US012799059B2

(12) United States Patent
Slivensky et al.

(10) Patent No.: US 12,799,059 B2
(45) Date of Patent: Nov. 17, 2026

(54) RECYCLE CONTENT GLYCOL ETHER AND GLYCOL ETHER ESTER COMPOSITIONS

(71) Applicant: ExxonMobil Product Solutions Company, Spring, TX (US)

(72) Inventors: David Eugene Slivensky, Tatum, TX (US); Daryl Bitting, Longview, TX (US); Kenny Randolph Parker, Afton, TN (US); Michael Gary Polasek, Longview, TX (US); William Lewis Trapp, Kingsport, TN (US); Xianchun Wu, Longview, TX (US)

(73) Assignee: Exxon Mobil Product Solutions Company, Spring, TX (US)

( * ) Notice: Subject to any disclaimer, the term of this patent is extended or adjusted under 35 U.S.C. 154(b) by 971 days.

(21) Appl. No.: 17/755,631

(22) PCT Filed: Nov. 6, 2020

(86) PCT No.: PCT/US2020/059312
§ 371 (c)(1),
(2) Date: May 4, 2022

(87) PCT Pub. No.: WO2021/092311
PCT Pub. Date: May 14, 2021

(65) Prior Publication Data

US 2022/0380283 A1 Dec. 1, 2022

Related U.S. Application Data

(60) Provisional application No. 62/932,029, filed on Nov. 7, 2019.

(51) Int. Cl.
*C07C 41/02* (2006.01)
*C07C 29/10* (2006.01)
(Continued)

(52) U.S. Cl.
CPC ............ *C07C 41/02* (2013.01); *C07C 29/106* (2013.01); *C07C 67/08* (2013.01); *C10G 1/10* (2013.01); *C10G 9/00* (2013.01); *C10G 2400/20* (2013.01)

(58) Field of Classification Search
None
See application file for complete search history.

(56) References Cited

U.S. PATENT DOCUMENTS 1,048,530 A 12/1912 Harlow
1,219,162 A 3/1917 Runge
(Continued)

FOREIGN PATENT DOCUMENTS

DE 1014089 B 8/1957
EP 0189247 A1 1/1986
(Continued)

OTHER PUBLICATIONS

BASF ("BASF's ChemCycling project uses chemically recycled plastics in products", published Dec. 17, 2018 at < https://www.recyclingtoday.com/news/basf-uses-chemically-recycled-plastic/>) (Year: 2018).*

(Continued)

*Primary Examiner* — Amy C Bonaparte
(74) *Attorney, Agent, or Firm* — C. Tumey Law Group PLLC

(57) ABSTRACT

A recycle content glycol ether or glycol ether ester and method of making a recycle content glycol ether or glycol ether ester wherein the recycle content is derived directly or indirectly from the cracking of recycle content pyrolysis oil and/or gas. The cracking of the pyrolysis oil can be conducted in a gas furnace or a split furnace.

16 Claims, 22 Drawing Sheets

(51) Int. Cl.

| | |
|---|---|
| ***C07C 67/08*** | (2006.01) |
| ***C10G 1/10*** | (2006.01) |
| ***C10G 9/00*** | (2006.01) |

(56) References Cited

U.S. PATENT DOCUMENTS

| | | | | |
|---|---|---|---|---|
| 2,464,916 | A | | 3/1949 | Adams et al. |
| 3,174,463 | A | | 3/1965 | Reagan |
| 3,175,968 | A | | 3/1965 | Berger |
| 3,340,312 | A | | 9/1967 | Duke, Jr. et al. |
| 3,448,157 | A | | 6/1969 | Slaugh et al. |
| 3,641,190 | A | | 2/1972 | Kivlen et al. |
| 3,711,568 | A | | 1/1973 | Cooper |
| 3,920,760 | A | | 11/1975 | Heinz |
| 3,935,279 | A | | 1/1976 | Cocuzza et al. |
| 3,959,316 | A | | 5/1976 | Piccinini et al. |
| 4,021,496 | A | | 5/1977 | Wright |
| 4,148,830 | A | | 4/1979 | Pruett et al. |
| 4,166,830 | A | | 9/1979 | Guth |
| 4,169,861 | A | | 10/1979 | Hughes |
| 4,176,045 | A | | 11/1979 | Leftin et al. |
| 4,364,905 | A | | 12/1982 | Fahrig et al. |
| 4,593,127 | A | | 6/1986 | Bunning et al. |
| 4,625,068 | A | | 11/1986 | Young |
| 4,699,998 | A | | 10/1987 | Green |
| 4,993,473 | A | | 2/1991 | Newcomb |
| 5,202,463 | A | | 4/1993 | Ruszkay |
| 5,253,479 | A | | 10/1993 | Di Cintio et al. |
| 5,264,600 | A | | 11/1993 | Lappe et al. |
| 5,364,995 | A | | 11/1994 | Kirkwood et al. |
| 5,446,229 | A | | 8/1995 | Taylor et al. |
| 5,523,502 | A | | 6/1996 | Rubin |
| 5,538,625 | A | | 7/1996 | Sigaud et al. |
| 5,618,973 | A | * | 4/1997 | Papa ...................... C07C 67/08 560/263 |
| 5,639,937 | A | | 6/1997 | Hover et al. |
| 5,656,150 | A | | 8/1997 | Reed et al. |
| 5,713,483 | A | | 2/1998 | Ata et al. |
| 5,763,724 | A | | 6/1998 | Bellet et al. |
| 5,945,568 | A | * | 8/1999 | Nagata .................... C07C 41/03 568/618 |
| 6,203,693 | B1 | | 3/2001 | Picciotti et al. |
| 6,488,839 | B1 | | 12/2002 | Lenglet et al. |
| 6,492,564 | B1 | | 12/2002 | Wiese et al. |
| 7,049,473 | B2 | | 5/2006 | Mackewitz et al. |
| 7,261,807 | B2 | | 8/2007 | Henry et al. |
| 7,420,092 | B2 | | 9/2008 | Fujita et al. |
| 7,935,850 | B2 | | 5/2011 | Caers et al. |
| 8,071,833 | B2 | | 12/2011 | Grootjans et al. |
| 8,658,019 | B2 | | 2/2014 | Bridges |
| 8,864,977 | B2 | | 10/2014 | Spicer et al. |
| 8,895,790 | B2 | | 11/2014 | Narayanaswamy et al. |
| 9,809,529 | B2 | | 11/2017 | Frycek et al. |
| 10,344,226 | B2 | | 7/2019 | Schmidt et al. |
| 10,513,661 | B2 | | 12/2019 | Narayanaswamy et al. |
| 10,851,309 | B2 | | 12/2020 | Ramamurthy et al. |
| 10,927,315 | B2 | | 2/2021 | Ramamurthy et al. |
| 11,365,357 | B2 | | 6/2022 | Bitting et al. |
| 11,473,016 | B2 | | 10/2022 | Timken |
| 2004/0188323 | A1 | | 9/2004 | Tzatzov et al. |
| 2006/0100473 | A1 | | 5/2006 | Grootjans et al. |
| 2007/0090020 | A1 | | 4/2007 | Buchanan et al. |
| 2007/0179326 | A1 | | 8/2007 | Baker |
| 2008/0142411 | A1 | | 6/2008 | Barendregt et al. |
| 2008/0207974 | A1 | | 8/2008 | McCoy et al. |
| 2008/0230444 | A1 | | 9/2008 | Iwadate et al. |
| 2009/0050530 | A1 | | 2/2009 | Spicer et al. |
| 2009/0054716 | A1 | | 2/2009 | Baumgartner et al. |
| 2011/0308142 | A1 | | 12/2011 | Abhari et al. |
| 2012/0125813 | A1 | | 5/2012 | Bridges et al. |
| 2012/0271029 | A1 | | 10/2012 | Kronemayer et al. |
| 2013/0296619 | A1 | | 11/2013 | Iaccino et al. |
| 2014/0018556 | A1 | * | 1/2014 | Verhaak .................... C07C 1/20 568/865 |
| 2015/0284645 | A1 | | 10/2015 | Schmidt et al. |
| 2016/0031775 | A1 | | 2/2016 | O'Young et al. |
| 2016/0168479 | A1 | | 6/2016 | Spicer et al. |
| 2016/0168491 | A1 | | 6/2016 | Yao et al. |
| 2016/0264874 | A1 | | 9/2016 | Narayanaswamy et al. |
| 2016/0264883 | A1 | | 9/2016 | Narayanaswamy et al. |
| 2016/0264885 | A1 | | 9/2016 | Narayanaswamy et al. |
| 2016/0362609 | A1 | | 12/2016 | Ward et al. |
| 2017/0081594 | A1 | | 3/2017 | Spicer et al. |
| 2018/0002609 | A1 | | 1/2018 | Narayanaswamy et al. |
| 2018/0170832 | A1 | | 6/2018 | Janda et al. |
| 2018/0346838 | A1 | | 12/2018 | Vasudevan et al. |
| 2019/0055483 | A1 | | 2/2019 | Bafna et al. |
| 2019/0161683 | A1 | | 5/2019 | Narayanaswamy et al. |
| 2019/0177626 | A1 | | 6/2019 | Ramamurthy et al. |
| 2019/0233744 | A1 | | 8/2019 | Narayanaswamy et al. |
| 2019/0241838 | A1 | | 8/2019 | Scheibel |
| 2019/0270939 | A1 | | 9/2019 | Javeed et al. |
| 2019/0299491 | A1 | | 10/2019 | Stanislaus et al. |
| 2019/0367428 | A1 | | 12/2019 | Ramamurthy et al. |
| 2020/0017773 | A1 | | 1/2020 | Ramamurthy et al. |
| 2020/0299590 | A1 | | 9/2020 | Cintula et al. |
| 2020/0369965 | A1 | | 11/2020 | Bitting et al. |
| 2020/0369966 | A1 | | 11/2020 | Bitting et al. |
| 2021/0130262 | A1 | | 5/2021 | Wu et al. |
| 2021/0130699 | A1 | | 5/2021 | Bitting et al. |
| 2021/0130700 | A1 | | 5/2021 | Slivensky et al. |
| 2021/0139620 | A1 | | 5/2021 | Wu et al. |

FOREIGN PATENT DOCUMENTS

| | | | |
|---|---|---|---|
| EP | 0250168 | A1 | 12/1987 |
| EP | 0467860 | A1 | 7/1991 |
| EP | 0804398 | A1 | 11/1997 |
| EP | 0711747 | B1 | 7/1998 |
| EP | 2949728 | A1 | 2/2015 |
| JP | 09-157659 | A | 6/1997 |
| WO | WO 82/03856 | A1 | 11/1982 |
| WO | WO 98/17614 | A1 | 4/1998 |
| WO | WO 2005/111175 | A1 | 11/2005 |
| WO | WO 2012/061005 | A2 | 5/2012 |
| WO | WO 2015/024103 | A1 | 2/2015 |
| WO | WO 2017/152046 | A1 | 9/2017 |
| WO | WO 2018/025104 | A1 | 2/2018 |
| WO | WO 2018-069794 | A1 | 4/2018 |
| WO | WO 2022/017899 | A1 | 1/2022 |
| WO | WO 2022/017901 | A1 | 1/2022 |
| WO | WO 2022/017902 | A1 | 1/2022 |
| WO | WO 2022/017903 | A1 | 1/2022 |
| WO | WO 2022/017904 | A1 | 1/2022 |
| WO | WO 2022/017906 | A1 | 1/2022 |

OTHER PUBLICATIONS

Sharuddin ("A review on the pyrolysis of plastic wastes" Energy Conversion and Management, 2016, p. 308) (Year: 2016).*

Co-pending U.S. Appl. No. 17/663,219, filed May 13, 2022; Bitting et al.

USPTO Office Action dated Jan. 5, 2024 for co-pending U.S. Appl. No. 17/663,219.

USPTO Office Action dated Nov. 14, 2022 for co-pending U.S. Appl. No. 16/881,030.

USPTO Office Action dated Apr. 3, 2023 for co-pending U.S. Appl. No. 16/881,030.

USPTO Office Action dated Dec. 13, 2023 for co-pending U.S. Appl. No. 16/881,030.

USPTO Office Action dated Sep. 28, 2023 for co-pending U.S. Appl. No. 17/755,330.

USPTO Office Action dated Aug. 25, 2023 for co-pending U.S. Appl. No. 16/881,032.

USPTO Office Action dated Oct. 26, 2023 received in Co-pending U.S. Appl. No. 17/755,347.

USPTO Office Action dated Aug. 31, 2023 for co-pending U.S. Appl. No. 17/755,342.

Co-pending U.S. Appl. No. 17/755,342, filed Apr. 27, 2022; Polasek et al.

(56) References Cited

OTHER PUBLICATIONS

Simon, C.M. et al.; "Pyrolysis of polyolefins with steam to yield olefins"; Journal of Analytical and Applied Pyrolysis; 38 (1996) pp. 75-78.
Zimmermann, Heinz, et al.; "Ethylene" In: "Ullmann's Encyclopedia of Industrial Chemistry", Apr. 15, 2009.
European Search Report; Application No. 20814532.6 dated Feb. 13, 2023.
European Search Report; Application No. 20881471.5 dated Nov. 27, 2023.
European Search Report; Application No. 20881241.2 dated Nov. 27, 2023.
European Search Report; Application No. 20882795.6 dated Nov. 27, 2023.
European Search Report; Application No. 20881996.1 dated Nov. 27, 2023.
"BASF for the first time makes products with chemically recycled plastics"; https://www.basfcom/us/en/media/news-releases/2018/12/P-US-18-134.html; Published Dec. 13, 2018.
"ISCC 203—Traceability and Chain of Custody"; https://www.iscc-system.org/wp-content/uploads/2017/02/ISCC_203_Traceability_and_Chain-of-Custody_3.0.pdf; Published Aug. 9, 2016.
AIChE Academy; Co-Cracking Vs. Segregated "Hybrid" Cracking in Individual Furnaces—Design and Operational Considerations; http://web.archive.org/web/20150124050411/https://www.aiche.org/academy/videos/conference-presentations/co-cracking-vs-segregated-hybrid-cracking-individual-furnaces-design-and-operational-considerat; Published Jan. 24, 2015.
ASTM D2887 "Standard Test Method for Boiling Range Distribution of Petroleum Fractions by Gas Chromatography" Published Jan. 2020.
ASTM D5399 "Standard Test Method for Boiling Point Distribution of Hydrocarbon Solvents by Gas Chromatography" Published Dec. 2017.
Bridle Intellectual Property LTD; Third Party Observations on PCT/US2020/034157; Sep. 23, 2021.
Bridle Intellectual Property LTD; Third Party Observations on PCT/US2020/034163; Sep. 23, 2021.
Co-pending U.S. Appl. No. 16/881,035, filed May 22, 2020; Bitting et al. Published as US 2021-0363432.
USPTO Office Action dated May 12, 2021 for co-pending U.S. Appl. No. 16/881,035.
Notice of Allowance received from USPTO on Feb. 9, 2022 in Co-pending U.S. Appl. No. 16/881,035.
Notice of Allowance received from USPTO on Sep. 30, 2021 in Co-pending U.S. Appl. No. 16/881,035.
Co-pending U.S. Appl. No. 17/593,383, filed Sep. 17, 2021; Bitting et al.
Co-pending U.S. Appl. No. 16/881,030, filed May 22, 2020; Bitting et al. Published as US 2020-0369965.
USPTO Office Action dated Mar. 25, 2021 for co-pending U.S. Appl. No. 16/881,030.
USPTO Office Action dated Oct. 5, 2021 for co-pending U.S. Appl. No. 16/881,030.
USPTO Office Action dated Dec. 6, 2021 for co-pending U.S. Appl. No. 16/881,030.
Co-pending U.S. Appl. No. 17/595,510, filed Nov. 18, 2021; Bitting et al.
Co-pending U.S. Appl. No. 17/594,308, filed Oct. 11, 2021; Bitting et al.
Co-pending U.S. Appl. No. 17/755,330, filed Apr. 27, 2022; Bitting et al.
Co-pending U.S. Appl. No. 17/594,370, filed Oct. 13, 2021; Bitting et al.
Co-pending U.S. Appl. No. 16/881,032, filed May 22, 2020; Bitting et al. Published as US 2020-0369966.
USPTO Office Action dated Dec. 10, 2021 for co-pending U.S. Appl. No. 16/881,032.
USPTO Office Action dated Mar. 25, 2021 for co-pending U.S. Appl. No. 16/881,032.
Co-pending U.S. Appl. No. 17/755,347, filed Apr. 27, 2022; Polasek et al.
Co-pending U.S. Appl. No. 17/755,344, filed Apr. 27, 2022; Polasek et al.
Co-pending U.S. Appl. No. 17/755,637, filed May 4, 2022; Polasek et al.
Ellen MacArthur Foundation and CE100; "Driving circular economy with the mass balance approach: BASF joins forces with members of the Ellen MacArthur Foundation's CE100 network for White Paper Publication"; https://www.basf.com/us/en/who-we-are/sustainability/whats-new/sustainability-news/2019/EllenMacArthurfoundation-White_Paper-Mass-balance.html; Published May 10, 2019.
Laermann, Michael; Chemical Recycling of Plastic Waste No More?; https://sustainablebrands.com/read/chemistry-materials-packaging/chemical-recycling-of-plastic-waste-no-more; Published Apr. 10, 2019.
Li, Fuwei, et al., "Production of Light Olefins from Catalytic Cracking Bio-oil Model Compounds over La203-Modified ZSM-5 zeolite", Energy & Fuels, 2018, 32, pp. 5910-5922.
Miandad, Rashid et al.; "Catalytic Pyrolysis of Plastic Waste: Moving Toward Pyrolysis Based Biorefineries"; Frontiers in Energy Research, vol. 7m Article 27, pp. 1-17, Published Mar. 19, 2019.
Notification of Transmittal of the International Search Report and the Written Opinion of the International Searching Authority with Date of Mailing Aug. 27, 2020 for International Application No. PCT/US2020/034147.
Notification of Transmittal of the International Search Report and the Written Opinion of the International Searching Authority with Date of Mailing Feb. 19, 2021 for International Application No. PCT/US2020/057842.
Notification of Transmittal of the International Search Report and the Written Opinion of the International Searching Authority with Date of Mailing Feb. 22, 2021 for International Application No. PCT/US2020/057837.
Notification of Transmittal of the International Search Report and the Written Opinion of the International Searching Authority with Date of Mailing Feb. 23, 2021 for International Application No. PCT/US2020/057888.
Notification of Transmittal of the International Search Report and the Written Opinion of the International Searching Authority with Date of Mailing Feb. 26, 2021 for International Application No. PCT/US2020/059289.
Notification of Transmittal of the International Search Report and the Written Opinion of the International Searching Authority with Date of Mailing Feb. 26, 2021 for International Application No. PCT/US2020/059312.
Notification of Transmittal of the International Search Report and the Written Opinion of the International Searching Authority with Date of Mailing Feb. 9, 2021 for International Application No. PCT/US2020/057884.
Notification of Transmittal of the International Search Report and the Written Opinion of the International Searching Authority with Date of Mailing Sep. 10, 2020 for International Application No. PCT/US2020/034157.
Notification of Transmittal of the International Search Report and the Written Opinion of the International Searching Authority with Date of Mailing Sep. 4, 2020 for International Application No. PCT/US2020/034153.
Notification of Transmittal of the International Search Report and the Written Opinion of the International Searching Authority with Date of Mailing Sep. 4, 2020 for International Application No. PCT/US2020/034163.
Paben, Jared; "Pyrolysis firm unveils recycled chemicals to make olefins"; https://resource-recycling.com/plastics/2018/09/06/pyrolysis-firm-unveils-recycled-chemicals-to-make-olefins/; Published Sep. 6, 2018.
PCT Third Party Observation with Submission Date of Sep. 24, 2021 for International Application No. PCT/US2020/034147.
PCT Third Party Observation with Submission Date of Sep. 24, 2021 for International Application No. PCT/US2020/034153.
PCT Third Party Observation with Submission Date of Sep. 24, 2021 for International Application No. PCT/US2020/034157.

(56) References Cited

OTHER PUBLICATIONS

PCT Third Party Observation with Submission Date of Sep. 24, 2021 for International Application No. PCT/US2020/034163.
Scheirs, John et al.; “Feedstock Recycling and Pyrolysis of Waste Plastics”; Wiley Series in Polymer Science; Chapter 13, p. 345-361, (2006).
Shoji, Atsushi et al.; “Thermal weight analysis of the jet floor gasification process of wasteTen”; Journal of Chemical Engineering, 2000 pp. 27-34.
The Editors of Encyclopedia Britannica; “Pyrolysis—Chemical Reaction”; https://web.archibe.org/web/20160611215925/https://www.britannica.com/science/pyrolysis; Published Jun. 11, 2016.
The Editors of Encyclopedia Britannica; “Cracking—Chemical Process”; https://web.archive.org/web/20160629203035/https://www.britannica.com/technology/cracking-chemical-process; Publication Date Jun. 29, 2016.
Indian Office Action for IN Patent Application No. 202217026908 dated Mar. 13, 2025. English Translation, PDF file. 7 pages.

* cited by examiner

RECYCLE CONTENT GLYCOL ETHER AND GLYCOL ETHER ESTER COMPOSITIONS

CROSS-REFERENCE TO RELATED APPLICATION(S)

This application is a national stage filing under 35 USC § 371 of International Application Number PCT/US2020/059312, filed on, Nov. 6, 2020 which claims the benefit of the filing date to U.S. Provisional Application No. 62/932,029, filed on Nov. 7, 2019, the entire disclosures of which are incorporated by reference herein.

BACKGROUND OF THE INVENTION

Waste materials, especially non-biodegradable waste materials, can negatively impact the environment when disposed of in landfills after a single use. Thus, from an environmental standpoint, it is desirable to recycle as much waste material as possible. However, recycling waste materials can be challenging from an economic standpoint.

To maximize recycling efficiency, it would be desirable for large-scale production facilities to be able to process feedstocks having recycle content originating from a variety of waste materials. Some recycling efforts involve complicated and detailed segregation of waste streams, which contributes to the increased cost of obtaining streams of recycle waste content. It would be desirable to establish recycle content without the necessity for sorting down to a single type of plastic or waste material, or which can tolerate a variety of impurities in waste streams.

In some cases, it may be difficult to dedicate a product having recycle content to a particular customer or downstream synthetic process for making a derivative of the product, particularly if the recycle content product is a gas or difficult to isolate. It may be difficult to segregate and distribute a dedicated portion of a gas made exclusively from a recycle content feedstock since the gas infrastructure is continuously fluid and often commingles gas streams from a variety of sources.

Further, it may be desirable to move away from dependence on natural gas, ethane, or propane as the sole source for making products such as ethylene and propylene and their downstream derivatives.

It is also desirable to synthesize chemical compounds, such as glycol ethers and glycol ether esters, using existing equipment and processes and without the need to invest in additional and expensive equipment in order to establish a recycle content in the manufacture of the chemical compound.

It would be desirable to be able to determine the amount and timing of establishing recycle content in a chemical compound such as a glycol ether or glycol ether ester. Also, there may be a desire to provide glycol ethers and glycol ether esters, at certain times or for different batches, with more or less recycle content or no recycle content. The flexibility in this approach without the need to add significant assets is desirable.

SUMMARY OF THE INVENTION

There is now provided a method of obtaining a recycle content glycol ether and/or glycol ether ester composition, methods of reacting recycle content alkylene oxide or applying a recycle content value to make a recycle content glycol ether, methods of reacting recycle content glycol ether or applying a recycle content value to make a recycle content glycol ether ester, uses thereof, compositions thereof, and systems thereof, each as further described in the claims and detailed description.

DETAILED DESCRIPTION OF THE INVENTION

Figure 1:
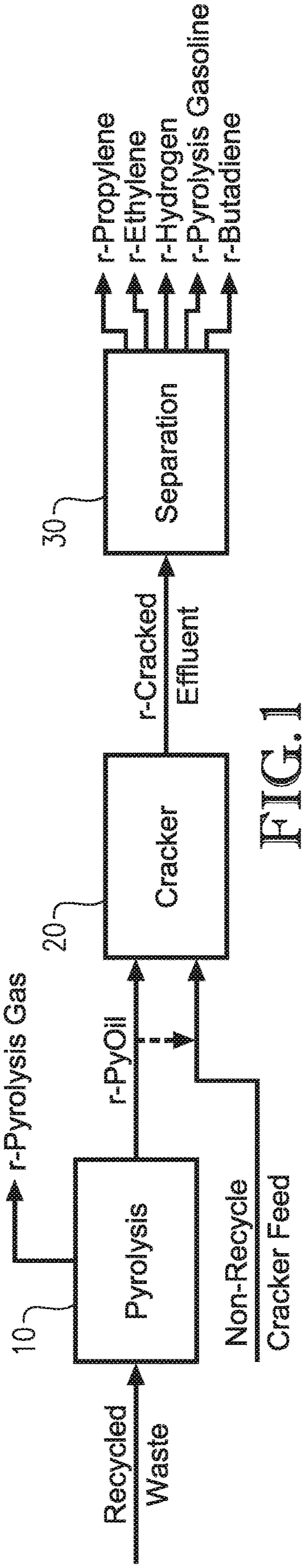
FIG. 1 is an illustrate of a process for employing a recycle content pyrolysis oil composition (r-pyoil) to make one or more recycle content compositions into r-compositions.

The word "containing" and "including" is synonymous with comprising. When a numerical sequence is indicated, it is to be understood that each number is modified the same as the first number or last number in the numerical sequence or in the sentence, e.g. each number is "at least," or "up to" or "not more than" as the case may be; and each number is in an "or" relationship. For example, "at least 10, 20, 30, 40, 50, 75 wt. % . . . " means the same as "at least 10 wt. %, or at least 20 wt. %, or at least 30 wt. %, or at least 40 wt. %, or at least 50 wt. %, or at least 75 wt. %," etc.; and "not more than 90 wt. %, 85, 70, 60 . . . " means the same as "not more than 90 wt. %, or not more than 85 wt. %, or not more than 70 wt. % . . . " etc.; and "at least 1%, 2%, 3%, 4%, 5%, 6%, 7%, 8%, 9% or 10% by weight . . . " means the same as "at least 1 wt. %, or at least 2 wt. %, or at least 3 wt. % . . . " etc.; and "at least 5, 10, 15, 20 and/or not more than 99, 95, 90 weight percent" means the same as "at least 5 wt. %, or at least 10 wt. %, or at least 15 wt. % or at least 20 wt. % and/or not more than 99 wt. %, or not more than 95 wt. %, or not more than 90 weight percent . . . " etc.; or "at least 500, 600, 750 °C . . . " means the same as "at least 500 °C, or at least 600 °C, or at least 750 °C . . . " etc.

In aspects, methods for making a recycle glycol ether ("r-GE") are provided that start with feeding a recycle content alkylene oxide composition at least a portion of which is derived directly or indirectly from pyrolyzing a recycled waste ("pr-AO") to a reactor to produce a glycol ether effluent comprising r-GE.

In aspects, methods for making a recycle glycol ether ester ("r-GEE") are provided that start with feeding a recycle content glycol ether composition at least a portion of which is derived directly or indirectly from pyrolyzing a recycled waste ("pr-GE") to a reactor to produce a glycol ether ester effluent comprising r-GEE.

Pyrolysis/Cracking Systems and Processes

All concentrations or amounts are by weight unless otherwise stated. An "olefin-containing effluent" is the furnace effluent obtained by cracking a cracker feed containing r-pyoil. A "non-recycle olefin-containing effluent" is the furnace effluent obtained by cracking a cracker feed that does not contain r-pyoil. Units on hydrocarbon mass flow rate, MF1, and MF2 are in kilo pounds/hr (klb/hr), unless otherwise stated as a molar flow rate.

As used herein, "containing" and "including" are open ended and synonymous with "comprising."

The term "recycle content" is used herein i) as a noun to refer to a physical component (e.g., compound, molecule, or atom) at least a portion of which is derived directly or indirectly from recycled waste or ii) as an adjective modifying a particular composition (e.g., a compound, polymer, feedstock, product, or stream) at least a portion of which is directly or indirectly derived from recycled waste.

As used herein, "recycle content composition," "recycle composition," and "r-composition" mean a composition having recycle content.

The term "pyrolysis recycle content" is used herein i) as a noun to refer to a physical component (e.g., compound, molecule, or atom) at least a portion of which is derived directly or indirectly from the pyrolysis of recycled waste or ii) as an adjective modifying a particular composition (e.g., a feedstock, product, or stream) at least a portion of which is directly or indirectly derived from the pyrolysis of recycled waste. For example, pyrolysis recycle content can be directly or indirectly derived from recycle content pyrolysis oil, recycle content pyrolysis gas, or the cracking of recycle content pyrolysis oil such as through thermal steam crackers or fluidized catalytic crackers.

As used herein, "pyrolysis recycle content composition," "pyrolysis recycle composition," and "pr-composition" mean a composition (e.g., a compound, polymer, feedstock, product, or stream) having pyrolysis recycle content. A pr-composition is a subset of a r-composition, where at least a portion of the recycle content of the r-composition is derived directly or indirectly from the pyrolysis of recycled waste.

As used herein, a composition (e.g., compound, polymer, feedstock, product, or stream) "directly derived" or "derived directly" from recycled waste has at least one physical component that is traceable to recycled waste, while a composition (e.g., a compound, polymer, feedstock, product, or stream) "indirectly derived" or "derived indirectly" from recycled waste has associated with it a recycle content allotment and may or may not contain a physical component that is traceable to recycled waste.

As used herein, a composition (e.g., compound, polymer, feedstock, product, or stream) "directly derived" or "derived directly" from the pyrolysis of recycled waste has at least one physical component that is traceable to the pyrolysis of recycled waste, while a composition (e.g., a compound, polymer, feedstock, product, or stream) "indirectly derived" or "derived indirectly" from the pyrolysis of recycled waste has associated with it a recycle content allotment and may or may not contain a physical component that is traceable to the pyrolysis of recycled waste.

As used herein, "pyrolysis oil" or "pyoil" mean a composition of matter that is liquid when measured at 25 °C and 1 atm and at least a portion of which is obtained from pyrolysis.

As used herein, "recycle content pyrolysis oil," "recycle pyoil," "pyrolysis recycle content pyrolysis oil" and "r-pyoil"" mean pyoil, at least a portion of which is obtained from pyrolysis, and having recycle content.

As used herein, "pyrolysis gas" and "pygas" mean a composition of matter that is gas when measured at 25 °C and 1 atm and at least a portion of which is obtained from pyrolysis.

As used herein, "recycle content pyrolysis gas," "recycle pygas," "pyrolysis content pyrolysis gas" and "r-pygas" mean pygas, at least a portion of which is obtained from pyrolysis, and having recycle content.

As used herein, "Et" is ethylene composition (e.g., a feedstock, product, or stream) and "Pr" is propylene composition (e.g., a feedstock, product, or stream).

As used herein, "recycle content ethylene," "r-ethylene" and "r-Et" mean Et having recycle content; and "recycle content propylene," "r-propylene" and "r-Pr" mean Pr having recycle content.

As used herein, "pyrolysis recycle content ethylene" and "pr-Et" mean r-Et having pyrolysis recycle content; and "pyrolysis recycle content propylene" and "pr-Pr" mean r-Pr having pyrolysis recycle content.

As used herein, "AO" is alkylene oxide composition (e.g., a feedstock, product, or stream).

As used herein, a “recycle content alkylene oxide” and “r-AO” mean AO having recycle content.

As used herein, a “pyrolysis content alkylene oxide” and “pr-AO” mean r-AO having pyrolysis recycle content.

As used herein, “GE” is glycol ether composition, i.e., ethylene glycol ether and/or propylene glycol ether (e.g., a feedstock, product, or stream).

As used herein, a “recycle content glycol ether” and “r-GE” mean GE having recycle content.

As used herein, a “pyrolysis content GE” and “pr-GE” mean r-GE having pyrolysis recycle content.

As used herein, “GEE” is a glycol ether ester composition (e.g., a feedstock, product, or stream).

As used herein, a “recycle content glycol ether ester” and “r-GEE” mean GEE having recycle content.

As used herein, a “pyrolysis content glycol ether ester” and “pr-GEE” mean r-GEE having pyrolysis recycle content.

As used throughout, the generic description of the compound, composition or stream does not require the presence of its species, but also does not exclude and may include its species. For example, a “GE” or “any GE” can include glycol ether made by any process and may or may not contain recycle content and may or may not be made from non-recycle content feedstocks or from recycle content feedstocks, and may or may not include r-GE or pr-GE. Likewise, r-GE may or may not include pr-GE, although the mention of r-GE does require it to have recycle content. In another example, an “Et” or “any Et” can include ethylene made by any process and may or may not have recycle content, and may or may not include r-Et or pr-Et. Likewise, r-Et may or may not include pr-Et, although the mention of r-Et does require it to have recycle content.

“Pyrolysis recycle content” is a specific subset/type (species) of “recycle content” (genus). Wherever “recycle content” and “r-” are used herein, such usage should be construed as expressly disclosing and providing claim support for “pyrolysis recycle content” and “pr-,” even if not expressly so stated. For example, whenever the term “recycle content glycol ether” or “r-GE” is used herein, it should be construed as also expressly disclosing and providing claim support for “pyrolysis recycle content glycol ether” and “pr-GE.”

As used throughout, whenever a cracking of r-pyoil is mentioned, such cracking can be conducted by a thermal cracker, or a thermal steam cracker, in a liquids fed furnace, or in a gas fed furnace, or in any cracking process. In one embodiment or in combination with any of the mentioned embodiments, the cracking is not catalytic or is conducted in the absence of an added catalyst or is not a fluidized catalytic cracking process.

As used throughout, whenever mention is made of pyrolysis of recycle waste, or r-pyoil, all embodiments also include (i) the option of cracking the effluent of pyrolyzing recycle waste or cracking r-pyoil and/or (ii) the option of cracking the effluent or r-pyoil as a feed to a gas fed furnace or to the tubes of gas furnace/cracker.

As used throughout, a “Family of Entities” means at least one person or entity that directly or indirectly controls, is controlled by, or is under common control with another person or entity, where control means ownership of at least 50% of the voting shares, or shared management, common use of facilities, equipment, and employees, or family interest. As used throughout, the mention of a person or entity provides claim support for and includes any person or entity among the Family of Entities.

In an embodiment or in combination with any other mentioned embodiments, the mention of r-Et also includes pr-Et, or pr-Et obtained directly or indirectly from the cracking of r-pyoil or obtained from r-pygas; and r-GE also includes pr-GE, or pr-GE obtained directly or indirectly from the cracking of r-pyoil or obtained from r-pygas.

In one embodiment or in combination with any of the mentioned embodiments, there is provided a method for making a r-GE composition by reacting AO (e.g., an AO composition) with alcohol. The AO can be a r-AO or a pr-AO or a dr-AO. In one embodiment, the method for making a r-GE starts with feeding r-AO to a reactor for making GE. In embodiments, the AO composition can be made by reacting O2 with an olefin (e.g., Et or Pr). The Et or Pr can be a r-Et or r-Pr, or a pr-Et or pr-PR, or a dr-Et or dr-Pr. In one embodiment, the AO is an r-AO made by feeding r-Et or r-Pr to a reactor for making AO.

In one embodiment or in combination with any of the mentioned embodiments, there is provided a method for making a r-GEE composition by reacting GE (e.g., a GE composition) with acid. The GE can be a r-GE or a pr-GE or a dr-GE. In one embodiment, the method for making a r-GEE starts with feeding r-GE to a reactor for making GEE.

FIG. 1 is a schematic depiction illustrating an embodiment or in combination with any embodiment mentioned herein of a process for employing a recycle content pyrolysis oil composition (r-pyoil) to make one or more recycle content compositions (e.g. ethylene, propylene, butadiene, hydrogen, and/or pyrolysis gasoline): the r-composition.

As shown in FIG. 1, recycled waste can be subjected to pyrolysis in pyrolysis unit 10 to produce a pyrolysis product/effluent comprising a recycle content pyrolysis oil composition (r-pyoil). The r-pyoil can be fed to a cracker 20, along with a non-recycle cracker feed (e.g., propone, ethane, and/or natural gasoline). A recycle content cracked effluent (r-cracked effluent) can be produced from the cracker and then subjected to separation in a separation train 30. In an embodiment or in combination with any embodiment mentioned herein, the r-composition can be separated and recovered from the r-cracked effluent. The r-propylene stream can contain predominantly propylene, while the r-ethylene stream can contain predominately ethylene.

Figure 5:
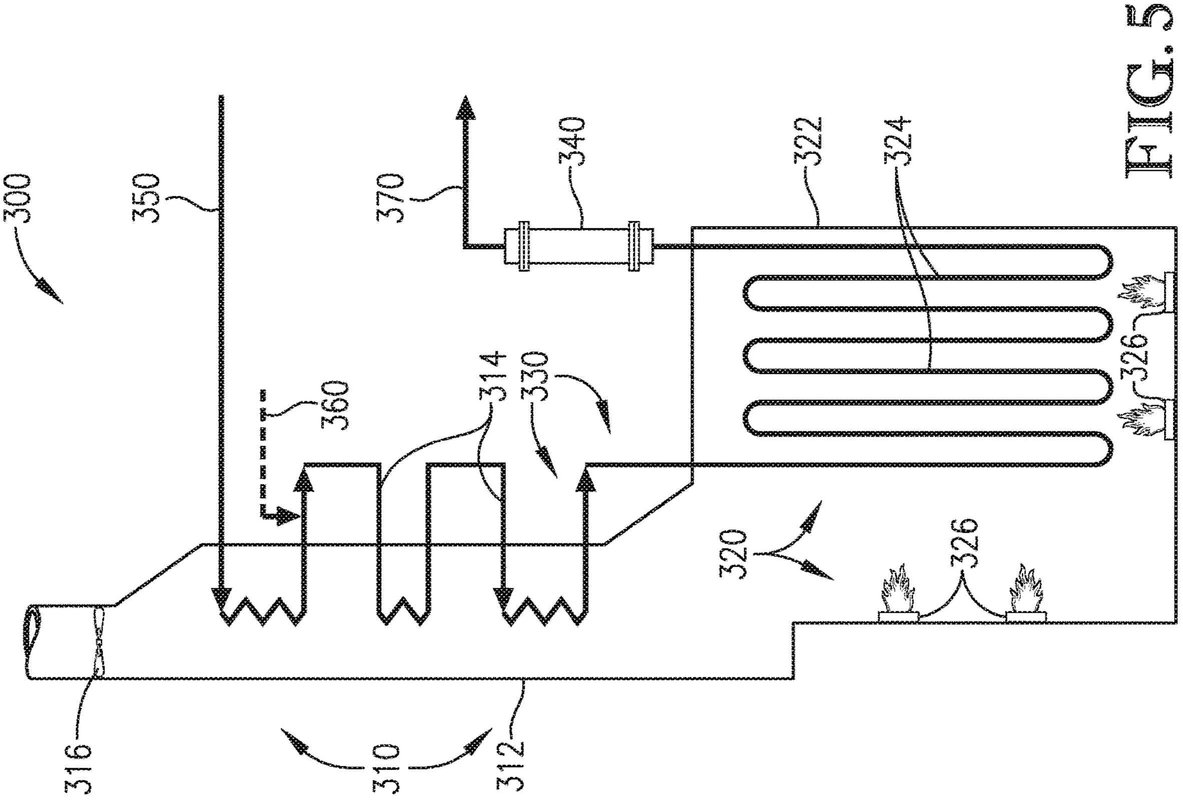
FIG. 5 is a schematic diagram of a cracker furnace suitable for receiving r-pyoil.

As used herein, a furnace includes the convection zone and the radiant zone. A convection zone includes the tubes and/or coils inside the convection box that can also continue outside the convection box downstream of the coil inlet at the entrance to the convection box. For example, as shown in FIG. 5, the convection zone 310 includes the coils and tubes inside the convection box 312 and can optionally extend or be interconnected with piping 314 outside the convection box 312 and returning inside the convection box 312. The radiant zone 320 includes radiant coils/tubes 324 and burners 326. The convection zone 310 and radiant zone 320 can be contained in a single unitary box, or in separate discrete boxes. The convection box 312 does not necessarily have to be a separate discrete box. As shown in FIG. 5, the convection box 312 is integrated with the firebox 322.

Unless otherwise specified, all component amounts provided herein (e.g. for feeds, feedstocks, streams, compositions, and products) are expressed on a dry basis.

As used herein, a “r-pyoil” or “r-pyrolysis oil” are interchangeable and mean a composition of matter that is liquid when measured at 25 °C and 1 atm, at least a portion of which is obtained from the pyrolysis, and which has recycle content. In embodiments, at least a portion of the composition is obtained from the pyrolysis of recycled waste (e.g., waste plastic or waste stream).

In embodiments, the "r-ethylene" can be a composition comprising: (a) ethylene obtained from cracking of a cracker feed containing r-pyoil, or (b) ethylene having a recycle content value attributed to at least a portion of the ethylene; and the "r-propylene" can be a composition comprising (a) propylene obtained from cracking of a cracker feed containing r-pyoil, or (b) propylene having a recycle content value attributed to at least a portion of the propylene.

Reference to a "r-ethylene molecule" means ethylene molecule derived directly or indirectly from recycled waste and reference to a "pr-ethylene molecule" means ethylene molecule derived directly or indirectly from r-pyrolysis effluent (e.g., r-pyoil and/or r-pygas).

As used herein, a "Site" means a largest continuous geographical boundary owned by a GE and/or GEE manufacturer, or by one person or entity, or combination of persons or entities, among its Family of Entities, wherein the geographical boundary contains one or more manufacturing facilities at least one of which is GE and/or GEE manufacturing facility.

As used herein, the term "predominantly" means more than 50 percent by weight, unless expressed in mole percent, in which case it means more than 50 mole %. For example, a predominantly propane stream, composition, feedstock, or product is a stream, composition, feedstock, or product that contains more than 50 weight percent propane, or if expressed as mole %, means a product that contains more than 50 mole % propane.

As used herein, a composition that is "directly derived" from cracking r-pyoil has at least one physical component that is traceable to an r-composition at least a portion of which is obtained by or with the cracking of r-pyoil, while a composition that is "indirectly derived" from cracking r-pyoil has associated with it a recycle content allotment and may or may not contain a physical component that is traceable to an r-composition at least a portion of which is obtained by or with the cracking of r-pyoil.

As used herein, "recycle content value" and "r-value" mean a unit of measure representative of a quantity of material having its origin in recycled waste. The r-value can have its origin in any type of recycled waste processed in any type of process.

As used herein, the term "pyrolysis recycle content value" and "pr-value" mean a unit of measure representative of a quantity of material having its origin in the pyrolysis of recycled waste. The pr-value is a specific subset/type of r-value that is tied to the pyrolysis of recycled waste. Therefore, the term r-value encompasses, but does not require, a pr-value.

The particular recycle content value (r-value or pr-value) can be by mass or percentage or any other unit of measure and can be determined according to a standard system for tracking, allocating, and/or crediting recycle content among various compositions. A recycle content value can be deducted from a recycle content inventory and applied to a product or composition to attribute recycle content to the product or composition. A recycle content value does not have to originate from making or cracking r-pyoil unless so stated. In one embodiment or in combination with any mentioned embodiments, at least a portion of the r-pyoil from which an allotment is obtained is also cracked in a cracking furnace as described throughout the one or more embodiments herein.

In one embodiment or in combination with any mentioned embodiments, at least a portion of the recycle content allotment or allotment or recycle content value deposited into a recycle content inventory is obtained from r-pyoil. Desirably, at least 60%, or at least 70%, or at least 80%, or at least 90% or at least 95%, or up to 100% of the:

a. allotments or
b. deposits into a recycle content inventory, or
c. recycle content value in a recycle content inventory, or
d. recycle content value applied to compositions to make a recycle content product, intermediate, or article (Recycle PIA) are obtained from r-pyoil.

A Recycle PIA is a product, intermediate or article which can include compounds or compositions containing compounds or polymers, and/or an article having an associated recycle content value. A PIA does not have a recycle content value associated with it. A PIA includes, and is not limited to, AO, or GE, or GEE.

As used herein, "recycle content allotment" or "allotment" means a recycle content value that is:

a. transferred from an originating composition (e.g., compound, polymer, feedstock, product, or stream) at least a portion of which is obtained from recycled waste or which has a recycle content value at least a portion of which originates from recycled waste, optionally originating from r-pyoil, to a receiving composition (the composition receiving the allotment, e.g., compound, polymer, feedstock, product, or stream) that may or may not have a physical component that is traceable to a composition at least a portion of which is obtained from recycled waste; or
b. deposited into a recycle inventory from an originating composition (e.g., compound, polymer, feedstock, product, or stream) at least a portion of which is obtained from or having a recycle content value or pr-value at least a portion of which originates from recycled waste.

As used herein, "pyrolysis recycle content allotment" and "pyrolysis allotment" or "pr-allotment" mean a pyrolysis recycle content value that is:

a. transferred from an originating composition (e.g., compound, polymer, feedstock, product, or stream) at least a portion of which is obtained from the pyrolysis of recycled waste or which has a recycle content value at least a portion of which originates from the pyrolysis of recycled waste, to a receiving composition (e.g., compound, polymer, feedstock, product, article or stream) that may or may not have a physical component that is traceable to a composition at least a portion of which is obtained from the pyrolysis of recycled waste; or
b. deposited into a recycle inventory from an originating composition (e.g., compound, polymer, feedstock, product, or stream) at least a portion of which is obtained from or having a recycle content value at least a portion of which originates from the pyrolysis of recycled waste.

A pyrolysis recycle content allotment is a specific type of recycle content allotment that is tied to the pyrolysis of recycled waste. Therefore, the term recycle content allotment encompasses pyrolysis recycle content allocation.

In one embodiment or in combination with any of the mentioned embodiments, a pyrolysis recycle content allotment or pyrolysis allotment may have a recycle content value that is:

a. transferred from an originating composition (e.g., compound, polymer, feedstock, product, or stream) at least a portion of which is obtained from the cracking (e.g. liquid or gas thermal steam cracking) of r-pyoil, or transferred from recycle waste used to make r-pyoil that is cracked, or transferred from r-pyoil that is or will be cracked, or which has a recycle content value at least a portion of which originates from the cracking (e.g. liquid or gas thermal steam cracking) of r-pyoil, to a receiving composition (e.g., compound, polymer, feedstock, product, or stream or PIA) that may or may not have a physical component that is traceable to a composition at least a portion of which is obtained from the cracking of r-pyoil; or b. deposited into a recycle content inventory and is obtained from a composition (e.g., compound, polymer, feedstock, product, or stream) at least a portion of which is obtained from or having a recycle content value at least a portion of which originates from the cracking (e.g. liquid or gas thermal steam cracking) of r-pyoil (whether or not the r-pyoil is cracked at the time of depositing the allotment into the recycle content inventory provided the r-pyoil from which the allotment is taken is ultimately cracked).

An allotment can be an allocation or a credit.

A recycle content allotment can include a recycle content allocation or a recycle content credit obtained with the transfer or use of a raw material. In one embodiment or in combination with any of the mentioned embodiments, the composition receiving the recycle content allotment can be a non-recycle composition, to thereby convert the non-recycle composition to an r-composition.

As used herein, "non-recycle" means a composition (e.g., compound, polymer, feedstock, product, or stream) none of which was directly or indirectly derived from recycled waste.

As used herein, a "non-recycle feed" in the context of a feed to the cracker or furnace means a feed that is not obtained from a recycled waste stream. Once a non-recycle feed obtains a recycle content allotment (e.g. either through a recycle content credit or recycle content allocation), the non-recycle feed become a recycle content feed, composition, or Recycle PIA.

As used herein, the term "recycle content allocation" is a type of recycle content allotment, where the entity or person supplying a composition sells or transfers the composition to the receiving person or entity, and the person or entity that made the composition has an allotment at least a portion of which can be associated with the composition sold or transferred by the supplying person or entity to the receiving person or entity. The supplying entity or person can be controlled by the same entity or person(s), or Family of Entities, or a different Family of Entities. In embodiments, a recycle content allocation travels with a composition and with the downstream derivates of the composition. In embodiments, an allocation may be deposited into a recycle content inventory and withdrawn from the recycle content inventory as an allocation and applied to a composition to make an r-composition or a Recycle PIA.

As used herein, "recycle content credit" and "credit" mean a type of recycle content allotment, where the allotment is not restricted to an association with compositions made from cracking r-pyoil or their downstream derivatives, but rather have the flexibility of being obtained from r-pyoil and (i) applied to compositions or PIA made from processes other than cracking feedstocks in a furnace, or (ii) applied to downstream derivatives of compositions, through one or more intermediate feedstocks, where such compositions are made from processes other than cracking feedstocks in a furnace, or (iii) available for sale or transfer to persons or entities other than the owner of the allotment, or (iv) available for sale or transfer by other than the supplier of the composition that is transferred to the receiving entity or person. For example, an allotment can be a credit when the allotment is taken from r-pyoil and applied by the owner of the allotment to a BTX composition, or cuts thereof, made by said owner or within its Family of Entities, obtained by refining and fractionation of petroleum rather than obtained by cracker effluent products; or it can be a credit if the owner of the allotment sells the allotment to a third party to allow the third party to either re-sell the product or apply the credit to one or more of a third party's compositions.

A credit can be available for sale or transfer or use, or can be sold or transferred or used, either:

a. without the sale of a composition, or b. with the sale or transfer of a composition but the allotment is not associated with the sale or transfer of the composition, or c. is deposited into or withdrawn from a recycle content inventory that does not track the molecules of a recycle content feedstock to the molecules of the resulting compositions which were made with the recycle content feedstocks, or which does have such tracking capability but which did not track the particular allotment as applied to a composition.

In one embodiment or in combination with any of the mentioned embodiments, an allotment may be deposited into a recycle content inventory, and a credit or allocation may be withdrawn from the inventory and applied to a composition. This would be the case where an allotment is created by making a first composition from the pyrolysis of recycle waste, or from r-pyoil or the cracking of r-pyoil, or by any other method of making a first composition from recycle waste, depositing the allocation associated with such first composition into a recycle content inventory, and deducting a recycle content value from the recycle content inventory and applying it to a second composition that is not a derivate of the first composition or that was not actually made by the first composition as a feedstock. In this system, one need not trace the source of a reactant back to the cracking of pyoil or back to any atoms contained in an olefin-containing effluent, but rather can use any reactant made by any process and have associated with such reactant a recycle content allotment.

In one embodiment or in combination with any mentioned embodiments, a composition receiving an allotment is used as a feedstock to make downstream derivatives of the composition, and such composition is a product of cracking a cracker feedstock in a cracker furnace. In one embodiment or in combination with any mentioned embodiments, there is provided a process in which:

a. a r-pyoil is obtained, b. a recycle content value (or allotment) is obtained from the r-pyoil and i. deposited into a recycle content inventory, and an allotment (or credit) is withdrawn from the recycle content inventory and applied to any composition to obtain a r-composition, or ii. applied directly to any composition, without depositing into a recycle content inventory, to obtain an r-composition; and c. at least a portion of the r-pyoil is cracked in a cracker furnace, optionally according to any of the designs or processes described herein; and d. optionally at least a portion of the composition in step b. originates from a cracking a cracker feedstock in a cracker furnace, optionally the composition having been obtained by any of the feedstocks, including r-pyoil, and methods described herein.

The steps b. and c. do not have to occur simultaneously. In one embodiment or in combination with any mentioned embodiments, they occur within a year of each other, or within six (6) months of each other, or within three (3) months of each other, or within one (1) month of each other, or within two (2) weeks of each other, or within one (1) week of each other, or within three (3) days of each other. The process allows for a time lapse between the time an entity or person receiving the r-pyoil and creating the allotment (which can occur upon receipt or ownership of the r-pyoil or deposit into inventory) and the actual processing of the r-pyoil in a cracker furnace.

As used herein, "recycle content inventory" and "inventory" mean a group or collection of allotments (allocations or credits) from which deposits and deductions of allotments in any units can be tracked. The inventory can be in any form (electronic or paper), using any or multiple software programs, or using a variety of modules or applications that together as a whole tracks the deposits and deductions. Desirably, the total amount of recycle content withdrawn (or applied to compositions) does not exceed the total amount of recycle content allotments on deposit in the recycle content inventory (from any source, not only from cracking of r-pyoil). However, if a deficit of recycle content value is realized, the recycle content inventory is rebalanced to achieve a zero or positive recycle content value available. The timing for rebalancing can be either determined and managed in accordance with the rules of a particular system of accreditation adopted by the olefin-containing effluent manufacturer or by one among its Family of Entities, or alternatively, is rebalanced within one (1) year, or within six (6) months, or within three (3) months, or within one (1) month of realizing the deficit. The timing for depositing an allotment into the recycle content inventory, applying an allotment (or credit) to a composition to make a r-composition, and cracking r-pyoil, need not be simultaneous or in any particular order. In one embodiment or in combination with any mentioned embodiments, the step of cracking a particular volume of r-pyoil occurs after the recycle content value or allotment from that volume of r-pyoil is deposited into a recycle content inventory. Further, the allotments or recycle content values withdrawn from the recycle content inventory need not be traceable to r-pyoil or cracking r-pyoil, but rather can be obtained from any waste recycle stream, and from any method of processing the recycle waste stream. Desirably, at least a portion of the recycle content value in the recycle content inventory is obtained from r-pyoil, and optionally at least a portion of r-pyoil, are processed in the one or more cracking processes as described herein, optionally within a year of each other and optionally at least a portion of the volume of r-pyoil from which a recycle content value is deposited into the recycle content inventory is also processed by any or more of the cracking processes described herein.

The determination of whether a r-composition is derived directly or indirectly from recycled waste is not on the basis of whether intermediate steps or entities do or do not exist in the supply chain, but rather whether at least a portion of the r-composition that is fed to the reactor for making an end product such as AO or GE or GEE can be traced to an r-composition made from recycled waste.

The determination of whether a pr-composition is derived directly or indirectly from the pyrolysis of recycled waste (e.g., from the cracking of r-pyoil or from r-pygas) is not on the basis of whether intermediate steps or entities do or do not exist in the supply chain, but rather whether at least a portion of the pr-composition that is fed to the reactor for making an end product such as GE can be traced to a pr-composition made from the pyrolysis of recycled waste.

As noted above, the end product is considered to be directly derived from cracking r-pyoil or from recycled waste if at least a portion of the reactant feedstock used to make the product can be traced back, optionally through one or more intermediate steps or entities, to at least a portion of the atoms or molecules that make up an r-composition produced from recycled waste or the cracking of r-pyoil fed to a cracking furnace or as an effluent from the cracking furnace.

The r-composition as an effluent may be in crude form that requires refining to isolate the particular r-composition. The r-composition manufacturer can, typically after refining and/or purification and compression to produce the desired grade of the particular r-composition, sell such r-composition to an intermediary entity who then sells the r-composition, or one or more derivatives thereof, to another intermediary for making an intermediate product or directly to the product manufacturer. Any number of intermediaries and intermediate derivates can be made before the final product is made.

The actual r-composition volume, whether condensed as a liquid, supercritical, or stored as a gas, can remain at the facility where it is made, or can be shipped to a different location, or held at an off-site storage facility before utilized by the intermediary or product manufacturer. For purposes of tracing, once an r-composition made from recycled waste (e.g., by cracking r-pyoil or from r-pygas) is mixed with another volume of the composition (e.g. r-ethylene mixed with non-recycle ethylene), for example in a storage tank, salt dome, or cavern, then the entire tank, dome, or cavern at that point becomes a r-composition source, and for purposes of tracing, withdrawal from such storage facility is withdrawing from an r-composition source until such time as when the entire volume or inventory of the storage facility is turned over or withdrawn and/or replaced with non-recycle compositions after the r-composition feed to the tank stops. Likewise, this applies also to any downstream storage facilities for storing the derivatives of the r-compositions, such as r-Et, r-Pr, pr-Et and pr-Pr compositions.

An r-composition is considered to be indirectly derived from recycled waste or pyrolysis of recycled waste or cracking of r-pyoil if it has associated with it a recycle content allotment and may or may not contain a physical component that is traceable to an r-composition at least a portion of which is obtained from recycled waste/pyrolysis of recycled waste/cracking of r-pyoil. For example, the (i) manufacturer of the product can operate within a legal framework, or an association framework, or an industry recognized framework for making a claim to a recycle content through, for example, a system of credits transferred to the product manufacturer regardless of where or from whom the r-composition, or derivatives thereof, or reactant feedstocks to make the product, is purchased or transferred, or (ii) a supplier of the r-composition or a derivate thereof ("supplier") operates within an allotment framework that allows for associating or applying a recycle content value or pr-value to a portion or all of an olefin-containing effluent or a compound within an olefin-containing effluent or derivate thereof to make an r-composition, and to transfer the recycle content value or allotment to the manufacturer of the product or any intermediary who obtains a supply of r-composition from the supplier. In this system, one need not trace the source of olefin volume back to the manufacture of r-composition from recycled waste/pyrolyzed recycled waste, but rather can use any ethylene composition made by any process and have associated with such ethylene composition a recycle content allotment, or an r-AO or r-GE or r-GEE manufacturer need not trace the source of r-Et or r-AO or r-GE or r-GEE feedstocks, respectively to a composition obtained by cracking r-pyoil or pyrolized recycle waste, but rather can use any ethylene/propylene or AO obtained from any source as a feedstock to make AO or GE or GEE, respectively and have associated with such AO or GE or GEE a recycle content allotment to make r-AO or r-GE or r-GEE.

Examples of how an olefin (e.g., Et) composition for making AO (and ultimately GE or GEE) can obtain recycle content include:

(i) a cracker facility in which the r-olefin (e.g. r-ethylene) is made at the facility, by cracking r-pyoil or obtained from r-pygas, can be in fluid communication, continuously or intermittently and directly or indirectly through intermediate facilities, with an olefin-derived petrochemical (e.g. AO or GE or GEE) formation facility (which can be to a storage vessel at the olefin-derived petrochemical facility or directly to the olefin-derived petrochemical formation reactor) through interconnected pipes, optionally through one or more storage vessels and valves or interlocks, and the r-olefin (e.g. r-ethylene) feedstock is drawn through the interconnected piping:
   a. from the cracker facility while r-olefin (e.g. r-ethylene) is being made or thereafter within the time for the r-olefin (e.g. r-ethylene) to transport through the piping to the olefin-derived petrochemical (e.g. AO or GE or GEE) formation facility; or
   b. from the one or more storage tanks at any time provided that at least one of the storage tanks was fed with r-olefin (e.g. r-ethylene), and continue for so long as the entire volume of the one or more storage tanks is replaced with a feed that does not contain r-olefin (e.g. r-ethylene); or (ii) transporting olefin (e.g. ethylene) from a storage vessel, dome, or facility, or in an isotainer via truck or rail or ship or a means other than piping, that contains or has been fed with r-olefin (e.g. r-ethylene) until such time as the entire volume of the vessel, dome or facility has been replaced with an olefin (e.g. ethylene) feed that does not contain r-olefin (e.g. r-ethylene); or (iii) the manufacturer of the olefin-derived petrochemical (e.g. AO or GE or GEE) certifies, represents to its customers or the public, or advertises that its olefin-derived petrochemical contains recycle content or is obtained from feedstock containing or obtained from recycle content, where such recycle content claim is based in whole or in part on obtaining r-olefin (e.g. ethylene feedstock associated with an allocation from ethylene made from cracking r-pyoil or obtained from r-pygas); or (iv) the manufacturer of the olefin-derived petrochemical (e.g. AO or GE or GEE) has acquired:
   a. an olefin (e.g. ethylene or propylene) volume made from r-pyoil under a certification, representation, or as advertised, or
   b. has transferred credits or allocation with the supply of olefin to the manufacturer of the olefin-derived petrochemical (e.g. AO or GE or GEE) sufficient to allow the manufacturer of the olefin-derived petrochemical (e.g. AO or GE or GEE) to satisfy the certification requirements or to make its representations or advertisements, or
   c. an olefin that has an associated recycle content value where such recycle content value was obtained, through one or more intermediary independent entities, from r-pyoil or cracking r-pyoil or an olefin obtained from cracking r-pyoil or obtained from r-pygas.

As discussed above, the recycle content can be a pyrolysis recycle content that is directly or indirectly derived from the pyrolysis of recycled waste (e.g., from cracking r-pyoil or from r-pygas).

In one embodiment or in combination with any of the mentioned embodiments, the recycle content input or creation (recycle content feedstock or allotments) can be to or at a first Site, and recycle content values from said inputs are transferred to a second Site and applied to one or more compositions made at a second Site. The recycle content values can be applied symmetrically or asymmetrically to the compositions at the second Site. A recycle content value that is directly or indirectly "derived from cracking r-pyoil", or a recycle content value that is "obtained from cracking r-pyoil" or originating in cracking r-pyoil does not imply the timing of when the recycle content value or allotment is taken, captured, deposited into a recycle content inventory, or transferred. The timing of depositing the allotment or recycle content value into a recycle content inventory, or realizing, recognizing, capturing, or transferring it, is flexible and can occur as early as receipt of r-pyoil onto the site within a Family of Entities, possessing it, or bringing the r-pyoil into inventory by the entity or person, or within the Family of Entities, owning or operating the cracker facility. Thus, an allotment or recycle content value on a volume of r-pyoil can be obtained, captured, deposited into an inventory, or transferred to a product without having yet fed that volume to cracker furnace and cracked. The allotment can also be obtained during feeding r-pyoil to a cracker, during cracking, or when an r-composition is made. An allotment taken when r-pyoil is owned, possessed, or received and deposited into a recycle content inventory is an allotment that is associated with, obtained from, or originates from cracking r-pyoil even though, at the time of taking or depositing the allotment, the r-pyoil has not yet been cracked, provided that the r-pyoil is at some future point in time cracked.

In one embodiment or in combination with any mentioned embodiments, the olefin-containing effluent manufacturer generates an allotment from r-pyoil, and either:
   a. applies the allotment to any PIA made directly or indirectly (e.g. through a reaction scheme of several intermediates) from cracking r-pyoil; or
   b. applies the allotment to any PIA not made directly or indirectly from cracking r-pyoil, such as would be the case where the PIA is already made and stored in inventory or future made PIA; or
   c. deposited into an inventory from which is deducted any allotment that is applied to PIA; and the deposited allotment either is or is not associated with the particular allotment applied to the PIA; or
   d. is deposited into an inventory and stored for use at a later time.

In one embodiment or in combination with any mentioned embodiments, one may communicate recycle content information about the Recycle PIA to a third party where such recycle content information is based on or derived from at least a portion of the allocation or credit. The third party may be a customer of the olefin-containing effluent manufacturer or of the Recycle PIA manufacturer or may be any other person or entity or governmental organization other than the entity owning the either of them. The communication may electronic, by document, by advertisement, or any other means of communication.

In one embodiment or in combination with any mentioned embodiments, there is provided a system or package comprising:

a. Recycle PIA, and
b. an identifier such as a credit, label or certification associated with said PIA, where the identifier is a representation that the PIA has, or is sourced from, a recycle content (which does not have to identify the source of the recycle content or allotment);

provided that the Recycle PIA made thereby has an allotment, or is made from a reactant, at least in part associated with r-pyoil.

As used throughout, the step of deducting an allotment from a recycle content inventory does not require its application to a Recycle PIA product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allotments on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allotment to a PIA where such allotment was deducted from inventory also does not require the allotment to be applied physically to a Recycle PIA product or to any document issued in association with the Recycle PIA product sold. For example, a Recycle PIA manufacturer may ship Recycle PIA product to a customer and satisfy the "application" of the allotment to the Recycle PIA product by electronically transferring a recycle content credit to the customer.

There is also provided a use for r-pyoil, the use including converting r-pyoil in a gas cracker furnace to make an olefin-containing effluent. There is also provided a use for a r-pyoil that includes converting a reactant in a synthetic process to make a PIA and applying at least a portion of an allotment to the PIA, where the allotment is associated with r-pyoil or has its origin in an inventory of allotments where at least one deposit made into the inventory is associated with r-pyoil.

In one embodiment or in combination with any mentioned embodiments, there is provided a Recycle PIA that is obtained by any of the methods described above.

In an embodiment, the process for making Recycle PIA can be an integrated process. One such example is a process to make Recycle PIA by:

a. cracking r-pyoil to make an olefin-containing effluent; and
b. separating compounds in said olefin-containing effluent to obtain a separated compound; and
c. reacting any reactant in a synthetic process to make a PIA;
d. depositing an allotment into an inventory of allotments, said allotment originating from r-pyoil; and
e. applying any allotment from said inventory to the PIA to thereby obtain a Recycle PIA.

In one embodiment or in combination with any mentioned embodiments, one may integrate two or more facilities and make Recycle PIA. The facilities to make Recycle PIA, or the olefin-containing effluent, can be stand-alone facilities or facilities integrated to each other. For example, one may establish a system of producing and consuming a reactant, as follows:

a. provide an olefin-containing effluent manufacturing facility configured to produce a reactant;
b. provide a PIA manufacturing facility having a reactor configured to accept a reactant from the olefin-containing effluent manufacturing facility; and
c. a supply system providing fluid communication between these two facilities and capable of supplying a reactant from the olefin-containing effluent manufacturing facility to the PIA manufacturing facility, wherein the olefin-containing effluent manufacturing facility generates or participates in a process to generate allotments and cracks r-pyoil, and:

(i) said allotments are applied to the reactants or to the PIA, or
(ii) are deposited into an inventory of allotments, and optionally an allotment is withdrawn from the inventory and applied to the reactants or to the PIA.

The Recycle PIA manufacturing facility can make Recycle PIA by accepting any reactant from the olefin-containing effluent manufacturing facility and applying a recycle content to Recycle PIA made with the reactant by deducting allotments from its inventory and applying them to the PIA.

In one embodiment or in combination with any mentioned embodiments, there is also provided a system for producing Recycle PIA as follows:

a. provide an olefin-containing effluent manufacturing facility configured to produce an output composition comprising an olefin-containing effluent;
b. provide a reactant manufacturing facility configured to accept a compound separated from the olefin-containing effluent and making, through a reaction scheme one or more downstream products of said compound to make an output composition comprising a reactant;
c. provide a PIA manufacturing facility having a reactor configured to accept a reactant and making an output composition comprising PIA; and
d. a supply system providing fluid communication between at least two of these facilities and capable of supplying the output composition of one manufacturing facility to another one or more of said manufacturing facilities.

The PIA manufacturing facility can make Recycle PIA. In this system, the olefin-containing effluent manufacturing facility can have its output in fluid communication with the reactant manufacturing facility which in turn can have its output in fluid communication with the PIA manufacturing facility. Alternatively, the manufacturing facilities of a) and b) alone can be in fluid communication, or only b) and c). In the latter case, the PIA manufacturing facility can make Recycle PIA by deducting allotments from it recycle content inventory and applying them to the PIA. The allotments obtained and stored in inventory can be obtained by any of the methods described above.

The fluid communication can be gaseous or liquid or both. The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment or in combination with any mentioned embodiments, the integrated process includes at least two facilities co-located within 5, or within 3, or within 2, or within 1 mile of each other (measured as a straight line). In one embodiment or in combination with any mentioned embodiments, at least two facilities are owned by the same Family of Entities.

There is also provided a circular manufacturing process comprising:

a. providing a r-pyoil, and
b. cracking the r-pyoil to produce an olefin-containing effluent, and
   (i) reacting a compound separated from said olefin-containing effluent to make a Recycle PIA, or
   (ii) associating a recycle content allotment, obtained from said r-pyoil, to the PIA made from compounds separated from a non-recycle olefin-containing effluent, to produce a Recycle PIA; and
c. taking back at least a portion of any of said Recycle PIA or any other articles, compounds, or polymer made from said Recycle PIA, as a feedstock to make said r-pyoil.

In the above described process, an entirely circular or closed loop process is provided in which Recycle PIA can be recycled multiple times.

Examples of articles that are included in PIA are fibers, yarns, tow, continuous filaments, staple fibers, rovings, fabrics, textiles, flake, film (e.g. polyolefin films), sheet, compounded sheet, plastic containers, and consumer articles.

In one embodiment or in combination with any mentioned embodiments, the Recycle PIA is a polymer or article of the same family or classification of polymers or articles used to make r-pyoil.

The terms "recycled waste," "waste stream," and "recycled waste stream" are used interchangeably to mean any type of waste or waste-containing stream that is reused in a production process, rather than being permanently disposed of (e.g., in a landfill or incinerator). The recycled waste stream is a flow or accumulation of recycled waste from industrial and consumer sources that is at least in part recovered.

A recycled waste stream includes materials, products, and articles (collectively "material(s)" when used alone). Recycled waste materials can be solid or liquid. Examples of a solid recycled waste stream include plastics, rubber (including tires), textiles, wood, biowaste, modified celluloses, wet laid products, and any other material capable of being pyrolyzed. Examples of liquid waste streams include industrial sludge, oils (including those derived from plants and petroleum), recovered lube oil, or vegetable oil or animal oil, and any other chemical streams from industrial plants.

In one embodiment or in combination with any of the mentioned embodiments, the recycled waste stream that is pyrolyzed includes a stream containing at least in part post-industrial, or post-consumer, or both a post-industrial and post-consumer materials. In one embodiment or in combination with any of the mentioned embodiments, a post-consumer material is one that has been used at least once for its intended application for any duration of time regardless of wear, or has been sold to an end use customer, or which is discarded into a recycle bin by any person or entity other than a manufacturer or business engaged in the manufacture or sale of the material.

In one embodiment or in combination with any of the mentioned embodiments, a post-industrial material is one which has been created and has not been used for its intended application, or has not been sold to the end use customer, or discarded by a manufacturer or any other entity engaged in the sale of the material. Examples of post-industrial materials include rework, regrind, scrap, trim, out of specification materials, and finished materials transferred from a manufacturer to any downstream customer (e.g. manufacturer to wholesaler to distributor) but not yet used or sold to the end use customer.

The form of the recycled waste stream, which can be fed to a pyrolysis unit, is not limited, and can include any of the forms of articles, products, materials, or portions thereof. A portion of an article can take the form of sheets, extruded shapes, moldings, films, laminates, foam pieces, chips, flakes, particles, fibers, agglomerates, briquettes, powder, shredded pieces, long strips, or randomly shaped pieces having a wide variety of shapes, or any other form other than the original form of the article and adapted to feed a pyrolysis unit.

In one embodiment or in combination with any of the mentioned embodiments, the recycled waste material is size reduced. Size reduction can occur through any means, including chopping, shredding, harrowing, confrication, pulverizing, cutting a feedstock, molding, compression, or dissolution in a solvent.

Recycled waste plastics can be isolated as one type of polymer stream or may be a stream of mixed recycled waste plastics. The plastics can be any organic synthetic polymer that is solid at 25 °C at 1 atm. The plastics can be thermosetting, thermoplastic, or elastomeric plastics. Examples of plastics include high density polyethylene and copolymers thereof, low density polyethylene and copolymers thereof, polypropylene and copolymers thereof, other polyolefins, polystyrene, polyvinyl chloride (PVC), polyvinylidene chloride (PVDC), polyesters including polyethylene terephthalate, copolyesters and terephthalate copolyesters (e.g. containing residues of TMCD, CHDM, propylene glycol, or NPG monomers), polyethylene terephthalate, polyamides, poly(methyl methacrylate), polytetrafluoroethylene, acrylobutadienestyrene (ABS), polyurethanes, cellulosics and derivates thereof such as cellulose acetate, cellulose diacetate, cellulose triacetate, cellulose propionate, cellulose butyrate; regenerated cellulosics such as viscose and rayons, epoxy, polyamides, phenolic resins, polyacetal, polycarbonates, polyphenylene-based alloys, polypropylene and copolymers thereof, polystyrene, styrenic compounds, vinyl based compounds, styrene acrylonitrile, thermoplastic elastomers, and urea based polymers and melamine containing polymers.

Suitable recycled waste plastics also include any of those having a resin ID code numbered 1-7 within the chasing arrow triangle established by the SPI. In one embodiment or in combination with any of the mentioned embodiments, the r-pyoil is made from a recycled waste stream at least a portion of which contains plastics that are not generally recycled. These would include plastics having numbers 3 (polyvinyl chloride), 5 (polypropylene), 6 (polystyrene), and 7 (other). In one embodiment or in combination with any of the mentioned embodiments, the recycled waste stream that is pyrolyzed contains less than 10 weight percent, or not more than 5 weight percent, or not more than 3 weight percent, or not more than 2 weight percent, or not more than 1 weight percent, or not more than 0.5 weight percent, or not more than 0.2 weight percent, or not more than 0.1 weight percent, or not more and 0.05 weight percent plastics with a number 3 designation (polyvinyl chloride), or optionally plastics with a number 3 and 6 designation, or optionally with a number 3, 6 and 7 designation.

Examples of recycled rubber include natural and synthetic rubber. The form of the rubber is not limited, and includes tires.

Examples of recycled waste wood include soft and hard woods, chipped, pulped, or as finished articles. The source of much recycled waste wood is industrial, construction, or demolition.

Examples of recycled biorecycled waste includes household biorecycled waste (e.g. food), green or garden biorecycled waste, and biorecycled waste from the industrial food processing industry.

Examples of recycled textiles includes natural and/or synthetic fibers, rovings, yarns, nonwoven webs, cloth, fabrics and products made from or containing any of the aforementioned items. Textiles can be woven, knitted, knotted, stitched, tufted, pressing of fibers together such as would be done in a felting operation, embroidered, laced, crocheted, braided, or nonwoven webs and materials. Textiles include fabrics, and fibers separated from a textile or other product containing fibers, scrap or off spec fibers or yarns or fabrics, or any other source of loose fibers and yarns. A textile also includes staple fibers, continuous fibers, threads, tow bands, twisted and/or spun yarns, grey fabrics made from yarns, finished fabrics produced by wet processing gray fabrics, and garments made from the finished fabrics or any other fabrics. Textiles include apparels, interior furnishings, and industrial types of textiles.

Examples of recycled textiles in the apparel category (things humans wear or made for the body) include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category include furniture upholstery and slipcovers, carpets and rugs, curtains, bedding such as sheets, pillow covers, duvets, comforters, mattress covers; linens, table cloths, towels, washcloths, and blankets. Examples of industrial textiles include transportation (auto, airplanes, trains, buses) seats, floor mats, trunk liners, and headliners; outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The recycled nonwoven webs can also be dry laid nonwoven webs. Examples of suitable articles that may be formed from dry laid nonwoven webs as described herein can include those for personal, consumer, industrial, food service, medical, and other types of end uses. Specific examples can include, but are not limited to, baby wipes, flushable wipes, disposable diapers, training pants, feminine hygiene products such as sanitary napkins and tampons, adult incontinence pads, underwear, or briefs, and pet training pads. Other examples include a variety of different dry or wet wipes, including those for consumer (such as personal care or household) and industrial (such as food service, health care, or specialty) use. Nonwoven webs can also be used as padding for pillows, mattresses, and upholstery, batting for quilts and comforters. In the medical and industrial fields, nonwoven webs of the present invention may be used for medical and industrial face masks, protective clothing, caps, and shoe covers, disposable sheets, surgical gowns, drapes, bandages, and medical dressings. Additionally, nonwoven webs may be used for environmental fabrics such as geotextiles and tarps, oil and chemical absorbent pads, as well as building materials such as acoustic or thermal insulation, tents, lumber and soil covers and sheeting. Nonwoven webs may also be used for other consumer end use applications, such as for, carpet backing, packaging for consumer, industrial, and agricultural goods, thermal or acoustic insulation, and in various types of apparel. The dry laid nonwoven webs may also be used for a variety of filtration applications, including transportation (e.g., automotive or aeronautical), commercial, residential, industrial, or other specialty applications. Examples can include filter elements for consumer or industrial air or liquid filters (e.g., gasoline, oil, water), including nanofiber webs used for microfiltration, as well as end uses like tea bags, coffee filters, and dryer sheets. Further, nonwoven webs may be used to form a variety of components for use in automobiles, including, but not limited to, brake pads, trunk liners, carpet tufting, and under padding.

The recycled textiles can include single type or multiple type of natural fibers and/or single type or multiple type of synthetic fibers. Examples of textile fiber combinations include all natural, all synthetic, two or more type of natural fibers, two or more types of synthetic fibers, one type of natural fiber and one type of synthetic fiber, one type of natural fibers and two or more types of synthetic fibers, two or more types of natural fibers and one type of synthetic fibers, and two or more types of natural fibers and two or more types of synthetic fibers.

Examples of recycled wet laid products include cardboard, office paper, newsprint and magazine, printing and writing paper, sanitary, tissue/toweling, packaging/container board, specialty papers, apparel, bleached board, corrugated medium, wet laid molded products, unbleached Kraft, decorative laminates, security paper and currency, grand scale graphics, specialty products, and food and drink products.

Examples of modified cellulose include cellulose acetate, cellulose diacetate, cellulose triacetate, regenerated cellulose such a viscose, rayon, and Lyocel™ products, in any form, such as tow bands, staple fibers, continuous fibers, films, sheets, molded or stamped products, and contained in or on any article such as cigarette filter rods, ophthalmic products, screwdrivers handles, optical films, and coatings.

Examples of recycled vegetable oil or animal oil include the oils recovered from animal processing facilities and recycled waste from restaurants.

The source for obtaining recycled post-consumer or post-industrial recycled waste is not limited, and can include recycled waste present in and/or separated from municipal solid recycled waste streams ("MSW"). For example, an MSW stream can be processed and sorted to several discrete components, including textiles, fibers, papers, wood, glass, metals, etc. Other sources of textiles include those obtained by collection agencies, or by or for or on behalf of textile brand owners or consortiums or organizations, or from brokers, or from postindustrial sources such as scrap from mills or commercial production facilities, unsold fabrics from wholesalers or dealers, from mechanical and/or chemical sorting or separation facilities, from landfills, or stranded on docks or ships.

In one embodiment or in combination with any of the mentioned embodiments, the feed to the pyrolysis unit can comprise at least 30, or at least 35, or at least 40, or at least 45, or at least 50, or at least 55, or at least 60, or at least 65, or at least 70, or at least 75, or at least 80, or at least 85, or at least 90, or at least 95, or at least 99, in each case weight percent of at least one, or at least two, or at least three, or at least four, or at least five, or at least six different kinds of recycled waste. Reference to a "kind" is determined by resin ID code 1-7. In one embodiment or in combination with any of the mentioned embodiments, the feed to the pyrolysis unit contains less than 25, or not more than 20, or not more than 15, or not more than 10, or not more than 5, or not more than 1, in each case weight percent of polyvinyl chloride and/or polyethylene terephthalate. In one embodiment or in combination with any of the mentioned embodiments, the recycled waste stream contains at least one, two, or three kinds of plasticized plastics.

Figure 2:
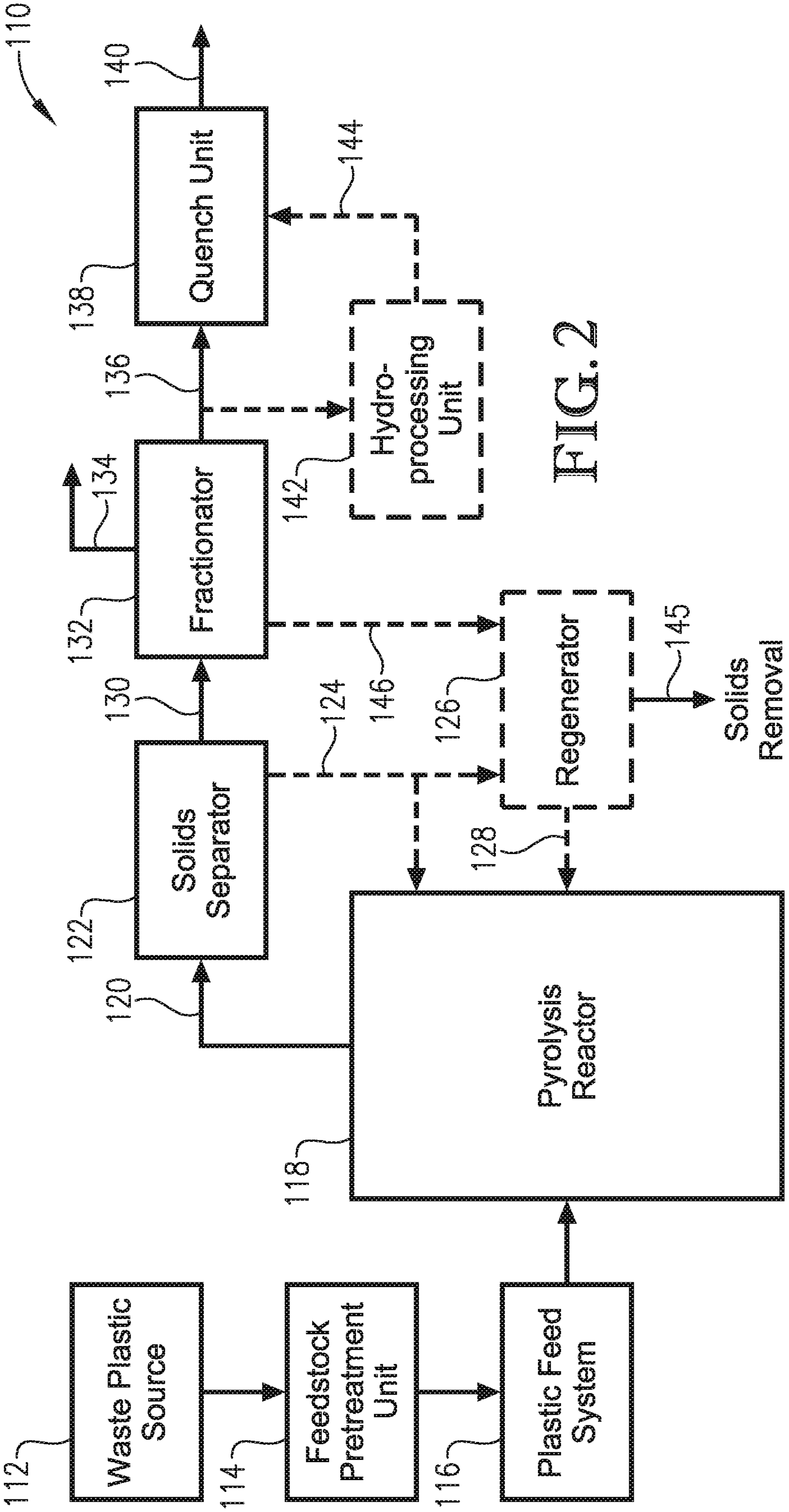
FIG. 2 is an illustration of an exemplary pyrolysis system to at least partially convert one or more recycled waste, particularly recycled plastic waste, into various useful r-products.

FIG. 2 depicts an exemplary pyrolysis system 110 that may be employed to at least partially convert one or more recycled waste, particularly recycled plastic waste, into various useful pyrolysis-derived products. It should be understood that the pyrolysis system shown in FIG. 2 is just one example of a system within which the present disclosure can be embodied. The present disclosure may find application in a wide variety of other systems where it is desirable to efficiently and effectively pyrolyze recycled waste, particularly recycled plastic waste, into various desirable end products. The exemplary pyrolysis system illustrated in FIG. 2 will now be described in greater detail.

As shown in FIG. 2, the pyrolysis system 110 may include a waste plastic source 112 for supplying one or more waste plastics to the system 110. The plastic source 112 can be, for example, a hopper, storage bin, railcar, over-the-road trailer, or any other device that may hold or store waste plastics. In an embodiment or in combination with any of the embodiments mentioned herein, the waste plastics supplied by the plastic source 112 can be in the form of solid particles, such as chips, flakes, or a powder. Although not depicted in FIG. 2, the pyrolysis system 110 may also comprise additional sources of other types of recycled wastes that may be utilized to provide other feed types to the system 110.

In an embodiment or in combination with any of the embodiments mentioned herein, the waste plastics can include one or more post-consumer waste plastic such as, for example, high density polyethylene, low density polyethylene, polypropylene, other polyolefins, polystyrene, polyvinyl chloride (PVC), polyvinylidene chloride (PVDC), polyethylene terephthalate, polyamides, poly(methyl methacrylate), polytetrafluoroethylene, or combinations thereof. In an embodiment or in combination with any of the embodiments mentioned herein, the waste plastics may include high density polyethylene, low density polyethylene, polypropylene, or combinations thereof. As used herein, "post-consumer" refers to non-virgin plastics that have been previously introduced into the consumer market.

In an embodiment or in combination with any of the embodiments mentioned herein, a waste plastic-containing feed may be supplied from the plastic source 112. In an embodiment or in combination with any of the embodiments mentioned herein, the waste plastic-containing feed can comprise, consist essentially of, or consist of high density polyethylene, low density polyethylene, polypropylene, other polyolefins, polystyrene, polyvinyl chloride (PVC), polyvinylidene chloride (PVDC), polyethylene terephthalate, polyamides, poly(methyl methacrylate), polytetrafluoroethylene, or combinations thereof.

In an embodiment or in combination with any of the embodiments mentioned herein, the waste plastic-containing feed can comprise at least 30, or at least 35, or at least 40, or at least 45, or at least 50, or at least 55, or at least 60, or at least 65, or at least 70, or at least 75, or at least 80, or at least 85, or at least 90, or at least 95, or at least 99, in each case weight percent of at least one, two, three, or four different kinds of waste plastic. In an embodiment or in combination with any of the embodiments mentioned herein, the plastic waste may comprise not more than 25, or not more than 20, or not more than 15, or not more than 10, or not more than 5, or not more than 1, in each case weight percent of polyvinyl chloride and/or polyethylene terephthalate. In an embodiment or in combination with any of the embodiments mentioned herein, the waste plastic-containing feed can comprise at least one, two, or three kinds of plasticized plastics. Reference to a "kind" is determined by resin ID code 1-7.

As depicted in FIG. 2, the solid waste plastic feed from the plastic source 112 can be supplied to a feedstock pretreatment unit 114. While in the feedstock pretreatment unit 114, the introduced waste plastics may undergo a number of pretreatments to facilitate the subsequent pyrolysis reaction. Such pretreatments may include, for example, washing, mechanical agitation, flotation, size reduction or any combination thereof. In an embodiment or in combination with any of the embodiments mentioned herein, the introduced plastic waste may be subjected to mechanical agitation or subjected to size reduction operations to reduce the particle size of the plastic waste. Such mechanical agitation can be supplied by any mixing, shearing, or grinding device known in the art which may reduce the average particle size of the introduced plastics by at least 10, or at least 25, or at least 50, or at least 75, in each case percent.

Next, the pretreated plastic feed can be introduced into a plastic feed system 116. The plastic feed system 116 may be configured to introduce the plastic feed into the pyrolysis reactor 118. The plastic feed system 116 can comprise any system known in the art that is capable of feeding the solid plastic feed into the pyrolysis reactor 118. In an embodiment or in combination with any of the embodiments mentioned herein, the plastic feed system 116 can comprise a screw feeder, a hopper, a pneumatic conveyance system, a mechanic metal train or chain, or combinations thereof.

While in the pyrolysis reactor 118, at least a portion of the plastic feed may be subjected to a pyrolysis reaction that produces a pyrolysis effluent comprising a pyrolysis oil (e.g., r-pyoil) and a pyrolysis gas (e.g., r-pyrolysis gas). The pyrolysis reactor 118 can be, for example, an extruder, a tubular reactor, a tank, a stirred tank reactor, a riser reactor, a fixed bed reactor, a fluidized bed reactor, a rotary kiln, a vacuum reactor, a microwave reactor, an ultrasonic or supersonic reactor, or an autoclave, a film reactor, or a combination of these reactors.

Generally, pyrolysis is a process that involves the chemical and thermal decomposition of the introduced feed. Although all pyrolysis processes may be generally characterized by a reaction environment that is substantially free of oxygen, pyrolysis processes may be further defined, for example, by the pyrolysis reaction temperature within the reactor, the residence time in the pyrolysis reactor, the reactor type, the pressure within the pyrolysis reactor, and the presence or absence of pyrolysis catalysts.

In an embodiment or in combination with any of the embodiments mentioned herein, the pyrolysis reaction can involve heating and converting the plastic feed in an atmosphere that is substantially free of oxygen or in an atmosphere that contains less oxygen relative to ambient air. In an embodiment or in combination with any of the embodiments mentioned herein, the atmosphere within the pyrolysis reactor 118 may comprise not more than 5, or not more than 4, or not more than 3, or not more than 2, or not more than 1, or not more than 0.5, in each case weight percent of oxygen gas.

In an embodiment or in combination with any of the embodiments mentioned herein, the pyrolysis process may be carried out in the presence of an inert gas, such as nitrogen, carbon dioxide, and/or steam. Additionally, or alternatively, in an embodiment or in combination with any of the embodiments mentioned herein, the pyrolysis process can be carried out in the presence of a reducing gas, such as hydrogen and/or carbon monoxide.

In an embodiment or in combination with any of the embodiments mentioned herein, the temperature in the pyrolysis reactor 118 can be adjusted to as to facilitate the production of certain end products. In an embodiment or in combination with any of the embodiments mentioned herein, the pyrolysis temperature in the pyrolysis reactor 118 can be at least 325 °C, or at least 350 °C, or at least 375 °C, or at least 400 °C, or at least 425 °C, or at least 450 °C, or at least 475 °C, or at least 500 °C, or at least 525 °C, or at least 550 °C, or at least 575 °C, or at least 600 °C, or at least 625 °C, or at least 650 °C, or at least 675 °C, or at least 700 °C, or at least 725 °C, or at least 750 °C, or at least 775 °C, or at least 800 °C. Additionally, or alternatively, in an embodiment or in combination with any of the embodiments mentioned herein, the pyrolysis temperature in the pyrolysis reactor 118 can be not more than 1,100 °C, or not more than 1,050 °C, or not more than 1,000 °C, or not more than 950 °C, or not more than 900 °C, or not more than 850 °C, or not more than 800 °C, or not more than 750 °C, or not more than 700 °C, or not more than 650 °C, or not more than 600 °C, or not more than 550 °C, or not more than 525 °C, or not more than 500 °C, or not more than 475 °C, or not more than 450 °C, or not more than 425 °C, or not more than 400 °C. In an embodiment or in combination with any of the embodiments mentioned herein, the pyrolysis temperature in the pyrolysis reactor 118 can range from 325 to 1,100 °C, 350 to 900 °C, 350 to 700 °C, 350 to 550 °C, 350 to 475 °C, 500 to 1,100 °C, 600 to 1,100 °C, or 650 to 1,000 °C.

In an embodiment or in combination with any of the embodiments mentioned herein, the residence times of the pyrolysis reaction can be at least 1, or at least 2, or at least 3, or at least 4, in each case seconds, or at least 10, or at least 20, or at least 30, or at least 45, or at least 60, or at least 75, or at least 90, in each case minutes. Additionally, or alternatively, in an embodiment or in combination with any of the embodiments mentioned herein, the residence times of the pyrolysis reaction can be not more than 6 hours, or not more than 5, or not more than 4, or not more than 3, or not more than 2, or not more than 1, or not more than 0.5, in each case hours. In an embodiment or in combination with any of the embodiments mentioned herein, the residence times of the pyrolysis reaction can range from 30 minutes to 4 hours, or 30 minutes to 3 hours, or 1 hour to 3 hours, or 1 hour to 2 hours.

In an embodiment or in combination with any of the embodiments mentioned herein, the pressure within the pyrolysis reactor 118 can be maintained at a pressure of at least 0.1, or at least 0.2, or at least 0.3, in each case bar and/or not more than 60, or not more than 50, or not more than 40, or not more than 30, or not more than 20, or not more than 10, or not more than 8, or not more than 5, or not more than 2, or not more than 1.5, or not more than 1.1, in each case bar. In an embodiment or in combination with any of the embodiments mentioned herein, the pressure within the pyrolysis reactor 18 can be maintained at about atmospheric pressure or within the range of 0.1 to 100 bar, or 0.1 to 60 bar, or 0.1 to 30 bar, or 0.1 to 10 bar, or 1.5 bar, 0.2 to 1.5 bar, or 0.3 to 1.1 bar.

In an embodiment or in combination with any of the embodiments mentioned herein, a pyrolysis catalyst may be introduced into the plastic feed prior to introduction into the pyrolysis reactor 118 and/or introduced directly into the pyrolysis reactor 118 to produce an r-catalytic pyoil, or an r-pyoil made by a catalytic pyrolysis process. In an embodiment or in combination with any embodiment mentioned herein or in combination with any of the embodiments mentioned herein, the catalyst can comprise: (i) a solid acid, such as a zeolite (e.g., ZSM-5, Mordenite, Beta, Ferrierite, and/or zeolite-Y); (ii) a super acid, such as sulfonated, phosphated, or fluorinated forms of zirconia, titania, alumina, silica-alumina, and/or clays; (iii) a solid base, such as metal oxides, mixed metal oxides, metal hydroxides, and/or metal carbonates, particularly those of alkali metals, alkaline earth metals, transition metals, and/or rare earth metals; (iv) hydrotalcite and other clays; (v) a metal hydride, particularly those of alkali metals, alkaline earth metals, transition metals, and/or rare earth metals; (vi) an alumina and/or a silica-alumina; (vii) a homogeneous catalyst, such as a Lewis acid, a metal tetrachloroaluminate, or an organic ionic liquid; (viii) activated carbon; or (ix) combinations thereof.

In an embodiment or in combination with any of the embodiments mentioned herein, the pyrolysis reaction in the pyrolysis reactor 118 occurs in the substantial absence of a catalyst, particularly the above-referenced catalysts. In such embodiments, a non-catalytic, heat-retaining inert additive may still be introduced into the pyrolysis reactor 118, such as sand, in order to facilitate the heat transfer within the reactor 118.

In an embodiment or in combination with any of the embodiments mentioned herein, the pyrolysis reaction in the pyrolysis reactor 118 may occur in the substantial absence of a pyrolysis catalyst, at a temperature in the range of 350 to 550 °C, at a pressure ranging from 0.1 to 60 bar, and at a residence time of 0.2 seconds to 4 hours, or 0.5 hours to 3 hours.

Referring again to FIG. 2, the pyrolysis effluent 120 exiting the pyrolysis reactor 118 generally comprises pyrolysis gas, pyrolysis vapors, and residual solids. As used herein, the vapors produced during the pyrolysis reaction may interchangeably be referred to as a "pyrolysis oil," which refers to the vapors when condensed into their liquid state. In an embodiment or in combination with any of the embodiments mentioned herein, the solids in the pyrolysis effluent 20 may comprise particles of char, ash, unconverted plastic solids, other unconverted solids from the feedstock, and/or spent catalyst (if a catalyst is utilized).

In an embodiment or in combination with any of the embodiments mentioned herein, the pyrolysis effluent 120 may comprise at least 20, or at least 25, or at least 30, or at least 40, or at least 45, or at least 50, or at least 55, or at least 60, or at least 65, or at least 70, or at least 75, or at least or at least 80, in each case weight percent of the pyrolysis vapors, which may be subsequently condensed into the resulting pyrolysis oil (e.g., r-pyoil). Additionally, or alternatively, in an embodiment or in combination with any of the embodiments mentioned herein, the pyrolysis effluent 120 may comprise not more than 99, or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, in each case weight percent of the pyrolysis vapors. In an embodiment or in combination with any of the embodiments mentioned herein, the pyrolysis effluent 120 may comprise in the range of 20 to 99 weight percent, 40 to 90 weight percent, or 55 to 90 weight percent of the pyrolysis vapors.

In an embodiment or in combination with any of the embodiments mentioned herein, the pyrolysis effluent 120 may comprise at least 1, or at least 5, or at least 6, or at least 7, or at least 8, or at least 9, or at least 10, or at least 11, or at least 12, in each case weight percent of the pyrolysis gas (e.g., r-pyrolysis gas). As used herein, a "pyrolysis gas" refers to a composition that is produced via pyrolysis and is a gas at standard temperature and pressure (STP). Additionally, or alternatively, in an embodiment or in combination with any of the embodiments mentioned herein, the pyrolysis effluent 20 may comprise not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in each case weight percent of the pyrolysis gas. In an embodiment or in combination with any of the embodiments mentioned herein, the pyrolysis effluent 120 may comprise 1 to 90 weight percent, or 5 to 60 weight percent, or 10 to 60 weight percent, or 10 to 30 weight percent, or 5 to 30 weight percent of the pyrolysis gas.

In an embodiment or in combination with any of the embodiments mentioned herein, the pyrolysis effluent 120 may comprise not more than 15, or not more than 10, or not more than 9, or not more than 8, or not more than 7, or not more than 6, or not more than 5, or not more than 4 or not more than 3, in each case weight percent of the residual solids.

In one embodiment or in combination of any mentioned embodiments, there is provided a cracker feed stock composition containing r-pyoil, and the r-pyoil composition contains recycle content catalytic pyrolysis oil (r-catalytic pyoil) and a recycle content thermal pyrolysis oil (r-thermal pyoil). An r-thermal pyoil is pyoil made without the addition of a pyrolysis catalyst. The cracker feedstock can include at least 5, 10, 15, or 20 weight percent r-catalytic pyoil, optionally that has been hydrotreated. The r-pyoil containing r-thermal pyoil and r-catalytic pyoil can be cracked according to any of the processes described herein to provide an olefin-containing effluent stream. The r-catalytic pyoil can be blended with r-thermal pyoil to form a blended stream cracked in the cracker unit. Optionally, the blended stream can contain not more than 10, 5, 3, 2, 1 weight percent of r-catalytic pyoil that has not been hydrotreated.

In one embodiment or in combination with any mentioned embodiment, the r-pyoil does not contain r-catalytic pyoil.

As depicted in FIG. 2, the conversion effluent 120 from the pyrolysis reactor 118 can be introduced into a solids separator 122. The solids separator 122 can be any conventional device capable of separating solids from gas and vapors such as, for example, a cyclone separator or a gas filter or combination thereof. In an embodiment or in combination with any of the embodiments mentioned herein, the solids separator 122 removes a substantial portion of the solids from the conversion effluent 120. In an embodiment or in combination with any of the embodiments mentioned herein, at least a portion of the solid particles 24 recovered in the solids separator 122 may be introduced into an optional regenerator 126 for regeneration, generally by combustion. After regeneration, at least a portion of the hot regenerated solids 128 can be introduced directly into the pyrolysis reactor 118. In an embodiment or in combination with any of the embodiments mentioned herein, at least a portion of the solid particles 124 recovered in the solids separator 122 may be directly introduced back into the pyrolysis reactor 118, especially if the solid particles 124 contain a notable amount of unconverted plastic waste. Solids can be removed from the regenerator 126 through line 145 and discharged out of the system.

Turning back to FIG. 2, the remaining gas and vapor conversion products 130 from the solids separator 122 may be introduced into a fractionator 132. In the fractionator 132, at least a portion of the pyrolysis oil vapors may be separated from the pyrolysis gas to thereby form a pyrolysis gas product stream 134 and a pyrolysis oil vapor stream 136. Suitable systems to be used as the fractionator 132 may include, for example, a distillation column, a membrane separation unit, a quench tower, a condenser, or any other known separation unit known in the art. In an embodiment or in combination with any of the embodiments mentioned herein, any residual solids 146 accrued in the fractionator 132 may be introduced in the optional regenerator 126 for additional processing.

In an embodiment or in combination with any of the embodiments mentioned herein, at least a portion of the pyrolysis oil vapor stream 136 may be introduced into a quench unit 138 in order to at least partially quench the pyrolysis vapors into their liquid form (i.e., the pyrolysis oil). The quench unit 138 may comprise any suitable quench system known in the art, such as a quench tower. The resulting liquid pyrolysis oil stream 140 may be removed from the system 110 and utilized in the other downstream applications described herein. In an embodiment or in combination with any of the embodiments mentioned herein, the liquid pyrolysis oil stream 140 may not be subjected to any additional treatments, such as hydrotreatment and/or hydrogenation, prior to being utilized in any of the downstream applications described herein.

In an embodiment or in combination with any embodiment mentioned herein, at least a portion of the pyrolysis oil vapor stream 136 may be introduced into a hydroprocessing unit 142 for further refinement. The hydroprocessing unit 142 may comprise a hydrocracker, a catalytic cracker operating with a hydrogen feed stream, a hydrotreatment unit, and/or a hydrogenation unit. While in the hydroproces sing unit 142, the pyrolysis oil vapor stream 136 may be treated with hydrogen and/or other reducing gases to further saturate the hydrocarbons in the pyrolysis oil and remove undesirable byproducts from the pyrolysis oil. The resulting hydroprocessed pyrolysis oil vapor stream 144 may be removed and introduced into the quench unit 138. Alternatively, the pyrolysis oil vapor may be cooled, liquified, and then treated with hydrogen and/or other reducing gases to further saturate the hydrocarbons in the pyrolysis oil. In this case, the hydrogenation or hydrotreating is performed in a liquid phase pyrolysis oil. No quench step is required in this embodiment post-hydrogenation or post-hydrotreating.

The pyrolysis system 110 described herein may produce a pyrolysis oil (e.g., r-pyoil) and pyrolysis gases (e.g., r-pyrolysis gas) that may be directly used in various downstream applications based on their desirable formulations. The various characteristics and properties of the pyrolysis oils and pyrolysis gases are described below. It should be noted that, while all of the following characteristics and properties may be listed separately, it is envisioned that each of the following characteristics and/or properties of the pyrolysis oils or pyrolysis gases are not mutually exclusive and may be combined and present in any combination.

The pyrolysis oil may predominantly comprise hydrocarbons having from 4 to 30 carbon atoms per molecule (e.g., C4 to C30 hydrocarbons). As used herein, the term "Cx" or "Cx hydrocarbon," refers to a hydrocarbon compound including x total carbons per molecule, and encompasses all olefins, paraffins, aromatics, and isomers having that number of carbon atoms. For example, each of normal, iso, and tert butane and butene and butadiene molecules would fall under the general description "C4."

In an embodiment or in combination with any of the embodiments mentioned herein, the pyrolysis oil fed to the cracking furnace may have a C4-C30 hydrocarbon content of at least 55, or at least 60, or at least 65, or at least 70, or at least 75, or at least 80, or at least 85, or at least 90, or at least 95, in each case weight percent based on the weight of the pyrolysis oil.

In an embodiment or in combination with any of the embodiments mentioned herein, the pyrolysis oil fed to the furnace can predominantly comprise C5-C25, C5-C22, or C5-C20hydrocarbons, or may comprise at least about 55, or at least 60, or at least 65, or at least 70, or at least 75, or at least 80, or at least 85, or at least 90, or at least 95, in each case weight percent of C5-C25, C5-C22, or C5-C20hydrocarbons, based on the weight of the pyrolysis oil.

The gas furnace can tolerate a wide variety of hydrocarbon numbers in the pyrolysis oil feedstock, thereby avoiding the necessity for subjecting a pyrolysis oil feedstock to separation techniques to deliver a smaller or lighter hydrocarbon cut to the cracker furnace. In one embodiment or in any of the mentioned embodiments, the pyrolysis oil after delivery from a pyrolysis manufacturer is not subjected a separation process for separating a heavy hydrocarbon cut from a lighter hydrocarbon cut, relative to each other, prior to feeding the pyrolysis oil to a cracker furnace. The feed of pyrolysis oil to a gas furnace allows one to employ a pyrolysis oil that contains heavy tail ends or higher carbon numbers at or above 12. In one embodiment or in any of the mentioned embodiments, the pyrolysis oil fed to a cracker furnace is a C5 to C25 hydrocarbon stream containing at least 1 wt. %, 3 wt. %, or at least 5 wt. %, or at least 8 wt. %, or at least 10 wt. %, or at least 12 wt. %, or at least 15 wt. %, or at least 18 wt. %, or at least 20 wt. %, or at least 25 wt. % or at least 30 wt. %, or at least 35 wt. %, or at least 40 wt. %, or at least 45 wt. %, or at least 50 wt. %, or at least 55 wt. %, or at least 60 wt. % hydrocarbons within a range from C12 to C25, inclusive, or within a range of C14 to C25, inclusive, or within a range of C16 to C25, inclusive.

In an embodiment or in combination with any of the embodiments mentioned herein, the pyrolysis oil may have a C6 to C12 hydrocarbon content of at least 10, or at least 15, or at least 20, or at least 25, or at least 30, or at least 35, or at least 40, or at least 45, or at least 50, or at least 55, in each case weight percent, based on the weight of the pyrolysis oil. Additionally, or alternatively, in an embodiment or in combination with any of the embodiments mentioned herein, the pyrolysis oil may have a C6-C12 hydrocarbon content of not more than 98.5, not more than 95, or not more than 90, or not more than 85, or not more than 80, or not more than 75, or not more than 70, or not more than 65, or not more than 60, in each case weight percent. In an embodiment or in combination with any of the embodiments mentioned herein, the pyrolysis oil may have a C6-C12 hydrocarbon content in the range of 10 to 95 weight percent, 20 to 80 weight percent, or 35 to 80 weight percent.

In an embodiment or in combination with any of the embodiments mentioned herein, the pyrolysis oil may have a C13 to C23 hydrocarbon content of at least 1, or at least 5, or at least 10, or at least 15, or at least 20, or at least 25, or at least 30, in each case weight percent. Additionally, or alternatively, in an embodiment or in combination with any of the embodiments mentioned herein, the pyrolysis oil may have a C13 to C23 hydrocarbon content of not more than 80, or not more than 75, or not more than 70, or not more than 65, or not more than 60, or not more than 55, or not more than 50, or not more than 45, or not more than 40, in each case weight percent. In an embodiment or in combination with any of the embodiments mentioned herein, the pyrolysis oil may have a C13 to C23 hydrocarbon content in the range of 1 to 80 weight percent, 5 to 65 weight percent, or 10 to 60 weight percent.

In an embodiment or in combination with any of the embodiments mentioned herein, the r-pyrolysis oil, or r-pyoil fed to a cracker furnace, or r-pyoil fed to a cracker furnace that, prior to feeding-pyoil, accepts a predominately C2-C4 feedstock (and the mention of r-pyoil or pyrolysis oil throughout includes any of these embodiments), may have a C24+ hydrocarbon content of at least 1, or at least 2, or at least 3, or at least 4, or at least 5, in each case weight percent. Additionally, or alternatively, in an embodiment or in combination with any of the embodiments mentioned herein, the pyrolysis oil may have a C24+ hydrocarbon content of not more than 15, or not more than 10, or not more than 9, or not more than 8, or not more than 7, or not more than 6, in each case weight percent. In an embodiment or in combination with any of the embodiments mentioned herein, the pyrolysis oil may have a C24+ hydrocarbon content in the range of 1 to 15 weight percent, 3 to 15 weight percent, 2 to 5 weight percent, or 5 to 10 weight percent.

The pyrolysis oil may also include various amounts of olefins, aromatics, and other compounds. In an embodiment or in combination with any of the embodiments mentioned herein, the pyrolysis oil includes at least 1, or at least 2, or at least 5, or at least 10, or at least 15, or at least 20, in each case weight percent olefins and/or aromatics. Additionally, or alternatively, in an embodiment or in combination with any of the embodiments mentioned herein, the pyrolysis oil may include not more than 50, or not more than 45, or not more than 40, or not more than 35, or not more than 30, or not more than 25, or not more than 20, or not more than 15, or not more than 10, or not more than 5, or not more than 2, or not more than 1, in each case weight percent olefins and/or aromatics.

In an embodiment or in combination with any of the embodiments mentioned herein, the pyrolysis oil may have an aromatic content of not more than 25, or not more than 20, or not more than 15, or not more than 14, or not more than 13, or not more than 12, or not more than 11, or not more than 10, or not more than 9, or not more than 8, or not more than 7, or not more than 6, or not more than 5, or not more than 4, or not more than 3, or not more than 2, or not more than 1, in each case weight percent. In one embodiment or in combination with any mentioned embodiments, the pyrolysis oil has an aromatic content that is not higher than 15, or not more than 10, or not more than 8, or not more than 6, in each case weight percent.

In an embodiment or in combination with any of the embodiments mentioned herein, the pyrolysis oil may have a naphthene content of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, in each case weight percent. Additionally, or alternatively, in an embodiment or in combination with any of the embodiments mentioned herein, the pyrolysis oil may have a naphthene content of not more than 50, or not more than 45, or not more than 40, or not more than 35, or not more than 30, or not more than 25, or not more than 20, or not more than 10, or not more than 5, or not more than 2, or not more than 1, or not more than 0.5, or no detectable amount, in each case weight percent. In an embodiment or in combination with any of the embodiments mentioned herein, the pyrolysis oil may have a naphthene content of not more than 5, or not more than 2, or not more than 1 wt. %, or no detectable amount, or naphthenes. Alternatively, the pyrolysis oil may contain in the range of 1 to 50 weight percent, 5 to 50 weight percent, or 10 to 45 weight percent naphthenes, especially if the r-pyoil was subjected to a hydrotreating process.

In an embodiment or in combination with any of the embodiments mentioned herein, the pyrolysis oil may have a paraffin content of at least 25, or at least 30, or at least 35, or at least 40, or at least 45, or at least 50, in each case weight percent. Additionally, or alternatively, in an embodiment or in combination with any of the embodiments mentioned herein, the pyrolysis oil may have a paraffin content of not more than 90, or not more than 85, or not more than 80, or not more than 75, or not more than 70, or not more than 65, or not more than 60, or not more than 55, in each case weight percent. In an embodiment or in combination with any of the embodiments mentioned herein, the pyrolysis oil may have a paraffin content in the range of 25 to 90 weight percent, 35 to 90 weight percent, or 40 to 80, or 40-70, or 40-65 weight percent.

In an embodiment or in combination with any of the embodiments mentioned herein, the pyrolysis oil may have an n-paraffin content of at least 5, or at least 10, or at least 15, or at least 25, or at least 30, or at least 35, or at least 40, or at least 45, or at least 50, in each case weight percent. Additionally, or alternatively, in an embodiment or in combination with any of the embodiments mentioned herein, the pyrolysis oil may have an n-paraffin content of not more than 90, or not more than 85, or not more than 80, or not more than 75, or not more than 70, or not more than 65, or not more than 60, or not more than 55, in each case weight percent. In an embodiment or in combination with any of the embodiments mentioned herein, the pyrolysis oil may have an n-paraffin content in the range of 25 to 90 weight percent, 35 to 90 weight percent, or 40-70, or 40-65, or 50 to 80 weight percent.

In an embodiment or in combination with any of the embodiments mentioned herein, the pyrolysis oil may have a paraffin to olefin weight ratio of at least 0.2:1, or at least 0.3:1, or at least 0.4:1, or at least 0.5:1, or at least 0.6:1, or at least 0.7:1, or at least 0.8:1, or at least 0.9:1, or at least 1:1. Additionally, or alternatively, in an embodiment or in combination with any of the embodiments mentioned herein, the pyrolysis oil may have a paraffin to olefin weight ratio not more than 3:1, or not more than 2.5:1, or not more than 2:1, or not more than 1.5:1, or not more than 1.4:1, or not more than 1.3:1. In an embodiment or in combination with any of the embodiments mentioned herein, the pyrolysis oil may have a paraffin to olefin weight ratio in the range of 0.2:1 to 5:1, or 1:1 to 4.5:1, or 1.5:1 to 5:1, or 1.5:1:4.5:1, or 0.2:1 to 4:1, or 0.2:1 to 3:1, 0.5:1 to 3:1, or 1:1 to 3:1.

In an embodiment or in combination with any of the embodiments mentioned herein, the pyrolysis oil may have an n-paraffin to i-paraffin weight ratio of at least 0.001:1, or at least 0.1:1, or at least 0.2:1, or at least 0.5:1, or at least 1:1, or at least 2:1, or at least 3:1, or at least 4:1, or at least 5:1, or at least 6:1, or at least 7:1, or at least 8:1, or at least 9:1, or at least 10:1, or at least 15:1, or at least 20:1. Additionally, or alternatively, in an embodiment or in combination with any of the embodiments mentioned herein, the pyrolysis oil may have an n-paraffin to i-paraffin weight ratio of not more than 100:1, 7 or not more than 5:1, or not more than 50:1, or not more than 40:1, or not more than 30:1. In an embodiment or in combination with any of the embodiments mentioned herein, the pyrolysis oil may have an n-paraffin to i-paraffin weight ratio in the range of 1:1 to 100:1, 4:1 to 100:1, or 15:1 to 100:1.

It should be noted that all of the above-referenced hydrocarbon weight percentages may be determined using gas chromatography-mass spectrometry (GC-MS).

In an embodiment or in combination with any of the embodiments mentioned herein, the pyrolysis oil may exhibit a density at 15 °C of at least 0.6 g/cm3, or at least 0.65 g/cm3, or at least 0.7 g/cm3. Additionally, or alternatively, in an embodiment or in combination with any of the embodiments mentioned herein, the pyrolysis oil may exhibit a density at 15 °C of not more than 1 g/cm3, or not more than 0.95 g/cm3, or not more than 0.9 g/cm3, or not more than 0.85 g/cm3. In an embodiment or in combination with any of the embodiments mentioned herein, the pyrolysis oil exhibits a density at 15 °C at a range of 0.6 to 1 g/cm3, 0.65 to 0.95 g/cm3, or 0.7 to 0.9 g/cm3.

In an embodiment or in combination with any of the embodiments mentioned herein, the pyrolysis oil may exhibit an API gravity at 15 °C of at least 28, or at least 29, or at least 30, or at least 31, or at least 32, or at least 33. Additionally, or alternatively, in an embodiment or in combination with any of the embodiments mentioned herein, the pyrolysis oil may exhibit an API gravity at 15 °C of not more than 50, or not more than 49, or not more than 48, or not more than 47, or not more than 46, or not more than 45, or not more than 44. In an embodiment or in combination with any of the embodiments mentioned herein, the pyrolysis oil exhibits an API gravity at 15 °C at a range of 28 to 50, 29 to 58, or 30 to 44.

In an embodiment or in combination with any of the embodiments mentioned herein, the pyrolysis oil may have a mid-boiling point of at least 75 °C, or at least 80 °C, or at least 85 °C, or at least 90 °C, or at least 95 °C, or at least 100 °C, or at least 105 °C, or at least 110 °C, or at least 115 °C. The values can be measured according to the procedures described in either according to ASTM D-2887, or in the working examples. A mid-boiling point having the stated value are satisfied if the value is obtained under either method. Additionally, or alternatively, in an embodiment or in combination with any of the embodiments mentioned herein, the pyrolysis oil may have a mid-boiling point of not more than 250 °C, or not more than 245 °C, or not more than 240 °C, or not more than 235 °C, or not more than 230 °C, or not more than 225 °C, or not more than 220 °C, or not more than 215 °C, or not more than 210 °C, or not more than 205 °C, or not more than 200 °C, or not more than 195 °C, or not more than 190 °C, or not more than 185 °C, or not more than 180 °C, or not more than 175 °C, or not more than 170 °C, or not more than 165 °C, or not more than 160 °C, 1 or not more than 55 °C, or not more than 150 °C, or not more than 145 °C, or not more than 140 °C, or not more than 135 °C, or not more than 130 °C, or not more than 125 °C, or not more than 120 °C. The values can be measured according to the procedures described in either according to ASTM D-2887, or in the working examples. A mid-boiling point having the stated value are satisfied if the value is obtained under either method. In an embodiment or in combination with any of the embodiments mentioned herein, the pyrolysis oil may have a mid-boiling point in the range of 75 to 250 °C, 90 to 225 °C, or 115 to 190 °C. As used herein, "mid-boiling point" refers to the median boiling point temperature of the pyrolysis oil when 50 weight percent of the pyrolysis oil boils above the mid-boiling point and 50 weight percent boils below the mid-boiling point.

In an embodiment or in combination with any of the embodiments mentioned herein, the boiling point range of the pyrolysis oil may be such that not more than 10 percent of the pyrolysis oil has a final boiling point (FBP) of 250 °C, 280 °C, 290 °C, 300 °C, or 310 °C, to determine the FBP, the procedures described in either according to ASTM D-2887, or in the working examples, can be employed and a FBP having the stated values are satisfied if the value is obtained under either method.

Turning to the pyrolysis gas, the pyrolysis gas can have a methane content of at least 1, or at least 2, or at least 5, or at least 10, or at least 11, or at least 12, or at least 13, or at least 14, or at least 15, or at least 16, or at least 17, or at least 18, or at least 19, or at least 20 weight percent. Additionally, or alternatively, in an embodiment or in combination with any of the embodiments mentioned herein, the pyrolysis gas can have a methane content of not more than 50, or not more than 45, or not more than 40, or not more than 35, or not more than 30, or not more than 25, in each case weight percent. In an embodiment or in combination with any of the embodiments mentioned herein, the pyrolysis gas can have a methane content in the range of 1 to 50 weight percent, 5 to 50 weight percent, or 15 to 45 weight percent.

In an embodiment or in combination with any of the embodiments mentioned herein, the pyrolysis gas can have a C3 hydrocarbon content of at least 1, or at least 2, or at least 3, or at least 4, or at least 5, or at least 6, or at least 7, or at least 8, or at least 9, or at least 10, or at least 15, or at least 20, or at least 25, in each case weight percent. Additionally, or alternatively, in an embodiment or in combination with any of the embodiments mentioned herein, the pyrolysis gas can have a C3 hydrocarbon content of not more than 50, or not more than 45, or not more than 40, or not more than 35, or not more than 30, in each case weight percent. In an embodiment or in combination with any of the embodiments mentioned herein, the pyrolysis gas can have a C3 hydrocarbon content in the range of 1 to 50 weight percent, 5 to 50 weight percent, or 20 to 50 weight percent.

In an embodiment or in combination with any of the embodiments mentioned herein, the pyrolysis gas can have a C4 hydrocarbon content of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, in each case weight percent. Additionally, or alternatively, in an embodiment or in combination with any of the embodiments mentioned herein, the pyrolysis gas can have a C4 hydrocarbon content of not more than 50, or not more than 45, or not more than 40, or not more than 35, or not more than 30, or not more than 25, in each case weight percent. In an embodiment or in combination with any of the embodiments mentioned herein, the pyrolysis gas can have a C4 hydrocarbon content in the range of 1 to 50 weight percent, 5 to 50 weight percent, or 20 to 50 weight percent.

In an embodiment or in combination with any of the embodiments mentioned herein, the pyrolysis oils of the present invention may be a recycle content pyrolysis oil composition (r-pyoil).

Various downstream applications that may utilize the above-disclosed pyrolysis oils and/or the pyrolysis gases are described in greater detail below. In an embodiment or in combination with any of the embodiments mentioned herein, the pyrolysis oil may be subjected to one or more treatment steps prior to being introduced into downstream units, such as a cracking furnace. Examples of suitable treatment steps can include, but are not limited to, separation of less desirable components (e.g., nitrogen-containing compounds, oxygenates, and/or olefins and aromatics), distillation to provide specific pyrolysis oil compositions, and preheating.

Figure 3:
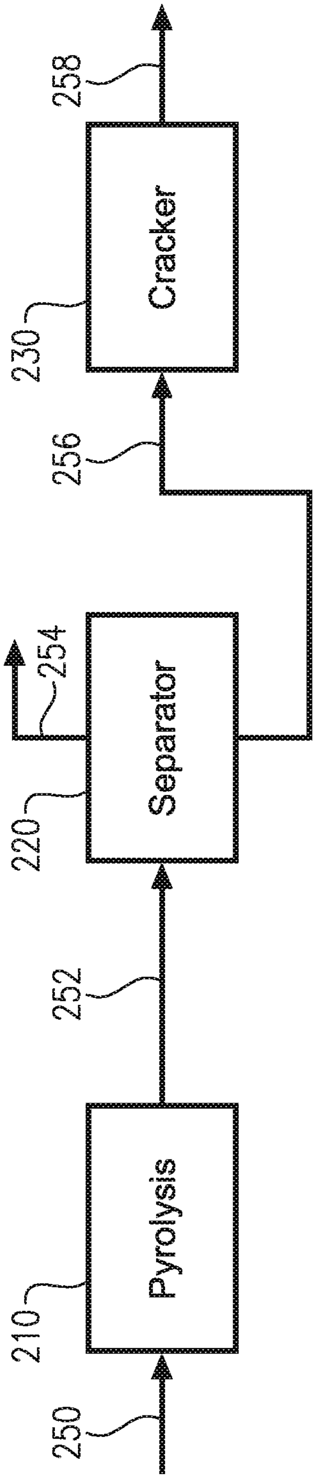
FIG. 3 is a schematic depiction of pyrolysis treatment through production of olefin containing products.

Turning now to FIG. 3, a schematic depiction of a treatment zone for pyrolysis oil according to an embodiment or in combination with any of the embodiments mentioned herein is shown.

As shown in the treatment zone 220 illustrated in FIG. 3, at least a portion of the r-pyoil 252 made from a recycle waste stream 250 in the pyrolysis system 210 may be passed through a treatment zone 220 such as, for example, a separator, which may separate the r-pyoil into a light pyrolysis oil fraction 254 and a heavy pyrolysis oil fraction 256. The separator 220 employed for such a separation can be of any suitable type, including a single-stage vapor liquid separator or "flash" column, or a multi-stage distillation column. The vessel may or may not include internals and may or may not employ a reflux and/or boil-up stream.

In an embodiment or in combination with any of the embodiments mentioned herein, the heavy fraction may have a C4 to C7 content or a C8+ content of at least 10, 15, 20, 25, 30, 35, 40, 45, 50, 55, 60, 65, 70, 75, 80, or 85 weight percent. The light fraction may include at least about 10, 15, 20, 25, 30, 35, 40, 45, 50, 55, 60, 65, 70, 75, 80, or 85 percent of C3 and lighter (C3-) or C7 and lighter (C7-) content. In some embodiments, separator may concentrate desired components into the heavy fraction, such that the heavy fraction may have a C4 to C7 content or a C8+ content that is at least 10, 15, 20, 25, 30, 35, 40, 45, 50, 55, 60, 65, 70, 7, 80, 85, 90, 95, 100, 105, 110, 115, 120, 125, 130, 135, 140, 145, or 150% greater than the C4 to C7 content or the C8+ content of the pyrolysis oil withdrawn from the pyrolysis zone. As shown in FIG. 3, at least a portion of the heavy fraction may be sent to the cracking furnace 230 for cracking as or as part of the r-pyoil composition to form an olefin-containing effluent 258, as discussed in further detail below.

In an embodiment or in combination with any of the embodiments mentioned herein, the pyrolysis oil is hydrotreated in a treatment zone, while, in other embodiments, the pyrolysis oil is not hydrotreated prior to entering downstream units, such as a cracking furnace. In an embodiment or in combination with any of the embodiments mentioned herein, the pyrolysis oil is not pretreated at all before any downstream applications and may be sent directly from the pyrolysis oil source. The temperature of the pyrolysis oil exiting the pre-treatment zone can be in the range of 15 to 55 °C, 30 to 55 °C, 49 to 40 °C, 15 to 50 °C, 20 to 45 °C, or 25 to 40 °C.

In an embodiment or in combination with any of the embodiments mentioned herein, the r-pyoil may be combined with the non-recycle cracker stream in order to minimize the amount of less desirable compounds present in the combined cracker feed. For example, when the r-pyoil has a concentration of less desirable compounds (such as, for example, impurities like oxygen-containing compounds, aromatics, or others described herein), the r-pyoil may be combined with a cracker feedstock in an amount such that the total concentration of the less desirable compound in the combined stream is at least 40, 50, 55, 60, 65, 70, 75, 80, 85, 90, or 95 percent less than the original content of the compound in the r-pyoil stream (calculated as the difference between the r-pyoil and combined streams, divided by the r-pyoil content, expressed as a percentage). In some cases, the amount of non-recycle cracker feed to combine with the r-pyoil stream may be determined by comparing the measured amount of the one or more less desirable compounds present in the r-pyoil with a target value for the compound or compounds to determine a difference and, then, based on that difference, determining the amount of non-recycle hydrocarbon to add to the r-pyoil stream. The amounts of r-pyoil and non-recycle hydrocarbon can be within one or more ranges described herein.

At least a portion of the r-ethylene can be derived directly or indirectly from the cracking of r-pyoil. The process for obtaining r-olefins from cracking (r-pyoil) can be as follows and as described in FIG. 4.

Figure 4:
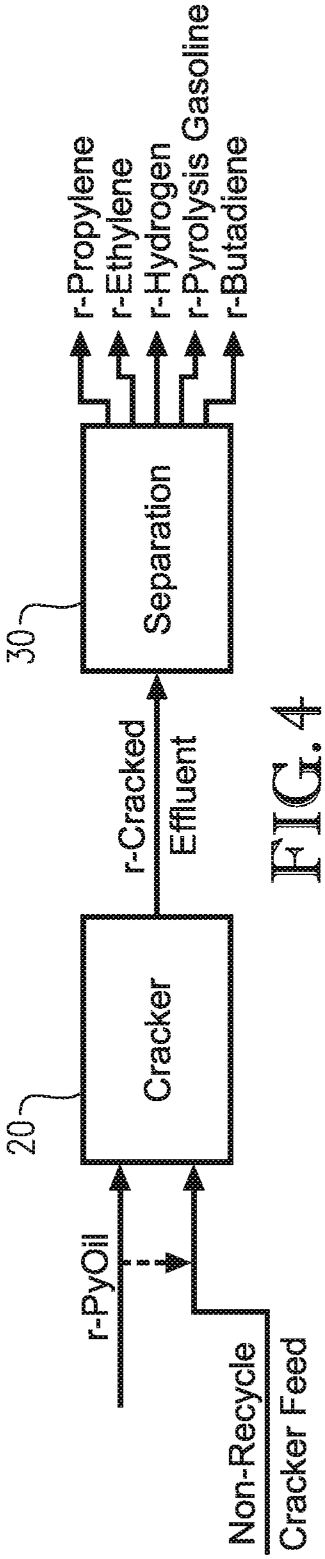
FIG. 4 is a block flow diagram illustrating steps associated with the cracking furnace and separation zones of a system for producing an r-composition obtained from cracking r-pyoil and non-recycle cracker feed.

Turning now to FIG. 4, a block flow diagram illustrating steps associated with the cracking furnace 20 and separation zones 30 of a system for producing an r-composition obtained from cracking r-pyoil. As shown in FIG. 4, a feed stream comprising r-pyoil (the r-pyoil containing feed stream) may be introduced into a cracking furnace 20, alone or in combination with a non-recycle cracker feed stream. A pyrolysis unit producing r-pyoil can be co-located with the production facility. In other embodiments, the r-pyoil can be sourced from a remote pyrolysis unit and transported to the production facility.

In an embodiment or in combination with any of the embodiments mentioned herein, the r-pyoil containing feed stream may contain r-pyoil in an amount of at least 1, or at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, or at least 97, or at least 98, or at least 99, or at least or 100, in each case weight percent and/or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, in each case weight percent, based on the total weight of the r-pyoil containing feed stream.

In an embodiment or in combination with any of the embodiments mentioned herein, at least 1, or at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90 or at least 97, or at least 98, or at least 99, or 100, in each case weight percent and/or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15 or not more than 10, in each case weight percent of the r-pyoil is obtained from the pyrolysis of a waste stream. In an embodiment or in combination with any of the embodiments mentioned herein, at least a portion of the r-pyoil is obtained from pyrolysis of a feedstock comprising plastic waste. Desirably, at least 90, or at least 95, or at least 97, or at least 98, or at least 99, or at least or 100, in each case wt. %, of the r-pyoil is obtained from pyrolysis of a feedstock comprising plastic waste, or a feedstock comprising at least 50 wt. % plastic waste, or a feedstock comprising at least 80 wt. % plastic waste, or a feedstock comprising at least 90 wt. % plastic waste, or a feedstock comprising at least 95 wt. % plastic waste.

In an embodiment or in combination with any of the embodiments mentioned herein, the r-pyoil can have any one or combination of the compositional characteristics described above with respect to pyrolysis oil.

In an embodiment or in combination with any of the embodiments mentioned herein, the r-pyoil may comprise at least 55, or at least 60, or at least 65, or at least 70, or at least 75, or at least 80, or at least 85, or at least 90, or at least 95, in each case weight percent of C4-C30 hydrocarbons, and as used herein, hydrocarbons include aliphatic, cycloaliphatic, aromatic, and heterocyclic compounds. In an embodiment or in combination with any of the embodiments mentioned herein, the r-pyoil can predominantly comprise C5-C25, C5-C22, or C5-C20 hydrocarbons, or may comprise at least 55, 60, 65, 70, 75, 80, 85, 90, or 95 weight percent of C5-C25, C5-C22, or C5-C20 hydrocarbons.

In an embodiment or in combination with any embodiment mentioned herein, the r-pyoil composition can comprise C4-C12 aliphatic compounds (branched or unbranched alkanes and alkenes including diolefins, and alicyclics) and C13-C22 aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil.

In an embodiment or in combination with any embodiment mentioned herein, the r-pyoil composition can comprise C13-C22 aliphatic compounds (branched or unbranched alkanes and alkenes including diolefins, and alicyclics) and C4-C12 aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil.

In an embodiment, the two aliphatic hydrocarbons (branched or unbranched alkanes and alkenes, and alicyclics) having the highest concentration in the r-pyoil are in a range of C5-C18, or C5-C16, or C5-C14, or C5-C10, or C5-C8, inclusive.

The r-pyoil can include one or more of paraffins, naphthenes or cyclic aliphatic hydrocarbons, aromatics, aromatic containing compounds, olefins, oxygenated compounds and polymers, heteroatom compounds or polymers, and other compounds or polymers.

For example, in an embodiment or in combination with any of the embodiments mentioned herein, the r-pyoil may comprise at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent and/or not more than 99, or not more than 97, or not more than 95, or not more than 93, or not more than 90, or not more than 87, or not more than 85, or not more than 83, or not more than 80, or not more than 78, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in each case weight percent of paraffins (or linear or branched alkanes), based on the total weight of the r-pyoil. In an embodiment or in combination with any of the embodiments mentioned herein, the pyrolysis oil may have a paraffin content in the range of 25 to 90, 35 to 90, or 40 to 80, or 40-70, or 40-65 weight percent, or 5-50, or 5 to 40, or 5 to 35, or 10- to 35, or 10 to 30, or 5 to 25, or 5 to 20, in each case as wt. % based on the weight of the r-pyoil composition.

In an embodiment or in combination with any of the embodiments mentioned herein, the r-pyoil can include naphthenes or cyclic aliphatic hydrocarbons in amount of zero, or at least 1, or at least 2, or at least 5, or at least 8, or at least 10, or at least 15, or at least 20, in each case weight percent and/or not more than 50, or not more than 45, or not more than 40, or not more than 35, or not more than 30, or not more than 25, or not more than 20, or not more than 15, or not more than 10, or not more than 5, or not more than 2, or not more than 1, or not more than 0.5, or no detectable amount, in each case weight percent. In an embodiment or in combination with any of the embodiments mentioned herein, the r-pyoil may have a naphthene content of not more than 5, or not more than 2, or not more than 1 wt. %, or no detectable amount, or naphthenes. Examples of ranges for the amount of naphthenes (or cyclic aliphatic hydrocarbons) contained in the r-pyoil is from 0-35, or 0-30, or 0-25, or 2-20, or 2-15, or 2-10, or 1-10, in each case as wt. % based on the weight of the r-pyoil composition.

In an embodiment or in combination with any of the embodiments mentioned herein, the r-pyoil may have a paraffin to olefin weight ratio of at least 0.2:1, or at least 0.3:1, or at least 0.4:1, or at least 0.5:1, or at least 0.6:1, or at least 0.7:1, or at least 0.8:1, or at least 0.9:1, or at least 1:1. Additionally, or alternatively, in an embodiment or in combination with any of the embodiments mentioned herein, the r-pyoil may have a paraffin to olefin weight ratio not more than 3:1, or not more than 2.5:1, or not more than 2:1, or not more than 1.5:1, or not more than 1.4:1, or not more than 1.3:1. In an embodiment or in combination with any of the embodiments mentioned herein, the r-pyoil may have a paraffin to olefin weight ratio in the range of 0.2:1 to 5:1, or 1:1 to 4.5:1, or 1.5:1 to 5:1, or 1.5:1:4.5:1, or 0.2:1 to 4:1, or 0.2:1 to 3:1, 0.5:1 to 3:1, or 1:1 to 3:1.

In an embodiment or in combination with any of the embodiments mentioned herein, the r-pyoil may have an n-paraffin to i-paraffin weight ratio of at least 0.001:1, or at least 0.1:1, or at least 0.2:1, or at least 0.5:1, or at least 1:1, or at least 2:1, or at least 3:1, or at least 4:1, or at least 5:1, or at least 6:1, or at least 7:1, or at least 8:1, or at least 9:1, or at least 10:1, or at least 15:1, or at least 20:1. Additionally, or alternatively, in an embodiment or in combination with any of the embodiments mentioned herein, the r-pyoil may have an n-paraffin to i-paraffin weight ratio of not more than 100:1, or not more than 50:1, or not more than 40:1, or not more than 30:1. In an embodiment or in combination with any of the embodiments mentioned herein, the r-pyoil may have an n-paraffin to i-paraffin weight ratio in the range of 1:1 to 100:1, 4:1 to 100:1, or 15:1 to 100:1.

In an embodiment, the r-pyoil comprises not more than 30, or not more than 25, or not more than 20, or not more than 15, or not more than 10, or not more than 8, or not more than 5, or not more than 2, or not more than 1, in each case weight percent of aromatics, based on the total weight of the r-pyoil. As used herein, the term “aromatics” refers to the total amount (in weight) of benzene, toluene, xylene, and styrene. The r-pyoil may include at least 1, or at least 2, or at least 5, or at least 8, or at least 10, in each case weight percent of aromatics, based on the total weight of the r-pyoil.

In an embodiment or in combination with any of the embodiments mentioned herein, the r-pyoil can include aromatic containing compounds in an amount of not more than 30, or not more than 25, or not more than 20, or not more than 15, or not more than 10, or not more than 8, or not more than 5, or not more than 2, or not more than 1, in each case weight, or not detectable, based on the total weight of the r-pyoil. Aromatic containing compounds includes the above-mentioned aromatics and any compounds containing an aromatic moiety, such as terephthalate residues and fused ring aromatics such as the naphthalenes and tetrahydronaphthalene.

In an embodiment or in combination with any of the embodiments mentioned herein, the r-pyoil can include olefins in amount of at least 1, or at least 2, or at least 5, or at least 8, or at least 10, or at least 15, or at least 20, or at least 30, or at least 40, or at least 45, or at least 50, or at least 55, or at least 60, or at least or at least 65, in each case weight percent olefins and/or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, or not more than 10, in each case weight percent, based on the weight of a r-pyoil. Olefins include mono- and di-olefins. Examples of suitable ranges include olefins present in an amount ranging from 5 to 45, or 10-35, or 15 to 30, or 40-85, or 45-85, or 50-85, or 55-85, or 60-85, or 65-85, or 40-80, or 45-80, or 50-80, or 55-80, or 60-80, or 65-80, 45-80, or 50-80, or 55-80, or 60-80, or 65-80, or 40-75, or 45-75, or 50-75, or 55-75, or 60-75, or 65-75, or 40-70, or 45-70, or 50-70, or 55-70, or 60-70, or 65-70, or 40-65, or 45-65, or 50-65, or 55-65, in each case as wt. % based on the weight of the r-pyoil.

In an embodiment or in combination with any of the embodiments mentioned herein, the r-pyoil can include oxygenated compounds or polymers in amount of zero or at least 0.01, or at least 0.1, or at least 1, or at least 2, or at least 5, in each case weight percent and/or not more than 20, or not more than 15, or not more than 10, or not more than 8, or not more than 6, or not more than 5, or not more than 3, or not more than 2, in each case weight percent oxygenated compounds or polymers, based on the weight of a r-pyoil. Oxygenated compounds and polymers are those containing an oxygen atom. Examples of suitable ranges include oxygenated compounds present in an amount ranging from 0-20, or 0-15, or 0-10, or 0.01-10, or 1-10, or 2-10, or 0.01-8, or 0.1-6, or 1-6, or 0.01-5, in each case as wt. % based on the weight of the r-pyoil.

In an embodiment or in combination with any embodiment mentioned herein, the amount of oxygen atoms in the r-pyoil can be not more than 10, or not more than 8, or not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.05, in each case wt. %, based on the weight of the r-pyoil. Examples of the amount of oxygen in the r-pyoil can be from 0-8, or 0-5, or 0-3, or 0-2.5 or 0-2, or 0.001-5, or 0.001-4, or 0.001-3, or 0.001-2.75, or 0.001-2.5, or 0.001-2, or 0.001-1.5, or 0.001-1, or 0.001-0.5, or 0.001-0.1, in each case as wt. % based on the weight of the r-pyoil.

In an embodiment or in combination with any of the embodiments mentioned herein, the r-pyoil can include heteroatom compounds or polymers in amount of at least 1, or at least 2, or at least 5, or at least 8, or at least 10, or at least 15, or at least 20, in each case weight percent and/or not more than 25, or not more than 20, or not more than 15, or not more than 10, or not more than 8, or not more than 6, or not more than 5, or not more than 3, or not more than 2, in each case weight percent, based on the weight of a r-pyoil. A heterocompound or polymer is defined in this paragraph as any compound or polymer containing nitrogen, sulfur, or phosphorus. Any other atom is not regarded as a heteroatom for purposes of determining the quantity of heteroatoms, heterocompounds, or heteropolymers present in the r-pyoil. The r-pyoil can contain heteroatoms present in an amount of not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.075, or not more than 0.05, or not more than 0.03, or not more than 0.02, or not more than 0.01, or not more than 0.008, or not more than 0.006, or not more than 0.005, or not more than 0.003, or not more than 0.002, in each case wt. %, based on the weight of the r-pyoil.

In an embodiment or in combination with any embodiment mentioned herein, the solubility of water in the r-pyoil at 1 atm and 25 °C is less than 2 wt. %, water, or not more than 1.5, or not more than 1, or not more than 0.5, or not more than 0.1, or not more than 0.075, or not more than 0.05, or not more than 0.025, or not more than 0.01, or not more than 0.005, in each case wt. % water based on the weight of the r-pyoil. Desirably, the solubility of water in the r-pyoil is not more than 0.1 wt. % based on the weight of the r-pyoil. In an embodiment or in combination with any embodiment mentioned herein, the r-pyoil contains not more than 2 wt. %, water, or not more than 1.5, or not more than 1, or not more than 0.5, desirably or not more than 0.1, or not more than 0.075, or not more than 0.05, or not more than 0.025, or not more than 0.01, or not more than 0.005, in each case wt. % water based on the weight of the r-pyoil.

In an embodiment or in combination with any embodiment mentioned herein, the solids content in the r-pyoil does not exceed 1, or is not more than 0.75, or not more than 0.5, or not more than 0.25, or not more than 0.2, or not more than 0.15, or not more than 0.1, or not more than 0.05, or not more than 0.025, or not more than 0.01, or not more than 0.005, or does not exceed 0.001, in each case wt. % solids based on the weight of the r-pyoil.

In an embodiment or in combination with any embodiment mentioned herein, the sulfur content of the r-pyoil does not exceed 2.5 wt. %, or is not more than 2, or not more than 1.75, or not more than 1.5, or not more than 1.25, or not more than 1, or not more than 0.75, or not more than 0.5, or not more than 0.25, or not more than 0.1, or not more than 0.05, desirably or not more than 0.03, or not more than 0.02, or not more than 0.01, or not more than 0.008, or not more than 0.006, or not more than 0.004, or not more than 0.002, or is not more than 0.001, in each case wt. % based on the weight of the r-pyoil.

In an embodiment or in combination with any embodiment mentioned herein, the r-pyoil can have the following compositional content:

carbon atom content of at least 75 wt. %, or at least or at least 77, or at least 80, or at least 82, or at least 85, in each case wt. %, and/or up to 90, or up to 88, or not more than 86, or not more than 85, or not more than 83, or not more than 82, or not more than 80, or not more than 77, or not more than 75, or not more than 73, or not more than 70, or not more than 68, or not more than 65, or not more than 63, or up to 60, in each case wt. %, desirably at least 82% and up to 93%, and/or hydrogen atom content of at least 10 wt. %, or at least 13, or at least 14, or at least 15, or at least 16, or at least 17, or at least 18, or not more than 19, or not more than 18, or not more than 17, or not more than 16, or not more than 15, or not more than 14, or not more than 13, or up to 11, in each case wt. %, an oxygen atom content not to exceed 10, or not more than 8, or not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.05, in each case wt. %, in each case based on the weight of the r-pyoil.

In an embodiment or in combination with any embodiment mentioned herein, the amount of hydrogen atoms in the r-pyoil can be in a range of from 10-20, or 10-18, or 11-17, or 12-16 or 13-16, or 13-15, or 12-15, in each case as wt. % based on the weight of the r-pyoil.

In an embodiment or in combination with any embodiment mentioned herein, the metal content of the r-pyoil is desirably low, for example, not more than 2 wt. %, or not more than 1, or not more than 0.75, or not more than 0.5, or not more than 0.25, or not more than 0.2, or not more than 0.15, or not more than 0.1, or not more than 0.05, in each case wt. % based on the weight of the r-pyoil.

In an embodiment or in combination with any embodiment mentioned herein, the alkali metal and alkaline earth metal or mineral content of the r-pyoil is desirably low, for example, not more than 2 wt. %, or not more than 1, or not more than 0.75, or not more than 0.5, or not more than 0.25, or not more than 0.2, or not more than 0.15, or not more than 0.1, or not more than 0.05, in each case wt. % based on the weight of the r-pyoil.

In an embodiment or in combination with any embodiment mentioned herein, the weight ratio of paraffin to naphthene in the r-pyoil can be at least 1:1, or at least 1.5:1, or at least 2:1, or at least 2.2:1, or at least 2.5:1, or at least 2.7:1, or at least 3:1, or at least 3.3:1, or at least 3.5:1, or at least 3.75:1, or at least 4:1, or at least 4.25:1, or at least 4.5:1, or at least 4.75:1, or at least 5:1, or at least 6:1, or at least 7:1, or at least 8:1, or at least 9:1, or at least 10:1, or at least 13:1, or at least 15:1, or at least 17:1, based on the weight of the r-pyoil.

In an embodiment or in combination with any embodiment mentioned herein, the weight ratio of paraffin and naphthene combined to aromatics can be at least 1:1, or at least 1.5:1, or at least 2:1, or at least 2.5:1, or at least 2.7:1, or at least 3:1, or at least 3.3:1, or at least 3.5:1, or at least 3.75:1, or at least 4:1, or at least 4.5:1, or at least 5:1, or at least 7:1, or at least 10:1, or at least 15:1, or at least 20:1, or at least 25:1, or at least 30:1, or at least 35:1, or at least 40:1, based on the weight of the r-pyoil. In an embodiment or in combination with any embodiment mentioned herein, the ratio of paraffin and naphthene combined to aromatics in the r-pyoil can be in a range of from 50:1-1:1, or 40:1-1:1, or 30:1-1:1, or 20:1-1:1, or 30:1-3:1, or 20:1-1:1, or 20:1-5:1, or 50:1-5:1, or 30:1-5:1, or 1:1-7:1, or 1:1-5:1, 1:1-4:1, or 1:1-3:1.

In an embodiment or in combination with any of the embodiments mentioned herein, the r-pyoil may have a boiling point curve defined by one or more of its 10%, its 50%, and its 90% boiling points, as defined below. As used herein, "boiling point" refers to the boiling point of a composition as determined by ASTM D2887 or according to the procedure described in the working examples. A boiling point having the stated values are satisfied if the value is obtained under either method. Additionally, as used herein, an "x % boiling point," refers to a boiling point at which x percent by weight of the composition boils per either of these methods.

As used throughout, an x % boiling at a stated temperature means at least x % of the composition boils at the stated temperature. In an embodiment or in combination with any of the embodiments mentioned herein, the 90% boiling point of the cracker feed stream or composition can be not more than 350, or not more than 325, or not more than 300, or not more than 295, or not more than 290, or not more than 285, or not more than 280, or not more than 275, or not more than 270, or not more than 265, or not more than 260, or not more than 255, or not more than 250, or not more than 245, or not more than 240, or not more than 235, or not more than 230, or not more than 225, or not more than 220, or not more than 215, not more than 200, not more than 190, not more than 180, not more than 170, not more than 160, not more than 150, or not more than 140, in each case °C and/or at least 200, or at least 205, or at least 210, or at least 215, or at least 220, or at least 225, or at least 230, in each case °C and/or not more than 25, 20, 15, 10, 5, or 2 weight percent of the r-pyoil may have a boiling point of 300 °C or higher.

Referring again to FIG. 3, the r-pyoil may be introduced into a cracking furnace or coil or tube alone (e.g., in a stream comprising at least 85, or at least 90, or at least 95, or at least 99, or 100, in each case wt. % percent pyrolysis oil based on the weight of the cracker feed stream), or combined with one or more non-recycle cracker feed streams. When introduced into a cracker furnace, coil, or tube with a non-recycle cracker feed stream, the r-pyoil may be present in an amount of at least 1, or at least 2, or at least 5, or at least 8, or at least 10, or at least 12, or at least 15, or at least 20, or at least 25, or at least 30, in each case wt. % and/or not more than 40, or not more than 35, or not more than 30, or not more than 25, or not more than 20, or not more than 15, or not more than 10, or not more than 8, or not more than 5, or not more than 2, in each case weight percent based on the total weight of the combined stream. Thus, the non-recycle cracker feed stream or composition may be present in the combined stream in an amount of at least 20, or at least 25, or at least 30, or at least 35, or at least 40, or at least 45, or at least 50, or at least 55, or at least 60, or at least 65, or at least 70, or at least 75, or at least 80, or at least 85, or at least 90, in each case weight percent and/or not more than 99, or not more than 95, or not more than 90, or not more than 85, or not more than 80, or not more than 75, or not more than 70, or not more than 65, or not more than 60, or not more than 55, or not more than 50, or not more than 45, or not more than 40, in each case weight percent based on the total weight of the combined stream. Unless otherwise noted herein, the properties of the cracker feed stream as described below apply either to the non-recycle cracker feed stream prior to (or absent) combination with the stream comprising r-pyoil, as well as to a combined cracker stream including both a non-recycle cracker feed and a r-pyoil feed.

In an embodiment or in combination with any of the embodiments mentioned herein, the cracker feed stream may comprise a predominantly C2-C4 hydrocarbon containing composition, or a predominantly C5-C22hydrocarbon containing composition. As used herein, the term "predominantly C2-C4 hydrocarbon," refers to a stream or composition containing at least 50 weight percent of C2-C4 hydrocarbon components. Examples of specific types of C2-C4 hydrocarbon streams or compositions include propane, ethane, butane, and LPG. In an embodiment or in combination with any of the embodiments mentioned herein, the cracker feed may comprise at least 50, or at least 55, or at least 60, or at least 65, or at least 70, or at least 75, or at least 80, or at least 85, or at least 90, or at least 95, in each case wt. % based on the total weight of the feed, and/or not more than 100, or not more than 99, or not more than 95, or not more than 92, or not more than 90, or not more than 85, or not more than 80, or not more than 75, or not more than 70, or not more than 65, or not more than 60, in each case weight percent C2-C4 hydrocarbons or linear alkanes, based on the total weight of the feed. The cracker feed can comprise predominantly propane, predominantly ethane, predominantly butane, or a combination of two or more of these components. These components may be non-recycle components. The cracker feed can comprise predominantly propane, or at least 50 mole % propane, or at least 80 mole % propane, or at least 90 mole % propane, or at least 93 mole % propane, or at least 95 mole % propane (inclusive of any recycle streams combined with virgin feed). The cracker feed can comprise HD5 quality propane as a virgin or fresh feed. The cracker can comprise at more than 50 mole % ethane, or at least 80 mole % ethane, or at least 90 mole % ethane, or at least 95 mole % ethane. These components may be non-recycle components.

In an embodiment or in combination with any of the embodiments mentioned herein, the cracker feed stream may comprise a predominantly C5-C22 hydrocarbon containing composition. As used herein, "predominantly C5-C22 hydrocarbon" refers to a stream or composition comprising at least 50 weight percent of C5-C22 hydrocarbon components. Examples include gasoline, naphtha, middle distillates, diesel, kerosene. In an embodiment or in combination with any of the embodiments mentioned herein, the cracker feed stream or composition may comprise at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case wt. % and/or not more than 100, or not more than 99, or not more than 95, or not more than 92, or not more than 90, or not more than 85, or not more than 80, or not more than 75, or not more than 70, or not more than 65, or not more than 60, in each case weight percent C5-C22, or C5-C20 hydrocarbons, based on the total weight of the stream or composition. In an embodiment or in combination with any of the embodiments mentioned herein, the cracker feed may have a C15 and heavier (C15+) content of at least 0.5, or at least 1, or at least 2, or at least 5, in each case weight percent and/or not more than 40, or not more than 35, or not more than 30, or not more than 25, or not more than 20, or not more than 18, or not more than 15, or not more than 12, or not more than 10, or not more than 5, or not more than 3, in each case weight percent, based on the total weight of the feed.

The cracker feed may have a boiling point curve defined by one or more of its 10%, its 50%, and its 90% boiling points, the boiling point being obtained by the methods described above Additionally, as used herein, an "x % boiling point," refers to a boiling point at which x percent by weight of the composition boils per the methods described above. In an embodiment or in combination with any of the embodiments mentioned herein, the 90% boiling point of the cracker feed stream or composition can be not more than 360, or not more than 355, or not more than 350, or not more than 345, or not more than 340, or not more than 335, or not more than 330, or not more than 325, or not more than 320, or not more than 315, or not more than 300, or not more than 295, or not more than 290, or not more than 285, or not more than 280, or not more than 275, or not more than 270, or not more than 265, or not more than 260, or not more than 255, or not more than 250, or not more than 245, or not more than 240, or not more than 235, or not more than 230, or not more than 225, or not more than 220, or not more than 215, in each case °C and/or at least 200, or at least 205, or at least 210, or at least 215, or at least 220, or at least 225, or at least 230, in each case °C.

In an embodiment or in combination with any of the embodiments mentioned herein, the 10% boiling point of the cracker feed stream or composition can be at least 40, at least 50, at least 60, at least 70, at least 80, at least 90, at least 100, at least 110, at least 120, at least 130, at least 140, at least 150, or at least 155, in each case °C and/or not more than 250, not more than 240, not more than 230, not more than 220, not more than 210, not more than 200, not more than 190, not more than 180, or not more than 170 in each case °C.

In an embodiment or in combination with any of the embodiments mentioned herein, the 50% boiling point of the cracker feed stream or composition can be at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, or at least 230, in each case °C, and/or not more than 300, not more than 290, not more than 280, not more than 270, not more than 260, not more than 250, not more than 240, not more than 230, not more than 220, not more than 210, not more than 200, not more than 190, not more than 180, not more than 170, not more than 160, not more than 150, or not more than 145 °C. The 50% boiling point of the cracker feed stream or composition can be in the range of 65 to 160, 70 to 150, 80 to 145, 85 to 140, 85 to 230, 90 to 220, 95 to 200, 100 to 190, 110 to 180, 200 to 300, 210 to 290, 220 to 280, 230 to 270, in each case in °C.

In an embodiment or in combination with any of the embodiments mentioned herein, the 90% boiling point of the cracker feedstock or stream or composition can be at least 350 °C, the 10% boiling point can be at least 60 °C; and the 50% boiling point can be in the range of from 95 °C to 200 °C. In an embodiment or in combination with any of the embodiments mentioned herein, the 90% boiling point of the cracker feedstock or stream or composition can be at least 150 °C, the 10% boiling point can be at least 60 °C, and the 50% boiling point can be in the range of from 80 to 145 °C. In an embodiment or in combination with any of the embodiments mentioned herein, the cracker feedstock or stream has a 90% boiling point of at least 350 °C, a 10% boiling point of at least 150 °C, and a 50% boiling point in the range of from 220 to 280 °C.

In an embodiment or in combination with any embodiment mentioned herein, the r-pyoil is cracked in a gas furnace. A gas furnace is a furnace having at least one coil which receives (or operated to receive), at the inlet of the coil at the entrance to the convection zone, a predominately vapor-phase feed (more than 50% of the weight of the feed is vapor) ("gas coil"). In an embodiment or in combination with any embodiment mentioned herein, the gas coil can receive a predominately C2-C4 feedstock, or a predominately a C2-C3 feedstock to the inlet of the coil in the convection section, or alternatively, having at least one coil receiving more than 50 wt. % ethane and/or more than 50% propane and/or more than 50% LPG, or in any one of these cases at least 60 wt. %, or at least 70 wt. %, or at least 80 wt. %, based on the weight of the cracker feed to the coil, or alternatively based on the weight of the cracker feed to the convection zone. The gas furnace may have more than one gas coil. In an embodiment or in combination with any embodiment mentioned herein, at least 25% of the coils, or at least 50% of the coils, or at least 60% of the coils, or all the coils in the convection zone or within a convection box of the furnace are gas coils. In an embodiment or in combination with any embodiment mentioned herein, the gas coil receives, at the inlet of the coil at the entrance to the convection zone, a vapor-phase feed in which at least 60 wt. %, or at least 70 wt. %, or at least 80 wt. %, or at least 90 wt. %, or at least 95 wt. %, or at least 97 wt. %, or at least 98 wt. %, or at least 99 wt. %, or at least 99.5 wt. %, or at least 99.9 wt. % of feed is vapor.

In an embodiment or in combination with any embodiment mentioned herein, the r-pyoil is cracked in a split furnace. A split furnace is a type of gas furnace. A split furnace contains at least one gas coil and at least one liquid coil within the same furnace, or within the same convection zone, or within the same convection box. A liquid coil is a coil which receives, at the inlet of coil at the entrance to the convection zone, a predominately liquid phase feed (more than 50% of the weight of the feed is liquid) ("liquid coil"). In an embodiment or in combination with any embodiment mentioned herein, the liquid coil can receive a predominately C5+ feedstock to the inlet of the coil at the entrance of the convection section ("liquid coil"). In an embodiment or in combination with any embodiment mentioned herein, the liquid coil can receive a predominately C6-C22 feedstock, or a predominately a C7-C16 feedstock to the inlet of the coil in the convection section, or alternatively, having at least one coil receiving more than 50 wt. % naphtha, and/or more than 50% natural gasoline, and/or more than 50% diesel, and/or more than JP-4, and/or more than 50% Stoddard Solvent, and/or more than 50% kerosene, and/or more than 50% fresh creosote, and/or more than 50% JP-8 or Jet-A, and/or more than 50% heating oil, and/or more than 50% heavy fuel oil, and/or more than 50% bunker C, and/or more than 50% lubricating oil, or in any one of these cases at least 60 wt. %, or at least 70 wt. %, or at least 80 wt. %, or at least 90 wt. %, or at least 95 wt. %, or at least 98 wt. %, or at least 99 wt. %, based on the weight of the cracker feed to the liquid coil, or alternatively based on the weight of the cracker feed to the convection zone. In an embodiment or in combination with any embodiment mentioned herein, at least one coil and not more than 75% of the coils, or not more than 50% of the coils, or not more than at least 40% of the coils in the convection zone or within a convection box of the furnace are liquid coils. In an embodiment or in combination with any embodiment mentioned herein, the liquid coil receives, at the inlet of the coil at the entrance to the convection zone, a liquid-phase feed in which at least 60 wt. %, or at least 70 wt. %, or at least 80 wt. %, or at least 90 wt. %, or at least 95 wt. %, or at least 97 wt. %, or at least 98 wt. %, or at least 99 wt. %, or at least 99.5 wt. %, or at least 99.9 wt. % of feed is liquid.

In an embodiment or in combination with any embodiment mentioned herein, the r-pyoil is cracked in a thermal gas cracker.

In an embodiment or in combination with any embodiment mentioned herein, the r-pyoil is cracked in a thermal steam gas cracker in the presence of steam. Steam cracking refers to the high-temperature cracking (decomposition) of hydrocarbons in the presence of steam.

In an embodiment or in combination with any embodiment mentioned herein, the r-composition is derived directly or indirectly from cracking r-pyoil in a gas furnace. The coils in the gas furnace can consist entirely of gas coils or the gas furnace can be a split furnace.

When the r-pyoil containing feed stream is combined with the non-recycle cracker feed, such a combination may occur upstream of, or within, the cracking furnace or within a single coil or tube. Alternatively, the r-pyoil containing feed stream and non-recycle cracker feed may be introduced separately into the furnace, and may pass through a portion, or all, of the furnace simultaneously while being isolated from one another by feeding into separate tubes within the same furnace (e.g., a split furnace). Ways of introducing the r-pyoil containing feed stream and the non-recycle cracker feed into the cracking furnace according to an embodiment or in combination with any of the embodiments mentioned herein are described in further detail below.

Turning now to FIG. 5, a schematic diagram of a cracker furnace suitable for use in an embodiment or in combination with any of the embodiments mentioned herein is shown.

In one embodiment or in combination of any of the mentioned embodiments, there is provided a method for making one or more olefins including:

(a) feeding a first cracker feed comprising a recycle content pyrolysis oil composition (r-pyoil) to a cracker furnace;

(b) feeding a second cracker feed into said cracker furnace, wherein said second cracker feed comprises none of said r-pyoil or less of said r-pyoil, by weight, than said first cracker feed stream; and (c) cracking said first and said second cracker feeds in respective first and second tubes to form an olefin-containing effluent stream.

The r-pyoil can be combined with a cracker stream to make a combined cracker stream, or as noted above, a first cracker stream. The first cracker stream can be 100% r-pyoil or a combination of a non-recycle cracker stream and r-pyoil. The feeding of step (a) and/or step (b) can be performed upstream of the convection zone or within the convection zone. The r-pyoil can be combined with a non-recycle cracker stream to form a combined or first cracker stream and fed to the inlet of a convection zone, or alternatively the r-pyoil can be separately fed to the inlet of a coil or distributor along with a non-recycle cracker stream to form a first cracker stream at the inlet of the convection zone, or the r-pyoil can be fed downstream of the inlet of the convection zone into a tube containing non-recycle cracker feed, but before a crossover, to make a first cracker stream or combined cracker stream in a tube or coil. Any of these methods includes feeding the first cracker stream to the furnace.

The amount of r-pyoil added to the non-recycle cracker stream to make the first cracker stream or combined cracker stream can be as described above; e.g. in an amount of at least 1, 5, 10, 15, 20, 25, 30, 35, 40, 45, 50, 55, 60, 65, 70, 75, 80, 85, 90, or 95, in each case weight percent and/or not more than 95, 90, 85, 80, 75, 70, 65, 60, 55, 60, 55, 50, 45, 40, 35, 30, 25, 20, 15, or 1, in each case weight percent, based on the total weight of the first cracker feed or combined cracker feed (either as introduced into the tube or within the tube as noted above). Further examples include 5-50, 5-40, 5-35, 5-30, 5-25, 5-20, or 5-15 wt. %.

The first cracker stream is cracked in a first coil or tube. The second cracker stream is cracked in a second coil or tube. Both the first and second cracker streams and the first and second coils or tubes can be within the same cracker furnace.

The second cracker stream can have none of the r-pyoil or less of said r-pyoil, by weight, than the first cracker feed stream. Also, the second cracker stream can contain only non-recycle cracker feed in the second coil or tube. The second cracker feed stream can be predominantly C2 to C4, or hydrocarbons (e.g. non-recycle content), or ethane, propane, or butane, in each case in amounts of at least 55, 60, 65, 70, 75, 80, 85, or at least 90 weight percent based on the second cracker feed within a second coil or tube. If r-pyoil is included in the second cracker feed, the amount of such r-pyoil can be at least 10% less, 20, 30, 40, 50, 60, 70, 80, 90, 95, 97, or 99% less by weight than the amount of r-pyoil in the first cracker feed.

In an embodiment or in combination with any embodiment mentioned herein, although not shown, a vaporizer can be provided to vaporize a condensed feedstock of C2-C5 hydrocarbons 350 to ensure that the feed to the inlet of the coils in the convection box 312, or the inlet of the convection zone 310, is a predominately vapor phase feed.

The cracking furnace shown in FIG. 5 includes a convection section or zone 310, a radiant section or zone 320, and a cross-over section or zone 330 located between the convection and radiant sections 310 and 320. The convection section 310 is the portion of the furnace 300 that receives heat from hot flue gases and includes a bank of tubes or coils 324 through which a cracker stream 350 passes. In the convection section 310, the cracker stream 350 is heated by convection from the hot flue gasses passing therethrough. The radiant section 320 is the section of the furnace 300 into which heat is transferred into the heater tubes primarily by radiation from the high-temperature gas. The radiant section 320 also includes a plurality of burners 326 for introducing heat into the lower portion of the furnace. The furnace includes a fire box 322 which surrounds and houses the tubes within the radiant section 320 and into which the burners are oriented. The cross-over section 330 includes piping for connecting the convection 310 and radiant sections 320 and may transfer the heated cracker stream internally or externally from one section to the other within the furnace 300.

As hot combustion gases ascend upwardly through the furnace stack, the gases may pass through the convection section 310, wherein at least a portion of the waste heat may be recovered and used to heat the cracker stream passing through the convection section 310. In an embodiment or in combination with any of the embodiments mentioned herein, the cracking furnace 300 may have a single convection (preheat) section 310 and a single radiant 320 section, while, in other embodiments, the furnace may include two or more radiant sections sharing a common convection section. At least one induced draft (I.D.) fan 316 near the stack may control the flow of hot flue gas and heating profile through the furnace, and one or more heat exchangers 340 may be used to cool the furnace effluent 370. In an embodiment or in combination with any of the embodiments mentioned herein (not shown), a liquid quench may be used in addition to, or alternatively with, the exchanger (e.g., transfer line heat exchanger or TLE) shown in FIG. 5, for cooling the cracked olefin-containing effluent.

The furnace 300 also includes at least one furnace coil 324 through which the cracker streams pass through the furnace. The furnace coils 324 may be formed of any material inert to the cracker stream and suitable for withstanding high temperatures and thermal stresses within the furnace. The coils may have any suitable shape and can, for example, have a circular or oval cross-sectional shape.

The coils in the convection section 310, or tubes within the coil, may have a diameter of at least 1, or at least 1.5, or at least 2, or at least 2.5, or at least 3, or at least 3.5, or at least 4, or at least 4.5, or at least 5, or at least 5.5, or at least 6, or at least 6.5, or at least 7, or at least 7.5, or at least 8, or at least 8.5, or at least 9, or at least 9.5, or at least 10, or at least 10.5, in each case cm and/or not more than 12, or not more than 11.5, or not more than 11, 1 or not more than 0.5, or not more than 10, or not more than 9.5, or not more than 9, or not more than 8.5, or not more than 8, or not more than 7.5, or not more than 7, or not more than 6.5, in each case cm. All or a portion of one or more coils can be substantially straight, or one or more of the coils may include a helical, twisted, or spiral segment. One or more of the coils may also have a U-tube or split U-tube design. In an embodiment or in combination with any of the embodiments mentioned herein, the interior of the tubes may be smooth or substantially smooth, or a portion (or all) may be roughened in order to minimize coking. Alternatively, or in addition, the inner portion of the tube may include inserts or fins and/or surface metal additives to prevent coke build up.

In an embodiment or in combination with any of the embodiments mentioned herein, all or a portion of the furnace coil or coils 324 passing through in the convection section 310 may be oriented horizontally, while all, or at least a portion of, the portion of the furnace coil passing through the radiant section 322 may be oriented vertically. In an embodiment or in combination with any of the embodiments mentioned herein, a single furnace coil may run through both the convection and radiant section. Alternatively, at least one coil may split into two or more tubes at one or more points within the furnace, so that cracker stream may pass along multiple paths in parallel. For example, the cracker stream (including r-pyoil) 350 may be introduced into multiple coil inlets in the convection zone 310, or into multiple tube inlets in the radiant 320 or cross-over sections 330. When introduced into multiple coil or tube inlets simultaneously, or nearly simultaneously, the amount of r-pyoil introduced into each coil or tube may not be regulated. In an embodiment or in combination with any of the embodiments mentioned herein, the r-pyoil and/or cracker stream may be introduced into a common header, which then channels the r-pyoil into multiple coil or tube inlets.

Figure 6:
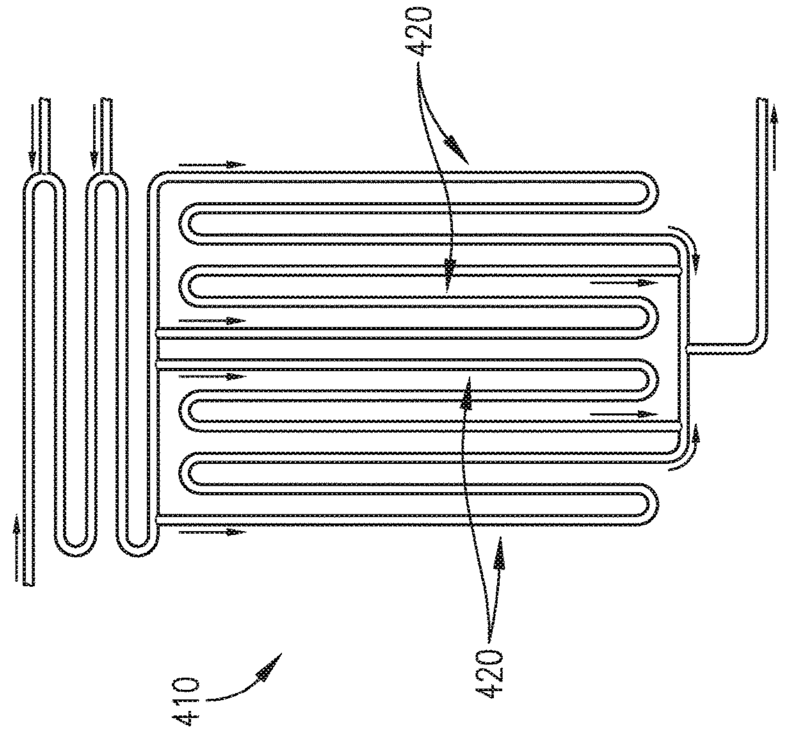
FIG. 6 illustrates a furnace coil configuration having multiple tubes.

A single furnace can have at least 1, or at least 2, or at least 3, or at least 4, or at least 5, or at least 6, or at least 7, or at least 8 or more, in each case coils. Each coil can be from 5 to 100, 10 to 75, or 20 to 50 meters in length and can include at least 1, or at least 2, or at least 3, or at least 4, or at least 5, or at least 6, or at least 7, or at least 8, or at least 10, or at least 12, or at least 14 or more tubes. Tubes of a single coil may be arranged in many configurations and in an embodiment or in combination with any of the embodiments mentioned herein may be connected by one or more 180 ° ("U") bends. One example of a furnace coil 410 having multiple tubes 420 is shown in FIG. 6.

An olefin plant can have a single cracking furnace, or it can have at least 2, or at least 3, or at least 4, or at least 5, or at least 6, or at least 7, or at least 8 or more cracking furnaces operated in parallel. Any one or each furnace(s) may be gas cracker, or a liquid cracker, or a split furnace. In an embodiment or in combination with any embodiment mentioned herein, the furnace is a gas cracker receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, based on the weight of all cracker feed to the furnace. In an embodiment or in combination with any embodiment mentioned herein, the furnace is a liquid or naphtha cracker receiving a cracker feed stream containing at least 50 wt. %, or at least 75 wt. %, or at least 85 wt. % liquid (when measured at 25 °C and 1 atm) hydrocarbons having a carbon number from C5-C22. through the furnace, or through at least one coil in a furnace, or through at least one tube in the furnace, based on the weight of all cracker feed to the furnace. In an embodiment or in combination with any embodiment mentioned herein, the cracker is a split furnace receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, and receiving a cracker feed stream containing at least 0.5 wt. %, or at least 0.1 wt. %, or at least 1 wt. %, or at least 2 wt. %, or at least 5 wt. %, or at least 7 wt. %, or at least 10 wt. %, or at least 13 wt. %, or at least 15 wt. %, or at least 20 wt. % liquid and/or r-pyoil (when measured at 25 °C and 1 atm), each based on the weight of all cracker feed to the furnace.

Figure 7:
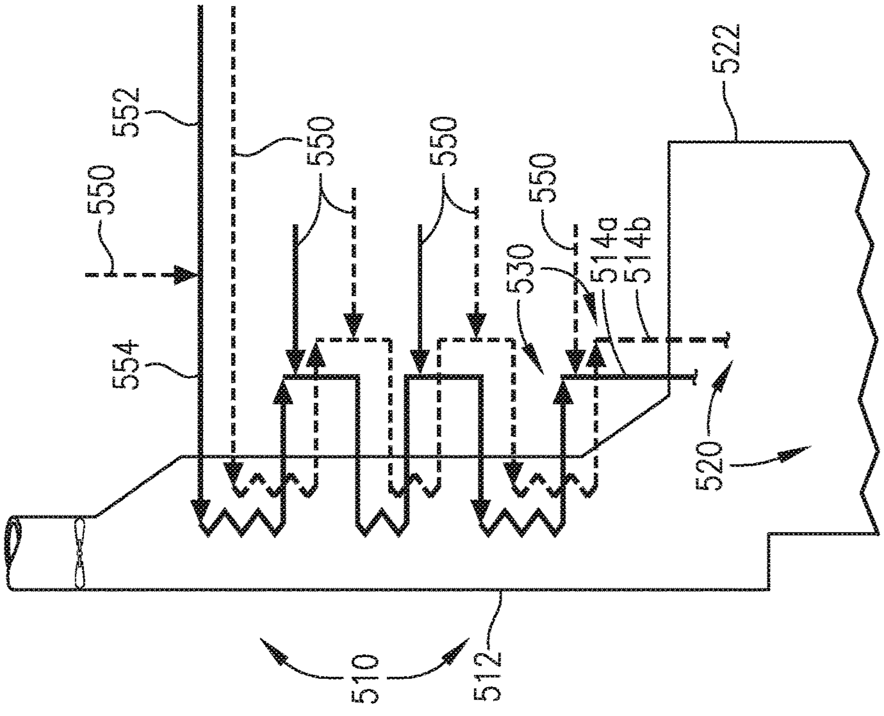
FIG. 7 illustrates a variety of feed locations for r-pyoil into a cracker furnace.

Turning now to FIG. 7, several possible locations for introducing the r-pyoil containing feed stream and the non-recycle cracker feed stream into a cracking furnace are shown.

In an embodiment or in combination with any of the embodiments mentioned herein, an r-pyoil containing feed stream 550 may be combined with the non-recycle cracker feed 552 upstream of the convection section to form a combined cracker feed stream 554, which may then be introduced into the convection section 510 of the furnace. Alternatively, or in addition, the r-pyoil containing feed 550 may be introduced into a first furnace coil, while the non-recycle cracker feed 552 is introduced into a separate or second furnace coil, within the same furnace, or within the same convection zone. Both streams may then travel in parallel with one another through the convection section 510 within a convection box 512, cross-over 530, and radiant section 520 within a radiant box 522, such that each stream is substantially fluidly isolated from the other over most, or all, of the travel path from the inlet to the outlet of the furnace. The pyoil stream introduced into any heating zone within the convection section 510 can flow through the convection section 510 and flow through as a vaporized stream **514*b* into the radiant box 522. In other embodiments, the r-pyoil containing feed stream 550 may be introduced into the non-recycle cracker stream 552 as it passes through a furnace coil in the convection section 510 flowing into the cross-over section 530 of the furnace to form a combined cracker stream 514*a*, as also shown in FIG. 7**.

In an embodiment or in combination with any embodiment mentioned herein, the r-pyoil 550 may be introduced into the first furnace coil, or an additional amount introduced into the second furnace coil, at either a first heating zone or a second heating zone as shown in FIG. 7. The r-pyoil 550 may be introduced into the furnace coil at these locations through a nozzle. A convenient method for introducing the feed of r-pyoil is through one or more dilution steam feed nozzles that are used to feed steam into the coil in the convection zone. The service of one or more dilution steam nozzles may be employed to inject r-pyoil, or a new nozzle can be fastened to the coil dedicated to the injection of the r-pyoil. In an embodiment or in combination with any embodiment mentioned herein, both steam and r-pyoil can be co-fed through a nozzle into the furnace coil downstream of the inlet to the coil and upstream of a crossover, optionally at the first or second heating zone within the convection zone as shown in FIG. 7.

The non-recycle cracker feed stream may be mostly liquid and have a vapor fraction of less than 0.25 by volume, or less than 0.25 by weight, or it may be mostly vapor and have a vapor fraction of at least 0.75 by volume, or at least 0.75 by weight, when introduced into the furnace and/or when combined with the r-pyoil containing feed. Similarly, the r-pyoil containing feed may be mostly vapor or mostly liquid when introduced into the furnace and/or when combined with the non-recycle cracker stream.

Figure 8:
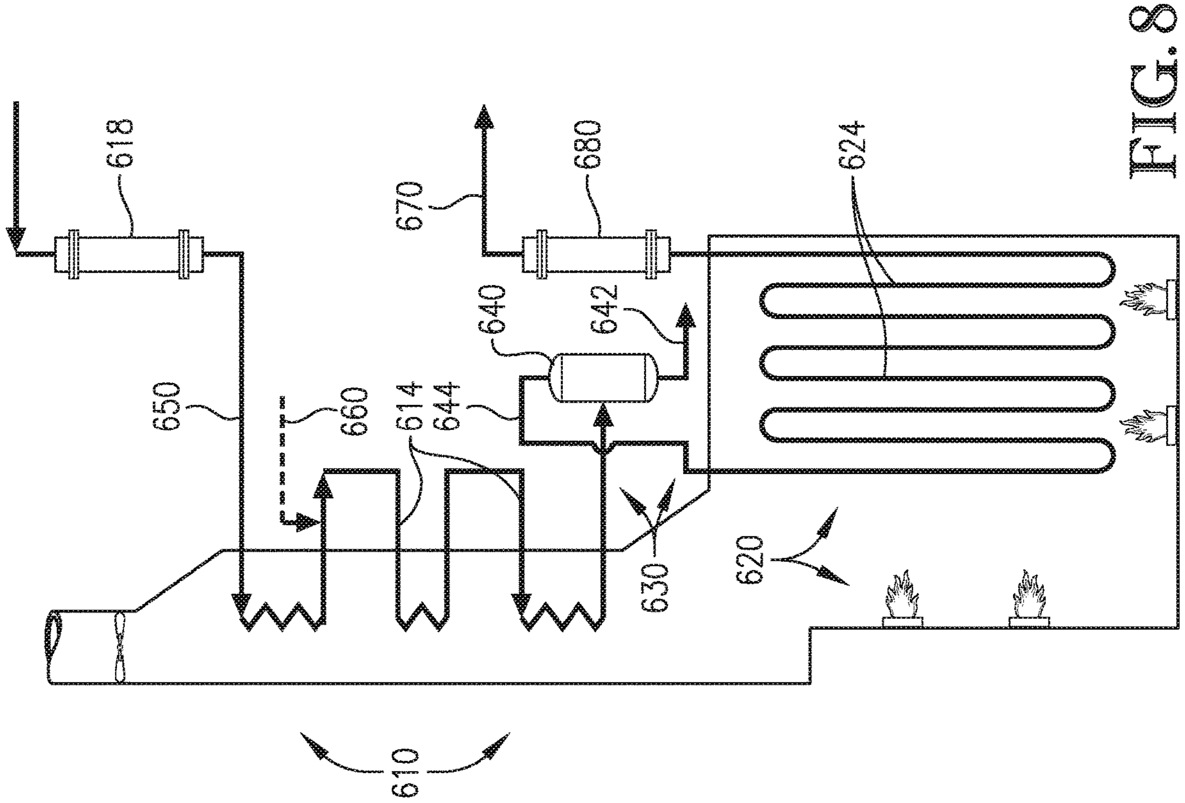
FIG. 8 illustrates a cracker furnace having a vapor-liquid separator.

In an embodiment or in combination with any of the embodiments mentioned herein, at least a portion or all of the r-pyoil stream or cracker feed stream may be preheated prior to being introduced into the furnace. As shown in FIG. 8, the preheating can be performed with an indirect heat exchanger 618 heated by a heat transfer media (such as steam, hot condensate, or a portion of the olefin-containing effluent) or via a direct fired heat exchanger 618. The preheating step can vaporize all or a portion of the stream comprising r-pyoil and may, for example, vaporize at least 50, 55, 60, 65, 70, 75, 80, 85, 90, 95, or 99 weight percent of the stream comprising r-pyoil.

The preheating, when performed, can increase the temperature of the r-pyoil containing stream to a temperature that is within about 50, 45, 40, 35, 30, 25, 20, 15, 10, 5, or 2 °C of the bubble point temperature of the r-pyoil containing stream. Additionally, or in the alternative, the preheating can increase the temperature of the stream comprising r-pyoil to a temperature at least 5, 10, 15, 20, 25, 30, 35, 40, 45, 50, 55, 60, 65, 70, 75, 80, 85, 90, or 100 °C below the coking temperature of the stream. In an embodiment or in combination with any of the embodiments mentioned herein, the preheated r-pyoil stream can have a temperature of at least 200, 225, 240, 250, or 260 °C and/or not more than 375, 350, 340, 330, 325, 320, or 315 °C, or at least 275, 300, 325, 350, 375, or 400 °C and/or not more than 600, 575, 550, 525, 500, or 475 °C. When the atomized liquid (as explained below) is injected into the vapor phase, heated cracker stream, the liquid may rapidly evaporate such that, for example, the entire combined cracker stream is vapor (e.g., 100 percent vapor) within 5, 4, 3, 2, or 1 second after injection.

In an embodiment or in combination with any of the embodiments mentioned herein, the heated r-pyoil stream (or cracker stream comprising the r-pyoil and the non-recycle cracker stream) can optionally be passed through a vapor-liquid separator to remove any residual heavy or liquid components, when present. The resulting light fraction may then be introduced into the cracking furnace, alone or in combination with one or more other cracker streams as described in various embodiments herein. For example, in an embodiment or in combination with any of the embodiments mentioned herein, the r-pyoil stream can comprise at least 1, 2, 5, 8, 10, or 12 weight percent C15 and heavier components. The separation can remove at least 50, 55, 60, 65, 70, 75, 80, 85, 90, 95, or 99 weight percent of the heavier components from the r-pyoil stream.

Turning back to FIG. 7, the cracker feed stream (either alone or when combined with the r-pyoil feed stream) may be introduced into a furnace coil at or near the inlet of the convection section. The cracker stream may then pass through at least a portion of the furnace coil in the convection section 510, and dilution steam may be added at some point in order to control the temperature and cracking severity in the furnace. In an embodiment or in combination with any of the embodiments mentioned herein, the steam may be added upstream of or at the inlet to the convection section, or it may be added downstream of the inlet to the convection section—either in the convection section, at the cross-over section, or upstream of or at the inlet to the radiant section. Similarly, the stream comprising the r-pyoil and the non-recycle cracker stream (alone or combined with the steam) may also be introduced into or upstream or at the inlet to the convection section, or downstream of the inlet to the convection section—either within the convection section, at the cross-over, or at the inlet to the radiant section. The steam may be combined with the r-pyoil stream and/or cracker stream and the combine stream may be introduced at one or more of these locations, or the steam and r-pyoil and/or non-recycle cracker stream may be added separately.

When combined with steam and fed into or near the cross-over section of the furnace, the r-pyoil and/or cracker stream can have a temperature of 500, 510, 520, 530, 540, 550, 560, 570, 580, 590, 600, 610, 620, 630, 640, 650, 660, 670, or 680 °C and/or not more than 850, 840, 830, 820, 810, 800, 790, 780, 770, 760, 750, 740, 730, 720, 710, 705, 700, 695, 690, 685, 680, 675, 670, 665, 660, 655, or 650 °C. The resulting steam and r-pyoil stream can have a vapor fraction of at least 0.75, 0.80, 0.85, 0.90, or at least 0.95 by weight, or at least 0.75, 0.80, 0.85, 0.90, and 0.95 by volume.

When combined with steam and fed into or near the inlet to the convection section 510, the r-pyoil and/or cracker stream can have a temperature of at least 30, 35, 40, 45, 50, 55, 60, or 65 and/or not more than 100, 90, 80, 70, 60, 50, or 45 °C.

The amount of steam added may depend on the operating conditions, including feed type and desired product, but can be added to achieve a steam-to-hydrocarbon ratio can be at least 0.10:1, 0.15:1, 0.20:1, 0.25:1, 0.27:1, 0.30:1, 0.32:1, 0.35:1, 0.37:1, 0.40:1, 0.42:1, 0.45:1, 0.47:1, 0.50:1, 0.52:1, 0.55:1, 0.57:1, 0.60:1, 0.62:1, 0.65:1 and/or not more than about 1:1.0.95:1, 0.90:1, 0.85:1, 0.80:1, 0.75:1, 0.72:1, 0.70:1, 0.67:1, 0.65:1, 0.62:1, 0.60:1, 0.57:1, 0.55:1, 0.52:1, 0.50:1, or it can be in the range of from 0.1:1 to 1.0:1, 0.15:1 to 0.9:1, 0.2:1 to 0.8:1, 0.3:1 to 0.75:1, or 0.4:1 to 0.6:1. When determining the "steam-to-hydrocarbon" ratio, all hydrocarbon components are included and the ratio is by weight. In an embodiment or in combination with any of the embodiments mentioned herein, the steam may be produced using separate boiler feed water/steam tubes heated in the convection section of the same furnace (not shown in FIG. 7). Steam may be added to the cracker feed (or any intermediate cracker stream within the furnace) when the cracker stream has a vapor fraction of 0.60 to 0.95, or 0.65 to 0.90, or 0.70 to 0.90.

When the r-pyoil containing feed stream is introduced into the cracking furnace separately from a non-recycle feed stream, the molar flow rate of the r-pyoil and/or the r-pyoil containing stream may be different than the molar flow rate of the non-recycle feed stream. In one embodiment or in combination with any other mentioned embodiment, there is provided a method for making one or more olefins by:

(a) feeding a first cracker stream having r-pyoil to a first tube inlet in a cracker furnace;

(b) feeding a second cracker stream containing, or predominately containing $C_2$ to $C_4$ hydrocarbons to a second tube inlet in the cracker furnace, wherein said second tube is separate from said first tube and the total molar flow rate of the first cracker stream fed at the first tube inlet is lower than the total molar flow rate of the second cracker stream to the second tube inlet, calculated without the effect of steam. The feeding of step (a) and step (b) can be to respective coil inlets.

For example, the molar flow rate of the r-pyoil or the first cracker stream as it passes through a tube in the cracking furnace may be at least 5, 7, 10, 12, 15, 17, 20, 22, 25, 27, 30, 35, 40, 45, 50, 55, or 60 percent lower than the flow rate of the hydrocarbon components (e.g., C2-C4 or C5-C22) components in the non-recycle feed stream, or the second cracker stream, passing through another or second tube. When steam is present in both the r-pyoil containing stream, or first cracker stream, and in the second cracker stream or the non-recycle feed stream, the total molar flow rate of the r-pyoil containing stream, or first cracker stream, (including r-pyoil and dilution steam) may be at least 5, 7, 10, 12, 15, 17, 20, 22, 25, 27, 30, 35, 40, 45, 50, 55, or 60 percent higher than the total molar flow rate (including hydrocarbon and dilution steam) of the non-recycle cracker feedstock, or second cracker stream (wherein the percentage is calculated as the difference between the two molar flow rates divided by the flow rate of the non-recycle stream).

In an embodiment or in combination with any of the embodiments mentioned herein, the molar flow rate of the r-pyoil in the r-pyoil containing feed stream (first cracker stream) within the furnace tube may be at least 0.01, 0.02, 0.025, 0.03, 0.035 and/or not more than 0.06, 0.055, 0.05, 0.045 kmol-lb/hr lower than the molar flow rate of the hydrocarbon (e.g., C2-C4 or C5-C22) in the non-recycle cracker stream (second cracker stream). In an embodiment or in combination with any of the embodiments mentioned herein, the molar flow rates of the r-pyoil and the cracker feed stream may be substantially similar, such that the two molar flow rates are within 0.005, 0.001, or 0.0005 kmol-lb/hr of one another. The molar flow rate of the r-pyoil in the furnace tube can be at least 0.0005, 0.001, 0.0025, 0.005, 0.01, 0.02, 0.03, 0.04, 0.05, 0.06, 0.07, 0.08, 0.09, 0.10, 0.11, 0.12, 0.13, 0.14, or 0.15 kilo moles-pound per hour (kmol-lb/hr) and/or not more than 0.25, 0.24, 0.23, 0.22, 0.21, 0.20, 0.19, 0.18, 0.17, 0.16, 0.15, 0.14, 0.13, 0.08, 0.05, 0.025, 0.01, or 0.008 kmol-lb/hr, while the molar flow rate of the hydrocarbon components in the other coil or coils can be at least 0.02, 0.03, 0.04, 0.05, 0.06, 0.07, 0.08, 0.09, 0.10, 0.11, 0.12, 0.13, 0.14, 0.15, 0.16, 0.17, 0.18 and/or not more than 0.30, 0.29, 0.28, 0.27, 0.26, 0.25, 0.24, 0.23, 0.22, 0.21, 0.20, 0.19, 0.18, 0.17, 0.16, 0.15 kmol-lb/hr.

In an embodiment or in combination with any of the embodiments mentioned herein, the total molar flow rate of the r-pyoil containing stream (first cracker stream) can be at least 0.01, 0.02, 0.03, 0.04, 0.05, 0.06, 0.07, 0.08, 0.09 and/or not more than 0.30, 0.25, 0.20, 0.15, 0.13, 0.10, 0.09, 0.08, 0.07, or 0.06 kmol-lb/hr lower than the total molar flow rate of the non-recycle feed stream (second cracker stream), or the same as the total molar flow rate of the non-recycle feed stream (second cracker stream). The total molar flow rate of the r-pyoil containing stream (first cracker stream) can be at least 0.01, 0.02, 0.03, 0.04, 0.05, 0.06, 0.07 and/or not more than 0.10, 0.09, 0.08, 0.07, or 0.06 kmol-lb/hr higher than the total molar flow rate of the second cracker stream, while the total molar flow rate of the non-recycle feed stream (second cracker stream) can be at least 0.20, 0.21, 0.22, 0.23, 0.24, 0.25, 0.26, 0.27, 0.28, 0.29, 0.30, 0.31, 0.32, 0.33 and/or not more than 0.50, 0.49, 0.48, 0.47. 0.46, 0.45, 0.44, 0.43, 0.42, 0.41, 0.40 kmol-lb/hr.

In an embodiment or in combination with any of the embodiments mentioned herein, the r-pyoil containing stream, or first cracker stream, has a steam-to-hydrocarbon ratio that is at least 5, 10, 15, 20, 25, 30, 35, 40, 45, 50, 55, 60, 65, 70, 75, or 80 percent different than the steam-to-hydrocarbon ratio of the non-recycle feed stream, or second cracker stream. The steam-to-hydrocarbon ratio can be higher or lower. For example, the steam-to-hydrocarbon ratio of the r-pyoil containing stream or first cracker stream can be at least 0.01, 0.025, 0.05, 0.075, 0.10, 0.125, 0.15, 0.175, or 0.20 and/or not more than 0.3, 0.27, 0.25, 0.22, or 0.20 different than the steam-to-hydrocarbon ratio of the non-recycle feed stream or second cracker stream. The steam-to-hydrocarbon ratio of the r-pyoil containing stream or first cracker stream can be at least 0.3, 0.32, 0.35, 0.37, 0.4, 0.42, 0.45, 0.47, 0.5 and/or not more than 0.7, 0.67, 0.65, 0.62, 0.6, 0.57, 0.55, 0.52, or 0.5, and the steam-to-hydrocarbon ratio of the non-recycle cracker feed or second cracker stream can be at least 0.02, 0.05, 0.07, 0.10, 0.12, 0.15, 0.17, 0.20, 0.25 and/or not more than 0.45, 0.42, 0.40, 0.37, 0.35, 0.32, or 0.30.

In an embodiment or in combination with any embodiments mentioned herein, the temperature of the r-pyoil containing stream as it passes through a cross-over section in the cracking furnace can be different than the temperature of the non-recycle cracker feed as it passes through the cross-over section, when the streams are introduced into and passed through the furnace separately. For example, the temperature of the r-pyoil stream as it passes through the cross-over section may be at least 0.01, 0.5, 1, 1.5, 2, 5, 10, 15, 20, 25, 30, 35, 40, 45, 50, 55, 60, 65, 70, or 75 percent different than the temperature of the non-recycle hydrocarbon stream (e.g., C2-C4 or C5-C22) passing through the cross-over section in another coil. The percentage can be calculated based on the temperature of the non-recycle stream according to the following formula:

[(temperature of r-pyoil stream−temperature of non-recycle cracker stream)]/(temperature of non-recycle cracker steam),expressed as a percentage.

The difference can be higher or lower. The average temperature of the r-pyoil containing stream at the cross-over section can be at least 400, 425, 450, 475, 500, 525, 550, 575, 580, 585, 590, 595, 600, 605, 610, 615, 620, or 625 °C and/or not more than 705, 700, 695, 690, 685, 680, 675, 670, 665, 660, 655, 650, 625, 600, 575, 550, 525, or 500 °C, while the average temperature of the non-recycle cracker feed can be at least 401, 426, 451, 476, 501, 526, 551, 560, 565, 570, 575, 580, 585, 590, 595, 600, 605, 610, 615, 620, or 625 °C and/or not more than 705, 700, 695, 690, 685, 680, 675, 670, 665, 660, 655, 650, 625, 600, 575, 550, 525, or 500 °C.

The heated cracker stream, which usually has a temperature of at least 500, 510, 520, 530, 540, 550, 560, 570, 580, 590, 600, 610, 620, 630, 640, 650, 660, 670, or 680 °C and/or not more than 850, 840, 830, 820, 810, 800, 790, 780, 770, 760, 750, 740, 730, 720, 710, 705, 700, 695, 690, 685, 680, 675, 670, 665, 660, 655, or 650 °C, or in the range of from 500 to 710 °C, 620 to 740 °C, 560 to 670 °C, or 510 to 650 °C, may then pass from the convection section of the furnace to the radiant section via the cross-over section.

In an embodiment or in combination with any of the embodiments mentioned herein, the r-pyoil containing feed stream may be added to the cracker stream at the cross-over section. When introduced into the furnace in the cross-over section, the r-pyoil may be at least partially vaporized by, for example, preheating the stream in a direct or indirect heat exchanger. When vaporized or partially vaporized, the r-pyoil containing stream has a vapor fraction of at least 0.5, 0.55, 0.6, 0.65, 0.7, 0.75, 0.8, 0.85, 0.9, 0.95, or 0.99 by weight, or in one embodiment or in combination with any mentioned embodiments, by volume.

When the r-pyoil containing stream is atomized prior to entering the cross-over section, the atomization can be performed using one or more atomizing nozzles. The atomization can take place within or outside the furnace. In an embodiment or in combination with any of the embodiments mentioned herein, an atomizing agent may be added to the r-pyoil containing stream during or prior to its atomization. The atomizing agent can include steam, or it may include predominantly ethane, propane, or combinations thereof. When used the atomizing agent may be present in the stream being atomized (e.g., the r-pyoil containing composition) in an amount of at least 1, 2, 4, 5, 8, 10, 12, 15, 10, 25, or 30 weight percent and/or not more than 50, 45, 40, 35, 30, 25, 20, 15, or 10 weight percent.

The atomized or vaporized stream of r-pyoil may then be injected into or combined with the cracker stream passing through the cross-over section. At least a portion of the injecting can be performed using at least one spray nozzle. At least one of the spray nozzles can be used to inject the r-pyoil containing stream into the cracker feed stream may be oriented to discharge the atomized stream at an angle within about 45, 50, 35, 30, 25, 20, 15, 10, 5, or 0 ° from the vertical. The spray nozzle or nozzles may also be oriented to discharge the atomized stream into a coil within the furnace at an angle within about 30, 25, 20, 15, 10, 8, 5, 2, or 1 ° of being parallel, or parallel, with the axial centerline of the coil at the point of introduction. The step of injecting the atomized r-pyoil may be performed using at least two, three, four, five, six or more spray nozzles, in the cross-over and/or convection section of the furnace.

In an embodiment or in combination with any embodiments mentioned herein, atomized r-pyoil can be fed, alone or in combination with an at least partially non-recycle cracker stream, into the inlet of one or more coils in the convection section of the furnace. The temperature of such an atomization can be at least 30, 35, 40, 45, 50, 55, 60, 65, 70, 75, or 80 °C and/or not more than 120, 110, 100, 90, 95, 80, 85, 70, 65, 60, or 55 °C.

In an embodiment or in combination with any embodiments mentioned herein, the temperature of the atomized or vaporized stream can be at least 5, 10, 15, 20, 25, 30, 35, 40, 45, 50, 75, 100, 125, 150, 175, 200, 225, 250, 275, 300, 325, 350 °C and/or not more than 550, 525, 500, 475, 450, 425, 400, 375, 350, 325, 300, 275, 250, 225, 200, 175, 150, 125, 100, 90, 80, 75, 70, 60, 55, 50, 45, 40, 30, or 25 °C cooler than the temperature of the cracker stream to which it is added. The resulting combined cracker stream comprises a continuous vapor phase with a discontinuous liquid phase (or droplets or particles) dispersed therethrough. The atomized liquid phase may comprise r-pyoil, while the vapor phase may include predominantly C2-C4 components, ethane, propane, or combinations thereof. The combined cracker stream may have a vapor fraction of at least 0.7, 0.75, 0.8, 0.85, 0.9, 0.95, or 0.99 by weight, or in one embodiment or in combination with any mentioned embodiments, by volume.

The temperature of the cracker stream passing through the cross-over section can be at least 500, 510, 520, 530, 540, 550, 555, 560, 565, 570, 575, 580, 585, 590, 595, 600, 605, 610, 615, 620, 625, 630, 635, 640, 645, 650, 660, 670, or 680 °C and/or not more than 850, 840, 830, 820, 810, 800, 795, 790, 785, 780, 775, 770, 765, 760, 755, 750, 745, 740, 735, 730, 725, 720, 715, 710, 705, 700, 695, 690, 685, 680, 675, 670, 665, 660, 655, 650, 645, 640, 635, or 630 °C, or in the range of from 620 to 740 °C, 550 to 680 °C, 510 to 630 °C.

The resulting cracker feed stream then passes into the radiant section. In an embodiment or in combination with any of the embodiments mentioned herein, the cracker stream (with or without the r-pyoil) from the convection section may be passed through a vapor-liquid separator to separate the stream into a heavy fraction and a light fraction before cracking the light fraction further in the radiant section of the furnace. One example of this is illustrated in FIG. 8.

In an embodiment or in combination with any of the embodiments mentioned herein, the vapor-liquid separator 640 may comprise a flash drum, while in other embodiments it may comprise a fractionator. As the stream 614 passes through the vapor-liquid separator 640, a gas stream impinges on a tray and flows through the tray, as the liquid from the tray fall to an underflow 642. The vapor-liquid separator may further comprise a demister or chevron or other device located near the vapor outlet for preventing liquid carry-over into the gas outlet from the vapor-liquid separator 640.

Within the convection section 610, the temperature of the cracker stream may increase by at least 50, 75, 100, 150, 175, 200, 225, 250, 275, or 300 °C and/or not more than about 650, 600, 575, 550, 525, 500, 475, 450, 425, 400, 375, 350, 325, 300, or 275 °C, so that the passing of the heated cracker stream exiting the convection section 610 through the vapor-liquid separator 640 may be performed at a temperature of least 400, 425, 450, 475, 500, 525, 550, 575, 600, 625, 650 °C and/or not more than 800, 775, 750, 725, 700, 675, 650, 625 °C. When heavier components are present, at least a portion or nearly all of the heavy components may be removed in the heavy fraction as an underflow 642. At least a portion of the light fraction 644 from the separator 640 may be introduced into the cross-over section or the radiant zone tubes 624 after the separation, alone or in combination with one or more other cracker streams, such as, for example, a predominantly C5-C22 hydrocarbon stream or a C2-C4 hydrocarbon stream.

Referencing FIGS. 5 and 6, the cracker feed stream (either the non-recycle cracker feed stream or when combined with the r-pyoil feed stream) 350 and 650 may be introduced into a furnace coil at or near the inlet of the convection section. The cracker feed stream may then pass through at least a portion of the furnace coil in the convection section 310 and 610, and dilution steam 360 and 660 may be added at some point in order to control the temperature and cracking severity in the radiant section 320 and 620. The amount of steam added may depend on the furnace operating conditions, including feed type and desired product distribution, but can be added to achieve a steam-to-hydrocarbon ratio in the range of from 0.1 to 1.0, 0.15 to 0.9, 0.2 to 0.8, 0.3 to 0.75, or 0.4 to 0.6, calculated by weight. In an embodiment or in combination with any of the embodiments mentioned herein, the steam may be produced using separate boiler feed water/steam tubes heated in the convection section of the same furnace (not shown in FIG. 5). Steam 360 and 660 may be added to the cracker feed (or any intermediate cracker feed stream within the furnace) when the cracker feed stream has a vapor fraction of 0.60 to 0.95, or 0.65 to 0.90, or 0.70 to 0.90 by weight, or in one embodiment or in combination with any mentioned embodiments, by volume.

The heated cracker stream, which usually has a temperature of at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case °C and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case °C, or in the range of from 500 to 710 °C, 620 to 740 °C, 560 to 670 °C, or 510 to 650 °C, may then pass from the convection section 610 of the furnace to the radiant section 620 via the cross-over section 630. In an embodiment or in combination with any of the embodiments mentioned herein, the r-pyoil containing feed stream 550 may be added to the cracker stream at the cross-over section 530 as shown in FIG. 8. When introduced into the furnace in the cross-over section, the r-pyoil may be at least partially vaporized or atomized prior to being combined with the cracker stream at the cross-over. The temperature of the cracker stream passing through the cross-over 530 or 630 can be at least 400, 425, 450, 475, or at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case °C and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case °C, or in the range of from 620 to 740 °C, 550 to 680 °C, 510 to 630 °C.

The resulting cracker feed stream then passes through the radiant section, wherein the r-pyoil containing feed stream is thermally cracked to form lighter hydrocarbons, including olefins such as ethylene, propylene, and/or butadiene. The residence time of the cracker feed stream in the radiant section can be at least 0.1, or at least 0.15, or at least 0.2, or at least 0.25, or at least 0.3, or at least 0.35, or at least 0.4, or at least 0.45, in each case seconds and/or not more than 2, or not more than 1.75, or not more than 1.5, or not more than 1.25, or not more than 1, or not more than 0.9, or not more than 0.8, or not more than 0.75, or not more than 0.7, or not more than 0.65, or not more than 0.6, or not more than 0.5, in each case seconds. The temperature at the inlet of the furnace coil is at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case °C and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case °C, or in the range of from 550 to 710 °C, 560 to 680 °C, or 590 to 650 °C, or 580 to 750 °C, 620 to 720 °C, or 650 to 710 °C.

The coil outlet temperature can be at least 640, or at least 650, or at least 660, or at least 670, or at least 680, or at least 690, or at least 700, or at least 720, or at least 730, or at least 740, or at least 750, or at least 760, or at least 770, or at least 780, or at least 790, or at least 800, or at least 810, or at least 820, in each case °C and/or not more than 1000, or not more than 990, or not more than 980, or not more than 970, or not more than 960, or not more than 950, or not more than 940, or not more than 930, or not more than 920, or not more than 910, or not more than 900, or not more than 890, or not more than 880, or not more than 875, or not more than 870, or not more than 860, or not more than 850, or not more than 840, or not more than 830, in each case °C, in the range of from 730 to 900 °C, 750 to 875 °C, or 750 to 850 °C.

The cracking performed in the coils of the furnace may include cracking the cracker feed stream under a set of processing conditions that include a target value for at least one operating parameter. Examples of suitable operating parameters include, but are not limited to maximum cracking temperature, average cracking temperature, average tube outlet temperature, maximum tube outlet temperature, and average residence time. When the cracker stream further includes steam, the operating parameters may include hydrocarbon molar flow rate and total molar flow rate. When two or more cracker streams pass through separate coils in the furnace, one of the coils may be operated under a first set of processing conditions and at least one of the other coils may be operated under a second set or processing conditions. At least one target value for an operating parameter from the first set of processing conditions may differ from a target value for the same parameter in the second set of conditions by at least 0.01, 0.03, 0.05, 0.1, 0.25, 0.5, 1, 2, 5, 7, 10, 15, 20, 25, 30, 35, 40, 45, 50, 55, 60, 65, 70, 75, 80, 85, 90, or 95 percent and/or not more than about 95, 90, 85, 80, 75, 70, 65, 60, 55, 50, 45, 40, 35, 30, 25, 20, or 15 percent. Examples include 0.01 to 30, 0.01 to 20, 0.01 to 15, 0.03 to 15 percent. The percentage is calculated according to the following formula:

[(measured value for operating parameter)−(target value for operating parameter]/[(target value for operating parameter)],expressed as a percentage.

As used herein, the term "different," means higher or lower.

The coil outlet temperature can be at least 640, 650, 660, 670, 680, 690, 700, 720, 730, 740, 750, 760, 770, 780, 790, 800, 810, 820 °C and/or not more than 1000, 990, 980, 970, 960, 950, 940, 930, 920, 910, 900, 890, 880, 875, 870, 860, 850, 840, 830 °C, in the range of from 730 to 900 °C, 760 to 875 °C, or 780 to 850 °C.

In an embodiment or in combination with any of the embodiments mentioned herein, the addition of r-pyoil to a cracker feed stream may result in changes to one or more of the above operating parameters, as compared to the value of the operating parameter when an identical cracker feed stream is processed in the absence of r-pyoil. For example, the values of one or more of the above parameters may be at least 0.01, 0.03, 0.05, 0.1, 0.25, 0.5, 1, 2, 5, 7, 10, 15, 20, 25, 30, 35, 40, 45, 50, 55, 60, 65, 70, 75, 80, 85, 90, or 95 percent different (e.g., higher or lower) than the value for the same parameter when processing an identical feed stream without r-pyoil, ceteris paribus. The percentage is calculated according to the following formula:

[(measured value for operating parameter)−(target value for operating parameter]/[(target value for operating parameter)],expressed as a percentage.

One example of an operating parameter that may be adjusted with the addition of r-pyoil to a cracker stream is coil outlet temperature. For example, in an embodiment or in combination with any embodiment mentioned herein, the cracking furnace may be operated to achieve a first coil outlet temperature (COT1) when a cracker stream having no r-pyoil is present. Next, r-pyoil may be added to the cracker stream, via any of the methods mentioned herein, and the combined stream may be cracked to achieve a second coil outlet temperature (COT2) that is different than COT1.

In some cases, when the r-pyoil is heavier than the cracker stream, COT2 may be less than COT1, while, in other case, when the r-pyoil is lighter than the cracker stream, COT2 may be greater than or equal to COT1. When the r-pyoil is lighter than the cracker stream, it may have a 50% boiling point that is at least 5, 10, 15, 20, 25, 30, 35, 40, 45, or 50 and/or not more than 80, 75, 70, 65, 60, 55, or 50 percent higher than the 50% boiling point of the cracker stream. The percentage is calculated according to the following formula:

[(50% boiling point of r-pyoil in ° R)−(50% boiling point of cracker stream)]/[(50% boiling point of cracker stream)],expressed as a percentage.

Alternatively, or in addition, the 50% boiling point of the r-pyoil may be at least 5, 10, 15, 20, 25, 30, 35, 40, 45, 50, 55, 60, 65, 70, 75, 80, 85, 90, 95, or 100 °C and/or not more than 300, 275, 250, 225, or 200 °C lower than the 50% boiling point of the cracker stream. Heavier cracker streams can include, for example, vacuum gas oil (VGO), atmospheric gas oil (AGO), or even coker gas oil (CGO), or combinations thereof.

When the r-pyoil is lighter than the cracker stream, it may have a 50% boiling point that is at least 5, 10, 15, 20, 25, 30, 35, 40, 45, or 50 and/or not more than 80, 75, 70, 65, 60, 55, or 50 percent lower than the 50% boiling point of the cracker stream. The percentage is calculated according to the following formula:

[(50% boiling point of r-pyoil)−(50% boiling point of cracker stream)]/[(50% boiling point of cracker stream)],expressed as a percentage.

Additionally, or in the alternative, the 50% boiling point of the r-pyoil may be at least 5, 10, 15, 20, 25, 30, 35, 40, 45, 50, 55, 60, 65, 70, 75, 80, 85, 90, 95, or 100 °C and/or not more than 300, 275, 250, 225, or 200 °C higher than the 50% boiling point of the cracker stream. Lighter cracker streams can include, for example, LPG, naphtha, kerosene, natural gasoline, straight run gasoline, and combinations thereof.

In some cases, COT1 can be at least 5, 10, 15, 20, 25, 30, 35, 40, 45, 50 °C and/or not more than about not more than 150, 140, 130, 125, 120, 110, 105, 100, 90, 80, 75, 70, or 65 °C different (higher or lower) than COT2, or COT1 can be at least 0.3, 0.6, 1, 2, 5, 10, 15, 20, or 25 and/or not more than 80, 75, 70, 65, 60, 50, 45, or 40 percent different than COT2 (with the percentage here defined as the difference between COT1 and COT2 divided by COT1, expressed as a percentage). At least one or both of COT1 and COT2 can be at least 730, 750, 77, 800, 825, 840, 850, 860, 870, 880, 890, 900, 910, 920, 930, 940, 950, 960, 970, 980, 990 and/or not more than 1200, 1175, 1150, 1140, 1130, 1120, 1110, 1100, 1090, 1080, 1070, 1060, 1050, 1040, 1030, 1020, 1010, 1000, 990, 980, 970, 960 950, 940, 930, 920, 910, or 900 °C.

In an embodiment or in combination with any of the embodiments mentioned herein, the mass velocity of the cracker feed stream through at least one, or at least two radiant coils (for clarity as determine across the entire coil as opposed to a tube within a coil) is in the range of 60 to 165 kilograms per second (kg/s) per square meter (m2) of cross-sectional area (kg/s/m2), 60 to 130 (kg/s/m2), 60 to 110 (kg/s/m2), 70 to 110 (kg/s/m2), or 80 to 100 (kg/s/m2). When steam is present, the mass velocity is based on the total flow of hydrocarbon and steam.

In one embodiment or in combination with any mentioned embodiments, there is provided a method for making one or more olefins by:

(a) cracking a cracker stream in a cracking unit at a first coil outlet temperature (COT1);
(b) subsequent to step (a), adding a stream comprising a recycle content pyrolysis oil composition (r-pyoil) to said cracker stream to form a combined cracker stream; and
(c) cracking said combined cracker stream in said cracking unit at a second coil outlet temperature (COT2), wherein said second coil outlet temperature is lower, or at least 3 °C lower, or at least 5 °C lower than said first coil outlet temperature.

The reason or cause for the temperature drop in the second coil outlet temperature (COT2) is not limited, provided that COT2 is lower than the first coil outlet temperature (COT1). In one embodiment or in combination with any mentioned embodiments, In one embodiment or in combination with any other mentioned embodiments, the COT2 temperature on the r-pyoil fed coils can be set to a temperature that lower than, or at least 1, 2, 3, 4, or at least 5 °C lower than COT1 ("Set" Mode), or it can be allowed to change or float without setting the temperature on the r-pyoil fed coils ("Free Float" Mode").

The COT2 can be set at least 5 °C lower than COT1 in a Set Mode. All coils in a furnace can be r-pyoil containing feed streams, or at least 1, or at least two of the coils can be r-pyoil containing feed streams. In either case, at least one of the r-pyoil containing coils can be in a Set Mode. By reducing the cracking severity of the combined cracking stream, one can take advantage of the lower heat energy required to crack r-pyoil when it has an average number average molecular weight that is higher than the cracker feed stream, such as a gaseous C2-C4 feed. While the cracking severity on the cracker feed (e.g. C2-C4) can be reduced and thereby increase the amount of unconverted C2-C4 feed in a single pass, the higher amount of unconverted feed (e.g. C2-C4 feed) is desirable to increase the ultimate yield of olefins such as ethylene and/or propylene through multiple passes by recycling the unconverted C2-C4 feed through the furnace. Optionally, other cracker products, such as the aromatic and diene content, can be reduced.

In one embodiment or in combination with any mentioned embodiments, the COT2 in a coil can be fixed in a Set Mode to be lower than, or at least 1, 2, 3, 4, or at least 5 °C lower than the COT1 when the hydrocarbon mass flow rate of the combined cracker stream in at least one coil is the same as or less than the hydrocarbon mass flow rate of the cracker stream in step (a) in said coil. The hydrocarbon mass flow rate includes all hydrocarbons (cracker feed and if present the r-pyoil and/or natural gasoline or any other types of hydrocarbons) and other than steam. Fixing the COT2 is advantageous when the hydrocarbon mass flow rate of the combined cracker stream in step (b) is the same as or less than the hydrocarbon mass flow rate of the cracker stream in step (a) and the pyoil has a higher average molecular weight than the average molecular weight of the cracker stream. At the same hydrocarbon mass flow rates, when pyoil has a heavier average molecular weight than the cracker stream, the COT2 will tend to rise with the addition of pyoil because the higher molecular weight molecules require less thermal energy to crack. If one desires to avoid overcracking the pyoil, the lowered COT2 temperature can assist to reduce by-product formation, and while the olefin yield in the singe pass is also reduced, the ultimate yield of olefins can be satisfactory or increased by recycling unconverted cracker feed through the furnace.

In a Set Mode, the temperature can be fixed or set by adjusting the furnace fuel rate to burners.

In one embodiment or in combination with any other mentioned embodiments, the COT2 is in a Free Float Mode and is as a result of feeding pyoil and allowing the COT2 to rise or fall without fixing a temperature to the pyoil fed coils. In this embodiment, not all of the coils contain r-pyoil. The heat energy supplied to the r-pyoil containing coils can be supplied by keeping constant temperature on, or fuel feed rate to the burners on the non-recycle cracker feed containing coils. Without fixing or setting the COT2, the COT2 can be lower than COT1 when pyoil is fed to the cracker stream to form a combined cracker stream that has a higher hydrocarbon mass flow rate than the hydrocarbon mass flow rate of the cracker stream in step (a). Pyoil added to a cracker feed to increase the hydrocarbon mass flow rate of the combined cracker feed lowers the COT2 and can outweigh the temperature rise effect of using a higher average molecular weight pyoil. These effects can be seen while other cracker conditions are held constant, such as the dilution steam ratio, feed locations, composition of the cracker feed and pyoil, and fuel feed rates to the firebox burners in the furnace on the tubes containing only cracker feed and no feed of r-pyoil.

The COT2 can be lower than, or at least 1, 2, 3, 4, 5, 8, 10, 12, 15, 18, 20, 25, 30, 35, 40, 45, 50 °C and/or not more than about not more than 150, 140, 130, 125, 120, 110, 105, 100, 90, 80, 75, 70, or 65 °C lower than COT1.

Independent of the reason or cause of the temperature drop in COT2, the time period for engaging step (a) is flexible, but ideally, step (a) reaches a steady state before engaging step (b). In one embodiment or in combination with any mentioned embodiments, step (a) is in operation for at least 1 week, or at least 2 weeks, or at least 1 month, or at least 3 months, or at least 6 months, or at least 1 year, or at least 1.5 years, or at least 2 years. The step (a) can be represented by a cracker furnace in operation that has never accepted a feed of pyoil or a combined feed of cracker feed and pyoil. Step (b) can be the first time a furnace has accepted a feed of pyoil or a combined cracker feed containing pyoil. In one embodiment or in combination with any other mentioned embodiments, steps (a) and (b) can be cycled multiple times per year, such as at least 2 x/yr, or at least 3 x/yr, or at least 4 x/yr, or at least 5 x/yr, or at least 6 x/yr, or at least 8 x/yr, or at least 12 x/yr, as measured on a calendar year. Campaigning a feed of pyoil is representative of multiple cycling of steps (a) and (b). When the feed supply of pyoil is exhausted or shut off, the COT1 is allowed to reach a steady state temperature before engaging step (b).

Alternatively, the feed of pyoil to a cracker feed can be continuous over the entire course of at least 1 calendar year, or at least 2 calendar years.

In one embodiment or in combination with any other mentioned embodiments, the cracker feed composition used in steps (a) and (b) remains unchanged, allowing for regular compositional variations observed during the course of a calendar year. In one embodiment or in combination with any other mentioned embodiments, the flow of cracker feed in step (a) is continuous and remains continuous as pyoil is to the cracker feed to make a combined cracker feed. The cracker feed in steps (a) and (b) can be drawn from the same source, such as the same inventory or pipeline.

In one embodiment or in combination with any mentioned embodiments, the COT2 is lower than, or at least 1, 2, 3, 4, or at least 5 °C lower for at least 30% of the time that the pyoil is fed to the cracker stream to form the combined cracker stream, or at least 40% of the time, or at least 50% of the time, or at least 60% of the time, or at least 70% of the time, or at least 80% of the time, or at least 85% of the time, or at least 90% of the time, or at least 95% of the time, the time measured as when all conditions, other than COT's, are held constant, such as cracker and pyoil feed rates, steam ratio, feed locations, composition of the cracker feed and pyoil, etc.

In one embodiment or in combination with any mentioned embodiments, the hydrocarbon mass flow rate of combined cracker feed can be increased. There is now provided a method for making one or more olefins by:

(a) cracking a cracker stream in a cracking unit at a first hydrocarbon mass flow rate (MF1);
(b) subsequent to step (a), adding a stream comprising a recycle content pyrolysis oil composition (r-pyoil) to said cracker stream to form a combined cracker stream having a second hydrocarbon mass flow rate (MF2) that is higher than MF1; and
(c) cracking said combined cracker stream at MF2 in said cracking unit to obtain an olefin-containing effluent that has a combined output of ethylene and propylene that same as or higher than the output of ethylene and propylene obtained by cracking only said cracker stream at MF1.

The output refers to the production of the target compounds in weight per unit time, for example, kg/hr. Increasing the mass flow rate of the cracker stream by addition of r-pyoil can increase the output of combined ethylene and propylene, thereby increasing the throughput of the furnace. Without being bound to a theory, it is believed that this is made possible because the total energy of reaction is not as endothermic with the addition of pyoil relative to total energy of reaction with a lighter cracker feed such as propane or ethane. Since the heat flux on the furnace is limited and the total heat of reaction of pyoil is less endothermic, more of the limited heat energy becomes available to continue cracking the heavy feed per unit time. The MF2 can be increased by at least 1, 2, 3, 4, 5, 7, 10, 10, 13, 15, 18, or 20% through a r-pyoil fed coil, or can be increased by at least 1, 2, 3, 5, 7, 10, 10, 13, 15, 18, or 20% as measured by the furnace output provided that at least one coil processes r-pyoil. Optionally, the increase in combined output of ethylene and propylene can be accomplished without varying the heat flux in the furnace, or without varying the r-pyoil fed coil outlet temperature, or without varying the fuel feed rate to the burners assigned to heat the coils containing only non-recycle content cracker feed, or without varying the fuel feed rate to any of the burners in the furnace. The MF2 higher hydrocarbon mass flow rate in the r-pyoil containing coils can be through one or at least one coil in a furnace, or two or at least two, or 50% or at least 50%, or 75% or at least 75%, or through all of the coils in a furnace.

The olefin-containing effluent stream can have a total output of propylene and ethylene from the combined cracker stream at MF2 that is the same as or higher than the output of propylene and ethylene of an effluent stream obtained by cracking the same cracker feed but without r-pyoil by at least 0.5%, or at least 1%, or at least 2%, or at least 2.5%, determined as:

$$\% \text{ increase} = \frac{Omf2 - Omf1}{Omf1} \times 100$$

where $O_{mf1}$ is the combined output of propylene and ethylene content in the cracker effluent at MF1 made without r-pyoil; and $O_{mf2}$ is the combined output of propylene and ethylene content in the cracker effluent at MF2 made with r-pyoil.

The olefin-containing effluent stream can have a total output of propylene and ethylene from the combined cracker stream at MF2 that is least 1, 5, 10, 15, 20%, and/or up to 80, 70, 65% of the mass flow rate increase between MF2 and MF1 on a percentage basis. Examples of suitable ranges include 1 to 80, or 1 to 70, or 1 to 65, or 5 to 80, or 5 to 70, or 5 to 65, or 10 to 80, or 10 to 70, or 10 to 65, or 15 to 80, or 15 to 70, or 15 to 65, or 20 to 80, or 20 to 70, or 20 to 65, or 25 to 80, or 25 to 70, or 26 to 65, or 35 to 80, or 35 to 70, or 35 to 65, or 40 to 80, or 40 to 70, or 40 to 65, each expressed as a percent %. For example, if the percentage difference between MF2 and MF1 is 5%, and the total output of propylene and ethylene is increased by 2.5%, the olefin increase as a function of mass flow increase is 50% (2.5%/5%×100). This can be determined as:

$$\% \text{ relative increase} = \frac{\Delta O\%}{\Delta MF\%} \times 100$$

where ΔO % is percentage increase between the combined output of propylene and ethylene content in the cracker effluent at MF1 made without r-pyoil and MF2 made with r-pyoil (using the aforementioned equation); and ΔMF % is the percentage increase of MF2 over MF1.

Optionally, the olefin-containing effluent stream can have a total wt. % of propylene and ethylene from the combined cracker stream at MF2 that is the same as or higher than the wt. % of propylene and ethylene of an effluent stream obtained by cracking the same cracker feed but without r-pyoil by at least 0.5%, or at least 1%, or at least 2%, or at least 2.5%, determined as:

$$\% \text{ increase} = \frac{Emf2 - Emf1}{Emf1} \times 100$$

where $E_{mf1}$ is the combined wt. % of propylene and ethylene content in the cracker effluent at MF1 made without r-pyoil; and $E_{mf2}$ is the combined wt. % of propylene and ethylene content in the cracker effluent at MF2 made with r-pyoil.

There is also provided a method for making one or more olefins, said method comprising:

(a) cracking a cracker stream in a cracking furnace to provide a first olefin-containing effluent exiting the cracking furnace at a first coil outlet temperature (COT1);

(b) subsequent to step (a), adding a stream comprising a recycle content pyrolysis oil composition (r-pyoil) to said cracker stream to form a combined cracker stream; and (c) cracking said combined cracker stream in said cracking unit to provide a second olefin-containing effluent exiting the cracking furnace at a second coil outlet temperature (COT2), wherein, when said r-pyoil is heavier than said cracker stream, COT2 is equal to or less than COT1, wherein, when said r-pyoil is lighter than said cracker stream, COT2 is greater than or equal to COT1.

In this method, the embodiments described above for a COT2 lower than COT1 are also applicable here. The COT2 can be in a Set Mode or Free Float Mode. In one embodiment or in combination with any other mentioned embodiments, the COT2 is in a Free Float Mode and the hydrocarbon mass flow rate of the combined cracker stream in step (b) is higher than the hydrocarbon mass flow rate of the cracker stream in step (a). In one embodiment or in combination with any mentioned embodiments, the COT2 is in a Set Mode.

In one embodiment or in combination with any mentioned embodiments, there is provided a method for making one or more olefins by:

(a) cracking a cracker stream in a cracking unit at a first coil outlet temperature (COT1);

(b) subsequent to step (a), adding a stream comprising a recycle content pyrolysis oil composition (r-pyoil) to said cracker stream to form a combined cracker stream; and (c) cracking said combined cracker stream in said cracking unit at a second coil outlet temperature (COT2), wherein said second coil outlet temperature is higher than the first coil outlet temperature.

The COT2 can be at least 5, 8, 10, 12, 15, 18, 20, 25, 30, 35, 40, 45, 50 °C and/or not more than about not more than 150, 140, 130, 125, 120, 110, 105, 100, 90, 80, 75, 70, or 65 °C higher than COT1.

In one embodiment or in combination with any other mentioned embodiments, r-pyoil is added to the inlet of at least one coil, or at least two coils, or at least 50%, or at least 75%, or all of the coils, to form at least one combined cracker stream, or at least two combined cracker streams, or at least the same number of combined crackers streams as coils accepting a feed of r-pyoil. At least one, or at least two of the combined cracker streams, or at least all of the r-pyoil fed coils can have a COT2 that is higher than their respective COT1. In one embodiment or in combination with any mentioned embodiments, at least one, or at least two coils, or at least 50%, or at least 75% of the coils within said cracking furnace contain only non-recycle content cracker feed, with at least one of the coils in the cracking furnace being fed with r-pyoil, and the coil or at least some of multiple coils fed with r-pyoil having a COT2 higher than their respective COT1.

In one embodiment or in combination with any mentioned embodiments, the hydrocarbon mass flow rate of the combined stream in step (b) is substantially the same as or lower than the hydrocarbon mass flow rate of the cracker stream in step (a). By substantially the same is meant not more than a 2% difference, or not more than a 1% difference, or not more than a 0.25% difference. When the hydrocarbon mass flow rate of the combined cracker stream in step (b) is substantially the same as or lower than the hydrocarbon mass flow rate of the cracker stream (a), and the COT2 is allowed to operate in a Free Float Mode (where at least 1 of the tubes contains non-recycle content cracker stream), the COT2 on the r-pyoil containing coil can rise relative to COT1. This is the case even though the pyoil, having a larger number average molecular weight compared to the cracker stream, requires less energy to crack. Without being bound to a theory, it is believed that one or a combination of factors contribute to the temperature rise, including the following:

(i) Lower heat energy is required to crack pyoil in the combined stream.

(ii) The occurrence of exothermic reactions among cracked products of pyoil, such as diels-alder reactions.

This effect can be seen when the other process variables are constant, such as the firebox fuel rate, dilution steam ratio, location of feeds, and composition of the cracker feed.

In one embodiment or in combination with any mentioned embodiments, the COT2 can be set or fixed to a higher temperature than COT1 (the Set Mode). This is more applicable when the hydrocarbon mass flow rate of the combined cracker stream is higher than the hydrocarbon mass flow rate of the cracker stream which would otherwise lower the COT2. The higher second coil outlet temperature (COT2) can contribute to an increased severity and a decreased output of unconverted lighter cracker feed (e.g. C2-C4 feed), which can assist with downstream capacity restricted fractionation columns.

In one embodiment or in combination with any mentioned embodiments, whether the COT2 is higher or lower than COT1, the cracker feed compositions are the same when a comparison is made between COT2 with a COT1. Desirably, the cracker feed composition in step (a) is the same cracker composition as used to make the combined cracker stream in step (b). Optionally, the cracker composition feed in step (a) is continuously fed to the cracker unit, and the addition of pyoil in step (b) is to the continuous cracker feed in step (a). Optionally, the feed of pyoil to the cracker feed is continuous for at least 1 day, or at least 2 days, or at least 3 days, or at least 1 week, or at least 2 weeks, or at least 1 month, or at least 3 months, or at least 6 months or at least 1 year.

The amount of raising or lowering the cracker feed in step (b) in any of the mentioned embodiments can be at least 2%, or at least 5%, or at least 8%, or at least 10%. In one embodiment or in combination with any mentioned embodiments, the amount of lowering the cracker feed in step (b) can be an amount that corresponds to the addition of pyoil by weight. In one embodiment or in combination with any mentioned embodiments, the mass flow of the combined cracker feed is at least 1%, or at least 5%, or at least 8%, or at least 10% higher than the hydrocarbon mass flow rate of the cracker feed in step (a).

In any or all of the mentioned embodiments, the cracker feed or combined cracker feed mass flows and COT relationships and measurements are satisfied if any one coil in the furnace satisfies the stated relationships but can also be present in multiple tubes depending on how the pyoil is fed and distributed.

In an embodiment or in combination with any of the embodiments mentioned herein, the burners in the radiant zone provide an average heat flux into the coil in the range of from 60 to 160 kW/m2 or 70 to 145 kW/m2 or 75 to 130 kW/m2.

The maximum (hottest) coil surface temperature is in the range of 1035 to 1150 °C or 1060 to 1180 °C. The pressure at the inlet of the furnace coil in the radiant section is in the range of 1.5 to 8 bar absolute (bara), or 2.5 to 7 bara, while the outlet pressure of the furnace coil in the radiant section is in the range of from 1.03 to 2.75 bara, or 1.03 to 2.06 bara. The pressure drop across the furnace coil in the radiant section can be from 1.5 to 5 bara, or 1.75 to 3.5 bara, or 1.5 to 3 bara, or 1.5 to 3.5 bara.

In an embodiment or in combination with any of the embodiments mentioned herein, the yield of olefin—ethylene, propylene, butadiene, or combinations thereof—can be at least 15, or at least 20, or at least 25, or at least 30, or at least 35, or at least 40, or at least 45, or at least 50, or at least 55, or at least 60, or at least 65, or at least 70, or at least 75, or at least 80, in each case percent. As used herein, the term "yield" refers to the mass of product/mass of feedstock×100%. The olefin-containing effluent stream comprises at least about 30, or at least 40, or at least 50, or at least 60, or at least 70, or at least 75, or at least 80, or at least 85, or at least 90, or at least 95, or at least 97, or at least 99, in each case weight percent of ethylene, propylene, or ethylene and propylene, based on the total weight of the effluent stream.

In an embodiment or in combination with one or more embodiments mentioned herein, the olefin-containing effluent stream 670 can comprise C2 to C4 olefins, or propylene, or ethylene, or C4 olefins, in an amount of at least 5, 10, 15, 20, 25, 30, 35, 40, 45, 50, 55, 60, 65, 70, 75, 80, 85, or 90 weight percent, based on the weight of the olefin-containing effluent. The stream may comprise predominantly ethylene, predominantly propylene, or predominantly ethylene and propylene, based on the olefins in the olefin-containing effluent, or based on the weight of the C1-C5 hydrocarbons in the olefin-containing effluent, or based on the weight of the olefin-containing effluent stream. The weight ratio of ethylene-to-propylene in the olefin-containing effluent stream can be at least about 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, or 2:1 and/or not more than 3:1, 2.9:1, 2.8:1, 2.7:1, 2.5:1, 2.3:1, 2.2:1, 2.1:1, 2:1, 1.7:1, 1.5:1, or 1.25:1. In an embodiment or in combination with one or more embodiments mentioned herein, the olefin-containing effluent stream can have a ratio of propylene:ethylene that is higher than the propylene:ethylene ratio of an effluent stream obtained by cracking the same cracker feed but without r-pyoil at equivalent dilution steam ratios, feed locations, cracker feed compositions (other than the r-pyoil), and allowing the coils fed with r-pyoil to be in the Float Mode, or if all coils in a furnace are fed with r-pyoil, then at the same temperature prior to feeding r-pyoil. As discussed above, this is possible when the mass flow of the cracker feed remains substantially the same resulting in a higher hydrocarbon mass flow rate of the combined cracker stream when r-pyoil is added relative to the original feed of the cracker stream.

The olefin-containing effluent stream can have a ratio of propylene:ethylene that is at least 1% higher, or at least 2% higher, or at least 3% higher, or at least 4% higher, or at least 5% higher or at least 7% higher or at least 10% higher or at least 12% higher or at least 15% higher or at least 17% higher or at least 20% higher than the propylene:ethylene ratio of an effluent stream obtained by cracking the same cracker feed but without r-pyoil. Alternatively or in addition, the olefin-containing effluent stream can have a ratio of propylene:ethylene that is up to 50% higher, or up to 45% higher, or up to 40% higher, or up to 35% higher, or up to 25% higher, or up to 20% higher than the propylene:ethylene ratio of an effluent stream obtained by cracking the same cracker feed but without r-pyoil, in each case determined as:

$$\%\ \text{increase} = \frac{Er - E}{E} \times 100$$

where E is the propylene:ethylene ratio by wt. % in the cracker effluent made without r-pyoil; and $E_r$ is the propylene:ethylene ratio by wt. % in the cracker effluent made with r-pyoil.

In an embodiment or in combination with any of the embodiments mentioned herein, the amount of ethylene and propylene can remain substantially unchanged or increased in the cracked olefin-containing effluent stream relative to an effluent stream without r-pyoil. It is surprising that a liquid r-pyoil can be fed to a gas fed furnace that accepts and cracks a predominant C2-C4 composition and obtain an olefin-containing effluent stream that can remain substantially unchanged or improved in certain cases relative to a C2-C4 cracker feed without r-pyoil. The heavy molecular weight of r-pyoil could have predominately contributed to the formation of aromatics and participate in the formation of olefins (ethylene and propylene in particular) in only a minor amount. However, we have found that the combined weight percent of ethylene and propylene, and even the output, does not significantly drop, and in many cases stays the same or can increase when r-pyoil is added to a cracker feed to form a combined cracker feed at the same hydrocarbon mass flow rates relative to a cracker feed without r-pyoil. The olefin-containing effluent stream can have a total wt. % of propylene and ethylene that is the same as or higher than the propylene and ethylene content of an effluent stream obtained by cracking the same cracker feed but without r-pyoil by at least 0.5%, or at least 1%, or at least 2%, or at least 2.5%, determined as:

$$\%\text{ increase} = \frac{Er - E}{E} \times 100$$

where E is the combined wt. % of propylene and ethylene content in the cracker effluent made without r-pyoil; and $E_r$ is the combined wt. % of propylene and ethylene content in the cracker effluent made with r-pyoil.

In an embodiment or in combination with one or more embodiments mentioned herein, the wt. % of propylene can improve in an olefin-containing effluent stream when the dilution steam ratio (ratio of steam:hydrocarbons by weight) is above 0.3, or above 0.35, or at least 0.4. The increase in the wt. % of propylene when the dilution steam ratio is at least 0.3, or at least 0.35, or at least 0.4 can be up to 0.25 wt. %, or up to 0.4 wt. %, or up to 0.5 wt. %, or up to 0.7 wt. %, or up to 1 wt. %, or up to 1.5 wt. %, or up to 2 wt. %, where the increase is measured as the simple difference between the wt. % of propylene between an olefin-containing effluent stream made with r-pyoil at a dilution steam ratio of 0.2 and an olefin-containing effluent stream made with r-pyoil at a dilution steam ratio of at least 0.3, all other conditions being the same.

When the dilution steam ratio is increased as noted above, the ratio of propylene:ethylene can also increase, or can be at least 1% higher, or at least 2% higher, or at least 3% higher, or at least 4% higher, or at least 5% higher or at least 7% higher or at least 10% higher or at least 12% higher or at least 15% higher or at least 17% higher or at least 20% higher than the propylene:ethylene ratio of an olefin-containing effluent stream made with r-pyoil at a dilution steam ratio of 0.2.

In an embodiment or in combination with one or more embodiments mentioned herein, when the dilution steam ratio is increased, the olefin-containing effluent stream can have a reduced wt. % of methane, when measured relative to an olefin-containing effluent stream at a dilution steam ratio of 0.2. The wt. % of methane in the olefin-containing effluent stream can be reduced by at least 0.25 wt. %, or by at least 0.5 wt. %, or by at least 0.75 wt. %, or by at least 1 wt. %, or by at least 1.25 wt. %, or by at least 1.5 wt. %, measured as the absolute value difference in wt. % between the olefin-containing effluent stream at a dilution steam ratio of 0.2 and at the higher dilution steam ratio value.

In an embodiment or in combination with one or more embodiments mentioned herein, the amount of unconverted products in the olefin-containing effluent is decreased, when measured relative to a cracker feed that does not contain r-pyoil and all other conditions being the same, including hydrocarbon mass flow rate. For example, the amount of propane and/or ethane can be decreased by addition of r-pyoil. This can be advantageous to decrease the mass flow of the recycle loop to thereby (a) decrease cryogenic energy costs and/or (b) potentially increase capacity on the plant if the plant is already capacity constrained. Further it can debottleneck the propylene fractionator if it is already to its capacity limit. The amount of unconverted products in the olefin containing effluent can decrease by at least 2%, or at least 5%, or at least 8%, or at least 10%, or at least 13%, or at least 15%, or at least 18%, or at least 20%.

In an embodiment or in combination with one or more embodiments mentioned herein, the amount of unconverted products (e.g. combined propane and ethane amount) in the olefin-containing effluent is decreased while the combined output of ethylene and propylene does not drop and is even improved, when measured relative to a cracker feed that does not contain r-pyoil. Optionally, all other conditions are the same including the hydrocarbon mass flow rate and with respect to temperature, where the fuel feed rate to heat the burners to the non-recycle content cracker fed coils remains unchanged, or optionally when the fuel feed rate to all coils in the furnace remains unchanged. Alternatively, the same relationship can hold true on a wt. % basis rather than an output basis.

For example, the combined amount (either or both of output or wt. %) of propane and ethane in the olefin containing effluent can decrease by at least 2%, or at least 5%, or at least 8%, or at least 10%, or at least 13,%, or at least 15%, or at least 18%, or at least 20%, and in each case up to 40% or up to 35% or up to 30%, in each case without a decrease in the combined amount of ethylene and propylene, and even can accompany an increase in the combined amount of ethylene and propylene. In another example, the amount of propane in the olefin containing effluent can decrease by at least 2%, or at least 5%, or at least 8%, or at least 10%, or at least 13,%, or at least 15%, or at least 18%, or at least 20%, and in each case up to 40% or up to 35% or up to 30%, in each case without a decrease in the combined amount of ethylene and propylene, and even can accompany an increase in the combined amount of ethylene and propylene. In any one of these embodiments, the cracker feed (other than r-pyoil and as fed to the inlet of the convection zone) can be predominately propane by moles, or at least 90 mole % propane, or at least 95 mole % propane, or at least 96 mole % propane, or at least 98 mole % propane; or the fresh supply of cracker feed can be at least HD5 quality propane.

In an embodiment or in combination with one or more embodiments mentioned herein, the ratio of propane:(ethylene and propylene) in the olefin-containing effluent can decrease with the addition of r-pyoil to the cracker feed when measured relative to the same cracker feed without pyoil and all other conditions being the same, measured either as wt. % or output. The ratio of propane:(ethylene and propylene combined) in the olefin-containing effluent can be not more than 0.50:1, or less than 0.50:1, or not more than 0.48:1, or not more than 0.46:1, or no more than 0.43:1, or no more than 0.40:1, or no more than 0.38:1, or no more than 0.35:1, or no more than 0.33:1, or no more than 0.30:1. The low ratios indicate that a high amount of ethylene+ propylene can be achieved or maintained with a corresponding drop in unconverted products such as propane.

In an embodiment or in combination with one or more embodiments mentioned herein, the amount of C6+ products in the olefin-containing effluent can be increased, if such products are desired such as for a BTX stream to make derivates thereof, when r-pyoil and steam are fed downstream of the inlet to the convection box, or when one or both of r-pyoil and steam are fed at the cross-over location. The amount of C6+ products in the olefin-containing effluent can be increased by 5%, or by 10%, or by 15%, or by 20%, or by 30% when r-pyoil and steam are fed downstream of the inlet to the convection box, when measured against feeding r-pyoil at the inlet to the convection box, all other conditions being the same. The % increase can be calculated as:

$$\%\ \text{increase} = \frac{Ei - Ed}{Ei} \times 100$$

where $E_i$ is the $C_{6+}$ content in the olefin-containing cracker effluent made by introducing r-pyoil at the inlet of the convection box; and $E_d$ is the $C_{6+}$ content in the olefin-containing cracker effluent made by introducing r-pyoil and steam downstream of the inlet of the convection box.

In an embodiment or in combination with any of the embodiments mentioned herein, the cracked olefin-containing effluent stream may include relatively minor amounts of aromatics and other heavy components. For example, the olefin-containing effluent stream may include at least 0.5, 1, 2, or 2.5 weight percent and/or not more than about 20, 19, 18, 17, 16, 15, 14, 13, 12, 11, 10, 9, 8, 7, 6, 5, 4, 3, 2, or 1 weight percent of aromatics, based on the total weight of the stream. We have found that the level of C6+ species in the olefin-containing effluent can be not more than 5 wt. %, or not more than 4 wt. %, or not more than 3.5 wt. %, or not more than 3 wt. %, or not more than 2.8 wt. %, or not more than 2.5 wt. %. The C6+ species includes all aromatics, as well as all paraffins and cyclic compounds having a carbon number of 6 or more. As used throughout, the mention of amounts of aromatics can be represented by amounts of C6+ species since the amount of aromatics would not exceed the amount of C6+ species.

The olefin-containing effluent may have an olefin-to-aromatic ratio, by weight %, of at least 2:1, 3.1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, or 30:1 and/or not more than 100:1, 90:1, 85:1, 80:1, 75:1, 70:1, 65:1, 60:1, 55:1, 50:1, 45:1, 40:1, 35:1, 30:1, 25:1, 20:1, 15:1, 10:1, or 5:1. As used herein, "olefin-to-aromatic ratio" is the ratio of total weight of C2 and C3 olefins to the total weight of aromatics, as defined previously. In an embodiment or in combination with any of the embodiments mentioned herein, the effluent stream can have an olefin-to-aromatic ratio of at least 2.5:1, 2.75:1, 3.5:1, 4.5:1, 5.5:1, 6.5:1, 7.5:1, 8.5:1, 9.5:1, 10.5:1, 11.5:1, 12.5:1, or 13:5:1.

The olefin-containing effluent may have an olefin:C6+ ratio, by weight %, of at least 8.5:1, or at least 9.5:1, or at least 10:1, or at least 10.5:1, or at least 12:1, or at least 13:1, or at least 15:1, or at least 17:1, or at least 19:1, or at least 20:1, or at least 25:1, or least 28:1, or at least 30:1. In addition or in the alternative, the olefin-containing effluent may have an olefin:C6+ ratio of up to 40:1, or up to 35:1, or up to 30:1, or up to 25:1, or up to 23:1. As used herein, "olefin-to-aromatic ratio" is the ratio of total weight of C2 and C3 olefins to the total weight of aromatics, as defined previously.

Additionally, or in the alternative, the olefin-containing effluent stream can have an olefin-to-C6+ ratio of at least about 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, 5:1, 5.25:1, 5.5:1, 5.75:1, 6:1, 6.25:1, 6.5:1, 6.75:1, 7:1, 7.25:1, 7.5:1, 7.75:1, 8:1, 8.25:1, 8.5:1, 8.75:1, 9:1, 9.5:1, 10:1, 10.5:1, 12:1, 13:1, 15:1, 17:1, 19:1, 20:1, 25:1, 28:1, or 30:1.

In an embodiment or in combination with any of the embodiments mentioned herein, the olefin:aromatic ratio decreases with an increase in the amount of r-pyoil added to the cracker feed. Since r-pyoil cracks at a lower temperature, it will crack earlier than propane or ethane, and therefore has more time to react to make other products such as aromatics. Although the aromatic content in the olefin-containing effluent increases with an increasing amount of pyoil, the amount of aromatics produced is remarkably low as noted above.

The olefin-containing composition may also include trace amounts of aromatics. For example, the composition may have a benzene content of at least 0.25, 0.3, 0.4, 0.5 weight percent and/or not more than about 2, 1.7, 1.6, 1.5 weight percent. Additionally, or in the alternative, the composition may have a toluene content of at least 0.005, 0.010, 0.015, or 0.020 and/or not more than 0.5, 0.4, 0.3, or 0.2 weight percent. Both percentages are based on the total weight of the composition. Alternatively, or in addition, the effluent can have a benzene content of at least 0.2, 0.3, 0.4, 0.5, or 0.55 and/or not more than about 2, 1.9, 1.8, 1.7, or 1.6 weight percent and/or a toluene content of at least 0.01, 0.05, or 0.10 and/or not more than 0.5, 0.4, 0.3, or 0.2 weight percent.

In an embodiment or in combination with any of the embodiments mentioned herein, the olefin-containing effluent withdrawn from a cracking furnace which has cracked a composition comprising r-pyoil may include an elevated amount of one or more compounds or by-products not found in olefin-containing effluent streams formed by processing conventional cracker feed. For example, the cracker effluent formed by cracking r-pyoil (r-olefin) may include elevated amounts of 1,3-butadiene, 1,3-cyclopentadiene, dicyclopentadiene, or a combination of these components. In an embodiment or in combination with any of the embodiments mentioned herein, the total amount (by weight) of these components may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of 1,3-butadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of 1,3-cyclopentadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of dicyclopentadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The percent difference is calculated by dividing the difference in weight percent of one or more of the above components in the r-pyoil and conventional streams by the amount (in weight percent) of the component in the conventional stream, or:

$$\% \text{ increase} = \frac{Er - E}{E} \times 100$$

where E is the wt. % of the component in the cracker effluent made without r-pyoil; and $E_r$ is the wt. % of the component in the cracker effluent made with r-pyoil.

In an embodiment or in combination with any of the embodiments mentioned herein, the olefin-containing effluent stream may comprise acetylene. The amount of acetylene can be at least 2000 ppm, at least 5000 ppm, at least 8000 ppm, or at least 10,000 ppm based on the total weight of the effluent stream from the furnace. It may also be not more than 50,000 ppm, not more than 40,000 ppm, not more than 30,000 ppm, or not more than 25,000 ppm, or not more than 10,000 ppm, or not more than 6,000 ppm, or not more than 5000 ppm.

In an embodiment or in combination with any of the embodiments mentioned herein, the olefin-containing effluent stream may comprise methyl acetylene and propadiene (MAPD). The amount of MAPD may be at least 2 ppm, at least 5 ppm, at least 10 ppm, at least 20 pm, at least 50 ppm, at least 100 ppm, at least 500 ppm, at least 1000 ppm, at least 5000 ppm, or at least 10,000 ppm, based on the total weight of the effluent stream. It may also be not more than 50,000 ppm, not more than 40,000 ppm, or not more than 30,000 ppm, or not more than 10,000 ppm, or not more than 6,000 ppm, or not more than 5,000 ppm.

In an embodiment or in combination with any of the embodiments mentioned herein, the olefin-containing effluent stream may comprise low or no amounts of carbon dioxide. The olefin-containing effluent stream can have an amount, in wt. %, of carbon dioxide that is not more than the amount of carbon dioxide in an effluent stream obtained by cracking the same cracker feed but without r-pyoil at equivalent conditions, or an amount this is not higher than 5%, or not higher than 2% of the amount of carbon dioxide, in wt. %, or the same amount as a comparative effluent stream without r-pyoil. Alternatively or in addition, the olefin-containing effluent stream can have an amount of carbon dioxide that is not more than 1000 ppm, or not more than 500 ppm, or not more than 100 ppm, or not more than 80 ppm, or not more than 50 ppm, or not more than 25 ppm, or not more than 10 ppm, or not more than 5 ppm.

Figure 9:
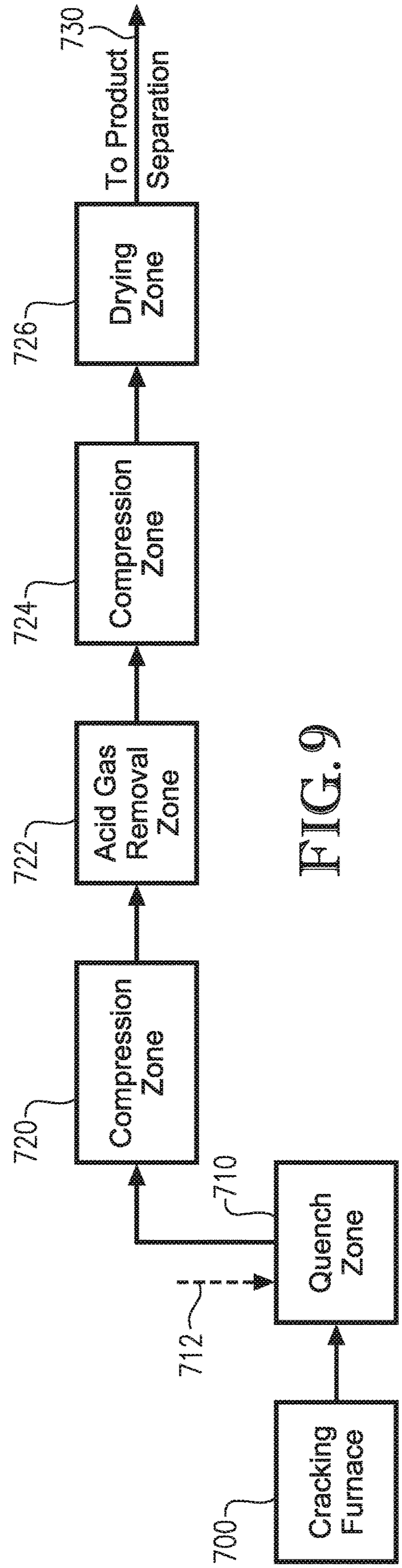
FIG. 9 is a block diagram illustrating the treatment of a recycle content furnace effluent.

Turning now to FIG. 9, a block diagram illustrating the main elements of the furnace effluent treatment section are shown.

As shown in FIG. 9, the olefin-containing effluent stream from the cracking furnace 700, which includes recycle content) is cooled rapidly (e.g., quenched) in a transfer line exchange ("TLE") 680 as shown in FIG. 8 in order to prevent production of large amounts of undesirable by-products and to minimize fouling in downstream equipment, and also to generate steam. In an embodiment or in combination with any of the embodiments mentioned herein, the temperature of the r-composition-containing effluent from the furnace can be reduced by 35 to 485 °C, 35 to 375 °C, or 90 to 550 °C to a temperature of 500 to 760 °C. The cooling step is performed immediately after the effluent stream leaves the furnace such as, for example, within 1 to 30, 5 to 20, or 5 to 15 milliseconds. In an embodiment or in combination with any of the embodiments mentioned herein, the quenching step is performed in a quench zone 710 via indirect heat exchange with high-pressure water or steam in a heat exchanger (sometimes called a transfer line exchanger as shown in FIG. 5 as TLE 340 and FIG. 8 as TLE 680), while, in other embodiments, the quench step is carried out by directly contacting the effluent with a quench liquid 712 (as generally shown in FIG. 9). The temperature of the quench liquid can be at least 65, or at least 80, or at least 90, or at least 100, in each case °C and/or not more than 210, or not more than 180, or not more than 165, or not more than 150, or not more than 135, in each case °C. When a quench liquid is used, the contacting may occur in a quench tower and a liquid stream may be removed from the quench tower comprising gasoline and other similar boiling-range hydrocarbon components. In some cases, quench liquid may be used when the cracker feed is predominantly liquid, and a heat exchanger may be used when the cracker feed is predominantly vapor.

The resulting cooled effluent stream is then vapor liquid separated and the vapor is compressed in a compression zone 720, such as in a gas compressor having, for example, between 1 and 5 compression stages with optional inter-stage cooling and liquid removal. The pressure of the gas stream at the outlet of the first set of compression stages is in the range of from 7 to 20 bar gauge (barg), 8.5 to 18 psig (0.6-1.3 barg), or 9.5 to 14 barg.

The resulting compressed stream is then treated in an acid gas removal zone 722 for removal of acid gases, including CO, CO2, and H2S by contact with an acid gas removal agent. Examples of acid gas removal agents can include, but are not limited to, caustic and various types of amines. In an embodiment or in combination with any of the embodiments mentioned herein, a single contactor may be used, while, in other embodiments, a dual column absorber-stripper configuration may be employed.

The treated compressed olefin-containing stream may then be further compressed in another compression zone 724 via a compressor, optionally with inter-stage cooling and liquid separation. The resulting compressed stream, which has a pressure in the range of 20 to 50 barg, 25 to 45 barg, or 30 to 40 barg. Any suitable moisture removal method can be used including, for example, molecular sieves or other similar process to dry the gas in a drying zone 726. The resulting stream 730 may then be passed to the fractionation section, wherein the olefins and other components may be separated in to various high-purity product or intermediate streams.

Figure 10:
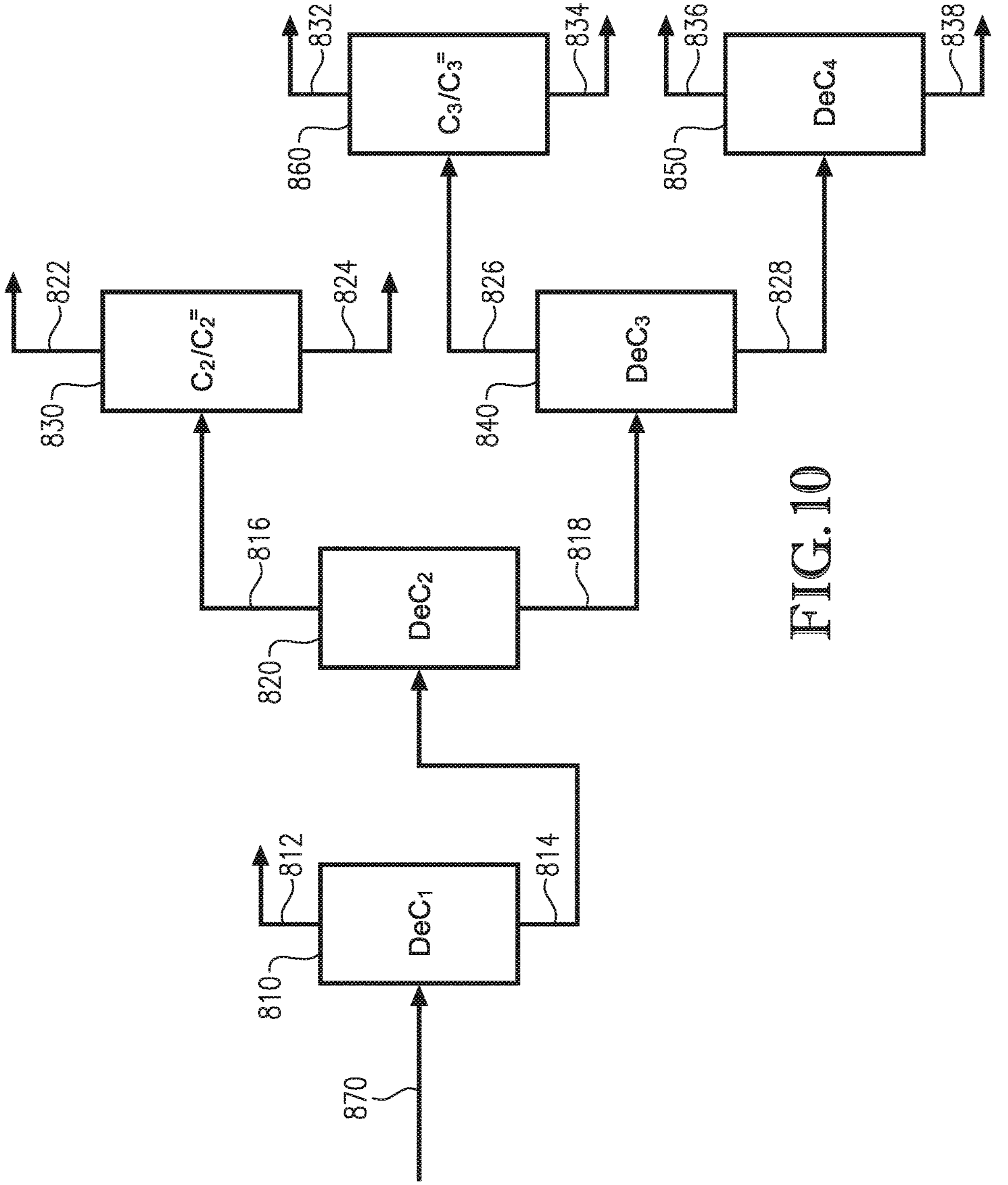
FIG. 10 illustrates a fractionation scheme in a Separation section, including a demethanizer, dethanizer, depropanizer, and the fractionation columns to separate and isolate the main r-compositions, including r-propylene, r-ethylene, r-butylene, and others.

Turning now to FIG. 10, a schematic depiction of the main steps of the fractionation section is provided. In an embodiment or in combination with any of the embodiments mentioned herein, the initial column of the fractionation train may not be a demethanizer 810, but may be a deethanizer 820, a depropanizer 840, or any other type of column. As used herein, the term "demethanizer," refers to a column whose light key is methane. Similarly, "deethanizer," and "depropanizer," refer to columns with ethane and propane as the light key component, respectively.

As shown in FIG. 10, a feed stream 870 from the quench section may introduced into a demethanizer (or other) column 810, wherein the methane and lighter (CO, CO2, H2) components 812 are separated from the ethane and heavier components 814. The demethanizer is operated at a temperature of at least −145, or at least −142, or at least −140, or at least −135, in each case °C and/or not more than −120, −125, −130, −135 °C. The bottoms stream 814 from the demethanizer column, which includes at least 50, or at least 55, or at least 60, or at least 65, or at least 70, or at least 75, or at least 80, or at least 85, or at least 90, or at least 95 or at least 99, in each case percent of the total amount of ethane and heavier components introduced into the column, is then introduced into a deethanizer column 820, wherein the C2 and lighter components 816 are separated from the C3 and heavier components 818 by fractional distillation. The deethanizer 820 can be operated with an overhead temperature of at least −35, or at least −30, or at least −25, or at least −20, in each case °C and/or not more than −5, −10, −10, −20 °C, and an overhead pressure of at least 3, or at least 5, or at least 7, or at least 8, or at least 10, in each case barg and/or not more than 20, or not more than 18, or not more than 17, or not more than 15, or not more than 14, or not more than 13, in each case barg. The deethanizer column 820 recovers at least 60, or at least 65, or at least 70, or at least 75, or at least 80, or at least 85, or at least 90, or at least 95, or at least 97, or at least 99, in each case percent of the total amount of C2 and lighter components introduced into the column in the overhead stream. In an embodiment or in combination with any of the embodiments mentioned herein, the overhead stream 816 removed from the deethanizer column comprises at least 50, or at least 55, or at least 60, or at least 65, or at least 70, or at least 75, or at least 80, or at least 85, or at least 90, or at least 95, in each case weight percent of ethane and ethylene, based on the total weight of the overhead stream.

As shown in FIG. 10, the C2 and lighter overhead stream 816 from the deethanizer 820 is further separated in an ethane-ethylene fractionator column (ethylene fractionator) 830. In the ethane-ethylene fractionator column 830, an ethylene and lighter component stream 822 can be withdrawn from the overhead of the column 830 or as a side stream from the top ½ of the column, while the ethane and any residual heavier components are removed in the bottoms stream 824. The ethylene fractionator 830 may be operated at an overhead temperature of at least −45, or at least −40, or at least −35, or at least −30, or at least −25, or at least −20, in each case °C and/or not more than −15, or not more than −20, or not more than −25, in each case °C, and an overhead pressure of at least 10, or at least 12, or at least 15, in each case barg and/or not more than 25, 22, 20 barg. The overhead stream 822, which is enriched in ethylene, can include at least 70, or at least 75, or at least 80, or at least 85, or at least 90, or at least 95, or at least 97, or at least 98, or at least 99, in each case weight percent ethylene, based on the total weight of the stream and may be sent to downstream processing unit for further processing, storage, or sale. The overhead ethylene stream 822 produced during the cracking of a cracker feedstock containing r-pyoil is a r-ethylene composition or stream. In an embodiment or in combination with any of the embodiments mentioned herein, the r-ethylene stream may be used to make one or more petrochemicals.

The bottoms stream from the ethane-ethylene fractionator 824 may include at least 40, or at least 45, or at least 50, or at least 55, or at least 60, or at least 65, or at least 70, or at least 75, or at least 80, or at least 85, or at least 90, or at least 95, or at least 98, in each case weight percent ethane, based on the total weight of the bottoms stream. All or a portion of the recovered ethane may be recycled to the cracker furnace as additional feedstock, alone or in combination with the r-pyoil containing feed stream, as discussed previously.

The liquid bottoms stream 818 withdrawn from the deethanizer column, which may be enriched in C3 and heavier components, may be separated in a depropanizer 840, as shown in FIG. 10. In the depropanizer 840, C3 and lighter components are removed as an overhead vapor stream 826, while C4 and heavier components may exit the column in the liquid bottoms 828. The depropanizer 840 can be operated with an overhead temperature of at least 20, or at least 35, or at least 40, in each case °C and/or not more than 70, 65, 60, 55 °C, and an overhead pressure of at least 10, or at least 12, or at least 15, in each case barg and/or not more than 20, or not more than 17, or not more than 15, in each case barg. The depropanizer column 840 recovers at least 60, or at least 65, or at least 70, or at least 75, or at least 80, or at least 85, or at least 90, or at least 95, or at least 97, or at least 99, in each case percent of the total amount of C3 and lighter components introduced into the column in the overhead stream 826. In an embodiment or in combination with any of the embodiments mentioned herein, the overhead stream 826 removed from the depropanizer column 840 comprises at least or at least 50, or at least 55, or at least 60, or at least 65, or at least 70, or at least 75, or at least 80, or at least 85, or at least 90, or at least 95, or at least 98, in each case weight percent of propane and propylene, based on the total weight of the overhead stream 826.

The overhead stream 826 from the depropanizer 840 are introduced into a propane-propylene fractionator (propylene fractionator) 860, wherein the propylene and any lighter components are removed in the overhead stream 832, while the propane and any heavier components exit the column in the bottoms stream 834. The propylene fractionator 860 may be operated at an overhead temperature of at least 20, or at least 25, or at least 30, or at least 35, in each case °C and/or not more than 55, 50, 45, 40 °C, and an overhead pressure of at least 12, or at least 15, or at least 17, or at least 20, in each case barg and/or not more than 20, or not more than 17, or not more than 15, or not more than 12, in each case barg. The overhead stream 860, which is enriched in propylene, can include at least 70, or at least 75, or at least 80, or at least 85, or at least 90, or at least 95, or at least 97, or at least 98, or at least 99, in each case weight percent propylene, based on the total weight of the stream and may be sent to downstream processing unit for further processing, storage, or sale. The overhead propylene stream produced during the cracking of a cracker feedstock containing r-pyoil is a r-propylene composition or stream. In an embodiment or in combination with any of the embodiments mentioned herein, the stream may be used to make one or more petrochemicals.

The bottoms stream 834 from the propane-propylene fractionator 860 may include at least 40, or at least 45, or at least 50, or at least 55, or at least 60, or at least 65, or at least 70, or at least 75, or at least 80, or at least 85, or at least 90, or at least 95, or at least 98, in each case weight percent propane, based on the total weight of the bottoms stream 834. All or a portion of the recovered propane may be recycled to the cracker furnace as additional feedstock, alone or in combination with r-pyoil, as discussed previously.

Referring again to FIG. 10, the bottoms stream 828 from the depropanizer column 840 may be sent to a debutanizer column 850 for separating C4 components, including butenes, butanes and butadienes, from C5+ components. The debutanizer can be operated with an overhead temperature of at least 20, or at least 25, or at least 30, or at least 35, or at least 40, in each case °C and/or not more than 60, or not more than 65, or not more than 60, or not more than 55, or not more than 50, in each case °C and an overhead pressure of at least 2, or at least 3, or at least 4, or at least 5, in each case barg and/or not more than 8, or not more than 6, or not more than 4, or not more than 2, in each case barg. The debutanizer column recovers at least 60, or at least 65, or at least 70, or at least 75, or at least 80, or at least 85, or at least 90, or at least 95, or at least 97, or at least 99, in each case percent of the total amount of C4 and lighter components introduced into the column in the overhead stream 836. In an embodiment or in combination with any of the embodiments mentioned herein, the overhead stream 836 removed from the debutanizer column comprises at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent of butadiene, based on the total weight of the overhead stream. The overhead stream 836 produced during the cracking of a cracker feedstock containing r-pyoil is a r-butadiene composition or stream. The bottoms stream 838 from the debutanizer includes mainly C5 and heavier components, in an amount of at least 50, or at least 60, or at least 70, or at least 80, or at least 90, or at least 95 weight percent, based on the total weight of the stream. The debutanizer bottoms stream 838 may be sent for further separation, processing, storage, sale or use.

The overhead stream 836 from the debutanizer, or the C4s, can be subjected to any conventional separation methods such as extraction or distillation processes to recover a more concentrated stream of butadiene.

The Glycol Ether and Glycol Ether Ester Processes

In one embodiment or in combination with any of the mentioned embodiments, there is now provided a method for processing pr-AO by feeding the pr-AO to a reactor in which is made glycol ethers or a GE composition. In another embodiment, there is provided a method for making a r-GE or pr-GE by reacting pr-AO with an alcohol composition to produce a GE effluent, optionally containing a pr-GE composition. There is also provided a r-GE or pr-GE, having a monomer derived from a pr-AO composition. Further, there is provided a pr-GE, and other compounds or polymers or articles made thereby.

In one embodiment or in combination with any of the mentioned embodiments, there is now provided a method for processing pr-GE by feeding the pr-GE to a reactor in which is made glycol ether esters or a GEE composition. In another embodiment, there is provided a method for making a r-GEE or pr-GEE by reacting pr-GE with an acid composition to produce a GEE effluent, optionally containing a pr-GEE composition. There is also provided a r-GEE or pr-GEE, having a monomer derived from a pr-GE composition. Further, there is provided a pr-GEE, and other compounds or polymers or articles made thereby.

GE compositions can be prepared by reacting, in the presence of a catalyst, pr-AO, with an alcohol. Optionally, at least a portion of the pr-AO is derived directly or indirectly from the cracking of r-pyoil to thereby obtain an r-AO composition.

In one embodiment or in combination with any of the mentioned embodiments, the concentration of pr-AO introduced into a reactor vessel is at least 90 wt. %, or at least 95 wt. %, or at least 97 wt. %, or at least 99 wt. %, based on the weight of the alkylene oxide composition fed to the reactor.

GEE compositions can be prepared by reacting pr-GE with an acid. Optionally, at least a portion of the pr-GE is derived directly or indirectly from the cracking of r-pyoil to thereby obtain an r-GE composition.

In one embodiment or in combination with any of the mentioned embodiments, the concentration of pr-GE introduced into a reactor vessel is at least 90 wt. %, or at least 95 wt. %, or at least 97 wt. %, or at least 99 wt. %, based on the weight of the glycol ether composition fed to the reactor.

In one embodiment or in combination with any of the mentioned embodiments, the AO and/or GE fed to the reaction vessel does not contain recycle content. In another embodiment, at least a portion of the AO composition and/or the GE composition fed to the reaction vessel is derived directly or indirectly from the cracking of r-pyoil or obtained from r-pygas. For example, at least 0.005 wt. %, or at least 0.01 wt. %, or at least 0.05 wt. %, or at least 0.1 wt. %, or at least 0.15 wt. %, or at least 0.2 wt. %, or at least 0.25 wt. %, or at least 0.3 wt. %, or at least 0.35 wt. %, or at least 0.4 wt. %, or at least 0.45 wt. %, or at least 0.5 wt. %, or at least 0.6 wt. %, or at least 0.7 wt. %, or at least 0.8 wt. %, or at least 0.9 wt. %, or at least 1 wt. %, or at least 2 wt. %, or at least 3 wt. %, or at least 4 wt. %, or at least 5 wt. %, or at least 6 wt. %, or at least 7 wt. %, or at least 8 wt. %, or at least 9 wt. %, or at least 10 wt. %, or at least 11 wt. %, or at least 13 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 70 wt. %, or at least 80 wt. %, or at least 90 wt. %, or at least 95 wt. %, or at least 98 wt. %, or at least 99 wt. %, or 100 wt. % of: (i) the alkylene oxide composition is r-AO or pr-AO and/or (ii) the glycol ether composition is r-GE or pr-GE. In addition, or in the alternative, up to 100 wt. %, or up to 98 wt. %, or up to 95 wt. %, or up to 90 wt. %, or up to 80 wt. %, or up to 75 wt. %, or up to 70 wt. %, or up to 60 wt. %, or up to 50 wt. %, or up to 40 wt. %, or up to 30 wt. %, or up to 20 wt. %, or up to 10 wt. %, or up to 8 wt. %, or up to 5 wt. %, or up to 4 wt. %, or up to 3 wt. %, or up to 2 wt. %, or up to 1 wt. %, or up to 0.8 wt. %, or up to 0.7 wt. %, or up to 0.6 wt. %, or up to 0.5 wt. %, or up to 0.4 wt. %, or up to 0.3 wt. %, or up to 0.2 wt. %, or up to 0.1 wt. %, or up to 0.09 wt. %, or up to 0.07 wt. %, or up to 0.05 wt. %, or up to 0.03 wt. %, or up to 0.02 wt. %, or up to 0.01 wt. % of: (i) the alkylene oxide composition is pr-AO and/or (ii) the glycol ether composition is pr-GE. In each case, the stated amounts are also applicable to not only alkylene oxide and glycol ether as fed into the reactor, but alternatively or in addition, to the pr-AO stock and/or pr-GE supplied to a manufacturer of GE or GEE, or can be used as a basis for associating or calculating the amount of recycle content in pr-AO and pr-GE, such as when blending a source of pr-AO with non-recycle content AO to make an alkylene oxide composition having pr-AO in quantities mentioned above.

In one embodiment or in combination with any of the mentioned embodiments, the GE composition and/or the GEE composition has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %, based on the weight of the compositions. The recycle content associated with the GE and GEE can be established by applying a recycle content value to the GE and GEE, such as through deducting the recycle content value from a recycle inventory populated with allotments (credit or allocation) or by reacting a r-AO or r-GE feedstock to make r-GE and r-GEE, respectively. The allotment can be contained in a recycle inventory created, maintained or operated by or for the GE and/or GEE manufacturer. The allotments are obtained from any source along any manufacturing chain of products. In one embodiment, the origin of the allotment is derived indirectly from pyrolyzing recycled waste, or from cracking r-pyoil or from r-pygas.

The amount of recycle content in an r-AO or r-GE raw material fed to a GE or GEE reactor, or the amount of recycle content applied to the r-GE or r-GEE, or the amount of r-AO or r-GE needed to feed the reactor to claim a desired amount of recycle content in the GE or GEE in the event that all the recycle content from the r-AO or r-GE is applied to the GE or GEE, respectively, can be determined or calculated by any of the following methods:

(i) the amount of an allotment associated with the r-AO or r-GE used to feed the reactor applied determined by the amount certified or declared by the supplier of the alkylene oxide composition or glycol ether composition transferred to the manufacturer of the GE or GEE, respectively, or (ii) the amount of allocation declared by the GE or GEE manufacturer as fed to the GE or GEE reactor, or (iii) using a mass balance approach to back-calculate the minimum amount of recycle content in the feedstock from an amount of recycle content declared, advertised, or accounted for by the manufacturer, whether or not accurate, as applied to the GE or GEE product, or (iv) blending of non-recycle content with recycle content feedstock AO or associating recycle content to a portion of the feedstock, using pro-rata mass approach Satisfying any one of the methods (i)-(iv) is sufficient to establish the portion of r-AO or r-GE that is derived directly or indirectly from recycled waste, the pyrolysis of recycled waste, pyrolysis gas produced from the pyrolysis of recycled waste, and/or the cracking of r-pyoil produced from the pyrolysis of recycled waste. In the event that a r-AO or r-GE feed is blended with a recycle feed from other recycle sources, a pro-rata approach to the mass of r-AO or r-GE directly or indirectly obtained from recycled waste, the pyrolysis of recycled waste, pyrolysis gas produced from the pyrolysis of recycled waste, and/or the cracking of r-pyoil produced from the pyrolysis of recycled waste to the mass of recycle alkylene oxides or glycol ethers from other sources is adopted to determine the percentage in the declaration attributable to r-AO or r-GE obtained directly or indirectly from recycled waste, the pyrolysis of recycled waste, pyrolysis gas produced from the pyrolysis of recycled waste, and/or the cracking of r-pyoil produced from the pyrolysis of recycled waste.

Methods (i)-(ii) need no calculation since they are determined based on what the AO, GE, or GEE manufacturers or suppliers declare, claim, or otherwise communicate to each other or the public. Method (iii) and (iv) are calculated.

In one embodiment or in combination with any of the mentioned embodiments, the minimum amount of recycle content ethylene oxide (EO) or propylene oxide (PO) fed to the reactor can be determined by knowing the amount of recycle content associated with the end product GE and assuming that the entire recycle content in the GE is attributable to the r-AO fed to the reactor and none to the alcohol fed to the reactor. Likewise, the minimum amount of recycle content GE fed to the GEE reactor can be determined by knowing the amount of recycle content associated with the end product GEE and assuming that the entire recycle content in the GEE is attributable to the r-GE fed to the reactor and none to the alcohol fed to the reactor. The minimum portion of r-AO or r-GE content derived directly or indirectly from recycled waste, the pyrolysis of recycled waste, pyrolysis gas produced from the pyrolysis of recycled waste, and/or the cracking of r-pyoil produced from the pyrolysis of recycled waste, to make a GE or GEE product associated with a particular amount of recycle content, can be calculated as:

$$P = \left(\frac{\%D}{100}\right) \times \left(\frac{Pm}{Rm}\right) \times \left(\frac{100}{Y}\right) \times 100$$

where P means the minimum portion of r-AO or r-GE derived directly or indirectly recycled waste, the pyrolysis of recycled waste, pyrolysis gas produced from the pyrolysis of recycled waste, and/or the cracking of r-pyoil produced from the pyrolysis of recycled waste, and % D means the percentage of recycle content declared in product r-GE or r-GEE, and Pm means the molecular weight of product GE or GEE, and Rm means the molecular weight of reactant EO or PO as a moiety in GE product or reactant GE as a moiety in GEE product, not to exceed the molecular weight of the reactant EO, reactant PO, or reactant GE, and Y means the percent yield of the product, e.g. GE, determined as an average annual yield regardless of whether or not the feedstock is r-AO. If an average annual yield is not known, the yield can be assumed to be industry average using the same process technology.

The amount of recycle content in the r-AO or r-GE feed can be greater than the minimum, resulting in excess recycle content left over if for a given designation of recycle content in the AO or GE. In such a case, the remainder of recycle content available may be reserved in a recycle inventory. The excess recycle content may be stored in a recycle inventory and applied to other GE or GEE products that either are not made with r-AO or r-GE or with a deficient amount of r-AO or r-GE recycle content relative to the amount of recycle content one desires to apply to the GEE. However, whether or not the r-AO or r-GE feedstock actually was designated by the manufacturer of the GE or GEE as containing the minimum amount of recycle content, an r-GE or r-GEE designated as containing a certain recycle content is nevertheless deemed to have been made from an r-AO or r-GE feedstock containing the minimum recycle content by the calculation method described above.

In the case of a pro-rata mass approach in method (iv), the portion of r-AO or r-GE derived directly or indirectly from recycled waste, the pyrolysis of recycled waste, pyrolysis gas produced from the pyrolysis of recycled waste, and/or the cracking of r-pyoil produced from the pyrolysis of recycled waste would be calculated on the basis of the mass of recycle content available to the GE or GEE manufacturer by way of purchase or transfer or created in case the EO or PO is integrated into r-AO production, that is attributed to the feedstock on a daily run divided by the mass of the r-AO or r-GE feedstock, or:

$$P = \frac{Mr}{Ma} \times 100$$

where P means the percentage of recycle content in the EO or PO feedstock stream, and where Mr is the mass of recycle content attributed to the r-AO stream on a daily basis, and Ma is the mass of the entire EO or PO feedstock used to make GE on the corresponding day.

For example, if a GE manufacturer has available 1000 kg of a recycle allocation or credit that has its origin in pyrolyzing recycled waste, and the GE manufacturer elects to attribute 10 kg of the recycle allocation to an EO feedstock used to make the GE, and the EO feedstock employs 100 kg per day to make GE, the portion P of the r-AO feedstock derived directly or indirectly from cracking pyoil would be 10 kg/100 kg, or 10 wt %. The EO feedstock composition would be considered to be a r-AO composition because a portion of the recycle allocation is applied to the EO feedstock used to make the GE.

In another embodiment, there is provided a variety of methods for apportioning the recycle content among the various products made by a GE or GEE manufacturer or the products made by any one entity or a combinations of entities among the Family of Entities of which the GE or GEE manufacturer is a part. For example, the GE or GEE manufacturer, of any combination or the entirety of its Family of Entities, or a Site, can:

a. adopt a symmetric distribution of recycle content values among its product(s) based on the same fractional percentage of recycle content in one or more feedstocks, or based on the amount of allotment received. For example, if 5 wt. % of the AO feedstock is r-AO, or if the allotment value is 5 wt. % of the entire AO feedstock, then all GE made with the AO feedstock may contain 5 wt. % recycle content value. In this case, the amount of recycle content in the products is proportional to the amount of recycle content in the feedstock to make the products; or b. adopt an asymmetric distribution of recycle content values among its product(s) based on the same fractional percentage of recycle content in the one or more feedstocks, or based on the amount of allotment received. For example, if 5 wt. % of the AO feedstock is r-AO, or if the allotment value is 5 wt. % of the entire AO feedstock, then one volume or batch of GE can receive a greater amount of recycle content value that other batches or volume of GE made, provided that the total amount of recycle content does not exceed the total amount of r-AO or allotment received, or the total amount of recycle content in the recycle inventory. One batch of GE can contain 5% recycle content by mass, and another batch can contain zero 0% recycle content, even though both volumes are made from the same volume of AO feedstock. In the asymmetric distribution of recycle content, a manufacturer can tailor the recycle content to volumes of GE sold as needed among customers, thereby providing flexibility among customers some of whom may need more recycle content than others in a GE volume.

Both the symmetric distribution and the asymmetric distribution of recycle content can be proportional on a site wide basis, or on a multi-site basis. In one embodiment or in combination with any of the mentioned embodiments, the recycle content input (recycle content feedstock or allotments) can be to a Site, and recycle content values from said inputs are applied to one or more products made at the same Site, and at least one of the products made at the Site is GE or GEE, and optionally at least a portion of the recycle content value is applied to the GE or GEE products. The recycle content values can be applied symmetrically or asymmetrically to the products at the Site. The recycle content values can be applied across different GE or GEE volumes symmetrically or asymmetrically, or applied across a combination of GE or GEE and other products made at the Site. For example, a recycle content value is transferred to a recycle inventory at a Site, created at a Site, or a feedstock containing recycle content value is reacted at a Site (collectively the "a recycle input"), and recycle content values obtained from said inputs are:

a. distributed symmetrically across at least a portion or across all GE or GEE volume made at the Site over a period of time (e.g. within 1 week, or within 1 month, or within 6 months, or within the same calendar year, or continuously); or b. distributed symmetrically across at least a portion or across all GE or GEE volume made at the Site and across at least a portion or across a second different product made at the same Site, each over the same period of time (e.g. within 1 week, or within 1 month, or within 6 months, or within the same calendar year, or continuously); or c. recycle content is distributed symmetrically across all products to which recycle content is actually applied that are made at the Site, over the same period of time (e.g. within the same day, or within 1 week, or within 1 month, or within 6 months, or within the same calendar year, or continuously). While a variety of products can be made at a Site, in this option, not all product have to receive a recycle content value, but for all products that do receive or to which are applied a recycle content value, the distribution is symmetrical; or d. distributed asymmetrically across at least two GE or GEE volumes made at the same Site, optionally either over the same period of time (e.g. within 1 day, or within 1 week, or within 1 month, or within 6 months, or within a calendar year, or continuously), or as sold to at least two different customers. For example, one volume of GE or GEE made can have a greater recycle content value than a second volume of GE or GEE made at the Site, or one volume of GE or GEE made at the Site and sold to one customer can have a greater recycle content value than a second volume of GE or GEE made at the Site and sold to a second different customer, or e. distributed asymmetrically across at least one volume of GE or GEE and at least one volume of a different product, each made at the same Site, optionally either over the same period of time (e.g. within 1 day, or within 1 week, or within 1 month, or within 6 months, or within a calendar year, or continuously), or as sold to at least two different customers.

In one embodiment or in combination with any of the mentioned embodiments, the recycle content input or creation (recycle content feedstock or allotments) can be to or at a first Site, and recycle content values from said inputs are transferred to a second Site and applied to one or more products made at a second Site, and at least one of the products made at the second Site is GE or GEE, and optionally at least a portion of the recycle content value is applied to GE products made at the second Site. The recycle content values can be applied symmetrically or asymmetrically to the products at the second Site. The recycle content values can be applied across different GE or GEE volumes symmetrically or asymmetrically, or applied across a combination of GE or GEE and other products made at the second Site. For example, a recycle content value is transferred to a recycle inventory at a first Site, created at a first Site, or a feedstock containing recycle content value is reacted at a first Site (collectively the "a recycle input"), and recycle content values obtained from said inputs are:

a. distributed symmetrically across at least a portion or across all GE or GEE volume made at a second Site over a period of time (e.g. within 1 week, or within 1 month, or within 6 months, or within the same calendar year, or continuously); or
b. distributed symmetrically across at least a portion or across all GE or GEE volume made at the second Site and across at least a portion or across a second different product made at the same second Site, each over the same period of time (e.g. within 1 week, or within 1 month, or within 6 months, or within the same calendar year, or continuously); or
c. recycle content is distributed symmetrically across all products to which recycle content is actually applied that are made at the second Site, over the same period of time (e.g. within the same day, or within 1 week, or within 1 month, or within 6 months, or within the same calendar year, or continuously). While a variety of products can be made at a second Site, in this option, not all product have to receive a recycle content value, but for all products that do receive or to which are applied a recycle content value, the distribution is symmetrical; or
d. distributed asymmetrically across at least two GE or GEE volumes made at the same second Site, optionally either over the same period of time (e.g. within 1 day, or within 1 week, or within 1 month, or within 6 months, or within a calendar year, or continuously), or as sold to at least two different customers. For example, one volume of GE or GEE made can have a greater recycle content value than a second volume of GE or GEE each made at the second Site, or one volume of GE or GEE made at the second Site and sold to one customer can have a greater recycle content value than a second volume of GE or GEE made at the second Site and sold to a second different customer, or
e. distributed asymmetrically across at least one volume of GE or GEE and at least one volume of a different product, each made at the same second Site, optionally either over the same period of time (e.g. within 1 day, or within 1 week, or within 1 month, or within 6 months, or within a calendar year, or continuously), or as sold to at least two different customers.

In one embodiment or in combination with any of the mentioned embodiments, the GE or GEE manufacturer, or one among its Family of Entities, can make GE, or can make GEE, or process an AO, or process AO and make an r-GE, or make r-GE, or process GE and make r-GEE, or make r-GEE by obtaining any source of an alkylene oxide composition or glycol ether composition from a supplier, whether or not such alkylene oxide composition or glycol ether composition has any direct or indirect recycle content, and either:

i. from the same supplier of the alkylene oxide composition or glycol ether composition, also obtain a recycle content allotment, or
ii. from any person or entity, obtaining a recycle content allotment without a supply of an alkylene oxide composition or glycol ether composition from the person or entity transferring the recycle content allotment.

The allotment in (i) is either obtained from an AO supplier or, and the AO supplier also supplies AO to the GE manufacturer or within its Family of Entities and/or obtained from an GE supplier or, and the GE supplier also supplies GE to the GEE manufacturer or within its Family of Entities. For example, the circumstance described in (i) allows a GE manufacturer to obtain a supply of an alkylene oxide composition that is a non-recycle content AO, yet obtain a recycle content allotment from the AO supplier. In one embodiment or in combination with any of the mentioned embodiments, the AO supplier transfers a recycle content allotment to the GE manufacturer and a supply of AO to the GE manufacturer, where the recycle content allotment is not associated with the AO supplied, or even not associated with any AO made by the AO supplier. The recycle content allotment does not have to be tied to an amount of recycle content in an alkylene oxide composition or to any monomer used to make GE, but rather the recycle content allotment transferred by the AO supplier can be associated with other products derived directly or indirectly from recycled waste, the pyrolysis of recycled waste, pyrolysis gas produced from the pyrolysis of recycled waste, and/or the cracking of r-pyoil produced from the pyrolysis of recycled waste or the recycle content of any downstream compounds obtained from the pyrolysis of recycled waste, such as r-ethylene, r-propylene, r-butadiene, r-aldehydes, r-alcohols, r-benzene, etc. For example, the AO supplier can transfer to the GE manufacturer a recycle content associated with r-propylene and also supply a quantity of ethylene oxide even though r-propylene was not used in the synthesis of the ethylene oxide. This allows flexibility among the AO supplier and GE manufacturer to apportion a recycle content among the variety of products they each make.

In one embodiment or in combination with any of the mentioned embodiments, the AO supplier transfers a recycle content allotment to the GE manufacturer and a supply of AO to the GE manufacturer, where the recycle content allotment is associated with AO. In this case, the AO transferred does not have to be a r-AO (one that is derived directly or indirectly from the pyrolysis of recycled waste); rather the AO supplied by the supplier can be any AO such as a non-recycle content AO, so long as the allocation supplied is associated with a manufacture of AO. Optionally, the AO being supplied can r-AO and at least a portion of the recycle content allotment being transferred can be the recycle content in the r-AO. The recycle content allotment transferred to the GE manufacturer can be up front with the AO supplied in installments, or with each AO installment, or apportioned as desired among the parties.

The allotment in (ii) is obtained by the GE manufacturer (or its Family of Entities) from any person or entity without obtaining a supply of AO from the person or entity. The person or entity can be an AO manufacturer that does not supply AO to the GE manufacturer or its Family of Entities, or the person or entity can be a manufacturer that does not make AO. In either case, the circumstances of (ii) allows a GE manufacturer to obtain a recycle content allotment without having to purchase any AO from the entity supplying the recycle content allotment. For example, the person or entity may transfer a recycle content allotment through a buy/sell model or contract to the GE manufacturer or its Family of Entities without requiring purchase or sale of an allotment (e.g. as a product swap of products that are not AO), or the person or entity may outright sell the allotment to the GE manufacturer or one among its Family of Entities. Alternatively, the person or entity may transfer a product, other than AO, along with its associated recycle content allotment to the GE manufacturer. This can be attractive to a GE manufacturer that has a diversified business making a variety of products other than GE requiring raw materials other than AO that the person or entity can supply to the GE manufacturer.

The GE or GEE manufacturer can deposit the allotment into a recycle inventory. The GE or GEE manufacturer also makes GE and/or GEE, whether or not a recycle content is applied to the GE or GEE so made and whether or not a recycle content value, if applied to the GE or GEE, is drawn from the recycle inventory. For example, the GE or GEE manufacturer, or any entity among its Family of Entities may:

a. deposit the allotment into a recycle inventory and merely store it; or
b. deposit the allotment into a recycle inventory and apply a recycle content value from the recycle inventory to products other than GE or GEE made by the GE or GEE manufacturer, or
c. sell or transfer an allotment from the recycle inventory into which the allotment obtained as noted above was deposited.

If desired, however, from that recycle inventory, any allotment can be deducted and applied to the GE or GEE product in any amount and at any time up to the point of sale or transfer of the GE or GEE to a third party. Thus, the recycle content allotment applied to the GE or GEE can be derived directly or indirectly from pyrolyzing recycled waste, or the recycle content allotment applied to the GE or GEE is not derived directly or indirectly from the pyrolysis of recycled waste. For example, a recycle inventory of allotments can be generated having a variety of sources for creating the allotments. Some recycle content allotments (credits) can have their origin in methanolysis of recycled waste, or from gasification of recycled waste, or from mechanical recycling of waste plastic or metal recycling, and/or from pyrolyzing recycled waste, or from any other chemical or mechanical recycling technology. The recycle inventory may or may not track the origin or basis of obtaining a recycle content, or the recycle inventory may not allow one to associate the origin or basis of an allocation to the allocation applied to GE or GEE. Thus, in this embodiment, it is sufficient that a recycle content value is deducted from recycle inventory and applied to GE or GEE regardless of the source or origin of the recycle content value, provided that an allotment derived from pyrolyzing recycled waste is also obtained by the GE or GEE manufacturer as specified in step (i) or step (ii), whether or not that allotment is actually deposited into the recycle inventory. In one embodiment or in combination with any of the mentioned embodiments, the allotment obtained in step (i) or (ii) is deposited into a recycle inventory of allotments. In one embodiment or in combination with any of the mentioned embodiments, the recycle content value deducted from the recycle inventory and applied to the GE or GEE originates from pyrolyzing recycled waste.

As used throughout, the recycle inventory of allotments can be owned by the GE or GEE manufacturer, operated by the GE or GEE manufacturer, owned or operated by other than the GE or GEE manufacturer but at least in part for the GE or GEE manufacturer, or licensed by the GE or GEE manufacturer. Also, as used throughout, the GE or GEE manufacturer may also include its Family of Entities. For example, while the GE manufacturer may not own or operate the recycle inventory, one among its Family of Entities may own such a platform, or license it from an independent vendor, or operate it for the GE or GEE manufacturer. Alternatively, an independent entity may own and/or operate the recycle inventory and for a service fee operate and/or manage at least a portion of the recycle inventory for the GE or GEE manufacturer.

In one embodiment or in combination with any of the mentioned embodiments, the GE or GEE manufacturer obtains a supply of AO from a supplier, and also obtains an allotment from either (i) the supplier or (ii) from any other person or entity, where such allotment is derived from recycled waste, the pyrolysis of recycled waste, pyrolysis gas produced from the pyrolysis of recycled waste, and/or the cracking of r-pyoil produced from the pyrolysis of recycled waste, and optionally the allotment is obtained from the AO supplier and can even be an allotment by virtue of obtaining a r-AO from the supplier. The GE or GEE manufacturer is deemed to obtain the supply of alkylene oxide from a supplier if the supply is obtained by a person or entity within the Family of Entities of the GE or GEE manufacturer. The GE or GEE manufacturer then carries out one or more of the following steps:

a. applying the allotment to GE or GEE made by the supply of AO;
b. applying the allotment to GE or GEE not made by the supply of AO, such as would be the case where GE or GEE is already made and stored in recycle inventory, or to future made GE or GEE; or
c. depositing the allotment into a recycle inventory from which is deducted a recycle content value and applying at least a portion of the recycle content value to:
    i. GE or GEE to thereby obtain r-GE or r-GEE, or
    ii. to a compound or composition other than GE or GEE, or
    iii. both;

whether or not r-AO is used to make the GE or GEE composition, and whether or not the recycle content value applied to GE or GEE was obtained from a recycle content value in the allotment obtained in step (i) or step (ii) or deposited into the recycle inventory; or d. as described above, can merely be deposited into a recycle inventory and stored.

It is not necessary in all embodiments that r-AO or r-GE is used to make the r-GE or r-GEE compositions, respectively, or that the r-GE or r-GEE were obtained from a recycle content allotment associated with an alkylene oxide composition or glycol ether composition. Further, it is not necessary that an allotment be applied to the feedstock for making the GE or GEE to which recycle content is applied. Rather, as noted above, the allotment, even if associated with an alkylene oxide composition or glycol ether composition when the compositions are obtained from a supplier, can be deposited into an electronic recycle inventory. In one embodiment or in combination with any of the mentioned embodiments, however, r-AO and/or r-GE are used to make the r-GE and/or r-GEE composition. In one embodiment or in combination with any of the mentioned embodiments, the r-GE and/or r-GEE is obtained from a recycle content allotment associated with an alkylene oxide composition and/or a glycol ether composition. In one embodiment or in combination with any of the mentioned embodiments, at least a portion of r-AO allotments are applied to GE to make a r-GE.

The glycol ether composition can be made from any source of an alkylene oxide composition, whether or not the alkylene oxide composition is a r-AO, and whether or not the AO is obtained from a supplier or made by the GE manufacturer or within its Family of Entities. Once a GE composition is made, it can be designated as having recycle content based on and derived from at least a portion of the allotment, again whether or not the r-AO is used to make the r-GE composition and regardless of the source of AO used to make the GE. The allocation can be withdrawn or deducted from recycle inventory. The amount of the deduction and/or applied to the GE can correspond to any of the methods described above, e.g. a mass balance approach.

The glycol ether ester composition can be made from any source of glycol ether composition, whether or not the glycol ether composition is a r-GE, and whether or not the GE is obtained from a supplier or made by the GEE manufacturer or within its Family of Entities. Once a GEE composition is made, it can be designated as having recycle content based on and derived from at least a portion of the allotment, again whether or not the r-GE is used to make the r-GEE composition and regardless of the source of GE used to make the GEE. The allocation can be withdrawn or deducted from recycle inventory. The amount of the deduction and/or applied to the GEE can correspond to any of the methods described above, e.g. a mass balance approach.

In one embodiment or in combination with any of the mentioned embodiments, a recycle content glycol ether composition can be made by reacting an alkylene oxide composition obtained from any source in a synthetic process to make an GE, and a recycle content value can be applied to at least a portion of the GE to thereby obtain r-GE. Optionally, a recycle content value can be obtained by deducting from a recycle inventory. The entire amount of recycle content value in the GE can correspond to the recycle content value deducted from the recycle inventory. Recycle content value deducted from the recycle inventory can be applied to both GE and products or compositions other that GE made by the GE manufacturer or a person or entity among its Family of Entities. The alkylene oxide composition can be obtained from a third party, or made by the GE manufacturer, or made by a person or entity amount the Family of Entities of the GE manufacturer and transferred to the GE manufacturer. In another example, the GE manufacturer or its Family of Entities can have a first facility for making alkylene oxide within a first Site, and a second facility within the first Site or a second facility within a second Site where the second facility makes GE, and transfer the alkylene oxide from the first facility or first Site to the second facility or second Site. The facilities or Sites can be in direct or indirect, continuous or discontinuous, fluid communication or pipe communication with each other. A recycle content value is then applied to (e.g. assigned to, designate to correspond to, attributed to, or associated with) the GE to make a r-GE. At least a portion of the recycle content value applied to the GE is obtained from a recycle inventory.

In one embodiment or in combination with any of the mentioned embodiments, a recycle content glycol ether ester composition can be made by reacting a glycol ether composition obtained from any source in a synthetic process to make a GEE, and a recycle content value can be applied to at least a portion of the GEE to thereby obtain r-GEE. Optionally, a recycle content value can be obtained by deducting from a recycle inventory. The entire amount of recycle content value in the GEE can correspond to the recycle content value deducted from the recycle inventory. Recycle content value deducted from the recycle inventory can be applied to both GEE and products or compositions other that GEE made by the GEE manufacturer or a person or entity among its Family of Entities. The glycol ether composition can be obtained from a third party, or made by the GEE manufacturer, or made by a person or entity amount the Family of Entities of the GEE manufacturer and transferred to the GEE manufacturer. In another example, the GEE manufacturer or its Family of Entities can have a first facility for making glycol ether within a first Site, and a second facility within the first Site or a second facility within a second Site where the second facility makes GEE, and transfer the glycol ether from the first facility or first Site to the second facility or second Site. The facilities or Sites can be in direct or indirect, continuous or discontinuous, fluid communication or pipe communication with each other. A recycle content value is then applied to (e.g. assigned to, designate to correspond to, attributed to, or associated with) the GEE to make a r-GEE. At least a portion of the recycle content value applied to the GEE is obtained from a recycle inventory.

Optionally, one may communicate to a third party that the r-GE and/or r-GEE has recycle content or is obtained or derived from recycled waste. In one embodiment or in combination with any of the mentioned embodiments, one may communicate recycle content information about the GE or GEE to a third party where such recycle content information is based on or derived from at least a portion of the allocation or credit. The third party may be a customer of the GE or GEE manufacturer or supplier, or may be any other person or entity or governmental organization other than the entity owning the GE or GEE. The communication may electronic, by document, by advertisement, or any other means of communication.

In one embodiment or in combination with any of the mentioned embodiments, a recycle content glycol ether composition is obtained by either making a first r-GE or r-GEE or by merely possessing (e.g. by way of purchase, transfer, or otherwise) a first r-GE or r-GEE already having a recycle content, and transferring a recycle content value between a recycle inventory and the first r-GE or first r-GEE to obtain a second r-GE or a second r-GEE having different recycle content value than the first r-GE or first r-GEE.

In one embodiment or in combination with any of the mentioned embodiments, the transferred recycle content value described above is deducted from the recycle inventory and applied to the first r-GE or first r-GEE to obtain a second r-GE or a second r-GEE, respectively, having a second recycle content value higher than the first r-GE or the first r-GEE contains, to thereby increase the recycle content in first r-GE or first r-GEE.

The recycle content in the first r-GE or first r-GEE need not be obtained from a recycle inventory, but rather can be attributed to GE or GEE by any of the methods described herein (e.g., by virtue of using a r-AO as a reactant feed), and the GE or GEE manufacturer may seek to further increase the recycle content in the first r-GE or the first r-GEE so made. In another example, a GE or GEE distributor may have r-GE or r-GEE in its inventory and seek to increase the recycle content value of the first r-GE or the first r-GEE in its possession. The recycle content in the first r-GE or first r-GEE can be increased by applying a recycle content value withdrawn from a recycle inventory.

The recycle content value quantity that is deducted from recycle inventory is flexible and will depend on the amount of recycle content applied to the GE or GEE. In one embodiment or in combination with any of the mentioned embodiments, it is at least sufficient to correspond with at least a portion of the recycle content in the r-GE or the r-GEE. This is useful if, as noted above, a portion of the GE or GEE was made with r-AO where the recycle content value in the r-AO was not deposited into a recycle inventory, resulting in a r-GE or r-GEE and one desires to increase the recycle content in the r-GE or r-GEE by applying a recycle content value withdrawn from a recycle inventory; or where one possesses r-GE or r-GEE (by way of purchase, transfer, or otherwise) and desires to increase its recycle content value. Alternatively, the entire recycle content in the r-GE or r-GEE can be obtained by applying a recycle content value to the GE or GEE obtained from a recycle inventory.

The method for calculating the recycle content value is not limited, and can include the mass balance approach or the methods of calculation described above. The recycle inventory can be established on any basis and be a mix of basis. Examples of the origin for obtaining allotments deposited into a recycle inventory can be from pyrolyzing recycled waste, gasification of recycled waste, depolymerization of recycled waste such as through hydrolysis or methanolysis, and so on. In one embodiment or in combination with any of the mentioned embodiments, at least a portion of the allocations deposited into the recycle inventory is attributable to pyrolyzing recycled waste (e.g. obtained from cracking r-pyoil or obtained from r-pygas). The recycle inventory may or may not track the origin of recycle content value deposited into the recycle inventory. In one embodiment or in combination with any of the mentioned embodiments, the recycle inventory distinguishes between a recycle content value obtained from pyrolyzing recycled waste (i.e., pyrolysis recycle content value) and recycle content values having their origin in other technologies (i.e., recycle content value). This may be accomplished simply by assigning distinguishing units of measure to the recycle content values having is origin in pyrolyzing recycled waste, or tracking the origin of the allocation by assigning or placing the allocation into a unique module, unique spreadsheet, unique column or row, unique database, unique taggants associated with a unit of measure, and the like to as to distinguish the:

a. Origin of technology used to create the allotment, or
b. The type of compound having recycle content from which the allocation is obtained, or
c. The supplier or Site identity, or
d. A combination thereof.

The recycle content value applied to the GE or GEE from the recycle inventory does not have to be obtained from allotments having their origin in pyrolyzing recycled waste. The recycle content values deducted from the recycle inventory and/or applied to the GE or GEE can be derived from any technology used to generate allocations from recycled waste, such as through methanolysis or gasification of recycled waste. In one embodiment or in combination with any of the mentioned embodiments, however, the recycle content value applied to the GE or GEE or withdrawn/deducted from the recycle inventory have their origins or are derived from allotments obtained from pyrolyzing recycled waste.

The following are examples of applying (designating, assigning, or declaring a recycle content) a recycle content value or allotment to GE, GEE, or alkylene oxide composition:

1. Applying at least a portion of a recycle content value to a GE or GEE composition where the recycle content value is derived directly or indirectly with a recycle content ethylene or propylene, where such recycle content ethylene or propylene is obtained directly or indirectly from cracking r-pyoil or obtained from r-pygas, and the alkylene oxide composition used to make the GE or GEE did not contain any recycle content or it did contain recycle content; or
2. Applying at least a portion of a recycle content value to a GE or GEE composition where the recycle content value is derived directly or indirectly from cracking r-pyoil or obtained from r-pygas; or
3. Applying at least a portion of a recycle content value to a GE or GEE composition where the recycle content value is derived directly or indirectly with a r-AO, whether or not such alkylene oxide volume is used to make the AA; or
4. Applying at least a portion of a recycle content value to a GE or GEE composition where the recycle content value is derived directly or indirectly with a r-AO, and the r-AO is used as a feedstock to make the r-GE or r-GEE to which the recycle content value is applied, and:
    a. all of the recycle content in the r-alkylene oxide is applied to determine the amount of recycle content in the GE or GEE, or
    b. only a portion of the recycle content in the r-alkylene oxide is applied to determine the amount of recycle content applied to the GE or GEE, the remainder stored in recycle inventory for use to future GE, or for application to other existing GE or GEE made from r-alkylene oxide not containing any recycle content, or to increase the recycle content on an existing r-GE or r-GEE, or a combination thereof, or
    c. none of the recycle content in the r-alkylene oxide is applied to the GE or GEE and instead is stored in a recycle inventory, and a recycle content from any source or origin is deducted from the recycle inventory and applied to GE or GEE; or
5. Applying at least a portion of a recycle content value to an alkylene oxide composition used to make a GE or GEE to thereby obtain a r-GE or r-GEE, where the recycle content value was obtained with the transfer or purchase of the same alkylene oxide composition used to make the GE or GEE and the recycle content value is associated with the recycle content in an alkylene oxide composition; or
6. Applying at least a portion of a recycle content value to an alkylene oxide composition used to make a GE or GEE to thereby obtain a r-GE or r-GEE, where the recycle content value was obtained with the transfer or purchase of the same alkylene oxide composition used to make the GE or GEE and the recycle content value is not associated with the recycle content in an alkylene oxide composition but rather on the recycle content of a monomer used to make the alkylene oxide composition, such as with propylene or ethylene; or
7. Applying at least a portion of a recycle content value to an alkylene oxide composition used to make a GE or GEE to thereby obtain a r-GE or r-GEE, where the recycle content value was not obtained with the transfer or purchase of the alkylene oxide composition and the recycle content value is associated with the recycle content in the alkylene oxide composition; or 8. Applying at least a portion of a recycle content value to an alkylene oxide composition used to make a GE or GEE to thereby obtain a r-GE or r-GEE, where the recycle content value was not obtained with the transfer or purchase of the alkylene oxide composition and the recycle content value is not associated with the recycle content in the alkylene oxide composition but rather with the recycle content of any monomers used to make the alkylene oxide composition, such as a recycle content value associated with recycle content in propylene or ethylene; or
9. Obtaining a recycle content value derived directly or indirectly from pyrolyzing recycled waste, such as from cracking of r-pyoil, or obtained from a r-pygas, or associated with a r-composition, or associated with a r-alkylene oxide, and:
   a. no portion of the recycle content value is applied to an alkylene oxide composition to make GE or GEE and at least a portion is applied to GE or GEE to make a r-GE or r-GEE; or
   b. less than the entire portion is applied to an alkylene oxide composition used to make GE or GEE and the remainder is stored in recycle inventory or is applied to future made GE or GEE or is applied to existing GE or GEE in recycle inventory.

As used throughout, the step of deducting an allocation from a recycle inventory does not require its application to a GE or GEE product. The deduction also does not mean that the quantity of the deduction disappears or is removed from the inventory logs. A deduction can be an adjustment of an entry, a withdrawal, an addition of an entry as a debit, or any other algorithm that adjusts inputs and outputs based on an amount of recycle content associated with a product and one or a cumulative amount of allocations on deposit in the recycle inventory. For example, a deduction can be a simple step of a reducing/debit entry from one column and an addition/credit to another column within the same program or books, or an algorithm that automates the deductions and entries/additions and/or applications or designations to a product slate. The step of applying a recycle content value to a GE or GEE product also does not require the recycle content value or allocation to be applied physically to a GE or GEE product or to any document issued in association with the GE or GEE product sold. For example, a GE or GEE manufacturer may ship GE or GEE product to a customer and satisfy the "application" of the recycle content value to the GE or GEE product by electronically transferring a recycle content credit or certification document to the customer, or by applying a recycle content value to a package or container containing the GE or GEE or r-AO.

Some GE or GEE manufacturers may be integrated into making downstream products using GE or GEE as a raw material, such as making dispersions, crop protection emulsions or suspensions, surfactants, metal working fluids, lubricants, scouring agents for gas sweetening, surfactants, polishes, urethane catalysts, solvents, dyes, rubber accelerator, emulsifiers, ink additives, and oil additives. They, and other non-integrated GE or GEE manufacturers, can also offer to sell or sell GE or GEE on the market as containing or obtained with an amount of recycle content. The recycle content designation can also be found on or in association with the downstream product made with the GE or GEE.

In one embodiment or in combination with any of the mentioned embodiments, the amount of recycle content in the r-AO, r-GE, or r-GEE will be based on the allocation or credit obtained by the manufacturer of the GE or GEE composition or the amount available in the GE or GEE manufacturer's recycle inventory. A portion or all of the recycle content value in an allocation or credit obtained by or in the possession of a manufacturer of GE or GEE can be designated and assigned to a r-AO, r-GE, or r-GEE on a mass balance basis. The assigned value of the recycle content to the r-AO, r-GE, or r-GEE should not exceed the total amount of all allocations and/or credits available to the manufacturer of the GE or GEE or other entity authorized to assign a recycle content value to the GE or GEE.

There is now also provided a method of introducing or establishing a recycle content in a glycol ether and/or glycol ether ester without necessarily using an r-alkylene oxide feedstock. In this method, a. an olefin supplier either:
   i. cracks a cracker feedstock comprising recycle pyoil to make an olefin composition at least a portion of which is obtained by cracking said recycle pyoil (r-olefin), or
   ii. makes a pygas at least a portion of which is obtained by pyrolyzing a recycled waste stream (r-pygas), or
   iii. both; and
b. a glycol ether and/or glycol ether ester manufacturer:
   i. obtaining an allotment derived directly or indirectly with said r-olefin or said r-pygas from the supplier or a third-party transferring said allotment,
   ii. making a glycol ether from an alkylene oxide and/or making a glycol ether ester from the glycol ether, and
   iii. associating at least a portion of the allotment with at least a portion of the glycol ether or glycol ether ester, whether or not the alkylene oxide used to make the glycol ether contains r-alkylene oxide.

In this method, the glycol ether or glycol ether ester manufacturer need not purchase r-alkylene oxide or r-glycol ether from any entity or from the supplier of alkylene oxide or glycol ether, and does not require the glycol ether manufacturer to purchase olefins, r-olefins, or alkylene oxide from a particular source or supplier, and does not require the glycol ether or glycol ether ester manufacturer to use or purchase an alkylene oxide composition having r-alkylene oxide and/or a glycol ether composition having r-GE in order to successfully establish a recycle content in the glycol ether composition or glycol ether ester composition. The alkylene oxide manufacturer or glycol ether manufacturer may use any source of alkylene oxide or glycol ether and apply at least a portion of the allocation or credit to at least a portion of the alkylene oxide feedstock, at least a portion of the glycol ether product, or at least a portion of the glycol ether ester product. When the allocation or credit is applied to the feedstock alkylene oxide, this would be an example of an r-alkylene oxide feedstock indirectly derived from the cracking of r-pyoil or obtained from r-pygas. The association by the glycol ether or the glycol ether ester manufacturer may come in any form, whether by on in its recycle inventory, internal accounting methods, or declarations or claims made to a third party or the public.

In another embodiment, an exchanged recycle content value is deducted from a first r-GE or a first r-GEE and added to the recycle inventory to obtain a second r-GE or a second r-GEE having a second recycle content value lower than the first r-GE or first r-GEE contains, to thereby decrease the recycle content in first r-GE or first r-GEE. This embodiment, the above description concerning adding a recycle content value from a recycle inventory to a first r-GE or first r-GEE applies in reverse to deducting a recycle content from first r-GE or first r-GEE and adding it to a recycle inventory.

The allotment can be obtained from a variety of sources in the manufacturing chain starting from pyrolyzing recycled waste up to making and selling a r-AO or a r-GE. The recycle content value applied to GE or GEE or the allocation deposited into the recycle inventory need not be associated with r-AO or r-GE. In one embodiment or in combination with any of the mentioned embodiments, the process for making r-GE or r-GEE can be flexible and allow for obtaining an allocation anywhere along the manufacturing chain to make GE or GEE starting from pyrolyzing recycled waste. For example, one can make r-GE by:

a. pyrolyzing a pyrolysis feed comprising a recycled waste material to thereby form a pyrolysis effluent that contains r-pyoil and/or r-pygas. An allotment associated with the r-pyoil or r-pygas is automatically created by creation of pyoil or pygas from a recycled waste stream. The allotment may travel with the pyoil or pygas, or be dissociated from the pyoil or pygas such as by way of depositing the allotment into a recycle inventory; and
b. optionally cracking a cracker feed that contains at least a portion of the r-pyoil made in step a) to thereby produce a cracker effluent containing r-olefins; or optionally cracking a cracker feed without r-pyoil to make olefins and applying a recycle content value to the olefins so made by deducting a recycle content value from a recycle inventory (in the case that can be owned, operated, or for the benefit of an olefin producer or its Family of Entities) and applying the recycle content value to the olefins to make r-olefins;
c. reacting any olefin volume in a synthetic process to make an alkylene oxide composition; optionally using the olefin made in step b) and optionally using a r-olefin made in step b) and optionally applying a recycle content value associated the manufacture of the alkylene oxides made to make r-AO; and
d. reacting any alkylene oxide in a synthetic process to make a glycol ether; optionally using the alkylene oxide made in step c) and optionally using a r-AO made in step c); and
e. applying a recycle content value to at least a portion of said glycol ether composition based on:
   i. feeding r-AO as a feedstock or
   ii. depositing at least a portion of an allotment obtained from any one or more of steps a) or b) or c) into a recycle inventory and deducting from said inventory a recycle content value and applying at least a portion of either or both of said values to GE to thereby obtain r-GE.

In one embodiment or in combination with any of the mentioned embodiments, there is also provided a comprehensive process for making recycle content glycol ethers or recycle content glycol ether esters by:

a. making a r-olefin by either cracking the r-pyoil or separating an olefin from the r-pygas; and
b. converting at least a portion of the r-olefin in a synthetic process to make alkylene oxide; and
c. converting at least a portion of any or said alkylene oxide to a glycol ether; and
d. optionally converting at least a portion of any or said glycol ether to a glycol ether ester; and
e. applying a recycle content value to said glycol ether or said glycol ether ester to make a r-GE or r-GEE, respectively; and
f. optionally, also making a r-pyoil or r-pygas or both by pyrolyzing a recycle feedstock In this embodiment, all steps a)-e) can be practiced by and within a Family of Entities, or optionally on the same Site.

In another method, the direct method, a recycle content can be introduced or established in glycol ether or glycol ether ester by:

a. obtaining recycle alkylene oxide composition at least a portion of which is directly derived from cracking r-pyoil or obtained from r-pygas ("r-AO"),
b. making a glycol ether composition from a feedstock comprising r-AO,
c. optionally making a glycol ether ester composition from a feedstock comprising the glycol ester composition, and
d. applying a recycle content value to at least a portion of any glycol ether composition or glycol ether ester composition made by the same entity that made the glycol ether composition in step b) or the glycol ether ester composition in step c), and the recycle content value is based at least partly on the amount of recycle content contained in the r-AO or r-GE.

In another more detailed direct method, a recycle content can be introduced or established in glycol ether or glycol ether ester by:

a. making a recycle olefin composition (e.g., ethylene or propylene) at least a portion of which is directly derived from the pyrolysis of recycle waste or from cracking r-pyoil or obtained from r-pygas ("dr-propylene"),
b. making an alkylene oxide with a feedstock containing dr-propylene or dr-ethylene,
c. designating at least a portion of the alkylene oxide as containing a recycle content corresponding to at least a portion of the amount of dr-propylene or dr-ethylene contained in the feedstock to obtain a dr-alkylene oxide,
d. making a glycol ether with a feedstock containing r-alkylene oxide,
e. optionally making a glycol ether ester with a feedstock comprising the glycol ether,
f. designating at least a portion of the glycol ether or glycol ether ester as containing a recycle content corresponding to at least a portion of the amount of dr-alkylene oxide contained in the feedstock to obtain a dr-glycol ether or dr-glycol ether ester,
g. and optionally offering to sell or selling the r-glycol ether or r-glycol ether ester as containing or obtained with recycle content corresponding with such designation.

In these direct methods, the r-alkylene oxide content used to make the glycol ether would be traceable to the olefin made by a supplier by cracking r-pyoil or obtained from r-pygas. Not all of the amount of r-olefin used to make the alkylene oxide need be designated or associated with the alkylene oxide. For example, if 1000 kg of r-ethylene is used to make r-AO, the AO manufacturer can designate less than 1000 kg of recycle content toward a particular batch of feedstock used to make the AO and may instead spread out the 1000 kg recycle content amount over various productions runs to make alkylene oxide. The alkylene oxide manufacturer may elect to offer for sale its dr-glycol ether and in doing so may also elect to represent the r-glycol ether that is sold as containing, or obtained with sources that contain, a recycle content.

There is also provided a use for an alkylene oxide derived directly or indirectly from cracking r-pyoil or obtained from r-pygas, the use including converting r-alkylene oxide in any synthetic process to make glycol ethers.

There is also provided a use for a r-alkylene oxide allotment or an r-olefin allotment that includes converting an alkylene oxide in a synthetic process to make glycol ethers and applying at least a portion of an r-alkylene oxide allotment or the r-olefin allotment to the glycol ether. An r-alkylene oxide allotment or an r-olefin allotment is an allotment that is created by pyrolyzing recycled waste. Desirably, the allotments originate from the cracking of r-pyoil, or cracking of r-pyoil in a gas furnace, or from r-pygas.

There is also provided a use for an alcohol compound by reacting an alcohol compound with an r-AO to make a glycol ether, where the r-AO is derived directly or indirectly from pyrolyzing recycled waste.

There is also provided a use for an alcohol compound by reacting an acid compound with an r-GE to make a glycol ether ester, where the r-GE is derived directly or indirectly from pyrolyzing recycled waste.

There is also provided a use for an alcohol by reacting the alcohol with an alkylene oxide to make a glycol ether, and applying at least a portion of a recycle content allotment to at least a portion of the glycol ether to make a r-glycol ether. At least a portion of the recycle inventory from which the recycle content allotment is applied to the glycol ether are allotments originating from pyrolyzing recycled waste. Desirably, the allotments originate from the cracking of r-pyoil, or cracking of r-pyoil in a gas furnace, or from r-pygas. Also, the allotment applied to the glycol ether can be a recycle content allotment originating from pyrolyzing recycled waste.

There is also provided a use for an acid by reacting the acid with glycol ether to make a glycol ether ester, and applying at least a portion of a recycle content allotment to at least a portion of the glycol ether ester to make a r-glycol ether ester. At least a portion of the recycle inventory from which the recycle content allotment is applied to the glycol ether esters are allotments originating from pyrolyzing recycled waste. Desirably, the allotments originate from the cracking of r-pyoil, or cracking of r-pyoil in a gas furnace, or from r-pygas. Also, the allotment applied to the glycol ether can be a recycle content allotment originating from pyrolyzing recycled waste In one embodiment or in combination with any of the mentioned embodiments, there is also provided a use of a recycle inventory by converting any alkylene oxide composition in a synthetic process to make a glycol ether composition ("GE"); deducting a recycle content value from the recycle inventory and applying at least a portion of the deducted recycle content value to the GE or GEE, and at least a portion of the inventory contains a recycle content allotment. The recycle content allotment can be present in the inventory at the time of deducting a recycle content value from the recycle inventory, or a recycle content allotment deposit is made into the recycle inventory before deducting a recycle content value (but need not be present or accounted for when a deduction is made), or it can be present within a year from the deduction, or within the same calendar year as the deduction, or within the same month as the deduction, or within the same week as the deduction. In one embodiment or in combination with any of the mentioned embodiments, the recycle content deduction is withdrawn against a recycle content allotment.

In one embodiment or in combination with any of the mentioned embodiments, there is provided a glycol ether composition and/or glycol ether ester composition that are obtained by any of the methods described above.

The same operator, owner, of Family of Entities may practice each of these steps, or one or more steps may be practiced among different operators, owners, or Family of Entities.

The alkylene oxide, such as EO or PO, and/or the glycol ether can be stored in a storage vessel and transferred to a GE or GEE manufacturing facility by way of truck, pipe, or ship, or as further described below, the AO and/or GE production facility can be integrated with the GE facility. The alkylene oxide or glycol ether may be shipped or transferred to the operator or facility that makes the glycol ether or glycol ether ester.

In one embodiment or in combination with any of the mentioned embodiments, one may integrate two or more facilities and make r-GE and/or r-GEE. The facilities to make r-GEE, r-GE, the alkylene oxide, the olefins, and the r-pyoil and/or r-pygas, can be stand-alone facilities or facilities integrated to each other. For example, one may establish a system of producing and consuming a recycle alkylene oxide composition at least a portion of which is obtained from directly or indirectly from cracking r-pyoil or obtaining r-pygas; or a method of making r-GE and/or r-GEE, as follows:

a. providing an alkylene oxide manufacturing facility that produces at least in part an alkylene oxide composition ("AO");
b. providing a glycol ether manufacturing facility that makes a glycol ether composition ("GE") and comprising a reactor configured to accept AO;
c. providing a glycol ether ester manufacturing facility that makes a glycol ether ester composition ("GEE") and comprising a reactor configured to accept GE;
d. feeding at least a portion of said AO from the alkylene oxide manufacturing facility to the glycol ether manufacturing facility through a supply system providing fluid communication between said facilities; and
e. feeding at least a portion of said GE from the glycol ether manufacturing facility to the glycol ether ester manufacturing facility through a supply system providing fluid communication between said facilities, wherein any one or both of the alkylene oxide manufacturing facility or glycol ether manufacturing facility makes or supplies a r-AO (r-AO) or recycle content glycol ether (r-GE), respectively, and optionally, wherein the alkylene oxide manufacturing facility supplies r-AO to the glycol ether manufacturing facility through the supply system.

The feeding in step c) and d) can be a supply system providing fluid communication between these facilities and capable of supplying an alkylene oxide composition from the alkylene oxide manufacturing facility to the GE manufacturing facility and a glycol ether composition from the glycol ether manufacturing facility to the GEE manufacturing facility, such as a piping system that has a continuous or discontinuous flow.

The GE manufacturing facility can make r-GE, and can make the r-GE directly or indirectly from the pyrolysis of recycled waste or the cracking of r-pyoil or from r-pygas. Likewise, the GEE manufacturing facility can make r-GEE, and can make the r-GEE directly or indirectly from the pyrolysis of recycled waste or the cracking of r-pyoil or from r-pygas. For example, in a direct method, the GE manufacturing facility can make r-GE by accepting r-alkylene oxide from the alkylene oxide manufacturing facility and feeding the r-alkylene oxide as a feed stream to a reactor to make GE. Alternatively, for example, the GE manufacturing facility can make r-GE by accepting any alkylene oxide composition from the alkylene oxide manufacturing facility and applying a recycle content to GE made with the alkylene oxide composition by deducting recycle content value from its recycle inventory and applying them to the GE, optionally in amounts using the methods described above. The allotments obtained and stored in recycle inventory can be obtained by any of the methods described above, and need not necessarily be allotments associated with r-alkylene oxide or r-GE.

In one embodiment or in combination with any of the mentioned embodiments, there is also provided a system for producing r-GE and/or r-GEE as follows:

a. Provide an olefin manufacturing facility configured to produce an output composition comprising a recycle content propylene or recycle content ethylene or both ("r-olefin");
b. provide an AO manufacturing facility configured to accept an olefin stream from the olefin manufacturing facility and making an output composition comprising an alkylene oxide composition;
c. provide a glycol ether (GE) manufacturing facility having a reactor configured to accept an alkylene oxide composition and making an output composition comprising a r-GE;
d. provide a glycol ether ester (GEE) manufacturing facility having a reactor configured to accept a GE composition and making an output composition comprising a r-GEE; and
e. a supply system providing fluid communication between at least two of these facilities and capable of supplying the output composition of one manufacturing facility to another one or more of said manufacturing facilities.

The GE manufacturing facility can make r-GE, and can make the r-GE directly or indirectly from the pyrolysis of recycled waste. Likewise, the GEE manufacturing facility can make r-GEE, and can make the r-GEE directly or indirectly from the pyrolysis of recycled waste. In this system, the olefin manufacturing facility can have its output in fluid communication with the AO manufacturing facility which in turn can have its output in fluid communication with the GE manufacturing facility. Additionally, the GE manufacturing facility can have its output in fluid communication with the GEE manufacturing facility. Alternatively, for example, the manufacturing facilities of a) and b) alone can be in fluid communication, or only b) and c). In the latter case, the GE manufacturing facility can make r-GE directly by having the r-olefin produced in the olefin manufacturing facility converted all the way to GE, or indirectly by accepting any alkylene oxide composition from the AO manufacturing facility and applying a recycle content to GE by deducting allotments from its recycle inventory and applying them to the GE, optionally in amounts using the methods described above. The allotments obtained and stored in recycle inventory can be obtained by any of the methods described above, and need not necessarily be allotments associated with r-alkylene oxide or the r-olefins. For example, the allotments can be obtained from any facility or source, so long as they originate from the pyrolysis of recycled waste, or the cracking r-pyoil or obtained from r-pygas.

The fluid communication can be gaseous, or liquid if compressed. The fluid communication need not be continuous and can be interrupted by storage tanks, valves, or other purification or treatment facilities, so long as the fluid can be transported from one facility to the subsequent facility through, for example, an interconnecting pipe network and without the use of truck, train, ship, or airplane. For example, one or more storage vessels may be placed in the supply system so that the r-AO facility feeds r-AO to a storage facility and r-AO can be withdrawn from the storage facility as needed by the GE manufacturing facility, with valving and pumps and compressors utilized an in line with the piping network as needed. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment or in combination with any of the mentioned embodiments, the integrated process includes at least two facilities co-located within 5, or within 3, or within 2, or within 1 mile of each other (measured as a straight line). In one embodiment or in combination with any of the mentioned embodiments, at least two facilities are owned by the same Family of Entities.

In one embodiment or in combination with any of the mentioned embodiments, there is also provided an integrated r-olefin, r-GE, and r-GEE generating and consumption system. This system includes:

a. Provide an olefin manufacturing facility configured to produce an output composition comprising a recycle content propylene or recycle content ethylene or both ("r-olefin");
b. provide an AO manufacturing facility configured to accept an olefin stream from the olefin manufacturing facility and making an output composition comprising an alkylene oxide composition;
c. provide glycol ethers (AA) manufacturing facility having a reactor configured to accept an alkylene oxide composition and making an output composition comprising a r-GE;
d. provide a glycol ether ester (GEE) manufacturing facility having a reactor configured to accept a GE composition and making an output composition comprising a r-GEE; and
e. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. In this system, ethylene or propylene made at the olefin manufacturing facility can be delivered to the AO facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the AO reactor or the cracker, but rather to a delivery and receiving point at the respective facilities. The same concept applies between the AO facility and the GE facility. The interconnecting pipework need not connect all three facilities to each other, but rather the interconnecting pipework can be between facilities a)-b), or b)-c), or between a)-b)-c).

There can now also be provided a package or a combination of a r-GE and/or r-GEE and a recycle content identifier associated with r-GE or r-GEE, where the identifier is or contains a representation that the GE or r-GEE contains, or is sourced from or associated with a recycle content. The package can be any suitable package for containing a glycol ether, such as a plastic or metal drum, railroad car, isotainer, totes, polytotes, IBC totes, bottles, jerricans, and polybags. The identifier can be a certificate document, a product specification stating the recycle content, a label, a logo or certification mark from a certification agency representing that the article or package contains contents or the GE or r-GEE contains, or is made from sources or associated with recycle content, or it can be electronic statements by the GE or r-GEE manufacturer that accompany a purchase order or the product, or posted on a website as a statement, representation, or a logo representing that the GE or r-GEE contains or is made from sources that are associated with or contain recycle content, or it can be an advertisement transmitted electronically, by or in a website, by email, or by television, or through a tradeshow, in each case that is associated with GE or r-GEE. The identifier need not state or represent that the recycle content is derived directly or indirectly from cracking r-pyoil or obtained from r-pygas. Rather, it is sufficient that the GE or r-GEE is directly or indirectly obtained at least in part from the cracking of r-pyoil, and the identifier can merely convey or communicate that the GE or r-GEE has or is sourced from a recycle content, regardless of the source.

In one embodiment or in combination with any of the mentioned embodiments, there is provided a system or package comprising:

a. glycol ethers ("GE") and/or glycol ether esters ("GEE"), and
b. an identifier (e.g. a credit, label or certification) associated with said glycol ether and/or said glycol ether ester, said identifier being a representation that said glycol ether and/or said glycol ether ester has recycle content or is made from a source having recycle content The system can be a physical combination, such as package having at least GE and/or GEE as its contents and the package has a label, such as a logo, that the contents such as the GE and/or GEE has or is sourced from a recycle content. Alternatively, the label or certification can be issued to a third party or customer as part of a standard operating procedure of an entity whenever it transfers or sells GE and/or GEE having or sourced from recycle content. The identifier does not have to be physically on the GE and/or GEE or on a package, and does not have to be on any physical document that accompanies or is associated with the GE and/or GEE. For example, the identifier can be an electronic credit or certification or representation transferred electronically by the GE and/or GEE manufacturer to a customer in connection with the sale or transfer of the GE and/or GEE product, and by sole virtue of being a credit, it is a representation that the GE and/or GEE has recycle content. The identifier, such as a label (such as a logo) or certification need not state or represent that the recycle content is derived directly or indirectly from cracking r-pyoil or obtained from r-pygas. Rather, it is sufficient that the GE and/or GEE is directly or indirectly obtained at least in part either (i) from pyrolyzing recycled waste or (ii) from a recycle inventory into which at least a portion of the deposits or credits in the recycle inventory have their origin in pyrolyzing recycled waste. The identifier itself need only convey or communicate that the GE and/or GEE has or is sourced from a recycle content, regardless of the source. In one embodiment or in combination with any of the mentioned embodiments, articles made from the GE and/or GEE may have the identifier, such as a stamp or logo embedded or adhered to the article. In one embodiment or in combination with any of the mentioned embodiments, the identifier is an electronic recycle content credit from any source. In one embodiment or in combination with any of the mentioned embodiments, the identifier is an electronic recycle content credit derived directly or indirectly from pyrolyzing recycled waste.

In one embodiment or in combination with any of the mentioned embodiments, the r-GE and/or r-GEE, or articles made thereby, can be offered for sale or sold as GE and/or GEE containing or obtained with, or an article containing or obtained with, recycle content. The sale or offer for sale can be accompanied with a certification or representation of the recycle content claim made in association with the GE and/or GEE or article made with the GE and/or GEE.

The obtaining of an allocation and designating (whether internally such as through a bookkeeping or a recycle inventory tracking software program or externally by way of declaration, certification, advertising, representing, etc.) can be by the GE and/or GEE manufacturer or within the GE and/or GEE manufacturer Family of Entities. The designation of at least a portion of the GE and/or GEE as corresponding to at least a portion of the allotment (e.g. allocation or credit) can occur through a variety of means and according to the system employed by the GE and/or GEE manufacturer, which can vary from manufacturer to manufacturer. For example, the designation can occur internally merely through a log entry in the books or files of the GE and/or GEE manufacturer or other inventory software program, or through an advertisement or statement on a specification, on a package, on the product, by way of a logo associated with the product, by way of a certification declaration sheet associated with a product sold, or through formulas that compute the amount deducted from recycle inventory relative to the amount of recycle content applied to a product.

Optionally, the GE and/or GEE can be sold. In one embodiment or in combination with any of the mentioned embodiments, there is provided a method of offering to sell or selling glycol ethers and/or glycol ether esters by:

a. converting an alkylene oxide composition in a synthetic process to make glycol ether composition ("GE"),
b. optionally converting the glycol ether composition into a glycol ether ester composition ("GEE");
c. applying a recycle content value to at least a portion of the GE and/or GEE to thereby obtain a recycle GE ("r-GE") and/or a r-GEE, and
d. offering to sell or selling the r-GE and/or r-GEE as having a recycle content or obtained or derived from recycled waste.

A GE and/or GEE manufacturer or its Family of Entities can obtain a recycle content allocation, and the allocation can be obtained by any of the means described herein and can be deposited into recycle inventory, the recycle content allocation derived directly or indirectly from the pyrolysis of recycled waste. The alkylene oxide converted in a synthetic process to make a glycol ether composition can be any alkylene oxide composition obtained from any source, including a non-r-AO composition, or it can be a r-alkylene oxide composition. The glycol ether converted in a synthetic process to make a glycol ether ester composition can be any glycol ether composition obtained from any source, including a non-r-GE composition, or it can be a r-GE composition. The r-GE and/or r-GEE sold or offered for sale can be designated (e.g. labelled or certified or otherwise associated) as having a recycle content value. In one embodiment or in combination with any of the mentioned embodiments, at least a portion of the recycle content value associated with the r-GE and/or r-GEE can be drawn from a recycle inventory. In another embodiment, at least a portion of the recycle content value in the GE and/or GEE is obtained by converting r-AO. The recycle content value deducted from the recycle inventory can be a non-pyrolysis recycle content value or can be a pyrolysis recycle content allocation; i.e., a recycle content value that has its origin in pyrolysis of recycled waste. The recycle inventory can optionally contain at least one entry that is an allocation derived directly or indirectly from pyrolysis of recycled waste. The designation can be the amount of allocation deducted from recycle inventory, or the amount of recycle content declared or determined by the GE and/or GEE manufacturer in its accounts. The amount of recycle content does not necessarily have to be applied to the GE and/or r-GEE product in a physical fashion. The designation can be an internal designation to or by the GE and/or GEE manufacturer or its Family of Entities or a service provider in contractual relationship to the GE and/or GEE manufacturer or its Family of Entities. The amount of recycle content represented as contained in the GE and/or GEE sold or offered for sale has a relationship or linkage to the designation. The amount of recycle content can be a 1:1 relationship in the amount of recycle content declared on a GE and/or GEE offered for sale or sold and the amount of recycle content assigned or designated to the GE and/or GEE by the GE and/or GEE manufacturer.

The steps described need not be sequential, and can be independent from each other. For example, the steps a) and b) can be simultaneous, such as would be the case if employs a r-AO composition to make the GE since the r-AO is both an alkylene oxide composition and has a recycle content allocation associated with it; or where the process of making GE is continuous and the application of the GE application of the recycle content value occurs during the manufacture of GE.

The Glycol Ether and Glycol Ether Ester Synthetic Processes

The synthetic process for making the GE using an alkylene oxide composition or a r-AO can be accomplished as follows. Generally, any conventional process for making glycol ethers is suitable.

As mentioned above, the process for making the glycol ether composition, including the r-GE, can be generally carried out in a reaction vessel by feeding to a vessel, or reacting in the vessel, an alkylene oxide with at least one alcohol. Generally, glycol ethers may be produced by reacting an alkylene oxide, such as ethylene oxide (EO) or propylene oxide (PO), with an alcohol such as methanol, ethanol, propanol, butanol, hexanol, or combinations thereof. Typically, the process is carried out under adiabatic and isothermal conditions.

The alcohol can comprise any alcohol and depends on the desired glycol ether to be produced. For instance, the alcohol may comprise an aliphatic monohydric alcohol, such as methanol, ethanol, or propanol; an aliphatic dihydric alcohol, such as ethylene glycol or propylene glycol; or a phenol, such as phenol or methylphenol.

The molar ratio of the alcohol to the alkylene oxide may vary, but may be maintained at a ratio of 2:1 to 20:1.

The reaction may also occur in the presence of a catalyst, such as an anionic exchange resin, an acid catalyst, a cation exchange resin, a lamellar clay catalyst, a basic catalyst, or combinations thereof.

The glycol ether production process may occur at a temperature in the range of 50 °C to 200 °C, generally from 60 ° to 120 °C. The reaction pressure may range from 1 to 50 bar.

The glycol ethers produced in accordance with the methods described herein can comprise ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, propylene glycol methyl ether, diethyleneglycol monomethyl ether, diethylene glycol monoethyl ether, dipropylene glycol monomethyl ether, or combinations thereof.

Exemplary processes for producing glycol ethers are described in U.S. Pat. Nos. 3,935,279 and 5,945,568; European Patent Application Publication No. EP0250168A1; and PCT Application No. WO 2015/024103, the disclosures of which are incorporated herein by reference in their entireties.

Generally, glycol ethers are either "E-series" or "P-series" glycol ethers, depending on whether they are made from ethylene oxide or propylene oxide, respectively. Typically, E-series glycol ethers may be used in pharmaceuticals, sunscreens, cosmetics, inks, dyes, and water-based paints, while P-series glycol ethers are typically used in degreasers, cleaners, aerosol paints and adhesives.

Both E-series glycol ethers and P-series glycol ethers can be used as intermediates that undergo further chemical reactions, such as for the production of glycol diethers and glycol ether acetates.

As noted above, the glycol ethers can also function as chemical intermediates and may be used to produce glycol ether esters. Generally, a glycol ether ester may be produced from the glycol ethers by introducing the glycol ether and at least one acid into a reaction vessel in the presence of a catalyst. Generally, any conventional process for making glycol ether esters is suitable.

One of the methods for producing glycol ether esters from glycol ethers may involve the Fischer esterification reaction, in which a stoichiometric excess of a glycol ether and an acid, such as a carboxylic acid, are heated in the presence of a catalytic amount of a strong acid (e.g., concentrated sulfuric acid or phosphoric acid) and an entrainer solvent (e.g., heptane or toluene) to yield the desired ester. The water byproduct may be removed by azeotropic distillation.

Generally, the acid used to produce the glycol ether esters may comprise a carboxylic acid. Exemplary carboxylic acids may include acetic acid, propionic acid, n-butyric acid, isobutyric acid, 2-methyl butyric acid, n-valeric acid, n-caproic acid, 2-ethyl hexanoic acid, benzoic acid, or combinations thereof.

The glycol ether ester production process may occur at a temperature in the range of 50 °C to 300 °C, generally from 100 ° to 280 °C. The reaction pressure may range from 1 to 50 bar.

Exemplary glycol ether esters that may be produced in accordance with the methods described herein can comprise ethylene glycol methyl ether acetate, ethylene glycol monoethyl ether acetate, ethylene glycol monobutyl ether acetate, propylene glycol methyl ether acetate, or combinations thereof.

The glycol ether esters may use in coatings, solvents, coalescent, and/or as plasticizers.

Exemplary processes for producing glycol ether esters are described in U.S. Pat. No. 9,809,529; European Patent No. EP0711747B1; and U.S. Patent Application Publication No. 2012/0258249, the disclosures of which are incorporated herein by reference in their entireties.

Alkylene Oxide Production

Any conventional process for making alkylene oxides or epoxides are suitable. In one example, an alkylene oxide can be produced by continuously contacting an oxygen rich gas with an olefin, such as ethylene and/or propylene, and in the presence of an epoxidation catalyst to make an alkylene oxide, such as ethylene oxide or propylene oxide. The oxygen rich gas can be air or any gas stream enriched in oxygen relative to the amount of oxygen in air, for example, at least 20.95 wt. % oxygen, or at least 21 wt. % oxygen, or at least 25 wt. % oxygen, or at least 30 wt. % oxygen, or at least 40 wt. % oxygen, or at least 50 wt. % oxygen, or at least 60 wt. % oxygen, or at least 70 wt. % oxygen, or at least 80 wt. % oxygen, or at least 90 wt. % oxygen, or at least 95 wt. % oxygen, or at least 98 wt. % oxygen. The amount of ethylene can be from 2 to 50 wt. %, from 0.5 to 30 wt. % oxygen, and the remainder inert materials, such as $CO_2$, nitrogen, water, other hydrocarbons such as methane, ethane, propane, etc., each based on the weight of all ingredients in the reaction chamber. The reaction can be in the vapor phase oxidation of the olefin, such as ethylene, and optionally in a fixed bed tubular reactor having multiple parallel tubes, typically in a shell. The epoxidation catalyst can be any conventional catalyst, such as a heterogenous supported silver-based epoxidation catalyst, optionally with a promoter such as a rhenium-containing compound and/or one or more alkali metals or alkali metal-containing compounds.

EXAMPLES r-Pyoil Examples 1-4

Table 1 shows the composition of r-pyoil samples by gas chromatography. The r-pyoil samples produced the material from waste high and low density polyethylene, polypropylene, and polystyrene. Sample 4 was a lab-distilled sample in which hydrocarbons greater than C21 were removed. The boiling point curves of these materials are shown in FIGS. 13-16.

TABLE 1

Gas Chromatography Analysis of r-Pyoil Examples

| | r-Pyoil Feed Examples | | | |
|---|---|---|---|---|
| Components | 1 | 2 | 3 | 4 |
| Propene | 0.00 | 0.00 | 0.00 | 0.00 |
| Propane | 0.00 | 0.19 | 0.20 | 0.00 |
| 1,3-Butadiene | 0.00 | 0.93 | 0.99 | 0.31 |
| Pentene | 0.16 | 0.37 | 0.39 | 0.32 |
| Pentane | 1.81 | 3.21 | 3.34 | 3.05 |
| 1,3-cyclopentadiene | 0.00 | 0.00 | 0.00 | 0.00 |
| 2-methyl-Pentene | 1.53 | 2.11 | 2.16 | 2.25 |
| 2-methyl-Pentane | 2.04 | 2.44 | 2.48 | 3.03 |
| Hexane | 1.37 | 1.80 | 1.83 | 2.10 |
| 2-methyl-1,3-cyclopentadiene | 0.00 | 0.00 | 0.00 | 0.00 |
| 1-methyl-1,3-cyclopentadiene | 0.00 | 0.00 | 0.00 | 0.00 |
| 2,4 dimethylpentene | 0.32 | 0.18 | 0.18 | 0.14 |
| Benzene | 0.00 | 0.16 | 0.16 | 0.00 |
| 5-methyl-1,3-cyclopentadiene | 0.00 | 0.17 | 0.17 | 0.20 |
| Heptene | 1.08 | 1.15 | 1.15 | 1.55 |
| Heptane | 2.51 | 0.17 | 2.89 | 3.61 |
| Toluene | 0.58 | 1.05 | 1.09 | 0.84 |
| 4-methylheptane | 1.50 | 1.67 | 1.68 | 1.99 |
| Octene | 1.37 | 1.35 | 1.37 | 1.88 |
| Octane | 2.56 | 2.72 | 2.78 | 3.40 |
| 2,4-dimethylheptene | 1.25 | 1.54 | 1.55 | 1.60 |
| 2,4-dimethylheptane | 5.08 | 4.01 | 4.05 | 6.40 |
| Ethylbenzene | 1.85 | 3.10 | 3.12 | 2.52 |
| m,p-xylene | 0.73 | 0.69 | 0.24 | 0.90 |
| Styrene | 0.40 | 0.13 | 1.13 | 0.53 |
| o-xylene | 0.12 | 0.36 | 0.00 | 0.00 |
| Nonane | 2.66 | 2.81 | 2.84 | 3.47 |
| Nonene | 1.12 | 0.00 | 0.00 | 1.65 |
| MW140 | 2.00 | 1.76 | 1.75 | 2.50 |
| Cumene | 0.56 | 0.96 | 0.97 | 0.73 |
| Decene/methylstyrene | 1.29 | 1.17 | 1.18 | 1.60 |
| Decane | 3.14 | 3.23 | 3.25 | 3.90 |
| Unknown 1 | 0.68 | 0.71 | 0.72 | 0.80 |
| Indene | 0.18 | 0.20 | 0.21 | 0.22 |
| Indane | 0.23 | 0.34 | 0.26 | 0.26 |
| C11 Alkene | 1.50 | 1.32 | 1.33 | 1.77 |
| C11 Alkane | 3.30 | 3.30 | 3.33 | 3.88 |
| C12 Alkene | 1.49 | 1.30 | 0.00 | 0.09 |
| Naphthalene | 0.10 | 0.12 | 3.24 | 3.73 |
| C12 Alkane | 3.34 | 3.21 | 1.31 | 1.66 |
| C13 Alkane | 3.20 | 2.90 | 2.97 | 3.40 |
| C13 Alkene | 1.46 | 1.20 | 1.17 | 1.53 |
| 2-methylnaphthalene | 0.86 | 0.63 | 0.64 | 0.85 |
| C14 Alkene | 1.07 | 0.84 | 0.84 | 1.04 |
| C14 Alkane | 3.34 | 3.04 | 3.05 | 3.24 |
| Acenaphthene | 0.31 | 0.28 | 0.28 | 0.28 |
| C15 Alkene | 1.16 | 0.87 | 0.87 | 0.96 |
| C15 Alkane | 3.41 | 3.00 | 3.02 | 2.84 |
| C16 Alkene | 0.85 | 0.58 | 0.58 | 0.56 |
| C16 Alkane | 3.25 | 2.67 | 2.68 | 2.12 |
| C17 Alkene | 0.70 | 0.46 | 0.46 | 0.35 |
| C17 Alkane | 3.04 | 2.43 | 2.44 | 1.50 |
| C18 Alkene | 0.51 | 0.33 | 0.33 | 0.19 |
| C18 Alkane | 2.71 | 2.11 | 2.13 | 0.99 |
| C19 Alkane | 2.39 | 1.82 | 0.38 | 0.15 |
| C19 Alkene | 0.60 | 0.38 | 1.83 | 0.61 |
| C20 Alkene | 0.42 | 0.18 | 0.26 | 0.00 |
| C20 Alkane | 2.05 | 1.55 | 1.55 | 0.37 |
| C21 Alkene | 0.31 | 0.00 | 0.00 | 0.00 |
| C21 Alkane | 1.72 | 1.45 | 1.30 | 0.23 |
| C22 Alkene | 0.00 | 0.00 | 0.00 | 0.00 |
| C22 Alkane | 1.43 | 1.11 | 1.12 | 0.00 |
| C23 Alkene | 0.00 | 0.00 | 0.00 | 0.00 |
| C23 Alkane | 1.09 | 0.87 | 0.88 | 0.00 |
| C24 Alkene | 0.00 | 0.00 | 0.00 | 0.00 |
| C24 Alkane | 0.82 | 0.72 | 0.72 | 0.00 |
| C25 Alkene | 0.00 | 0.00 | 0.00 | 0.00 |
| C25 Alkane | 0.61 | 0.58 | 0.56 | 0.00 |
| C26 Alkene | 0.00 | 0.00 | 0.00 | 0.00 |
| C26 Alkane | 0.44 | 0.47 | 0.44 | 0.00 |
| C27 Alkane | 0.31 | 0.37 | 0.32 | 0.00 |
| C28 Alkane | 0.22 | 0.29 | 0.23 | 0.00 |
| C29 Alkane | 0.16 | 0.22 | 0.15 | 0.00 |
| C30 Alkane | 0.00 | 0.16 | 0.00 | 0.00 |
| C31 Alkane | 0.00 | 0.00 | 0.00 | 0.00 |
| C32 Alkane | 0.00 | 0.00 | 0.00 | 0.00 |
| Unidentified | 13.73 | 18.59 | 15.44 | 15.91 |
| Percent C8+ | 74.86 | 67.50 | 67.50 | 66.69 |
| Percent C15+ | 28.17 | 22.63 | 22.25 | 10.87 |
| Percent Aromatics | 5.91 | 8.02 | 11.35 | 10.86 |
| Percent Paraffins | 59.72 | 54.85 | 54.19 | 51.59 |
| Percent C4 to C7 | 11.41 | 13.72 | 16.86 | 17.40 |

r-Pyoil Examples 5-10

Six r-pyoil compositions were prepared by distillation of r-pyoil samples. They were prepared by processing the material according the procedures described below.

Figure 17:
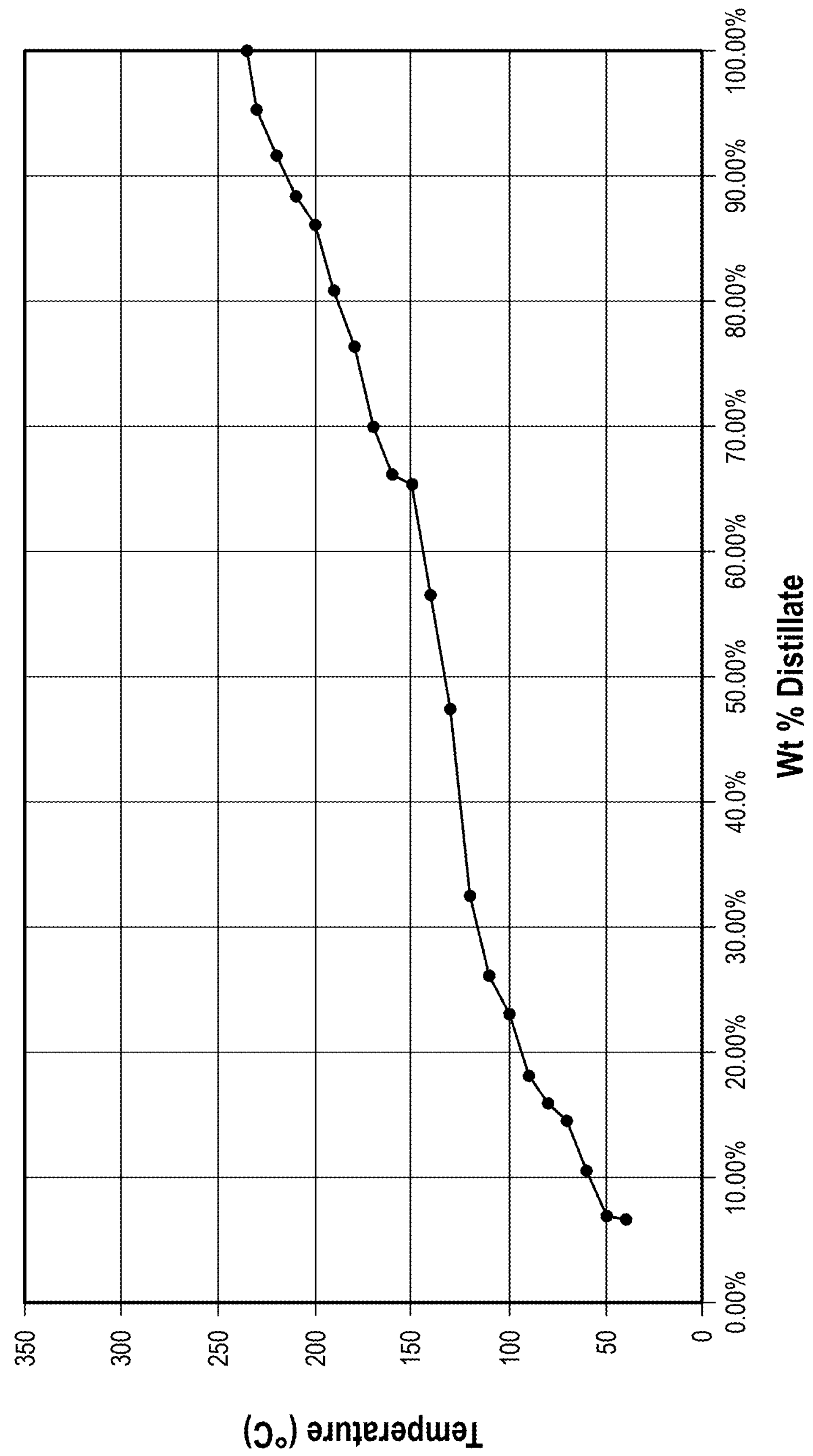
FIG. 17 is a graph of the boiling point curve of r-pyoil distilled in lab with at least 90% boiling by 350 °C, 50% boiling between 95 °C and 200 °C, and at least 10% boiling by 60 °C.

Example 5. R-Pyoil with at Least 90% Boiling by 350 °C, 50% Boiling Between 95 °C and 200 °C, and at Least 10% Boiling by 60 °C A 250 g sample of r-pyoil from Example 3 was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 20 mL, and the overhead temperature and mass recorded to construct the boiling curve presented in FIG. 17. The distillation was repeated until approximately 635 g of material was collected.

Figure 18:
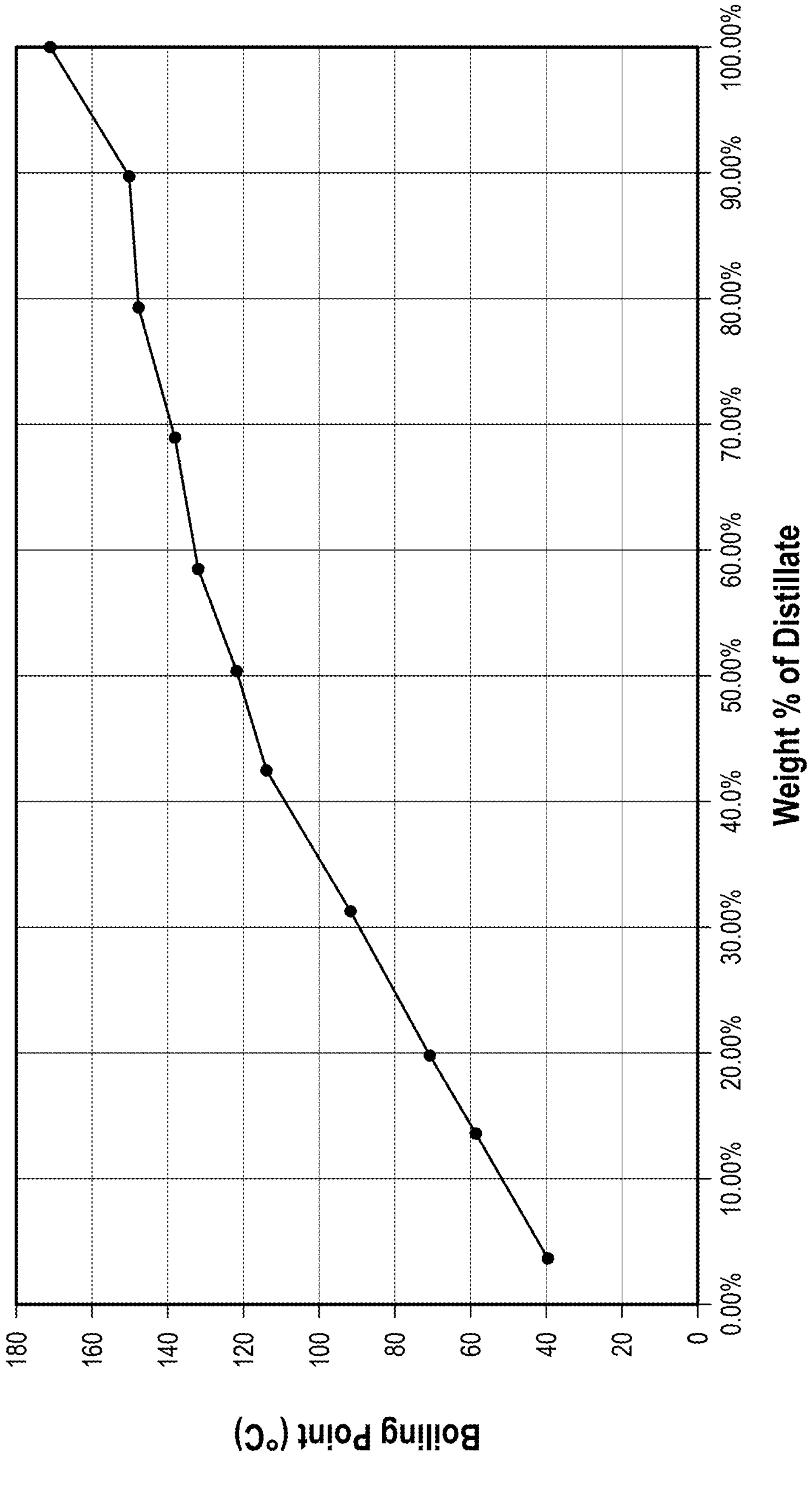
FIG. 18 is a graph of the boiling point curve of r-pyoil distilled in lab with at least 90% boiling by 150 °C, 50% boiling between 80 °C and 145 °C, and at least 10% boiling by 60 °C.

Example 6. R-Pyoil with at Least 90% Boiling by 150 °C, 50% Boiling Between 80 °C and 145 °C, and at Least 10% Boiling by 60 °C A 150 g sample of r-pyoil from Example 3 was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 20 mL, and the overhead temperature and mass recorded to construct the boiling curve presented in FIG. 18. The distillation was repeated until approximately 200 g of material was collected.

Figure 19:
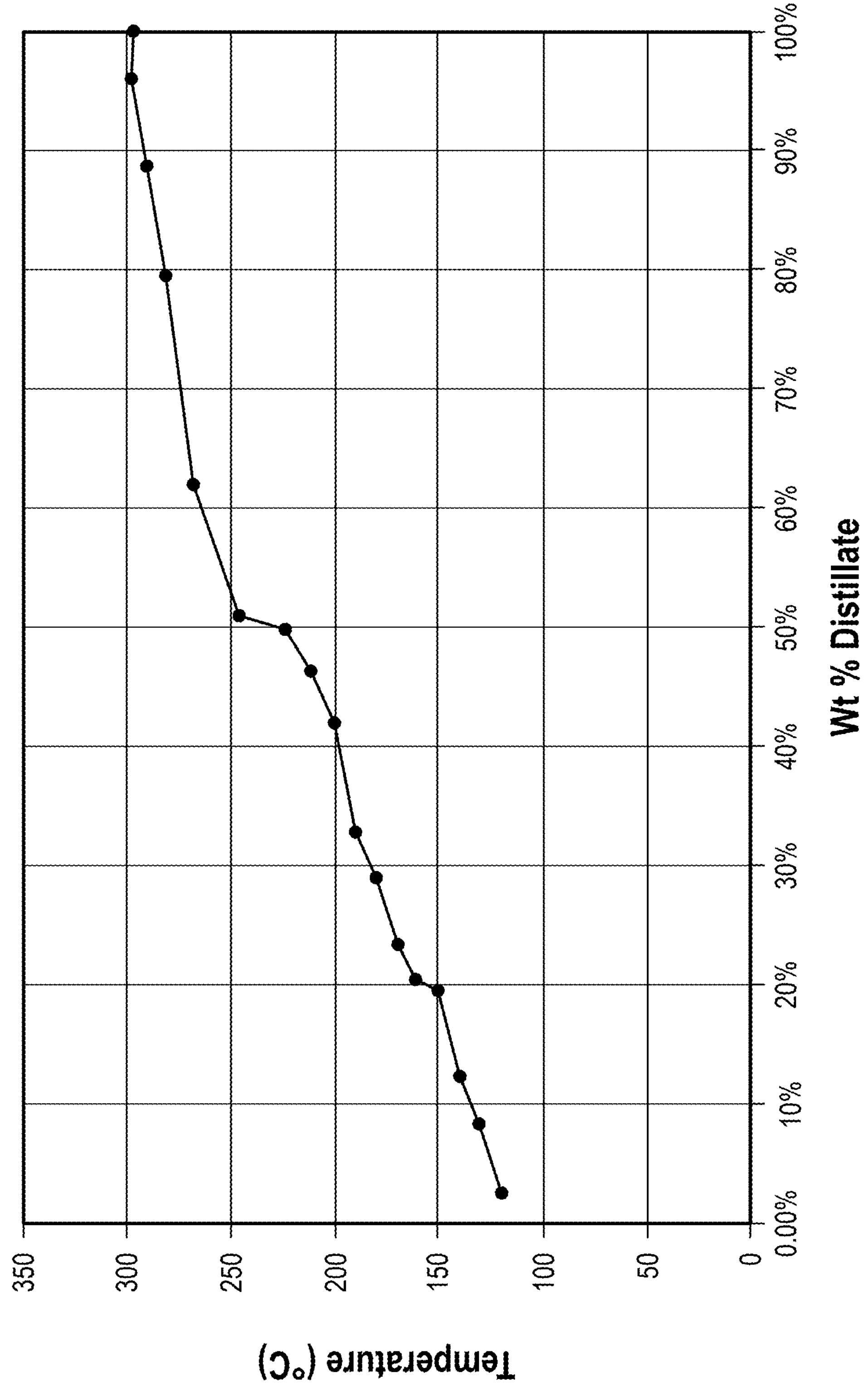
FIG. 19 is a graph of the boiling point curve of r-pyoil distilled in lab with at least 90% boiling by 350 °C, at least 10% by 150 °C, and 50% boiling between 220 °C and 280 °C.

Example 7. R-Pyoil with at Least 90% Boiling by 350 °C, at Least 10% by 150 °C, and 50% Boiling Between 220 °C and 280 °C A procedure similar to Example 8 was followed with fractions collected from 120 °C to 210 °C at atmospheric pressure and the remaining fractions (up to 300 °C, corrected to atmospheric pressure) under 75 torr vacuum to give a composition of 200 g with a boiling point curve described by FIG. 19.

Example 8. R-Pyoil with 90% Boiling Between 250-300 °C

Figure 20:
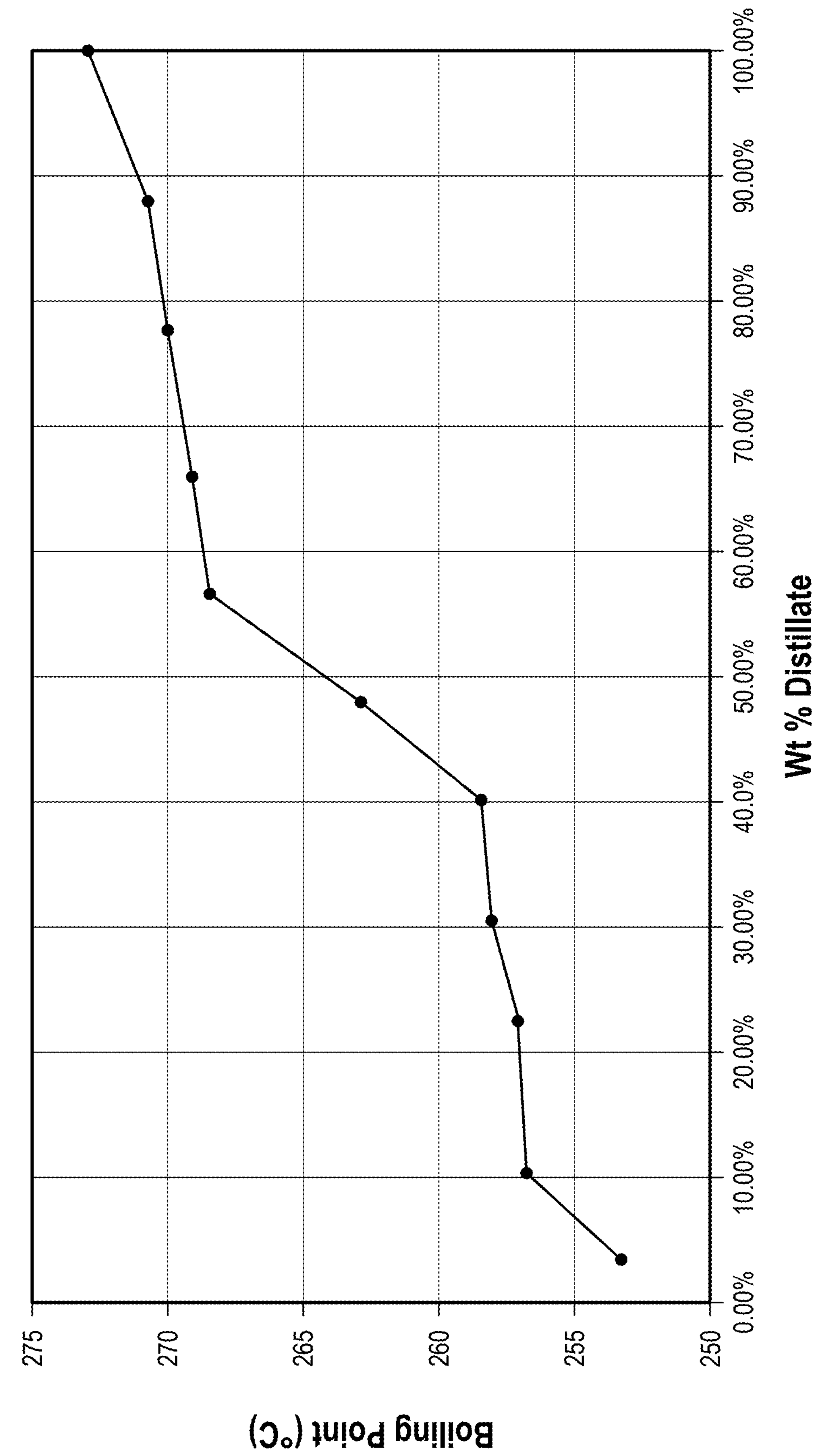
FIG. 20 is a graph of the boiling point curve of r-pyoil distilled in lab with 90% boiling between 250-300 °C.

Approximately 200 g of residuals from Example 6 were distilled through a 20-tray glass Oldershaw column fitted with glycol chilled condensers, thermowells containing thermometers, and a magnet operated reflux controller regulated by electronic timer. One neck of the base pot was fitted with a rubber septum, and a low flow $N_2$ purge was bubbled into the base mixture by means of an 18" long, 20-gauge steel thermometer. Batch distillation was conducted at 70 torr vacuum with a reflux rate of 1:2. Temperature measurement, pressure measurement, and timer control were provided by a Camille Laboratory Data Collection System. Liquid fractions were collected every 20 mL, and the overhead temperature and mass recorded. Overhead temperatures were corrected to atmospheric boiling point by means of the Clausius-Clapeyron Equation to construct the boiling curve presented in FIG. 20 below. Approximately 150 g of overhead material was collected.

Example 9. R-Pyoil with 50% Boiling Between 60-80 °C

Figure 21:
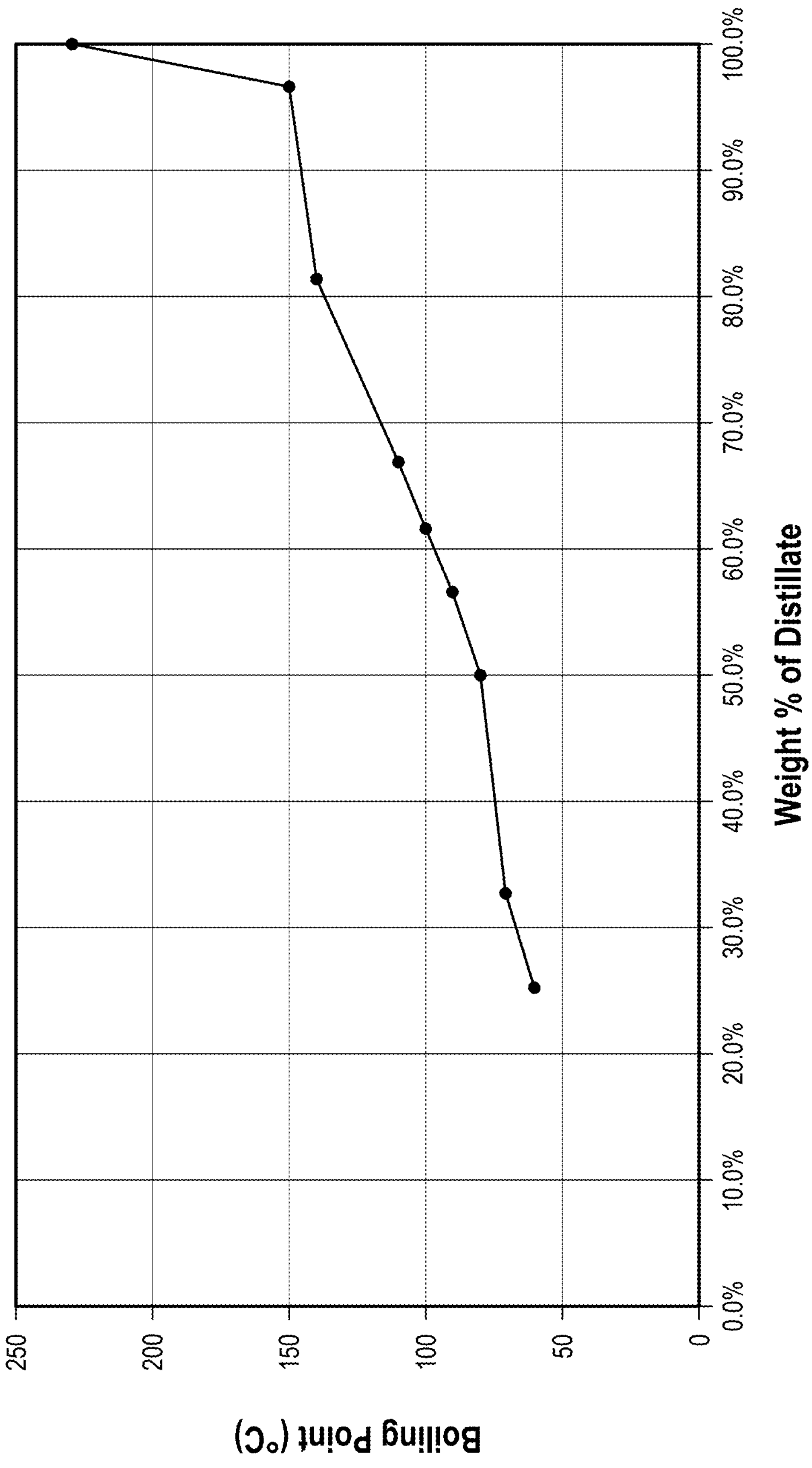
FIG. 21 is a graph of the boiling point curve of r-pyoil distilled in lab with 50% boiling between 60-80 °C.

A procedure similar to Example 5 was followed with fractions collected boiling between 60 °C and 230 °C to give a composition of 200 g with a boiling point curve described by FIG. 21.

Example 10. r-Pyoil with High Aromatic Content

Figure 22:
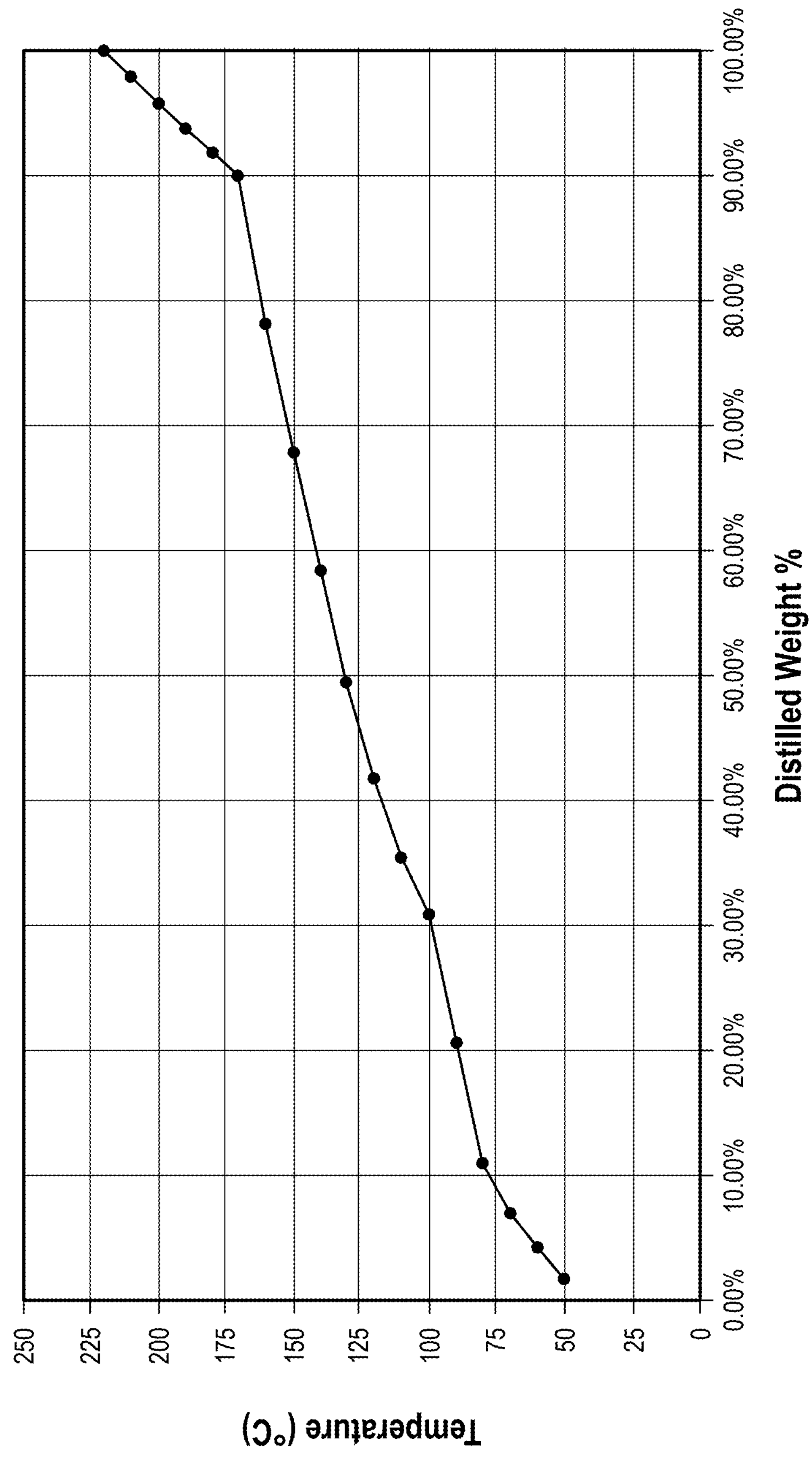
FIG. 22 is a graph of the boiling point curve of r-pyoil distilled in lab with 34.7% aromatic content.

A 250 g sample of r-pyoil with high aromatic content was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 10-20 mL, and the overhead temperature and mass recorded to construct the boiling curve presented in FIG. 22. The distillation ceased after approximately 200 g of material were collected. The material contains 34 weight percent aromatic content by gas chromatography analysis.

Table 2 shows the composition of Examples 5-10 by gas chromatography analysis.

TABLE 2

Gas Chromatography Analysis of r-Pyoil Examples 5-10.

| | r-Pyoil Examples | | | | | |
|---|---|---|---|---|---|---|
| Components | 5 | 6 | 7 | 8 | 9 | 10 |
| Propene | 0.00 | 0.00 | 0.00 | 0.00 | 0.00 | 0.00 |
| Propane | 0.00 | 0.10 | 0.00 | 0.00 | 0.00 | 0.00 |
| 1,3-r-Butadiene | 0.27 | 1.69 | 0.00 | 0.00 | 0.00 | 0.18 |
| Pentene | 0.44 | 1.43 | 0.00 | 0.00 | 0.00 | 0.48 |
| Pentane | 3.95 | 4.00 | 0.00 | 0.00 | 0.37 | 4.59 |
| Unknown 1 | 0.09 | 0.28 | 0.00 | 0.00 | 0.00 | 0.07 |
| 1,3-cyclopentadiene | 0.00 | 0.13 | 0.00 | 0.00 | 0.00 | 0.00 |
| 2-methyl-Pentene | 2.75 | 3.00 | 0.00 | 0.00 | 5.79 | 4.98 |
| 2-methyl-Pentane | 2.63 | 6.71 | 0.00 | 0.00 | 9.92 | 5.56 |
| Hexane | 0.75 | 4.77 | 0.00 | 0.00 | 11.13 | 3.71 |
| 2-methyl-1,3-cyclopentadiene | 0.00 | 0.20 | 0.00 | 0.00 | 0.96 | 0.30 |
| 1-methyl-1,3-cyclopentadiene | 0.00 | 0.00 | 0.00 | 0.00 | 0.00 | 0.00 |
| 2,4 dimethylpentene | 0.00 | 0.35 | 0.00 | 0.00 | 2.06 | 0.26 |
| Benzene | 0.00 | 0.24 | 0.00 | 0.00 | 1.11 | 0.26 |

TABLE 2-continued

Gas Chromatography Analysis of r-Pyoil Examples 5-10.

| Components | r-Pyoil Examples 5 | 6 | 7 | 8 | 9 | 10 |
|---|---|---|---|---|---|---|
| 5-methyl-1,3-cyclopentadiene | 0.00 | 0.09 | 0.00 | 0.00 | 0.15 | 0.15 |
| Heptene | 0.52 | 5.50 | 0.00 | 0.00 | 6.22 | 2.97 |
| Heptane | 0.13 | 7.35 | 0.17 | 0.00 | 10.16 | 6.85 |
| Toluene | 1.18 | 2.79 | 0.69 | 0.00 | 2.39 | 6.98 |
| 4-methylheptane | 2.54 | 2.46 | 3.29 | 0.00 | 1.16 | 3.92 |
| Octene | 3.09 | 4.72 | 2.50 | 0.00 | 0.48 | 2.62 |
| Octane | 5.77 | 6.27 | 3.49 | 0.00 | 0.65 | 4.50 |
| 2,4-dimethylheptene | 3.92 | 2.30 | 0.61 | 0.00 | 0.96 | 2.58 |
| 2,4-dimethylheptane | 9.47 | 5.80 | 1.30 | 0.00 | 3.74 | 0.00 |
| Ethylbenzene | 0.00 | 0.00 | 1.32 | 0.00 | 2.43 | 7.81 |
| m,p-xylene | 7.48 | 4.36 | 0.23 | 0.00 | 1.09 | 15.18 |
| Styrene | 0.90 | 1.80 | 0.40 | 0.00 | 2.32 | 1.47 |
| o-xylene | 0.28 | 0.00 | 0.12 | 0.00 | 0.00 | 0.00 |
| Nonane | 3.74 | 5.94 | 0.41 | 0.00 | 6.15 | 2.55 |
| Nonene | 1.45 | 3.87 | 0.84 | 0.00 | 2.53 | 1.14 |
| MW140 | 2.36 | 1.94 | 1.63 | 0.00 | 3.69 | 2.35 |
| Cumene | 1.30 | 1.23 | 0.54 | 0.00 | 2.13 | 2.43 |
| Decene/methylstyrene | 1.54 | 1.60 | 1.55 | 0.00 | 0.30 | 0.48 |
| Decane | 4.31 | 1.68 | 4.34 | 0.00 | 0.48 | 1.08 |
| Unknown 2 | 0.96 | 0.15 | 0.97 | 0.00 | 0.00 | 0.24 |
| Indene | 0.25 | 0.00 | 0.21 | 0.00 | 0.00 | 0.00 |
| Indane | 0.33 | 0.00 | 0.33 | 0.00 | 0.00 | 0.08 |
| C11 Alkene | 1.83 | 0.22 | 1.83 | 0.00 | 0.00 | 0.19 |
| C11 Alkane | 4.54 | 0.18 | 4.75 | 0.00 | 0.00 | 0.39 |
| C12 Alkene | 1.68 | 0.08 | 2.34 | 0.00 | 0.18 | 0.08 |
| Naphthalene | 0.09 | 0.00 | 0.11 | 0.00 | 0.00 | 0.00 |
| C12 Alkane | 4.28 | 0.09 | 6.14 | 0.00 | 0.84 | 0.16 |
| C13 Alkane | 4.11 | 0.00 | 6.80 | 3.32 | 0.68 | 0.08 |
| C13 Alkene | 1.67 | 0.00 | 2.85 | 0.38 | 0.37 | 0.00 |
| 2-methylnaphthalene | 0.70 | 0.00 | 0.00 | 0.93 | 0.14 | 0.00 |
| C14 Alkene | 0.08 | 0.00 | 1.81 | 3.52 | 0.00 | 0.00 |
| C14 Alkane | 0.14 | 0.09 | 6.20 | 14.12 | 0.00 | 0.00 |
| Acenaphthylene | 0.00 | 0.00 | 0.75 | 0.00 | 0.00 | 0.00 |
| C15 Alkene | 0.00 | 0.00 | 2.70 | 3.55 | 0.00 | 0.00 |
| C15 Alkane | 0.00 | 0.09 | 9.40 | 14.16 | 0.00 | 0.07 |
| C16 Alkene | 0.00 | 0.00 | 1.61 | 2.20 | 0.00 | 0.00 |
| C16 Alkane | 0.00 | 0.10 | 5.44 | 12.40 | 0.00 | 0.00 |
| C17 Alkene | 0.00 | 0.00 | 0.10 | 3.35 | 0.00 | 0.00 |
| C17 Alkane | 0.00 | 0.10 | 0.26 | 16.81 | 0.00 | 0.00 |
| C18 Alkene | 0.00 | 0.00 | 0.00 | 0.67 | 0.00 | 0.00 |
| C18 Alkane | 0.00 | 0.10 | 0.00 | 3.31 | 0.00 | 0.00 |
| C19 Alkane | 0.00 | 0.00 | 0.00 | 0.13 | 0.00 | 0.00 |
| C19 Alkene | 0.00 | 0.00 | 0.00 | 0.00 | 0.00 | 0.00 |
| C20 Alkene | 0.00 | 0.00 | 0.00 | 0.00 | 0.00 | 0.00 |
| C20 Alkane | 0.00 | 0.00 | 0.00 | 0.00 | 0.00 | 0.00 |
| C21 Alkene | 0.00 | 0.00 | 0.00 | 0.00 | 0.00 | 0.00 |
| Unidentified | 18.51 | 16.18 | 21.95 | 21.13 | 19.45 | 13.24 |
| Percent C4-C7 | 12.71 | 38.55 | 0.85 | 0.00 | 50.25 | 37.35 |
| Percent C8+ | 68.78 | 45.17 | 77.20 | 78.87 | 30.30 | 49.41 |
| Percent C15+ | 0.00 | 0.38 | 19.52 | 56.60 | 0.00 | 0.07 |
| Percent Aromatics | 14.04 | 12.02 | 6.27 | 0.93 | 11.90 | 34.70 |
| Percent Paraffins | 52.35 | 59.75 | 55.64 | 64.26 | 56.08 | 44.89 |

Examples 11-58 Involving Steam Cracking r-Pyoil in a Lab Unit

Figure 11:
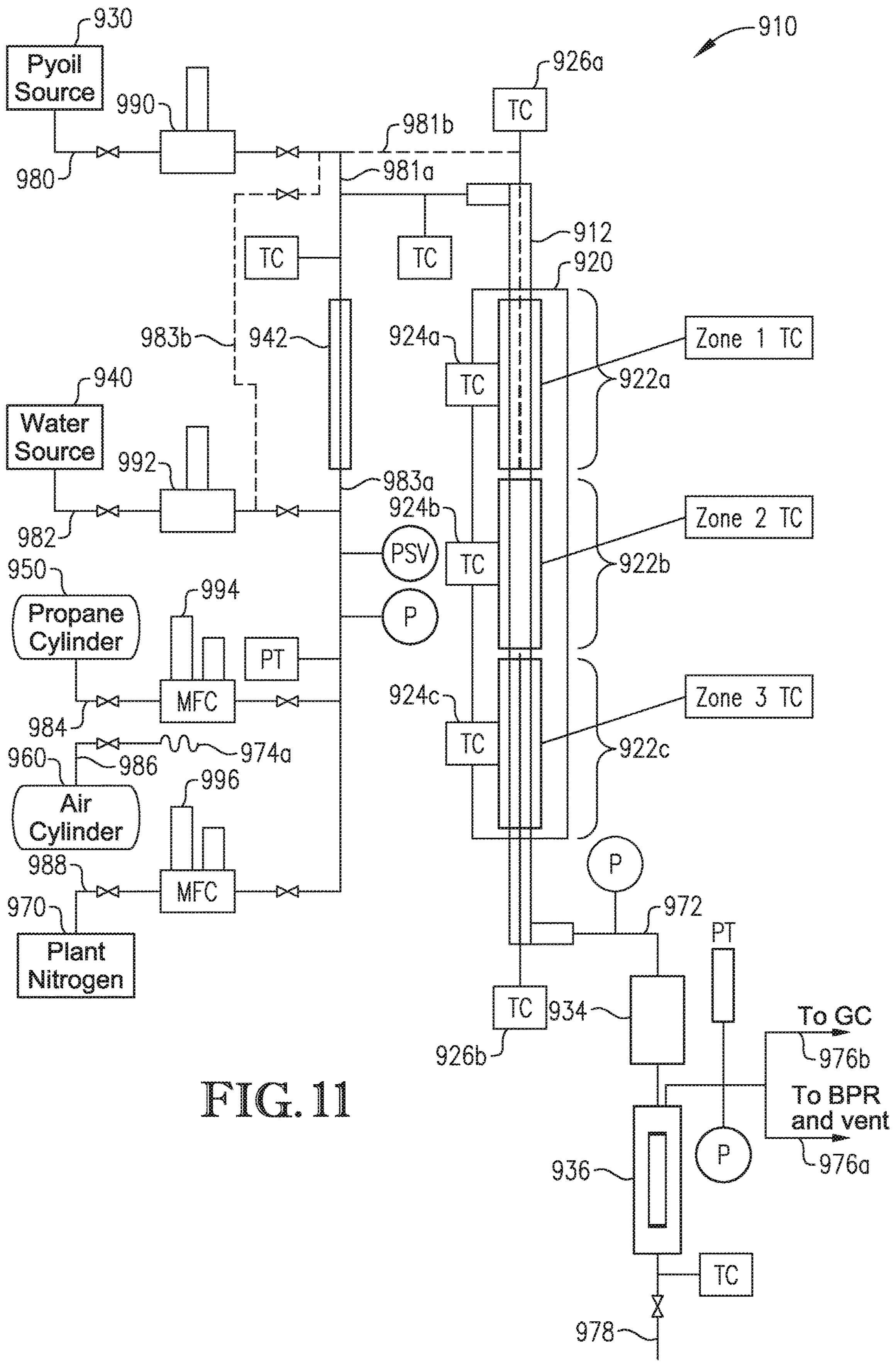
FIG. 11 illustrates the laboratory scale cracking unit design.

The invention is further illustrated by the following steam cracking examples. Examples were performed in a laboratory unit to simulate the results obtained in a commercial steam cracker. A drawing of the lab steam cracker is shown in FIG. 11. Lab Steam Cracker 910 consisted of a section of ⅜ inch Incoloy™tubing 912 that was heated in a 24-inch Applied Test Systems three zone furnace 920. Each zone (Zone 1 922*a*, Zone 2 922*b*, and Zone 3 922*c*) in the furnace was heated by a 7-inch section of electrical coils. Thermocouples 924*a*, 924*b*, and 924*c* were fastened to the external walls at the mid-point of each zone for temperature control of the reactor. Internal reactor thermocouples 926*a* and 926*b* were also placed at the exit of Zone 1 and the exit of Zone 2, respectively. The r-pyoil source 930 was fed through line 980 to Isco syringe pump 990 and fed to the reactor through line 981*a*. The water source 940 was fed through line 982 to ICSO syringe pump 992 and fed to preheater 942 through line 983*a* for conversion to steam prior to entering the reactor in line 981*a* with pyoil. A propane cylinder 950 was attached by line 984 to mass flow controller 994. The plant nitrogen source 970 was attached by line 988 to mass flow controller 996. The propane or nitrogen stream was fed through line 983*a* to preheater 942 to facilitate even steam generation prior to entering the reactor in line 981*a*. Quartz glass wool was placed in the 1 inch space between the three zones of the furnace to reduce temperature gradients between them. In an optional configuration, the top internal thermocouple 922*a* was removed for a few examples to feed r-pyoil either at the mid-point of Zone 1 or at the transition between Zone 1 and Zone 2 through a section of ⅛ inch diameter tubing. The dashed lines in FIG. 11 show the optional configurations. A heavier dashed line extends the feed point to the transition between Zone 1 and Zone 2. Steam was also optionally added at these positions in the reactor by feeding water from Isco syringe pump 992 through the dashed line 983*b*. r-Pyoil, and optionally steam, were then fed through dashed line 981*b* to the reactor. Thus, the reactor can be operated be feeding various combinations of components and at various locations. Typical operating conditions were heating the first zone to 600 °C, the second zone to about 700 °C, and the third zone to 375 °C while maintaining 3 psig at the reactor exit. Typical flow rates of hydrocarbon feed and steam resulted in a 0.5 sec residence time in one 7-inch section of the furnace. The first 7-inch section of the furnace 922*a* was operated as the convection zone and the second 7-inch section 922*b* as the radiant zone of a steam cracker. The gaseous effluent of the reactor exited the reactor through line 972. The stream was cooled with shell and tube condenser 934 and any condensed liquids were collected in glycol cooled sight glass 936. The liquid material was removed periodically through line 978 for weighing and gas chromatography analysis. The gas stream was fed through line 976*a* for venting through a back-pressure regulator that maintained about 3 psig on the unit. The flow rate was measured with a Sensidyne Gilian Gilibrator-2 Calibrator. Periodically a portion of the gas stream was sent in line 976*b* to a gas chromatography sampling system for analysis. The unit could be was operated in a decoking mode by physically disconnecting propane line 984 and attaching air cylinder 960 with line 986 and flexible tubing line 974*a* to mass flow controlled 994.

Analysis of reaction feed components and products was done by gas chromatography. All percentages are by weight unless specified otherwise. Liquid samples were analyzed on an Agilent 7890A using a Restek RTX-1 column (30 meters×320 micron ID, 0.5 micron film thickness) over a temperature range of 35 °C to 300 °C and a flame ionization detector. Gas samples were analyzed on an Agilent 8890 gas chromatograph. This GC was configured to analyze refinery gas up to C6 with $H_2S$ content. The system used four valves, three detectors, 2 packed columns, 3 micro-packed columns, and 2 capillary columns. The columns used were the following: 2 ft×1⁄16 in, 1 mm i.d. HayeSep A 80/100 mesh UltiMetal Plus 41 mm; 1.7 m×1⁄16 in, 1 mm i.d. HayeSep A 80/100 mesh UltiMetal Plus 41 mm; 2 m×1⁄16 in, 1 mm i.d. MolSieve 13X 80/100 mesh UltiMetal Plus 41 mm; 3 ft×⅛ in, 2.1 mm i.d. HayeSep Q 80/100 mesh in UltiMetal Plus; 8 ft×⅛ in, 2.1 mm i.d. Molecular Sieve 5A 60/80 mesh in UltiMetal Plus; 2 m×0.32 mm, Sum thickness DB-1 (123-1015, cut); 25 m×0.32 mm, 8 um thickness HP-AL/S (19091P-S12). The FID channel was configured to analyze the hydrocarbons with the capillary columns from $C_1$ to $C_5$, while C6/C6+ components are backflushed and measured as one peak at the beginning of the analysis. The first channel (reference gas He) was configured to analyze fixed gases (such as $CO_2$, CO, O2, N2, and $H_2S$). This channel was run isothermally, with all micro-packed columns installed inside a valve oven. The second TCD channel (third detector, reference gas N2) analyzed hydrogen through regular packed columns. The analyses from both chromatographs were combined based on the mass of each stream (gas and liquid where present) to provide an overall assay for the reactor.

A typical run was made as follows:

Nitrogen (130 sccm) was purged through the reactor system, and the reactor was heated (zone1, zone 2, zone 3 setpoints 300 °C, 450 °C, 300 °C, respectively). Preheaters and cooler for post-reactor liquid collection were powered on. After 15 minutes and the preheater was above 100 °C, 0.1 mL/min water was added to the preheater to generate steam. The reactor temperature setpoints were raised to 450 °C, 600 °C, and 350 °C for zones 1, 2, and 3, respectively. After another 10 minutes, the reactor temperature setpoints were raised to 600 °C, 700 °C, and 375 °C for zones 1, 2, and 3, respectively. The $N_2$ was decreased to zero as the propane flow was increased to 130 sccm. After 100 min at these conditions either r-pyoil or r-pyoil in naphtha was introduced, and the propane flow was reduced. The propane flow was 104 sccm, and the r-pyoil feed rate was 0.051 g/hr for a run with 80% propane and 20% r-pyoil. This material was steam cracked for 4.5 hr (with gas and liquid sampling). Then, 130 sccm propane flow was reestablished. After 1 hr, the reactor was cooled and purged with nitrogen.

Steam Cracking with r-Pyoil Example 1

Table 3 contains examples of runs made in the lab steam cracker with propane, r-pyoil from Example 1, and various weight ratios of the two. Steam was fed to the reactor in a 0.4 steam to hydrocarbon ratio in all runs. Nitrogen (5% by weight relative to the hydrocarbon) was fed with steam in the run with only r-pyoil to aid in even steam generation. Comparative Example 1 is an example involving cracking only propane.

TABLE 3

Steam Cracking Examples using r-pyoil from Example 1.

| Examples | Comparative Example 1 | 11 | 12 | 13 | 14 | 15 |
|---|---|---|---|---|---|---|
| Zone 2 Control Temp | 700 | 700 | 700 | 700 | 700 | 700 |
| Propane (wt %) | 100 | 85 | 80 | 67 | 50 | 0 |
| r-Pyoil (wt %) | 0 | 15 | 20 | 33 | 50 | 100* |
| Feed Wt, g/hr | 15.36 | 15.43 | 15.35 | 15.4 | 15.33 | 15.35 |
| Steam/Hydrocarbon Ratio | 0.4 | 0.4 | 0.4 | 0.4 | 0.4 | 0.4 |
| Total Accountability, % | 103.7 | 94.9 | 94.5 | 89.8 | 87.7 | 86 |
| Total Products | Weight Percent | | | | | |
| C6+ | 1.15 | 2.61 | 2.62 | 4.38 | 7.78 | 26.14 |
| methane | 18.04 | 18.40 | 17.68 | 17.51 | 17.52 | 12.30 |
| ethane | 2.19 | 2.59 | 2.46 | 2.55 | 2.88 | 2.44 |

TABLE 3-continued

| Steam Cracking Examples using r-pyoil from Example 1. | | | | | | |
|---|---|---|---|---|---|---|
| ethylene | 30.69 | 32.25 | 31.80 | 32.36 | 32.97 | 23.09 |
| propane | 24.04 | 19.11 | 20.25 | 16.87 | 11.66 | 0.33 |
| propylene | 17.82 | 17.40 | 17.63 | 16.80 | 15.36 | 7.34 |
| i-butane | 0.00 | 0.04 | 0.04 | 0.03 | 0.03 | 0.01 |
| n-butane | 0.03 | 0.02 | 0.02 | 0.02 | 0.02 | 0.02 |
| propydiene | 0.07 | 0.14 | 0.13 | 0.15 | 0.17 | 0.14 |
| acetylene | 0.24 | 0.40 | 0.40 | 0.45 | 0.48 | 0.41 |
| t-2-butene | 0.00 | 0.19 | 0.00 | 0.00 | 0.00 | 0.11 |
| 1-butene | 0.16 | 0.85 | 0.19 | 0.19 | 0.20 | 0.23 |
| i-butylene | 0.92 | 0.34 | 0.87 | 0.81 | 0.66 | 0.81 |
| c-2-butene | 0.12 | 0.15 | 0.40 | 0.56 | 0.73 | 0.11 |
| i-pentane | 0.13 | 0.00 | 0.00 | 0.00 | 0.00 | 0.00 |
| n-pentane | 0.00 | 0.01 | 0.01 | 0.02 | 0.02 | 0.02 |
| 1,3-butadiene | 1.73 | 2.26 | 2.31 | 2.63 | 3.02 | 2.88 |
| methyl acetylene | 0.20 | 0.26 | 0.26 | 0.30 | 0.32 | 0.28 |
| t-2-pentene | 0.11 | 0.08 | 0.12 | 0.12 | 0.12 | 0.05 |
| 2-methyl-2-butene | 0.02 | 0.01 | 0.03 | 0.03 | 0.02 | 0.02 |
| 1-pentene | 0.05 | 0.09 | 0.01 | 0.02 | 0.02 | 0.03 |
| c-2-pentene | 0.06 | 0.01 | 0.03 | 0.03 | 0.03 | 0.01 |
| pentadiene 1 | 0.00 | 0.01 | 0.02 | 0.02 | 0.02 | 0.08 |
| pentadiene 2 | 0.01 | 0.04 | 0.04 | 0.05 | 0.06 | 0.16 |
| pentadiene 3 | 0.12 | 0.21 | 0.23 | 0.27 | 0.30 | 0.26 |
| 1,3-Cyclopentadiene | 0.48 | 0.85 | 0.81 | 1.01 | 1.25 | 1.58 |
| pentadiene 4 | 0.00 | 0.08 | 0.08 | 0.09 | 0.10 | 0.07 |
| pentadiene 5 | 0.06 | 0.17 | 0.17 | 0.20 | 0.23 | 0.31 |
| CO2 | 0.00 | 0.00 | 0.00 | 0.00 | 0.00 | 0.00 |
| CO | 0.12 | 0.11 | 0.05 | 0.00 | 0.12 | 0.74 |
| hydrogen | 1.40 | 1.31 | 1.27 | 1.21 | 1.13 | 0.67 |
| Unidentified | 0.00 | 0.00 | 0.10 | 1.33 | 2.79 | 19.37 |
| Olefin/Aromatics Ratio | 45.42 | 21.07 | 20.91 | 12.62 | 7.11 | 1.42 |
| Total Aromatics | 1.15 | 2.61 | 2.62 | 4.38 | 7.78 | 26.14 |
| Propylene + Ethylene | 48.51 | 49.66 | 49.43 | 49.16 | 48.34 | 30.43 |
| Ethylene/Propylene Ratio | 1.72 | 1.85 | 1.80 | 1.93 | 2.15 | 3.14 |

*5% N2 was also added to facilitate steam generation. Analysis has been normalized to exclude it.

As the amount of r-pyoil used is increased relative to propane, there was an increase in the formation of dienes. For example, both r-butadiene and cyclopentadiene increased as more r-pyoil is added to the feed. Additionally, aromatics (C6+) increased considerably with increased r-pyoil in the feed.

Accountability decreased with increasing amounts of r-pyoil in these examples. It was determined that some r-pyoil in the feed was being held up in the preheater section. Due to the short run times, accountability was negatively affected. A slight increase in the slope of the reactor inlet line corrected the issue (see Example 24). Nonetheless, even with an accountability of 86% in Example 15, the trend was clear. The overall yield of r-ethylene and r-propylene decreased from about 50% to less than about 35% as the amount of r-pyoil in the feed increased. Indeed, feeding r-pyoil alone produced about 40% of aromatics (C6+) and unidentified higher boilers (see Example 15 and Example 24).

r-Ethylene Yield—r-Ethylene yield showed an increase from 30.7% to >32% as 15% r-pyoil was co-cracked with propane. The yield of r-ethylene then remained about 32% until >50% r-pyoil was used. With 100% r-pyoil, the yield of r-ethylene decreased to 21.5% due to a large amount of aromatics and unidentified high boilers (>40%). Since r-pyoil cracks faster than propane, a feed with an increased amount of r-pyoil will crack faster to more r-propylene. The r-propylene can then react to form r-ethylene, diene and aromatics. When the concentration of r-pyoil was increased the amount of r-propylene cracked products was also increased. Thus, the increased amount of dienes can react with other dienes and olefins (like r-ethylene) leading to even more aromatics formation. So, at 100% r-pyoil in the feed, the amount of r-ethylene and r-propylene recovered was lower due to the high concentration of aromatics that formed. In fact, the olefin/aromatic dropped from 45.4 to 1.4 as r-pyoil was increased to 100% in the feed. Thus, the yield of r-ethylene increased as more r-pyoil was added to the feed mixture, at least to about 50% r-pyoil. Feeding pyoil in propane provides a way to increase the ethylene/propylene ratio on a steam cracker.

r-Propylene Yield—r-Propylene yield decreased with more r-pyoil in the feed. It dropped from 17.8% with propane only to 17.4% with 15% r-pyoil and then to 6.8% as 100% r-pyoil was cracked. r-Propylene formation did not decrease in these cases. r-Pyoil cracks at lower temperature than propane. As r-propylene is formed earlier in the reactor it has more time to converted to other materials—like dienes and aromatics and r-ethylene. Thus, feeding r-pyoil with propane to a cracker provides a way to increase the yield of ethylene, dienes and aromatics.

The r-ethylene/r-propylene ratio increased as more r-pyoil was added to the feed because an increase concentration of r-pyoil made r-propylene faster, and the r-propylene reacted to other cracked products—like dienes, aromatics and r-ethylene.

The ethylene to propylene ratio increased from 1.72 to 3.14 going from 100% propane to 100% r-pyoil cracking. The ratio was lower for 15% r-pyoil (0.54) than 20% r-pyoil (0.55) due to experimental error with the small change in r-pyoil feed and the error from having just one run at each condition.

The olefin/aromatic ratio decreased from 45 with no r-pyoil in the feed to 1.4 with no propane in the feed. The decrease occurred mainly because r-pyoil cracked more readily than propane and thus more r-propylene was produced faster. This gave the r-propylene more time to react further—to make more r-ethylene, dienes, and aromatics.

Thus, aromatics increased, and r-propylene decreased with the olefin/aromatic ratio decreasing as a result.

r-Butadiene increased as the concentration of r-pyoil in the feed increased, thus providing a way to increase r-butadiene yield. r-Butadiene increased from 1.73% with propane cracking, to about 2.3% with 15-20% r-pyoil in the feed, to 2.63% with 33% r-pyoil, and to 3.02% with 50% r-pyoil. The amount was 2.88% at 100% r-pyoil. Example 24 showed 3.37% r-butadiene observed in another run with 100% r-pyoil. This amount may be a more accurate value based on the accountability problems that occurred in Example 15. The increase in r-butadiene was the result of more severity in cracking as products like r-propylene continued to crack to other materials.

Cyclopentadiene increased with increasing r-pyoil except for the decrease in going from 15%-20% r-pyoil (from 0.85 to 0.81). Again, some experimental error was likely. Thus, cyclopentadiene increased from 0.48% cracking propane only, to about 0.85% at 15-20% r-pyoil in the reactor feed, to 1.01% with 33% r-pyoil, to 1.25 with 50% r-pyoil, and 1.58% with 100% r-pyoil. The increase in cyclopentadiene was also the result of more severity in cracking as products like r-propylene continued to crack to other materials. Thus, cracking r-pyoil with propane provided a way to increase cyclopentadiene production.

Operating with r-pyoil in the feed to the steam cracker resulted in less propane in the reactor effluent. In commercial operation, this would result in a decreased mass flow in the recycle loop. The lower flow would decrease cryogenic energy costs and potentially increase capacity on the plant if it is capacity constrained. Additionally, lower propane in the recycle loop would debottleneck the r-propylene fractionator if it is already capacity limited.

Steam Cracking with r-Pyoil Examples 1-4

Table 4 contains examples of runs made with the r-pyoil samples found in Table1 with a propane/r-pyoil weight ratio of 80/20 and 0.4 steam to hydrocarbon ratio.

TABLE 4

Examples using r-PyOil Examples 1-4 under similar conditions.

| | Examples | | | |
|---|---|---|---|---|
| | 16 | 17 | 18 | 19 |
| | r-Pyoil from Table 1 | | | |
| | 1 | 2 | 3 | 4 |
| Zone 2 Control Temp | 700 | 700 | 700 | 700 |
| Propane (wt %) | 80 | 80 | 80 | 80 |
| r-Pyoil (wt %) | 20 | 20 | 20 | 20 |
| N2 (wt %) | 0 | 0 | 0 | 0 |
| Feed Wt, g/hr | 15.35 | 15.35 | 15.35 | 15.35 |
| Steam/Hydrocarbon Ratio | 0.4 | 0.4 | 0.4 | 0.4 |
| Total Accountability, % | 94.5 | 96.4 | 95.6 | 95.3 |
| Total Products | Weight Percent | | | |
| C6+ | 2.62 | 2.86 | 3.11 | 2.85 |
| methane | 17.68 | 17.36 | 17.97 | 17.20 |
| ethane | 2.46 | 2.55 | 2.67 | 2.47 |
| ethylene | 31.80 | 30.83 | 31.58 | 30.64 |
| propane | 20.25 | 21.54 | 19.34 | 21.34 |
| propylene | 17.63 | 17.32 | 17.18 | 17.37 |
| i-butane | 0.04 | 0.04 | 0.04 | 0.04 |
| n-butane | 0.02 | 0.01 | 0.02 | 0.03 |
| propadiene | 0.13 | 0.06 | 0.09 | 0.12 |
| acetylene | 0.40 | 0.11 | 0.26 | 0.37 |
| t-2-butene | 0.00 | 0.00 | 0.00 | 0.00 |
| 1-butene | 0.19 | 0.19 | 0.20 | 0.19 |
| i-butylene | 0.87 | 0.91 | 0.91 | 0.98 |
| c-2-butene | 0.40 | 0.44 | 0.45 | 0.52 |
| i-pentane | 0.00 | 0.14 | 0.16 | 0.16 |
| n-pentane | 0.01 | 0.03 | 0.03 | 0.03 |
| 1,3-butadiene | 2.31 | 2.28 | 2.33 | 2.27 |
| methyl acetylene | 0.26 | 0.23 | 0.23 | 0.24 |
| t-2-pentene | 0.12 | 0.13 | 0.14 | 0.13 |
| 2-methyl-2-butene | 0.03 | 0.04 | 0.04 | 0.03 |
| 1-pentene | 0.01 | 0.02 | 0.02 | 0.02 |
| c-2-pentene | 0.03 | 0.06 | 0.05 | 0.04 |
| pentadiene 1 | 0.02 | 0.00 | 0.00 | 0.00 |
| pentadiene 2 | 0.04 | 0.02 | 0.02 | 0.01 |
| pentadiene 3 | 0.23 | 0.17 | 0.00 | 0.25 |
| 1,3-Cyclopentadiene | 0.81 | 0.72 | 0.76 | 0.71 |
| pentadiene 4 | 0.08 | 0.00 | 0.00 | 0.00 |
| pentadiene 5 | 0.17 | 0.08 | 0.09 | 0.08 |
| CO2 | 0.00 | 0.00 | 0.00 | 0.00 |
| CO | 0.05 | 0.00 | 0.00 | 0.00 |
| hydrogen | 1.27 | 1.22 | 1.26 | 1.21 |
| Unidentified | 0.10 | 0.65 | 1.04 | 0.69 |
| Olefin/Aromatics Ratio | 20.91 | 18.66 | 17.30 | 18.75 |
| Total Aromatics | 2.62 | 2.86 | 3.11 | 2.85 |
| Propylene + Ethylene | 49.43 | 48.14 | 48.77 | 48.01 |
| Ethylene/Propylene Ratio | 1.80 | 1.78 | 1.84 | 1.76 |

Steam cracking of the different r-pyoil Examples 1~4 at the same conditions gave similar results. Even the lab distilled sample of r-pyoil (Example 19) cracked like the other samples. The highest r-ethylene and r-propylene yield was for Example 16, but the range was 48.01-49.43. The r-ethylene/r-propylene ratio varied from 1.76 to 1.84. The amount of aromatics (C6+) only varied from 2.62 to 3.11. Example 16 also produced the smallest yield of aromatics. The r-pyoil used for this example (r-Pyoil Example 1, Table 1) contained the largest amount of paraffins and the lowest amount of aromatics. Both are desirable for cracking to r-ethylene and r-propylene.

Steam Cracking with r-Pyoil Example 2

Table 5 contains runs made in the lab steam cracker with propane (Comparative Example 2), r-pyoil Example 2, and four runs with a propane/pyrolysis oil weight ratio of 80/20. Comparative Example 2 and Example 20 were run with a 0.2 steam to hydrocarbon ratio. Steam was fed to the reactor in a 0.4 steam to hydrocarbon ratio in all other examples. Nitrogen (5% by weight relative to the r-pyoil) was fed with steam in the run with only r-pyoil (Example 24).

TABLE 5

Examples using r-Pyoil Example 2.

| Examples | Comparative Example 2 | 20 | 21 | 22 | 23 | 24 |
|---|---|---|---|---|---|---|
| Zone 2 Control Temp | 700° C. | 700° C. | 700° C. | 700° C. | 700° C. | 700° C. |
| Propane (wt %) | 100 | 80 | 80 | 80 | 80 | 0 |
| r-Pyoil (wt %) | 0 | 20 | 20 | 20 | 20 | 100* |
| Feed Wt, g/hr | 15.36 | 15.35 | 15.35 | 15.35 | 15.35 | 15.35 |
| Steam/Hydrocarbon Ratio | 0.2 | 0.2 | 0.4 | 0.4 | 0.4 | 0.4 |
| Total Accountability, % | 100.3 | 93.8 | 99.1 | 93.4 | 96.4 | 97.9 |
| Total Products | | | Weight Percent | | | |
| C6+ | 1.36 | 2.97 | 2.53 | 2.98 | 2.86 | 22.54 |
| methane | 18.59 | 19.59 | 17.34 | 16.64 | 17.36 | 11.41 |
| ethane | 2.56 | 3.09 | 2.26 | 2.35 | 2.55 | 3.00 |
| ethylene | 30.70 | 32.51 | 31.19 | 29.89 | 30.83 | 24.88 |
| propane | 23.00 | 17.28 | 21.63 | 23.84 | 21.54 | 0.38 |
| propylene | 18.06 | 16.78 | 17.72 | 17.24 | 17.32 | 10.94 |
| i-butane | 0.04 | 0.03 | 0.03 | 0.05 | 0.04 | 0.02 |
| n-butane | 0.01 | 0.03 | 0.03 | 0.03 | 0.01 | 0.09 |
| propadiene | 0.05 | 0.10 | 0.12 | 0.12 | 0.06 | 0.12 |
| acetylene | 0.12 | 0.35 | 0.40 | 0.36 | 0.11 | 0.31 |
| t-2-butene | 0.00 | 0.00 | 0.00 | 0.00 | 0.00 | 0.00 |
| 1-butene | 0.17 | 0.20 | 0.18 | 0.18 | 0.19 | 0.25 |
| i-butylene | 0.87 | 0.80 | 0.91 | 0.94 | 0.91 | 1.22 |
| c-2-butene | 0.14 | 0.40 | 0.40 | 0.44 | 0.44 | 1.47 |
| i-pentane | 0.14 | 0.13 | 0.00 | 0.00 | 0.14 | 0.13 |
| n-pentane | 0.00 | 0.01 | 0.02 | 0.03 | 0.03 | 0.01 |
| 1,3-butadiene | 1.74 | 2.35 | 2.20 | 2.18 | 2.28 | 3.37 |
| methyl acetylene | 0.18 | 0.22 | 0.26 | 0.24 | 0.23 | 0.23 |
| t-2-pentene | 0.13 | 0.14 | 0.12 | 0.12 | 0.13 | 0.14 |
| 2-methyl-2-butene | 0.03 | 0.04 | 0.03 | 0.04 | 0.04 | 0.10 |
| 1-pentene | 0.01 | 0.03 | 0.01 | 0.01 | 0.02 | 0.05 |
| c-2-pentene | 0.04 | 0.04 | 0.03 | 0.04 | 0.06 | 0.18 |
| pentadiene 1 | 0.00 | 0.01 | 0.01 | 0.02 | 0.00 | 0.14 |
| pentadiene 2 | 0.01 | 0.02 | 0.03 | 0.02 | 0.02 | 0.19 |
| pentadiene 3 | 0.00 | 0.24 | 0.19 | 0.24 | 0.17 | 0.50 |
| 1,3-Cyclopentadiene | 0.52 | 0.83 | 0.65 | 0.71 | 0.72 | 1.44 |
| pentadiene 4 | 0.00 | 0.00 | 0.00 | 0.00 | 0.00 | 0.01 |
| pentadiene 5 | 0.06 | 0.09 | 0.08 | 0.08 | 0.08 | 0.15 |
| CO2 | 0.00 | 0.00 | 0.00 | 0.00 | 0.00 | 0.00 |
| CO | 0.07 | 0.00 | 0.00 | 0.00 | 0.00 | 0.19 |
| hydrogen | 1.36 | 1.28 | 1.28 | 1.21 | 1.22 | 0.63 |
| Unidentified | 0.00 | 0.00 | 0.34 | 0.00 | 0.65 | 15.89 |
| Olefin/Aromatics Ratio | 38.54 | 18.39 | 21.26 | 17.55 | 18.66 | 2.00 |
| Total Aromatics | 1.36 | 2.97 | 2.53 | 2.98 | 2.86 | 22.54 |
| Propylene +- Ethylene | 48.76 | 49.29 | 48.91 | 47.13 | 48.14 | 35.82 |
| Ethylene/Propylene Ratio | 1.70 | 1.94 | 1.76 | 1.73 | 1.78 | 2.27 |

*5% N2 was also added to facilitate steam generation. Analysis has been normalized to exclude it.

Comparing Example 20 to Examples 21-23 shows that the increased feed flow rate (from 192 sccm in Example 20 to 255 sccm with more steam in Examples 21-23) resulted in less conversion of propane and r-pyoil due to the 25% shorter residence time in the reactor (r-ethylene and r-propylene: 49.3% for Example 20 vs 47.1, 48.1, 48.9% for Examples 21-23). r-Ethylene was higher in Example 21 with the increased residence time since propane and r-pyoil cracked to higher conversion of r-ethylene and r-propylene and some of the r-propylene can then be converted to additional r-ethylene. And conversely, r-propylene was higher in the higher flow examples with a higher steam to hydrocarbon ratio (Example 21-23) since it has less time to continue reacting. Thus, Examples 21-23 produced a smaller amount of other components: r-ethylene, C6+(aromatics), r-butadiene, cyclopentadiene, etc., than found in Example 20.

Examples 21-23 were run at the same conditions and showed that there was some variability in operation of the lab unit, but it was sufficiently small that trends can be seen when different conditions are used.

Example 24, like example 15, showed that the r-propylene and r-ethylene yield decreased when 100% r-pyoil was cracked compared to feed with 20% r-pyoil. The amount decreased from about 48% (in Examples 21-23) to 36%. Total aromatics was greater than 20% of the product as in Example 15.

Steam Cracking with r-Pyoil Example 3

Table 6 contains runs made in the lab steam cracker with propane and r-pyoil Example 3 at different steam to hydrocarbon ratios.

TABLE 6

Examples using r-Pyoil Example 3.

| | Examples | |
|---|---|---|
| | 25 | 26 |
| Zone 2 Control Temp | 700° C | 700° C |
| Propane (wt %) | 80 | 80 |

TABLE 6-continued

Examples using r-Pyoil Example 3.

| | | |
|---|---|---|
| r-Pyoil (wt %) | 20 | 20 |
| N2 (wt %) | 0 | 0 |
| Feed Wt, g/hr | 15.33 | 15.33 |
| Steam/Hydrocarbon Ratio | 0.4 | 0.2 |
| Total Accountability, % | 95.6 | 92.1 |
| Total Products | Weight Percent | |
| C6+ | 3.11 | 3.42 |
| methane | 17.97 | 18.57 |
| ethane | 2.67 | 3.01 |
| ethylene | 31.58 | 31.97 |
| propane | 19.34 | 17.43 |
| propylene | 17.18 | 17.17 |
| i-butane | 0.04 | 0.04 |
| n-butane | 0.02 | 0.03 |
| propadiene | 0.09 | 0.10 |
| acetylene | 0.26 | 0.35 |
| t-2-butene | 0.00 | 0.00 |
| 1-butene | 0.20 | 0.20 |
| i-butylene | 0.91 | 0.88 |
| c-2-butene | 0.45 | 0.45 |
| i-pentane | 0.16 | 0.17 |
| n-pentane | 0.03 | 0.02 |
| 1,3-butadiene | 2.33 | 2.35 |
| methyl acetylene | 0.23 | 0.22 |
| t-2-pentene | 0.14 | 0.15 |
| 2-methyl-2-butene | 0.04 | 0.04 |
| 1-pentene | 0.02 | 0.02 |
| c-2-pentene | 0.05 | 0.04 |
| pentadiene 1 | 0.00 | 0.00 |
| pentadiene 2 | 0.02 | 0.02 |
| pentadiene 3 | 0.00 | 0.25 |
| 1,3-Cyclopentadiene | 0.76 | 0.84 |
| pentadiene 4 | 0.00 | 0.00 |
| pentadiene 5 | 0.09 | 0.10 |
| CO2 | 0.00 | 0.00 |
| CO | 0.00 | 0.00 |
| hydrogen | 1.26 | 1.24 |
| Unidentified | 1.04 | 0.92 |
| Olefin/Aromatics Ratio | 17.30 | 15.98 |
| Total Aromatics | 3.11 | 3.42 |
| Propylene + Ethylene | 48.77 | 49.14 |
| Ethylene/Propylene Ratio | 1.84 | 1.86 |

The same trends observed from cracking with r-pyoil Examples 1-2 were demonstrated for cracking with propane and r-pyoil Example 3. Example 25 compared to Example 26 showed that a decrease in the feed flow rate (to 192 sccm in Example 26 with less steam from 255 sccm in Example 25) resulted in greater conversion of the propane and r-pyoil due to the 25% greater residence time in the reactor (r-ethylene and r-propylene: 48.77% for Example 22 vs 49.14% for the lower flow in Example 26). r-Ethylene was higher in Example 26 with the increased residence time since propane and r-pyoil cracked to higher conversion of r-ethylene and r-propylene and some of the r-propylene was then converted to additional r-ethylene. Thus, Example 25, with the shorter residence time produced a smaller amount of other components: r-ethylene, C6+(aromatics), r-butadiene, cyclopentadiene, etc., than found in Example 26.

Steam Cracking with r-Pyoil Example 4

Table 7 contains runs made in the lab steam cracker with propane and pyrolysis oil sample 4 at two different steam to hydrocarbon ratios.

TABLE 7

Examples using Pyrolysis Oil Example 4.

| | Examples | |
|---|---|---|
| | 27 | 28 |
| Zone 2 Control Temp | 700° C | 700° C |
| Propane (wt %) | 80 | 80 |
| r-Pyoil (wt %) | 20 | 20 |
| N2 (wt %) | 0 | 0 |
| Feed Wt, g/hr | 15.35 | 15.35 |
| Steam/Hydrocarbon Ratio | 0.4 | 0.6 |
| Total Accountability, % | 95.3 | 95.4 |
| Total Products | Weight Percent | |
| C6+ | 2.85 | 2.48 |
| methane | 17.20 | 15.37 |
| ethane | 2.47 | 2.09 |
| ethylene | 30.64 | 28.80 |
| propane | 21.34 | 25.58 |
| propylene | 17.37 | 17.79 |
| i-butane | 0.04 | 0.05 |
| n-butane | 0.03 | 0.03 |
| propadiene | 0.12 | 0.12 |
| acetylene | 0.37 | 0.35 |
| t-2-butene | 0.00 | 0.00 |
| 1-butene | 0.19 | 0.19 |
| i-butylene | 0.98 | 1.03 |
| c-2-butene | 0.52 | 0.53 |
| i-pentane | 0.16 | 0.15 |
| n-pentane | 0.03 | 0.05 |
| 1,3-butadiene | 2.27 | 2.15 |
| methyl acetylene | 0.24 | 0.25 |
| t-2-pentene | 0.13 | 0.12 |
| 2-methyl-2-butene | 0.03 | 0.04 |
| 1-pentene | 0.02 | 0.02 |
| c-2-pentene | 0.04 | 0.05 |
| pentadiene 1 | 0.00 | 0.00 |
| pentadiene 2 | 0.01 | 0.02 |
| pentadiene 3 | 0.25 | 0.27 |
| 1,3-Cyclopentadiene | 0.71 | 0.65 |
| pentadiene 4 | 0.00 | 0.00 |
| pentadiene 5 | 0.08 | 0.08 |
| CO2 | 0.00 | 0.00 |
| CO | 0.00 | 0.00 |
| hydrogen | 1.21 | 1.15 |
| Unidentified | 0.69 | 0.63 |
| Olefin/Aromatics Ratio | 18.75 | 20.94 |
| Total Aromatics | 2.85 | 2.48 |
| Propylene + Ethylene | 48.01 | 46.59 |
| Ethylene/Propylene Ratio | 1.76 | 1.62 |

The results in Table 7 showed the same trends as discussed with Example 20 vs Examples 21-23 in Table 5 and Example 25 vs Example 26 in Table 6. At a smaller steam to hydrocarbon ratio, higher amounts of r-ethylene and r-propylene and higher amounts of aromatics were obtained at the increased residence time. The r-ethylene/r-propylene ratio was also greater.

Thus, comparing Example 20 with Examples 21-23 in Table 5, Example 25 with Example 26, and Example 27 with Example 28 showed the same effect. Decreasing the steam to hydrocarbon ratio decreased the total flow in the reactor. This increased the residence time. As a result, there was an increase in the amount of r-ethylene and r-propylene produced. The r-ethylene to r-propylene ratio was larger which indicated that some r-propylene reacted to other products like r-ethylene. There was also an increase in aromatics (C6+) and dienes.

Examples of Cracking r-Pyoils from Table 2 with Propane

Table 8 contains the results of runs made in the lab steam cracker with propane (Comparative example 3) and the six r-pyoil samples listed in Table 2. Steam was fed to the reactor in a 0.4 steam to hydrocarbon ratio in all runs.

Examples 30, 33, and 34 were the results of runs with r-pyoil having greater than 35% C4-C7. The r-pyoil used in Example 40 contained 34.7% aromatics. Comparative Example 3 was a run with propane only. Examples 29, 31, and 32 were the results of runs with r-pyoil containing less than 35% C4-C7.

for the 46.31% obtained with the r-pyoil with 34.7% aromatic content (using r-pyoil Example 10 in Example 34). Except for that difference, the r-pyoils performed similarly, and any of them can be fed with C-2 to C-4 in a steam cracker. r-Pyoils having high aromatic content like r-pyoil Example 10 may not be the preferred feed for a steam cracker, and a r-pyoil having less than about 20% aromatic

TABLE 8

Examples of steam cracking with propane and r-pyoils.

| Examples | Comparative Example 3 | 29 | 30 | 31 | 32 | 33 | 34 |
|---|---|---|---|---|---|---|---|
| r-Pyoil Feed from Table 2 | | 5 | 6 | 7 | 8 | 9 | 10 |
| Zone 2 Control Temp, ° C. | 700 | 700 | 700 | 700 | 700 | 700 | 700 |
| Propane (wt %) | 100 | 80 | 80 | 80 | 80 | 80 | 80 |
| r-Pyoil (wt %) | 0 | 20 | 20 | 20 | 20 | 20 | 20 |
| Feed Wt, g/hr | 15.36 | 15.32 | 15.33 | 15.33 | 15.35 | 15.35 | 15.35 |
| Steam/Hydrocarbon Ratio | 0.4 | 0.4 | 0.4 | 0.4 | 0.4 | 0.4 | 0.4 |
| Total Accountability, % | 103 | 100 | 100.3 | 96.7 | 96.3 | 95.7 | 97.3 |
| Total Products | Weight Percent | | | | | | |
| C6+ | 1.13 | 2.86 | 2.64 | 3.03 | 2.34 | 3.16 | 3.00 |
| methane | 17.69 | 17.17 | 15.97 | 17.04 | 16.42 | 18.00 | 16.41 |
| ethane | 2.27 | 2.28 | 2.12 | 2.26 | 2.59 | 2.63 | 2.19 |
| ethylene | 29.85 | 31.03 | 29.23 | 30.81 | 30.73 | 30.80 | 28.99 |
| propane | 24.90 | 21.86 | 25.13 | 21.70 | 23.79 | 20.99 | 24.57 |
| propylene | 18.11 | 17.36 | 17.78 | 17.23 | 18.08 | 17.90 | 17.32 |
| i-butane | 0.05 | 0.04 | 0.05 | 0.04 | 0.05 | 0.04 | 0.05 |
| n-butane | 0.02 | 0.02 | 0.04 | 0.02 | 0.00 | 0.00 | 0.02 |
| propadiene | 0.08 | 0.14 | 0.12 | 0.14 | 0.04 | 0.04 | 0.10 |
| acetylene | 0.31 | 0.42 | 0.36 | 0.42 | 0.04 | 0.06 | 0.31 |
| t-2-butene | 0.00 | 0.00 | 0.00 | 0.00 | 0.00 | 0.00 | 0.00 |
| 1-butene | 0.16 | 0.18 | 0.19 | 0.18 | 0.19 | 0.20 | 0.18 |
| i-butylene | 0.91 | 0.93 | 1.00 | 0.92 | 0.93 | 0.90 | 0.95 |
| c-2-butene | 0.13 | 0.51 | 0.50 | 0.50 | 0.34 | 0.68 | 0.61 |
| i-pentane | 0.14 | 0.00 | 0.15 | 0.00 | 0.16 | 0.16 | 0.15 |
| n-pentane | 0.00 | 0.04 | 0.05 | 0.04 | 0.00 | 0.00 | 0.06 |
| 1,3-butadiene | 1.64 | 2.28 | 2.15 | 2.26 | 2.48 | 2.23 | 2.04 |
| methyl acetylene | 0.19 | 0.28 | 0.24 | 0.28 | n/a | 0.24 | 0.24 |
| t-2-pentene | 0.12 | 0.12 | 0.12 | 0.12 | 0.13 | 0.13 | 0.11 |
| 2-methyl-2-butene | 0.03 | 0.03 | 0.03 | 0.03 | 0.04 | 0.03 | 0.03 |
| 1-pentene | 0.11 | 0.02 | 0.02 | 0.02 | 0.01 | 0.02 | 0.02 |
| c-2-pentene | 0.01 | 0.03 | 0.04 | 0.03 | 0.11 | 0.10 | 0.05 |
| pentadiene 1 | 0.00 | 0.02 | 0.00 | 0.02 | 0.00 | 0.00 | 0.00 |
| pentadiene 2 | 0.01 | 0.03 | 0.03 | 0.04 | 0.01 | 0.05 | 0.02 |
| pentadiene 3 | 0.14 | 0.25 | 0.00 | 0.25 | 0.00 | 0.00 | 0.00 |
| 1,3-Cyclopentadiene | 0.44 | 0.77 | 0.69 | 0.77 | 0.22 | 0.30 | 0.63 |
| pentadiene 4 | 0.00 | 0.00 | 0.00 | 0.00 | 0.00 | 0.00 | 0.00 |
| pentadiene 5 | 0.06 | 0.08 | 0.08 | 0.08 | 0.09 | 0.08 | 0.07 |
| CO2 | 0.00 | 0.00 | 0.00 | 0.00 | 0.00 | 0.00 | 0.00 |
| CO | 0.11 | 0.00 | 0.07 | 0.00 | 0.00 | 0.00 | 0.11 |
| hydrogen | 1.36 | 1.26 | 1.21 | 1.25 | 1.18 | 1.25 | 1.22 |
| unidentified | 0.00 | 0.00 | 0.00 | 0.52 | 0.00 | 0.00 | 0.56 |
| Olefin/Aromatics Ratio | 45.81 | 18.79 | 19.66 | 17.64 | 22.84 | 16.91 | 17.06 |
| Total Aromatics | 1.13 | 2.86 | 2.64 | 3.03 | 2.34 | 3.16 | 3.00 |
| Propylene + Ethylene | 47.96 | 48.39 | 47.01 | 48.04 | 48.82 | 48.70 | 46.31 |
| Ethylene/Propylene Ratio | 1.65 | 1.79 | 1.64 | 1.79 | 1.70 | 1.72 | 1.67 |

The examples in Table 8 involved using an 80/20 mix of propane with the various distilled r-pyoils. The results were like those in previous examples involving cracking r-pyoil with propane. All the examples produced an increase in aromatics and dienes relative to cracking propane only. As a result, the olefins to aromatic ratio was lower for cracking the combined feeds. The amount of r-propylene and r-ethylene produced was 47.01-48.82% for all examples except content should be considered a more preferred feed for co-cracking with ethane or propane.

Example of Steam Cracking r-Pyoils from Table 2 with Natural Gasoline

Table 9 contains the results of runs made in the lab steam cracker with a natural gasoline sample from a supplier and the r-pyoils listed in Table 2. The natural gasoline material was greater than 99% C5-C8 and contained greater than 70% identified paraffins and about 6% aromatics. The material had an initial boiling point of 100 °F, a 50% boiling point of 128 °F, a 95% boiling point of 208 °F, and a final boiling point of 240 °F. No component greater than C9 were identified in the natural gasoline sample. It was used as a typical naphtha stream for the examples.

The results presented in Table 9 include examples involving cracking the natural gasoline (Comparative example 4), or cracking a mixture of natural gasoline and the r-pyoil samples listed in Table 2. Steam was fed to the reactor in a 0.4 steam to hydrocarbon ratio in all runs. Nitrogen (5% by weight relative to the hydrocarbon) was fed with water to facilitate even steam generation. Examples 35, 37, and 38 involved runs with r-pyoils containing very little C15+. Example 38 illustrated the results of a run with greater than 50% C15+ in the r-pyoil.

The gas flow of the reactor effluent and the gas chromatography analysis of the stream were used to determine the weight of gas product, and then the weight of other liquid material needed for 100% accountability was calculated. This liquid material was typically 50-75% aromatics, and more typically 60-70%. An actual assay of the liquid sample was difficult for these examples. The liquid product in most of these examples was an emulsion that was hard to separate and assay. Since the gas analysis was reliable, this method allowed an accurate comparison of the gaseous products while still having an estimate of the liquid product if it was completely recovered.

TABLE 9

Results of Cracking r-Pyoil with Natural Gasoline.

| Examples | Comparative Example 4 | 35 | 36 | 37 | 38 | 39 | 40 |
|---|---|---|---|---|---|---|---|
| r-Pyoil Feed from Table 2 | Natural Gasoline | 5 | 6 | 7 | 8 | 9 | 10 |
| Zone 2 Control Temp | 700 | 700 | 700 | 700 | 700 | 700 | 700 |
| Natural Gasoline (wt %) | 100 | 80 | 80 | 80 | 80 | 80 | 80 |
| r-Pyoil (wt %) | 0 | 20 | 20 | 20 | 20 | 20 | 20 |
| N2 (wt %) | 5* | 5* | 5* | 5* | 5* | 5* | 5* |
| Feed Wt, g/hr | 15.4 | 15.3 | 15.4 | 15.4 | 15.4 | 15.4 | 15.4 |
| Gas Exit Flow, sccm | 221.2 | 206.7 | 204.5 | 211.8 | 211.3 | 202.6 | 207.8 |
| Gas Weight Accountability, % | 92.5 | 83.1 | 81.5 | 79.9 | 83.9 | 81.7 | 84.3 |
| Total Products | Weight Percent | | | | | | |
| C6+ | 9.54 | 7.86 | 6.32 | 8.05 | 7.23 | 7.15 | 5.75 |
| methane | 19.19 | 18.33 | 16.98 | 17.80 | 19.46 | 17.88 | 15.67 |
| ethane | 3.91 | 3.91 | 3.24 | 3.86 | 4.02 | 3.52 | 2.77 |
| ethylene | 27.34 | 26.14 | 28.24 | 24.96 | 27.74 | 26.42 | 29.39 |
| propane | 0.42 | 0.40 | 0.38 | 0.36 | 0.37 | 0.37 | 0.42 |
| propylene | 12.97 | 12.49 | 13.61 | 10.87 | 11.80 | 12.34 | 16.10 |
| i-butane | 0.03 | 0.03 | 0.03 | 0.02 | 0.02 | 0.02 | 0.03 |
| n-butane | 0.11 | 0.07 | 0.00 | 0.05 | 0.00 | 0.05 | 0.00 |
| propadiene | 0.22 | 0.18 | 0.10 | 0.18 | 0.08 | 0.22 | 0.11 |
| acetylene | 0.40 | 0.34 | 0.11 | 0.33 | 0.09 | 0.41 | 0.13 |
| t-2-butene | 0.00 | 0.00 | 0.00 | 0.00 | 0.00 | 0.00 | 0.00 |
| 1-butene | 0.44 | 0.39 | 0.40 | 0.32 | 0.38 | 0.39 | 0.46 |
| i-butylene | 0.91 | 0.89 | 0.91 | 0.65 | 0.76 | 0.86 | 1.30 |
| c-2-butene | 2.98 | 2.85 | 2.98 | 2.28 | 2.58 | 2.94 | 3.58 |
| i-pentane | 0.08 | 0.03 | 0.02 | 0.05 | 0.04 | 0.03 | 0.02 |
| n-pentane | 5.55 | 1.95 | 0.84 | 2.21 | 1.72 | 1.45 | 1.33 |
| 1,3-butadiene | 3.17 | 3.09 | 3.77 | 2.94 | 3.54 | 3.48 | 3.78 |
| methyl acetylene | 0.37 | 0.32 | 0.40 | 0.31 | 0.36 | 0.39 | n/a |
| t-2-pentene | 0.14 | 0.12 | 0.12 | 0.12 | 0.14 | 0.12 | 0.12 |
| 2-methyl-2-butene | 0.07 | 0.06 | 0.04 | 0.07 | 0.08 | 0.07 | 0.06 |
| 1-pentene | 0.10 | 0.08 | 0.08 | 0.09 | 0.11 | 0.10 | 0.09 |
| c-2-pentene | 0.20 | 0.17 | 0.07 | 0.19 | 0.12 | 0.09 | 0.08 |
| pentadiene 1 | 0.35 | 0.12 | 0.02 | 0.19 | 0.13 | 0.09 | 0.06 |
| pentadiene 2 | 0.80 | 0.52 | 0.16 | 0.59 | 0.54 | 0.40 | 0.29 |
| pentadiene 3 | 0.48 | 0.10 | 0.00 | 0.46 | 0.00 | 0.00 | 0.00 |
| 1,3-Cyclopentadiene | 1.03 | 1.00 | 0.56 | 0.98 | 0.56 | 1.09 | 0.56 |
| pentadiene 4 | 0.00 | 0.00 | 0.00 | 0.00 | 0.00 | 0.00 | 0.00 |
| pentadiene 5 | 0.11 | 0.11 | 0.13 | 0.10 | 0.13 | 0.12 | 0.00 |
| CO2 | 0.01 | 0.00 | 0.00 | 0.00 | 0.00 | 0.00 | 0.00 |
| CO | 0.00 | 0.00 | 0.10 | 0.00 | 0.00 | 0.06 | 0.13 |
| hydrogen | 1.00 | 0.92 | 0.94 | 0.87 | 0.95 | 0.93 | 1.03 |
| Other High Boilers-calculated** | 8.09 | 17.54 | 19.45 | 21.12 | 17.06 | 19.01 | 16.75 |
| C6+ and Other Calculated High Boilers | 17.63 | 25.40 | 25.77 | 29.17 | 24.28 | 26.17 | 22.50 |
| Ethylene and Propylene | 40.31 | 38.63 | 41.86 | 35.83 | 39.54 | 38.76 | 45.48 |
| Ethylene/Propylene Ratio | 2.11 | 2.09 | 2.07 | 2.30 | 2.35 | 2.14 | 1.83 |
| Olefin/Aromatics in gas effluent | 5.38 | 6.15 | 8.10 | 5.59 | 6.74 | 6.81 | 9.74 |

*5% Nitrogen was also added to facilitate steam generation. Analysis has been normalized to exclude it.

**Calculated theoretical amount needed for 100% accountability based on the actual reactor effluent gas flow rate and gas chromatography analysis.

The cracking examples in Table 9 involved using an 80/20 mix of natural gasoline with the various distilled r-pyoils. The natural gasoline and r-pyoils examples produced an increase in C6+(aromatics), unidentified high boilers, and dienes relative to cracking propane only or r-pyoil and propane (see Table 8). The increase in aromatics in the gas phase was about double compared to cracking 20% by weight r-pyoil with propane. Since the liquid product was typically greater than 60% aromatics, the total amount of aromatics was probably 5 times greater than cracking 20% by weight r-pyoil with propane. The amount of r-propylene and r-ethylene produced was generally lower by about 10%. The r-ethylene and r-propylene yield ranged from 35.83-41.86% for all examples except for the 45.48% obtained with high aromatic r-pyoil (using Example 10 material in Example 40). This is almost in the range of the yields obtained from cracking r-pyoil and propane (46.3-48.8% in Table 7). Example 40 produced the highest amount of r-propylene (16.1%) and the highest amount of r-ethylene (29.39%). This material also produced the lowest r-ethylene/r-propylene ratio which suggests that there was less conversion of r-propylene to other products than in the other examples. This result was unanticipated. The high concentration of aromatics (34.7%) in the r-pyoil feed appeared to inhibit further reaction of r-propylene. It is thought that r-pyoils having an aromatic content of 25-50% will see similar results. Co-cracking this material with natural gasoline also produced the lowest amount of C6+ and unidentified high boilers, but this stream produced the most r-butadiene. The natural gasoline and r-pyoil both cracked easier than propane so the r-propylene that formed reacted to give the increase in r-ethylene, aromatics, dienes, and others. Thus, the r-ethylene/r-propylene ratio was above 2 in all these examples, except in Example 40. The ratio in this example (1.83) was similar to the 1.65-1.79 range observed in Table 8 for cracking r-pyoil and propane. Except for these differences, the r-pyoils performed similarly and any of them can be fed with naphtha in a steam cracker.

Steam Cracking r-Pyoil with Ethane

Table 10 shows the results of cracking ethane and propane alone, and cracking with r-pyoil Example 2. The examples from cracking either ethane or ethane and r-pyoil were operated at three Zone 2 control temperatures: 700 °C, 705 °C, and 710 °C.

TABLE 10

Examples of Cracking Ethane and r-pyoil at different temperatures.

| Examples | Comparative Example 5 | 41 | Comparative Example 6 | 42 | Comparative Example 7 | 43 | Comparative Example 3 | Comparative Example 8 |
|---|---|---|---|---|---|---|---|---|
| Zone 2 Control Temp | 700° C. | 700° C. | 705° C. | 705° C. | 710° C. | 710° C. | 700° C. | 700° C. |
| Propane or Ethane in Feed | Ethane | Ethane | Ethane | Ethane | Ethane | Ethane | Propane | Propane |
| Propane or Ethane (wt %) | 100 | 80 | 100 | 80 | 100 | 80 | 100 | 80 |
| r-Pyoil (wt %) | 0 | 20 | 0 | 20 | 0 | 20 | 0 | 20 |
| Feed Wt, g/hr | 10.48 | 10.47 | 10.48 | 10.47 | 10.48 | 10.47 | 15.36 | 15.35 |
| Steam/Hydrocarbon Ratio | 0.4 | 0.4 | 0.4 | 0.4 | 0.4 | 0.4 | 0.4 | 0.4 |
| Total Accountability, % | 107.4 | 94.9 | 110.45 | 97.0 | 104.4 | 96.8 | 103.0 | 96.4 |
| Total Products | Weight Percent | | | | | | | |
| C6+ | 0.22 | 1.42 | 0.43 | 2.18 | 0.64 | 2.79 | 1.13 | 2.86 |
| methane | 1.90 | 6.41 | 2.67 | 8.04 | 3.69 | 8.80 | 17.69 | 17.36 |
| ethane | 46.36 | 39.94 | 38.75 | 33.77 | 32.15 | 26.82 | 2.27 | 2.55 |
| ethylene | 44.89 | 44.89 | 51.27 | 48.53 | 55.63 | 53.41 | 29.85 | 30.83 |
| propane | 0.08 | 0.18 | 0.09 | 0.18 | 0.10 | 0.16 | 24.90 | 21.54 |
| propylene | 0.66 | 2.18 | 0.84 | 1.99 | 1.03 | 1.86 | 18.11 | 17.32 |
| i-butane | 0.00 | 0.00 | 0.00 | 0.00 | 0.00 | 0.00 | 0.05 | 0.04 |
| n-butane | 0.00 | 0.00 | 0.00 | 0.00 | 0.00 | 0.00 | 0.02 | 0.01 |
| propadiene | 0.41 | 0.26 | 0.37 | 0.22 | 0.31 | 0.19 | 0.08 | 0.06 |
| acetylene | 0.00 | 0.01 | 0.00 | 0.01 | 0.00 | 0.01 | 0.31 | 0.11 |
| t-2-butene | 0.00 | 0.00 | 0.00 | 0.00 | 0.00 | 0.00 | 0.00 | 0.00 |
| 1-butene | 0.04 | 0.07 | 0.05 | 0.07 | 0.06 | 0.07 | 0.16 | 0.19 |
| i-butylene | 0.00 | 0.15 | 0.00 | 0.15 | 0.00 | 0.14 | 0.91 | 0.91 |
| c-2-butene | 0.12 | 0.19 | 0.13 | 0.11 | 0.13 | 0.08 | 0.13 | 0.44 |
| i-pentane | 0.59 | 0.05 | 0.04 | 0.06 | 0.05 | 0.06 | 0.14 | 0.14 |
| n-pentane | 0.01 | 0.01 | 0.00 | 0.00 | 0.00 | 0.00 | 0.00 | 0.03 |
| 1,3-butadiene | 0.96 | 1.45 | 1.34 | 1.69 | 1.72 | 2.06 | 1.64 | 2.28 |
| methyl acetylene | n/a | n/a | n/a | n/a | n/a | n/a | 0.19 | 0.23 |
| t-2-pentene | 0.03 | 0.04 | 0.02 | 0.04 | 0.03 | 0.05 | 0.12 | 0.13 |
| 2-methyl-2-butene | 0.02 | 0.00 | 0.03 | 0.00 | 0.03 | 0.00 | 0.03 | 0.04 |
| 1-pentene | 0.00 | 0.00 | 0.00 | 0.00 | 0.00 | 0.00 | 0.11 | 0.02 |
| c-2-pentene | 0.03 | 0.04 | 0.03 | 0.04 | 0.03 | 0.03 | 0.01 | 0.06 |
| pentadiene 1 | 0.00 | 0.00 | 0.00 | 0.00 | 0.00 | 0.00 | 0.00 | 0.00 |
| pentadiene 2 | 0.00 | 0.00 | 0.00 | 0.00 | 0.00 | 0.00 | 0.01 | 0.02 |
| pentadiene 3 | 0.00 | 0.00 | 0.00 | 0.00 | 0.00 | 0.00 | 0.14 | 0.17 |
| 1,3-Cyclopentadiene | 0.03 | 0.06 | 0.02 | 0.05 | 0.02 | 0.05 | 0.44 | 0.72 |
| pentadiene 4 | 0.00 | 0.00 | 0.00 | 0.00 | 0.00 | 0.00 | 0.00 | 0.00 |
| pentadiene 5 | 0.00 | 0.03 | 0.00 | 0.03 | 0.00 | 0.03 | 0.06 | 0.08 |
| CO2 | 0.00 | 0.00 | 0.00 | 0.00 | 0.00 | 0.00 | 0.00 | 0.00 |
| CO | 0.00 | 0.00 | 0.00 | 0.00 | 0.00 | 0.00 | 0.11 | 0.00 |
| hydrogen | 3.46 | 2.66 | 3.94 | 2.90 | 4.36 | 3.43 | 1.36 | 1.22 |
| unidentified | 0.00 | 0.00 | 0.00 | 0.00 | 0.00 | 0.00 | 0.00 | 0.65 |
| Olefin/Aromatics | 216.63 | 34.87 | 126.61 | 24.25 | 91.78 | 20.80 | 45.81 | 18.66 |

TABLE 10-continued

| Examples of Cracking Ethane and r-pyoil at different temperatures. | | | | | | | | |
|---|---|---|---|---|---|---|---|---|
| Total Aromatics | 0.22 | 1.42 | 0.43 | 2.18 | 0.64 | 2.79 | 1.13 | 2.86 |
| Propylene + Ethylene | 45.56 | 47.07 | 52.11 | 50.52 | 56.65 | 55.28 | 47.96 | 48.14 |
| Ethylene/Propylene Ratio | 67.53 | 20.59 | 60.95 | 24.44 | 54.13 | 28.66 | 1.65 | 1.78 |

A limited number of runs with ethane were made. As can be seen in the Comparative Examples 5-7 and Comparative Example 3, conversion of ethane to products occurred more slowly than with propane. Comparative Example 5 with ethane and Comparative Example 3 with propane were run at the same molar flow rates and temperatures. However, conversion of ethane was only 52% (100%— 46% ethane in product) vs 75% for propane. However, the r-ethylene/r-propylene ratio was much higher (67.53 vs 1.65) as ethane cracking produced mainly r-ethylene. The olefin to aromatics ratio for ethane cracking was also much higher for ethane cracking. The Comparative Examples 5-7 and Examples 41-43 compare cracking ethane to an 80/20 mixture of ethane and r-pyoil at 700 °C, 705 °C and 710 °C Production of total r-ethylene plus r-propylene increased with both ethane feed and the combined feed when the temperature was increased (an increase from about 46% to about 55% for both). Although the r-ethylene to r-propylene ratio decreased for ethane cracking with increasing temperature (from 67.53 at 700 °C to 60.95 at 705 °C to 54.13 at 710 °C), the ratio increased for the mixed feed (from 20.59 to 24.44 to 28.66). r-Propylene was produced from the r-pyoil and some continued to crack generating more cracked products such as r-ethylene, dienes and aromatics. The amount of aromatics in propane cracking with r-pyoil at 700 °C (2.86% in Comparative Example 8) was about the same as cracking ethane and r-pyoil at 710 °C (2.79% in Example 43).

Co-cracking ethane and r-pyoil required higher temperature to obtain more conversion to products compared to co-cracking with propane and r-pyoil. Ethane cracking produced mainly r-ethylene. Since a high temperature was required to crack ethane, cracking a mixture of ethane and r-pyoil produced more aromatics and dienes as some r-propylene reacted further. Operation in this mode would be appropriate if aromatics and dienes were desired with minimal production of r-propylene.

Examples of Cracking r-Pyoil and Propane 5 °C Higher or Lower than Cracking Propane Table 11 contains runs made in the lab steam cracker with propane at 695 °C, 700 °C, and 705 °C (Comparative examples 3, 9-10) and Examples 44-46 using 80/20 propane/r-pyoil weight ratios at these temperatures. Steam was fed to the reactor in a 0.4 steam to hydrocarbon ratio in all runs. r-Pyoil Example 2 was cracked with propane in these examples.

TABLE 11

Examples using r-Pyoil Example 2 at 700° C. +/− 5° C.

| Examples | Comparative Example 9 | Comparative Example 3 | Comparative Example 10 | 44 | 45 | 46 |
|---|---|---|---|---|---|---|
| Zone 2 Control Temp, ° C. | 695 | 700 | 705 | 695 | 700 | 705 |
| Propane (wt %) | 100 | 100 | 100 | 80 | 80 | 80 |
| r-Pyoil Example 2 (wt %) | 0 | 0 | 0 | 20 | 20 | 20 |
| Zone 2 Exit Temp, ° C. | 683 | 689 | 695 | 685 | 691 | 696 |
| Feed Wt, g/hr | 15.36 | 15.36 | 15.36 | 15.35 | 15.35 | 15.35 |
| Steam/Hydrocarbon Ratio | 0.4 | 0.4 | 0.4 | 0.4 | 0.4 | 0.4 |
| Total Accountability, % | 105 | 103 | 100.2 | 99.9 | 96.4 | 94.5 |
| **Total Products** | | | **Weight Percent** | | | |
| C6+ | 0.76 | 1.13 | 1.58 | 2.44 | 2.86 | 4.02 |
| methane | 15.06 | 17.69 | 20.02 | 14.80 | 17.36 | 19.33 |
| ethane | 1.92 | 2.27 | 2.49 | 2.20 | 2.55 | 2.63 |
| ethylene | 25.76 | 29.85 | 33.22 | 27.14 | 30.83 | 33.06 |
| propane | 33.15 | 24.90 | 18.96 | 28.21 | 21.54 | 15.38 |
| propylene | 18.35 | 18.11 | 16.61 | 17.91 | 17.32 | 15.43 |
| i-butane | 0.05 | 0.05 | 0.03 | 0.06 | 0.04 | 0.03 |
| n-butane | 0.02 | 0.02 | 0.02 | 0.03 | 0.01 | 0.02 |
| propadiene | 0.07 | 0.08 | 0.10 | 0.10 | 0.06 | 0.12 |
| acetylene | 0.22 | 0.31 | 0.42 | 0.27 | 0.11 | 0.47 |
| t-2-butene | 0.00 | 0.00 | 0.00 | 0.00 | 0.00 | 0.00 |
| 1-butene | 0.15 | 0.16 | 0.16 | 0.19 | 0.19 | 0.17 |
| i-butylene | 0.95 | 0.91 | 0.80 | 1.01 | 0.91 | 0.72 |
| c-2-butene | 0.11 | 0.13 | 0.13 | 0.49 | 0.44 | 0.33 |
| i-pentane | 0.12 | 0.14 | 0.13 | 0.15 | 0.14 | 0.12 |
| n-pentane | 0.00 | 0.00 | 0.00 | 0.02 | 0.03 | 0.02 |
| 1,3-butadiene | 1.22 | 1.64 | 2.00 | 1.93 | 2.28 | 2.39 |
| methyl acetylene | 0.14 | 0.19 | 0.23 | 0.20 | 0.23 | 0.26 |
| t-2-pentene | 0.11 | 0.12 | 0.12 | 0.12 | 0.13 | 0.12 |

TABLE 11-continued

| Examples using r-Pyoil Example 2 at 700° C. +/− 5° C. | | | | | | |
|---|---|---|---|---|---|---|
| 2-methyl-2-butene | 0.02 | 0.03 | 0.02 | 0.04 | 0.04 | 0.03 |
| 1-pentene | 0.11 | 0.11 | 0.05 | 0.02 | 0.02 | 0.01 |
| c-2-pentene | 0.01 | 0.01 | 0.06 | 0.04 | 0.06 | 0.03 |
| pentadiene 1 | 0.00 | 0.00 | 0.00 | 0.01 | 0.00 | 0.00 |
| pentadiene 2 | 0.00 | 0.01 | 0.01 | 0.01 | 0.02 | 0.01 |
| pentadiene 3 | 0.12 | 0.14 | 0.16 | 0.24 | 0.17 | 0.22 |
| 1,3-Cyclopentadiene | 0.30 | 0.44 | 0.59 | 0.59 | 0.72 | 0.83 |
| pentadiene 4 | 0.00 | 0.00 | 0.00 | 0.00 | 0.00 | 0.00 |
| pentadiene 5 | 0.05 | 0.06 | 0.06 | 0.07 | 0.08 | 0.08 |
| CO2 | 0.00 | 0.00 | 0.00 | 0.00 | 0.00 | 0.00 |
| CO | 0.00 | 0.11 | 0.47 | 0.00 | 0.00 | 0.00 |
| hydrogen | 1.21 | 1.36 | 1.50 | 1.09 | 1.22 | 1.32 |
| unidentified | 0.00 | 0.00 | 0.00 | 0.61 | 0.65 | 2.84 |
| Olefin/Aromatics Ratio | 62.38 | 45.81 | 34.23 | 20.43 | 18.66 | 13.33 |
| Total Aromatics | 0.76 | 1.13 | 1.58 | 2.44 | 2.86 | 4.02 |
| Propylene + Ethylene | 44.12 | 47.96 | 49.83 | 45.05 | 48.14 | 48.49 |
| Ethylene/Propylene Ratio | 1.40 | 1.65 | 2.00 | 1.52 | 1.78 | 2.14 |

Operating at a higher temperature in the propane tube gave a higher conversion of propane—mainly to r-ethylene and r-propylene (increasing from 44.12% to 47.96% to 49.83% in Comparative Example 9, 3, and 10 respectively). The higher the temperature the more r-ethylene was produced at the expense of r-propylene (r-ethylene/r-propylene ratio increased from 1.40 to 1.65 to 2.0 in Comparative Examples 9, 3, and 10). Aromatics also increased with higher temperature. The same trends were observed with cracking the mixed streams in Examples 44-46: increased r-ethylene and r-propylene from 45.05% to 48.49%), increased r-ethylene/r-propylene ratio (from 1.52 to 2.14), and an increase in total aromatics (from 2.44% to 4.02%). It is known that r-pyoil conversion to cracked products is greater at a given temperature relative to propane.

For the condition where the mixed feed has a 5 °C lower reactor outlet temperature consider the following two cases:

Case A. Comparative Example 3 (Propane at 700 °C) and Example 441 (80/20 at 695 °C)

Case B. Comparative Example 103 (Propane at 705 °C) and Example 452 (80/20 at 700 °C)

Operating the combined tube at 5 °C lower temperature allowed isolation of more r-propylene relative to the higher temperature. For example, operating at 700 °C in Example 45 vs 705 °C in Example 46, r-propylene was 17.32% vs 15.43%. Similarly, operating at 695 °C in Example 44 vs 700 °C in Example 45, r-propylene was 17.91% vs 17.32%. r-Propylene and r-ethylene yield increased as temperature was increased, but this occurred at the expense of r-propylene as shown by the increasing r-ethylene to r-propylene ratio (from 1.52 at 695 °C in Example 44 to 2.14 at 705 °C in Example 46). The ratio also increased for propane feed, but it started from a slightly lower level. Here, the ratio increased from 1.40 at 695 °C to 2.0 at 705 °C.

The lower temperature in the combined tube still gave almost as good conversion to r-ethylene and r-propylene (For Case A: 47.96% for propane cracking vs 45.05% for combined cracking and for Case B: 49.83% for propane cracking vs 48.15% combined). Operation of the combined tube at lower temperature also decreased aromatics and dienes. Thus, this mode is preferred if more r-propylene is desired relative to r-ethylene while minimizing production of C6+(aromatics) and dienes.

For the condition where the mixed tube has a 5 °C higher reactor outlet temperature, consider the following two cases:

Case A. Comparative Example 3 (Propane at 700 °C and Example 46 (80/20 at 705 °C)

Case B. Comparative Example 9 (Propane at 695 °C) and Example 45 (80/20 at 700 °C)

Running lower temperature in the propane tube decreased the conversion of propane and decreased the r-ethylene to r-propylene ratio. The ratio was lower at lower temperatures for both the combined feed and the propane feed cases. The r-pyoil conversion to cracked products was greater at a given temperature relative to propane. It was seen that operating 5 °C higher in the combined tube caused production of more r-ethylene and less r-propylene relative to the lower temperature. This mode—with the higher temperature in the combined tube—gave an increased conversion to r-ethylene plus r-propylene (For Case A: 47.96% for propane cracking in Comparative Example 3 vs 48.49% in Example 46 for combined cracking, and for Case B: 44.11% for propane cracking (Comparative Example 9) vs 48.15% for combined cracking (Example 45) at 5 °C higher temperature).

Operation in this mode (5 °C higher temperature in the combined tube) increases production of r-ethylene, aromatics, and dienes, if so desired. By operating the propane tube at a lower temperature—which operates at a lower ethylene to propylene ratio—the r-propylene production can be maintained compared to running both tubes at the same temperature. For example, operating the combined tube at 700 °C and the propane tube at 695 °C resulted in 18.35% and 17.32%, respectively, of r-propylene. Running both at 695 °C would give 0.6% more r-propylene in the combined tube. Thus, this mode is preferred if more aromatics, dienes, and slightly more r-ethylene is desired while minimizing production loss of r-propylene.

The temperatures were measured at the exit of Zone 2 which is operated to simulate the radiant zone of the cracking furnace. These temperatures are shown in Table 11. Although there were considerable heat loses in operating a small lab unit, the temperatures showed that the exit temperatures for the combined feed cases were 1-2 °C higher than for the corresponding propane only feed case. Steam cracking is an endothermic process. There is less heat needed in cracking with pyoil and propane than when cracking propane alone, and thus the temperature does not decrease as much.

Examples Feeding r-Pyoil or r-Pyoil and Steam at Various Locations

Table 12 contains runs made in the lab steam cracker with propane and r-pyoil Example 3. Steam was fed to the reactor in a 0.4 steam to hydrocarbon ratio in all runs. r-Pyoil and steam were fed at different locations (see configurations in FIG. 11). In Example 48, the reactor inlet temperature was controlled at 380 °C, and r-pyoil was fed as a gas. The reactor inlet temperature was usually controlled at 130-150 °C when r-pyoil was fed as a liquid (Example 49) in the typical reactor configuration.

TABLE 12

Examples with r-Pyoil and Steam Fed at Different Locations.

| Examples* | 47 | 48 | 49 | 50 | 51 | 52 |
|---|---|---|---|---|---|---|
| Zone 2 Control Temp | 700° C. | 700° C. | 700° C. | 700° C. | 700° C. | 700° C. |
| Propane (wt %) | 80 | 80 | 80 | 80 | 80 | 80 |
| r-Pyoil (wt %) | 20 | 20 | 20 | 20 | 20 | 20 |
| Feed Wt, g/hr | 15.33 | 15.33 | 15.33 | 15.33 | 15.33 | 15.33 |
| Steam/hydrocarbon ratio | 0.4 | 0.4 | 0.4 | 0.4 | 0.4 | 0.4 |
| Total Accountability, % | 95.8 | 97.1 | 97.83 | 97.33 | 96.5 | 97.3 |
| Total Products | Weight Percent | | | | | |
| C6+ | 3.03 | 3.66 | 4.50 | 3.32 | 3.03 | 3.38 |
| methane | 17.37 | 18.49 | 19.33 | 17.46 | 19.85 | 17.38 |
| ethane | 2.58 | 3.04 | 3.27 | 2.60 | 3.18 | 2.35 |
| ethylene | 30.30 | 31.07 | 31.53 | 30.93 | 32.10 | 30.75 |
| propane | 21.90 | 19.10 | 16.57 | 20.11 | 17.79 | 21.96 |
| propylene | 16.82 | 16.78 | 15.97 | 17.24 | 16.64 | 16.14 |
| i-butane | 0.04 | 0.04 | 0.03 | 0.04 | 0.03 | 0.04 |
| n-butane | 0.04 | 0.03 | 0.03 | 0.03 | 0.03 | 0.03 |
| propadiene | 0.10 | 0.09 | 0.09 | 0.11 | 0.11 | 0.12 |
| acetylene | 0.35 | 0.33 | 0.33 | 0.36 | 0.34 | 0.40 |
| t-2-butene | 0.00 | 0.00 | 0.00 | 0.00 | 0.00 | 0.00 |
| 1-butene | 0.19 | 0.19 | 0.19 | 0.19 | 0.18 | 0.18 |
| i-butylene | 0.94 | 0.79 | 0.72 | 0.86 | 0.73 | 0.86 |
| c-2-butene | 0.43 | 0.39 | 0.39 | 0.43 | 0.37 | 0.39 |
| i-pentane | 0.16 | 0.16 | 0.16 | 0.16 | 0.15 | 0.15 |
| n-pentane | 0.04 | 0.02 | 0.02 | 0.03 | 0.02 | 0.04 |
| 1,3-butadiene | 2.15 | 2.16 | 2.22 | 2.28 | 2.20 | 2.29 |
| methyl acetylene | 0.21 | 0.21 | 0.20 | 0.23 | 0.22 | 0.24 |
| t-2-pentene | 0.13 | 0.13 | 0.13 | 0.13 | 0.12 | 0.12 |
| 2-methyl-2-butene | 0.04 | 0.03 | 0.03 | 0.03 | 0.03 | 0.03 |
| 1-pentene | 0.02 | 0.01 | 0.02 | 0.02 | 0.02 | 0.02 |
| c-2-pentene | 0.05 | 0.03 | 0.03 | 0.03 | 0.03 | 0.04 |
| pentadiene 1 | 0.00 | 0.00 | 0.01 | 0.00 | 0.00 | 0.00 |
| pentadiene 2 | 0.03 | 0.02 | 0.02 | 0.02 | 0.01 | 0.01 |
| pentadiene 3 | 0.25 | 0.07 | 0.22 | 0.24 | 0.22 | 0.24 |
| 1,3-Cyclopentadiene | 0.72 | 0.76 | 0.83 | 0.80 | 0.79 | 0.81 |
| pentadiene 4 | 0.00 | 0.00 | 0.00 | 0.00 | 0.00 | 0.00 |
| pentadiene 5 | 0.08 | 0.08 | 0.08 | 0.08 | 0.08 | 0.08 |
| CO2 | 0.00 | 0.00 | 0.00 | 0.00 | 0.05 | 0.00 |
| CO | 0.00 | 0.00 | 0.00 | 0.00 | 0.23 | 0.00 |
| hydrogen | 1.24 | 1.23 | 1.23 | 1.21 | 1.42 | 1.25 |
| Unidentified | 0.79 | 1.09 | 1.80 | 1.06 | 0.00 | 0.71 |
| Olefin/Aromatics Ratio | 17.27 | 14.36 | 11.67 | 16.08 | 17.71 | 15.43 |
| Total Aromatics | 3.03 | 3.66 | 4.50 | 3.32 | 3.03 | 3.38 |
| Propylene + Ethylene | 47.12 | 47.85 | 47.50 | 48.17 | 48.75 | 46.89 |
| Ethylene/Propylene Ratio | 1.80 | 1.85 | 1.97 | 1.79 | 1.93 | 1.91 |

*Example 47-r-Pyoil fed between zone 1 and zone 2: Proxy For Crossover
*Example 48-r-Pyoil and steam fed between zone 1 and zone 2: Proxy for Crossover
*Example 49-r-Pyoil and steam fed at midpoint of zone 1: Proxy for Downstream of Inlet
*Example 50-r-Pyoil fed at midpoint of zone 1: Proxy for Downstream of Inlet
*Example 51-r-Pyoil fed as gas at inlet of zone 1
*Example 49-r-Pyoil fed as liquid at inlet of zone 1

Feeding propane and r-pyoil as a gas at reactor inlet (Example 51) gave a higher conversion to r-ethylene and r-propylene compared to Example 52 where the r-pyoil was fed as a liquid. Some conversion was due to heating the stream to near 400 °C where some cracking occurred. Since the r-pyoil was vaporized outside the reactor, no heat supplied for that purpose was required by the furnace. Thus, more heat was available for cracking. As a result, a greater amount of r-ethylene and r-propylene (48.75%) was obtained compared to that obtained when the r-pyoil was fed as a liquid at the top of the reactor (46.89% in Example 52). Additionally, r-pyoil entering the reactor as a gas decreased residence time in the reactor which resulted in lower total aromatics and an increased olefin/aromatics ratio for Example 51.

In the other examples (47-50) either r-pyoil or r-pyoil and steam was fed at the simulated crossover between the convection zone and the radiant zone of a steam cracking furnace (between Zone 1 and Zone 2 of the lab furnace) or at the mid-point of Zone 1. There was little difference in the cracking results except for the aromatic content in Example 49. Feeding r-pyoil and steam at the midpoint of Zone 1 resulted in the greatest amount of aromatics. The number of aromatics was also high when steam was cofed with r-pyoil between Zone 1 and Zone 2 (Example 48). Both examples had a longer overall residence time for propane to react before the streams were combined compared to the other Examples in the table. Thus, the particular combination of longer residence time for cracking propane and a slightly shorter residence time for r-pyoil cracking in Example 49 resulted in a greater amount of aromatics as cracked products.

Feeding r-pyoil as a liquid at the top of reactor (Example 52) gave the lowest conversion of all the conditions. This was due to the r-pyoil requiring vaporization which needed heat. The lower temperature in Zone 1 resulted in less cracking when compared to Example 51.

Higher conversion to r-ethylene and r-propylene was obtained by feeding the r-pyoil at the crossover or the midpoint of the convection section for one main reason. The propane residence time in the top of the bed—before introduction of r-pyoil or r-pyoil and steam—was lower. Thus, propane can achieve higher conversion to r-ethylene and r-propylene relative to Example 52 with a 0.5 sec residence time for the entire feed stream. Feeding propane and r-pyoil as a gas at reactor inlet (Example 51) gave the highest conversion to r-ethylene and r-propylene because none of the furnace heat was used in vaporization of r-pyoil as was required for the other examples.

Decoking Examples from Cracking r-Pyoil Example 5 with Propane or Natural Gasoline Propane was cracked at the same temperature and feed rate as an 80/20 mixture of propane and r-pyoil from Example 5 and an 80/20 mixture of natural gasoline and r-pyoil from Example 5. All examples were operated in the same way. The examples were run with a Zone 2 control temperature of 700 °C. When the reactor was at stable temperature, propane was cracked for 100 minutes, followed by 4.5 hr of cracking propane, or propane and r-pyoil, or natural gasoline and r-pyoil, followed by another 60 min of propane cracking. The steam/hydrocarbon ratio was varied in these comparative examples from 0.1 to 0.4. The propane cracking results are shown in Table 13 as Comparative Examples 11-13. The results presented in Table 14 include examples (Examples 53-58) involving cracking an 80/20 mixture of propane or natural gasoline with r-pyoil from Example 5 at different steam to hydrocarbon ratios. Nitrogen (5% by weight relative to the hydrocarbon) was fed with steam in the examples with natural gasoline and r-pyoil to provide even steam generation. In the examples involving cracking r-pyoil with natural gasoline, the liquid samples were not analyzed. Rather, the measured reactor effluent gas flow rate and gas chromatography analysis were used to calculate the theoretical weight of unidentified material for 100% accountability.

Following each steam cracking run, decoking of the reactor tube was performed. Decoking involved heating all three zones of the furnace to 700 °C under 200 sccm N2 flow and 124 sccm steam. Then, 110 sccm air was introduced to bring the oxygen concentration to 5%. Then, the air flow was slowly increased to 310 sccm as the nitrogen flow was decreased over two hours. Next, the furnace temperature was increased to 825 °C over two hours. These conditions were maintained for 5 hours. Gas chromatography analysis were performed every 15 minutes beginning with the introduction of the air stream. The amount of carbon was calculated based on the amount of CO2 and CO in each analysis. The amount of carbon was totalized until no CO was observed, and the amount of CO2 was less than 0.05%.

The results (mg carbon by gas chromatography analysis) from decoking the propane comparative examples are found in Table 13. The results from the r-pyoil examples is found in Table 14.

TABLE 13

Comparative Examples of Cracking with Propane.

| | Examples | | |
|---|---|---|---|
| | Comparative Example 11 | Comparative Example 12 | Comparative Example 13 |
| Zone 2 Control Temp, ° C. | 700° C. | 700° C. | 700° C. |
| Propane (wt %) | 100 | 100 | 100 |
| r-Pyoil (wt %) | 0 | 0 | 0 |
| N2 (wt %) | 0 | 0 | 0 |
| Feed Wt, g/hr | 15.36 | 15.36 | 15.36 |
| Steam/Hydrocarbon Ratio | 0.1 | 0.2 | 0.4 |
| Total Accountability, % | 98.71 | 101.30 | 99.96 |
| Total Products | Weight Percent | | |
| C6+ | 1.71 | 1.44 | 1.10 |
| Methane | 20.34 | 19.92 | 17.98 |
| Ethane | 3.04 | 2.83 | 2.25 |
| Ethylene | 32.48 | 32.29 | 30.43 |
| Propane | 19.04 | 20.26 | 24.89 |
| Propylene | 17.72 | 17.88 | 18.19 |
| i-butane | 0.04 | 0.04 | 0.04 |
| n-butane | 0.03 | 0.00 | 0.00 |
| Propadiene | 0.08 | 0.04 | 0.04 |
| Acetylene | 0.31 | 0.03 | 0.04 |
| t-2-butene | 0.00 | 0.00 | 0.00 |
| 1-butene | 0.18 | 0.18 | 0.17 |
| i-butylene | 0.78 | 0.82 | 0.93 |
| c-2-butene | 0.15 | 0.14 | 0.13 |
| i-pentane | 0.15 | 0.15 | 0.14 |
| n-pentane | 0.00 | 0.00 | 0.00 |
| 1,3-butadiene | 1.93 | 1.90 | 1.68 |
| methyl acetylene | 0.18 | 0.18 | 0.19 |
| t-2-pentene | 0.14 | 0.14 | 0.12 |
| 2-methyl-2-butene | 0.03 | 0.03 | 0.03 |
| 1-pentene | 0.01 | 0.01 | 0.01 |
| c-2-pentene | 0.01 | 0.11 | 0.10 |
| pentadiene 1 | 0.00 | 0.00 | 0.00 |
| pentadiene 2 | 0.01 | 0.01 | 0.01 |
| pentadiene 3 | 0.00 | 0.00 | 0.00 |
| 1,3-Cyclopentadiene | 0.17 | 0.16 | 0.14 |
| pentadiene 4 | 0.00 | 0.00 | 0.00 |
| pentadiene 5 | 0.07 | 0.00 | 0.01 |
| CO2 | 0.00 | 0.00 | 0.00 |
| CO | 0.00 | 0.00 | 0.00 |
| Hydrogen | 1.41 | 1.43 | 1.39 |
| Unidentified | 0.00 | 0.00 | 0.00 |
| Olefin/Aromatics Ratio | 31.53 | 37.20 | 47.31 |
| Total Aromatics | 1.71 | 1.44 | 1.10 |
| Propylene + Ethylene | 50.20 | 50.17 | 48.62 |
| Ethylene/Propylene Ratio | 1.83 | 1.81 | 1.67 |
| Carbon from Decoking, mg | 16 | 51 | 1.5 |

TABLE 14

Examples of Cracking Propane or Natural Gasoline and r-Pyoil.

| Examples | 53 | 54 | 55 | 56 | 57 | 58 |
|---|---|---|---|---|---|---|
| Propane or Natural Gasoline | Propane | Propane | Propane | Nat Gas | Nat Gas | Nat Gas |
| Zone 2 Control Temp | 700 | 700 | 700 | 700 | 700 | 700 |
| Propane/Nat Gas (wt %) | 80 | 80 | 80 | 80 | 80 | 80 |
| r-Pyoil (wt %) | 20 | 20 | 20 | 20 | 20 | 20 |
| N2 (wt %) | 0 | 0 | 0 | 5* | 5* | 5* |
| Feed Wt, g/hr | 15.32 | 15.32 | 15.32 | 15.29 | 15.29 | 15.29 |
| Steam/Hydrocarbon Ratio | 0.1 | 0.2 | 0.4 | 0.4 | 0.6 | 0.7 |
| Total Accountability, % | 95.4 | 99.4 | 97.5 | 100** | 100** | 100** |
| Total Products | | | Weight Percent | | | |
| C6+ | 2.88 | 2.13 | 2.30 | 5.69 | 4.97 | 5.62 |
| Methane | 18.83 | 16.08 | 16.62 | 15.60 | 16.81 | 18.43 |
| Ethane | 3.56 | 2.85 | 2.27 | 2.97 | 3.43 | 3.63 |
| Ethylene | 30.38 | 28.17 | 30.20 | 27.71 | 27.74 | 26.94 |
| Propane | 19.81 | 25.60 | 24.07 | 0.40 | 0.43 | 0.36 |
| Propylene | 18.37 | 18.83 | 18.13 | 14.76 | 14.48 | 12.04 |
| i-butane | 0.04 | 0.06 | 0.05 | 0.03 | 0.03 | 0.02 |
| n-butane | 0.00 | 0.00 | 0.00 | 0.00 | 0.00 | 0.00 |
| Propadiene | 0.05 | 0.05 | 0.04 | 0.09 | 0.09 | 0.08 |
| Acetylene | 0.04 | 0.04 | 0.05 | 0.12 | 0.10 | 0.10 |
| t-2-butene | 0.00 | 0.00 | 0.00 | 0.00 | 0.00 | 0.00 |
| 1-butene | 0.23 | 0.22 | 0.19 | 0.45 | 0.43 | 0.44 |
| i-butylene | 0.81 | 0.97 | 0.97 | 1.27 | 1.02 | 1.04 |
| c-2-butene | 0.63 | 0.76 | 0.55 | 3.38 | 3.31 | 2.94 |
| i-pentane | 0.19 | 0.18 | 0.16 | 0.02 | 0.02 | 0.03 |
| n-pentane | 0.01 | 0.01 | 0.04 | 1.27 | 1.12 | 2.08 |
| 1,3-butadiene | 2.11 | 2.29 | 2.45 | 3.64 | 3.52 | 3.45 |
| methyl acetylene | 0.17 | n/a | n/a | 0.41 | 0.37 | 0.37 |
| t-2-pentene | 0.16 | 0.13 | 0.12 | 0.12 | 0.12 | 0.13 |
| 2-methyl-2-butene | 0.03 | 0.03 | 0.03 | 0.05 | 0.06 | 0.09 |
| 1-pentene | 0.02 | 0.02 | 0.02 | 0.08 | 0.10 | 0.12 |
| c-2-pentene | 0.11 | 0.10 | 0.09 | 0.08 | 0.09 | 0.11 |
| pentadiene 1 | 0.00 | 0.00 | 0.00 | 0.05 | 0.08 | 0.14 |
| pentadiene 2 | 0.01 | 0.03 | 0.02 | 0.23 | 0.36 | 0.53 |
| pentadiene 3 | 0.00 | 0.00 | 0.00 | 0.00 | 0.00 | 0.00 |
| 1,3-Cyclopentadiene | 0.26 | 0.26 | 0.25 | 0.50 | 0.55 | 0.58 |
| pentadiene 4 | 0.00 | 0.00 | 0.00 | 0.00 | 0.00 | 0.00 |
| pentadiene 5 | 0.09 | 0.08 | 0.08 | 0.00 | 0.00 | 0.12 |
| CO2 | 0.00 | 0.00 | 0.00 | 0.02 | 0.00 | 0.00 |
| CO | 0.00 | 0.00 | 0.00 | 0.06 | 0.06 | 0.03 |
| Hydrogen | 1.21 | 1.12 | 1.24 | 0.96 | 0.95 | 0.95 |
| Unidentified | 0.00 | 0.00 | 0.00 | 20.04 | 19.77 | 19.63 |
| Olefin/Aromatics Ratio | 18.48 | 24.43 | 23.07 | 9.22 | 10.46 | 8.67 |
| Total Aromatics | 2.88 | 2.13 | 2.30 | 5.69 | 4.97 | 5.62 |
| Propylene +− Ethylene | 48.75 | 47.00 | 48.33 | 42.47 | 42.22 | 38.98 |
| Ethylene/Propylene Ratio | 1.65 | 1.50 | 1.67 | 1.88 | 1.92 | 2.24 |
| Carbon from Decoking, mg | 96 | 44 | 32 | 90 | 71 | 23 |

*5% N2 was also added to facilitate steam generation. Analysis has been normalized to exclude it.

**100% accountability based on actual reactor effluent gas flow rate and gas chromatography analysis and calculation to give theoretical mass of unidentified products.

The cracking results showed the same general trends that were seen in the other cases, such as r-propylene and r-ethylene yield and total aromatics increasing with a lower steam to hydrocarbon ratio due to the longer residence time in the reactor. These runs were made to determine the amount of carbon generated when a r-pyoil was cracked with propane or natural gasoline. These were short runs but they was sufficiently accurate to see trends in coking. Cracking propane produced the least coking. The carbon produced ranged from 16 to 51 mg at 0.2 or less steam/ghydrocarbon ratio. Coking was the smallest at a 0.4 steam/hydrocarbon ratio. In fact, only 1.5 mg of carbon was determined after decoking in Comparative 13. A much longer run time is needed to improve accuracy. Since most commercial plants operate at a steam to hydrocarbon ratio of 0.3 or higher, the 51 mg obtained at 0.2 ratio may not be unreasonable and may be considered a baseline for other feeds. For the r-pyoil/propane feed in Examples 53-55, increasing the ratio from 0.1 to 0.2 to 0.4 decreased the amount of carbon obtained from 96 mg (Example 53) to 32 mg (Example 55). Even the 44 mg of carbon at a 0.2 ratio (Example 54) was not unreasonable. Thus, using a 0.4 ratio for the combined r-pyoil and propane feed inhibited coke formation similar to using a 0.2-0.4 ratio for propane. Cracking r-pyoil with natural gasoline required a 0.7 ratio (Example 58) to decrease the carbon obtained to the 20-50 mg range. At a 0.6 ratio, (Example 57) 71 mg of carbon was still obtained. Thus, operation of an 80/20 mixture of natural gasoline and r-pyoil should use a ratio of 0.7 or greater to provide runtimes typical for operation of propane cracking.

Increasing the steam to hydrocarbon ratio decreased the amount of coke formed in cracking propane, propane and r-pyoil, and natural gasoline and r-pyoil. A higher ratio was required as a heavier feedstock was cracked. Thus, propane required the lowest ratio to obtain low coke formation. Cracking propane and r-pyoil required a ratio of about 0.4.

A range of 0.4 to 0.6 would be adequate to allow typical commercial runtimes between decoking. For the natural gasoline and r-pyoil mixture, even a higher ratio was required. In this case, a ratio of 0.7 or above is needed. Thus, operating at a steam to hydrocarbon ratio of 0.7 to 0.9 would be adequate to allow typical commercial runtimes between decoking.

Example 59—Plant Test

Figure 12:
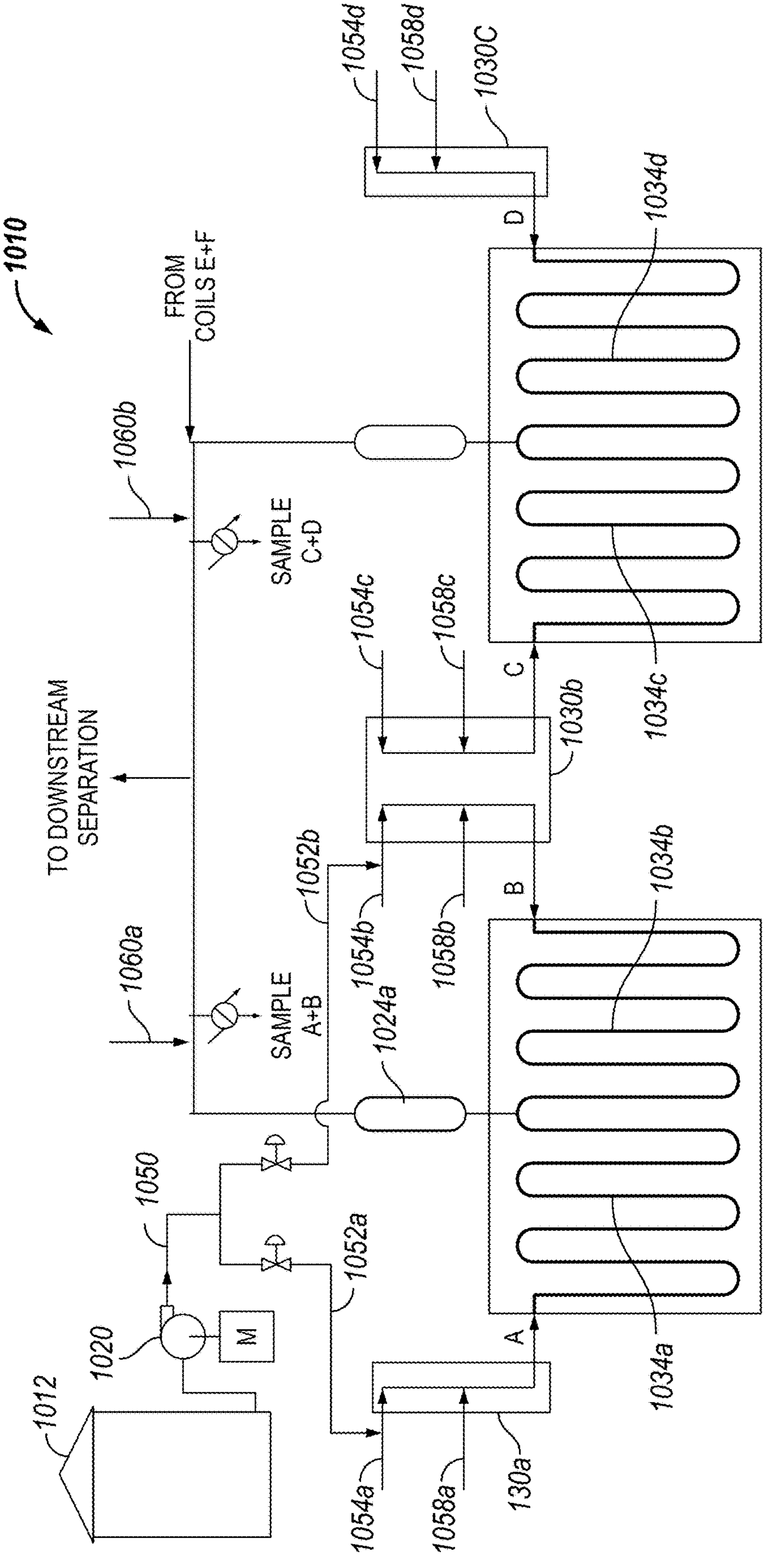
FIG. 12 illustrates design features of a plant-based trial feeding r-pyoil to a gas fed cracker furnace.
Figure 13:
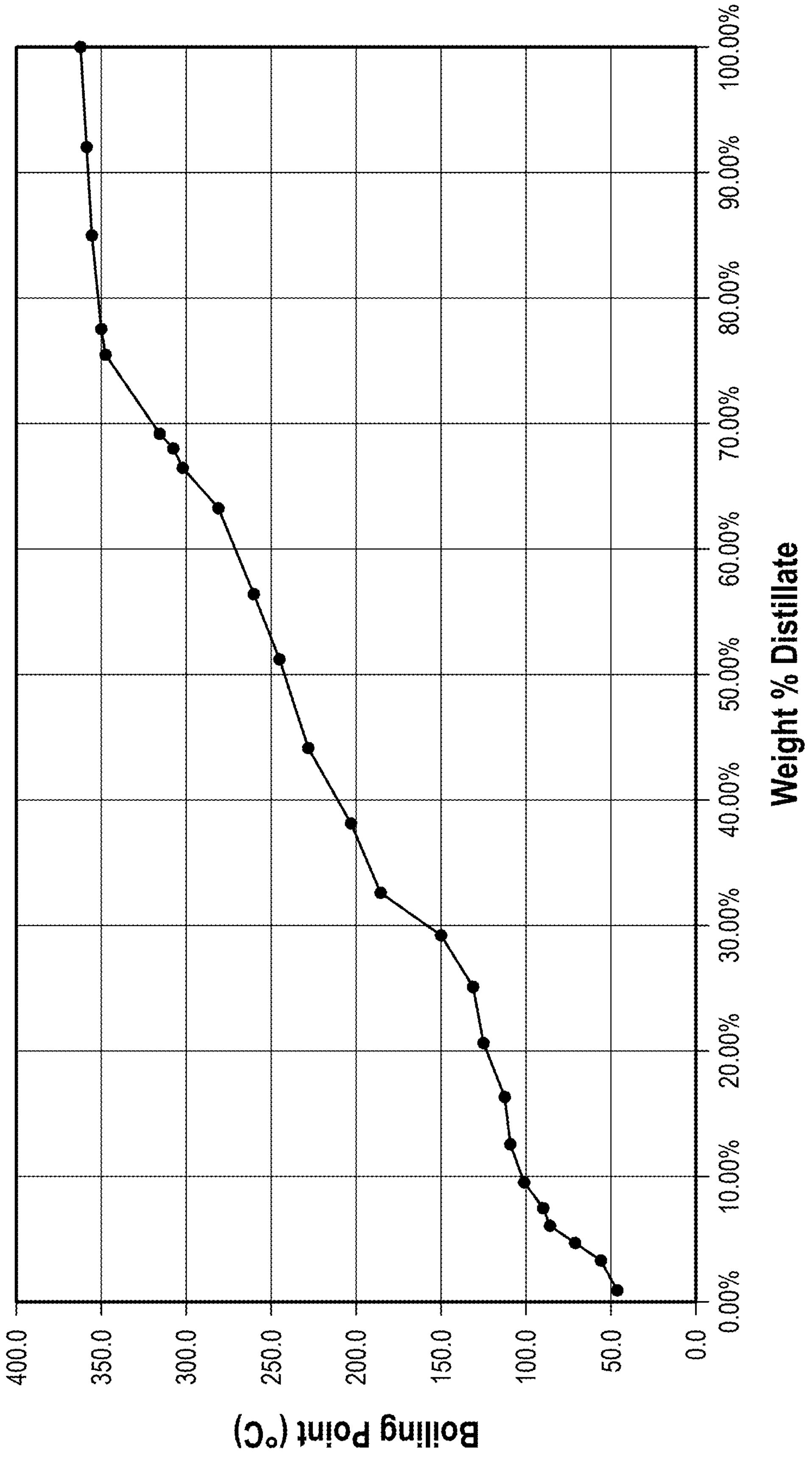
FIG. 13 is a graph of the boiling point curve of a r-pyoil having 74.86% C8+, 28.17% C15+, 5.91% aromatics, 59.72% paraffins, and 13.73% unidentified components by gas chromatography analysis.
Figure 14:
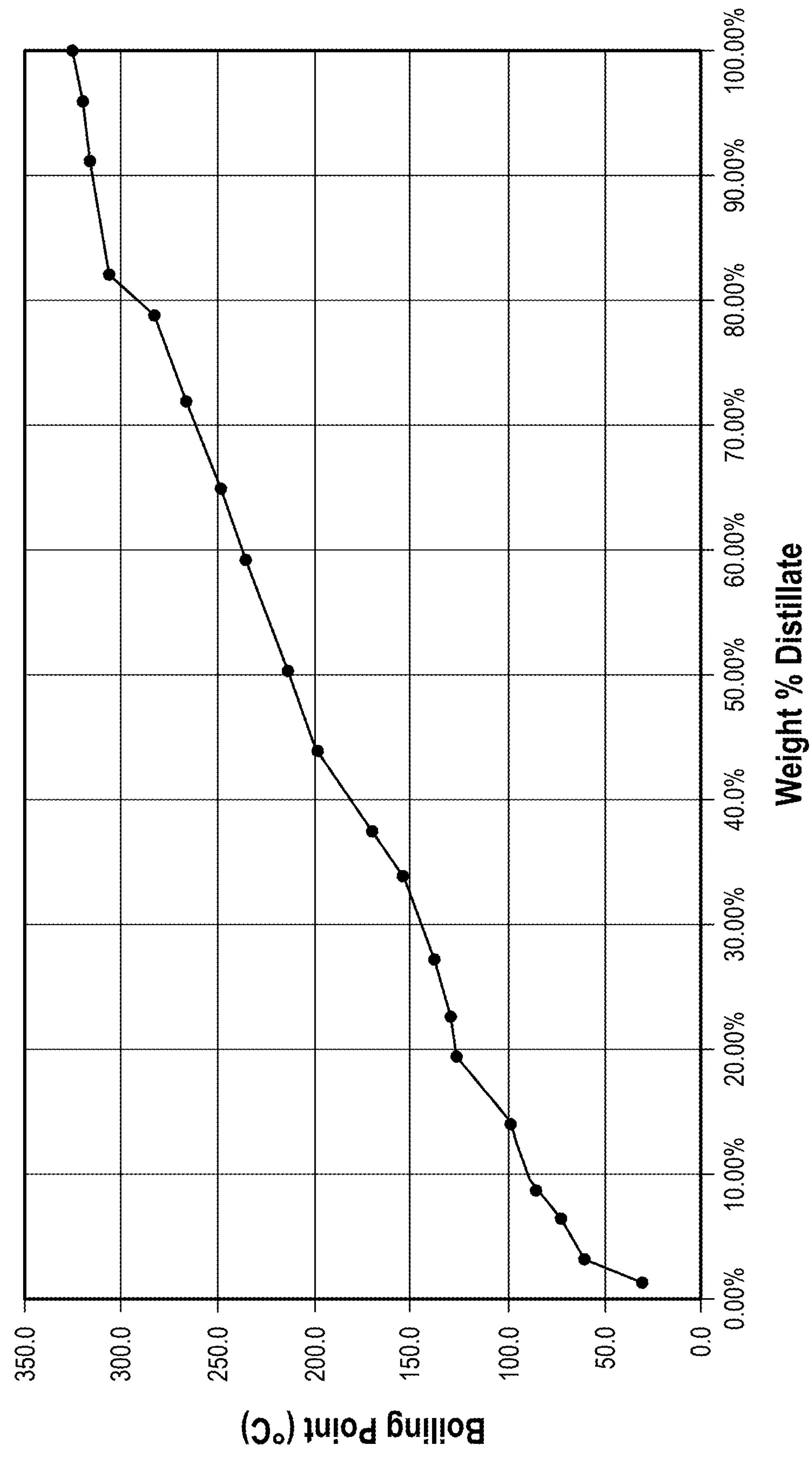
FIG. 14 is a graph of the boiling point curve of a r-pyoil obtained by gas chromatography analysis.
Figure 15:
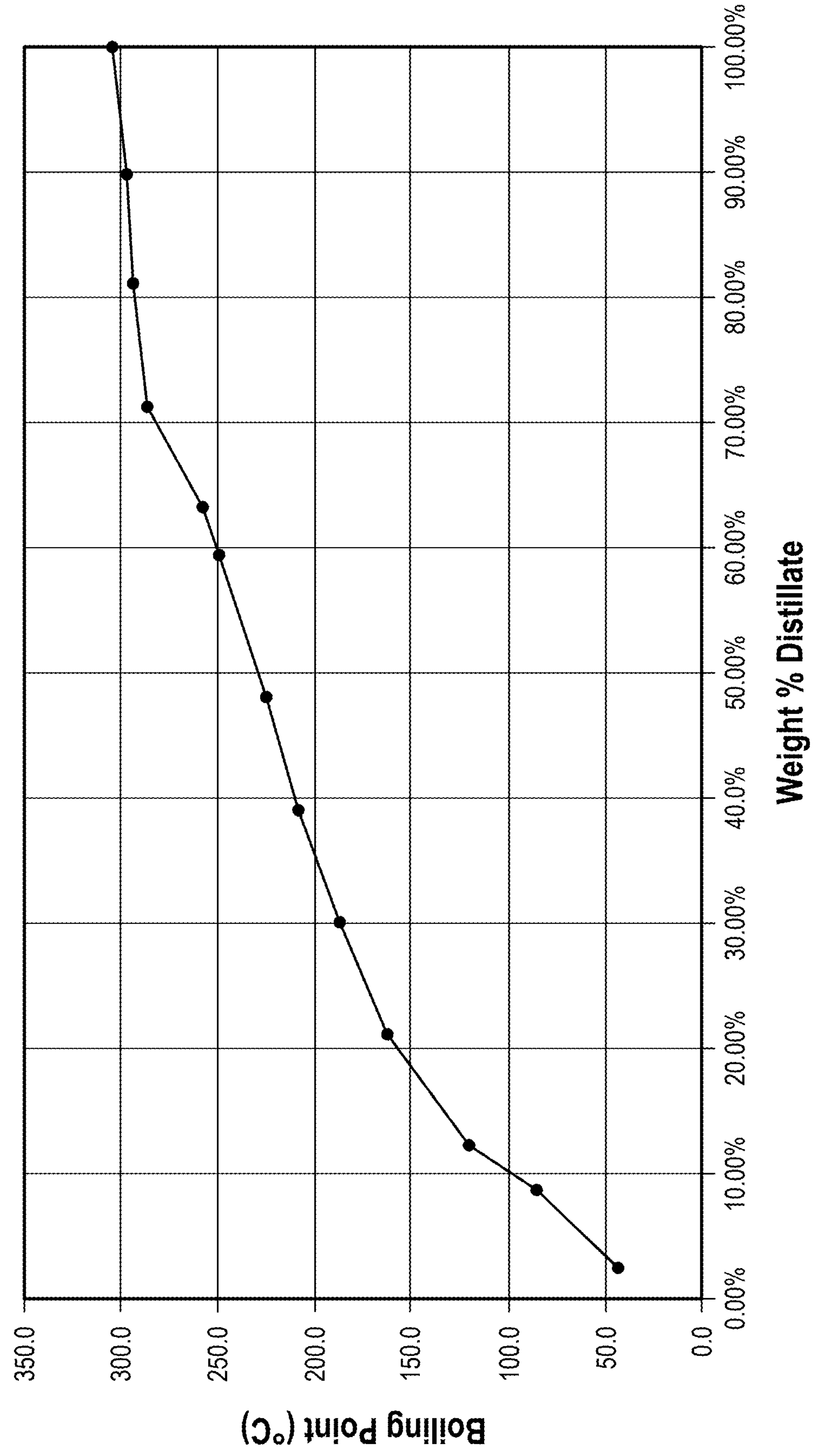
FIG. 15 is a graph of the boiling point curve of a r-pyoil obtained by gas chromatography analysis.
Figure 16:
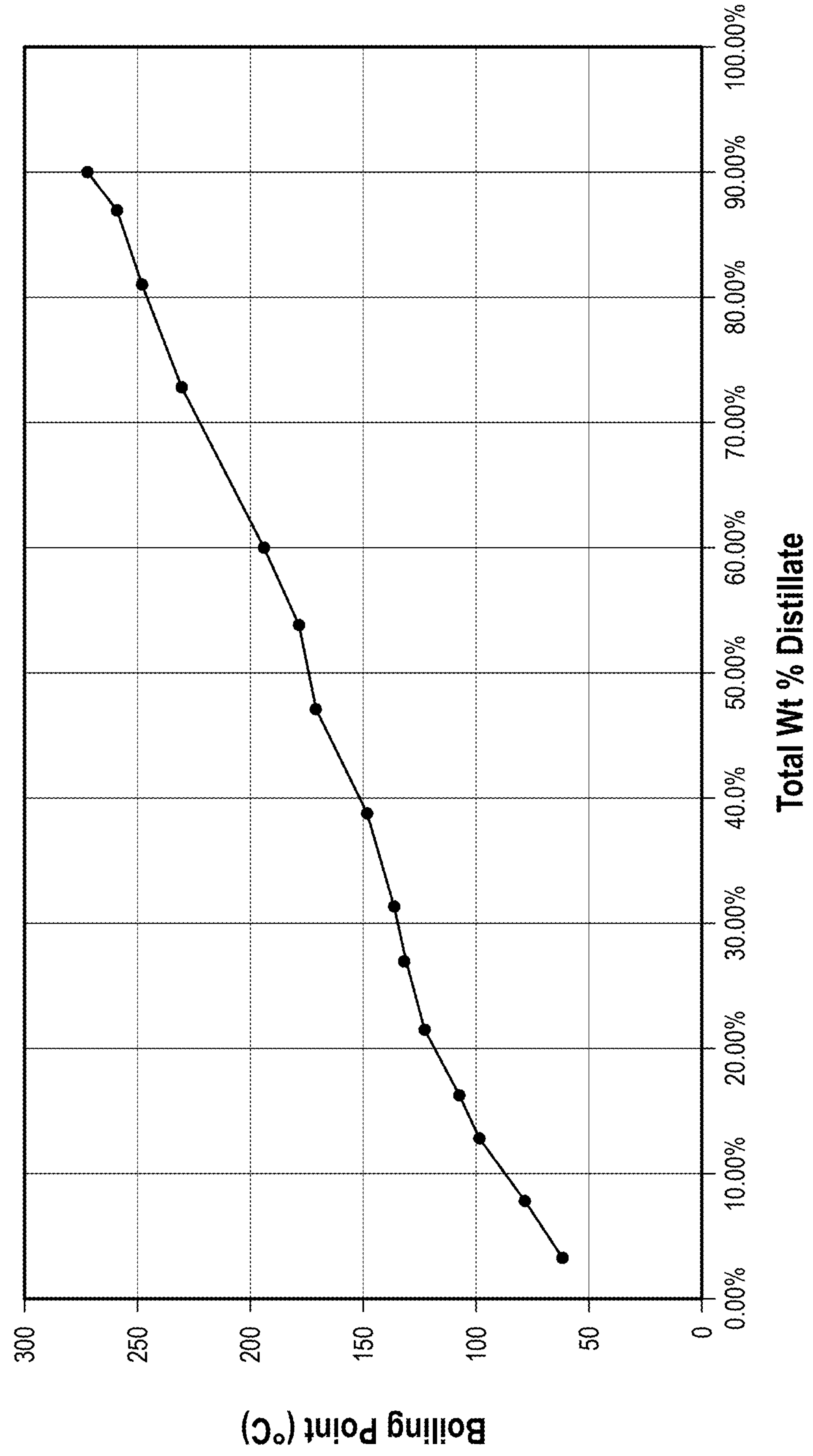
FIG. 16 is a graph of the boiling point curve of a r-pyoil distilled in a lab and obtained by chromatography analysis.

About 13,000 gallons from tank 1012 of r-pyoil were used in the plant test as show in FIG. 12. The furnace coil outlet temperature was controlled either by the testing coil (Coil-A 1034*a* or Coil-B 1034*b*) outlet temperature or by the propane coil (Coil C 1034*c*, coil D 1034*d* through F) outlet temperature, depending on the objective of the test. In FIG. 12 the steam cracking system with r-pyoil 1010; 1012 is the r-pyoil tank; 1020 is the r-pyoil tank pump; 1024*a* and 1226*b* are TLE (transfer line exchanger); 1030*a, b,c* is the furnace convection section; 1034*a, b, c, d* are the coils in furnace firebox (the radiant section); 1050 is the r-pyoil transfer line; 1052*a, b* are the r-pyoil feed that is added into the system; 1054*a, b, c, d* are the regular hydrocarbon feed; 1058*a, b, c, d*—are dilution steam; 1060*a* and 1060*b* are cracked effluent. The furnace effluent is quenched, cooled to ambient temperature and separated out condensed liquid, the gas portion is sampled and analyzed by gas chromatograph.

For the testing coils, propane flow 1054*a* and 1054*b* were controlled and measured independently. Steam flow 1058*a* and 1058*b* were either controlled by Steam/HC ratio controller or in an AUTO mode at a constant flow, depending on the objective of the test. In the non-testing coils, the propane flow was controlled in AUTO mode and steam flow was controlled in a ratio controller at Steam/Propane=0.3.

r-pyoil was obtained from tank 1012 through r-pyoil flow meters and flow control valves into propane vapor lines, from where r-pyoil flowed along with propane into the convection section of the furnace and further down into the radiant section also called the firebox. FIG. 12 shows the process flow.

Figure 23:
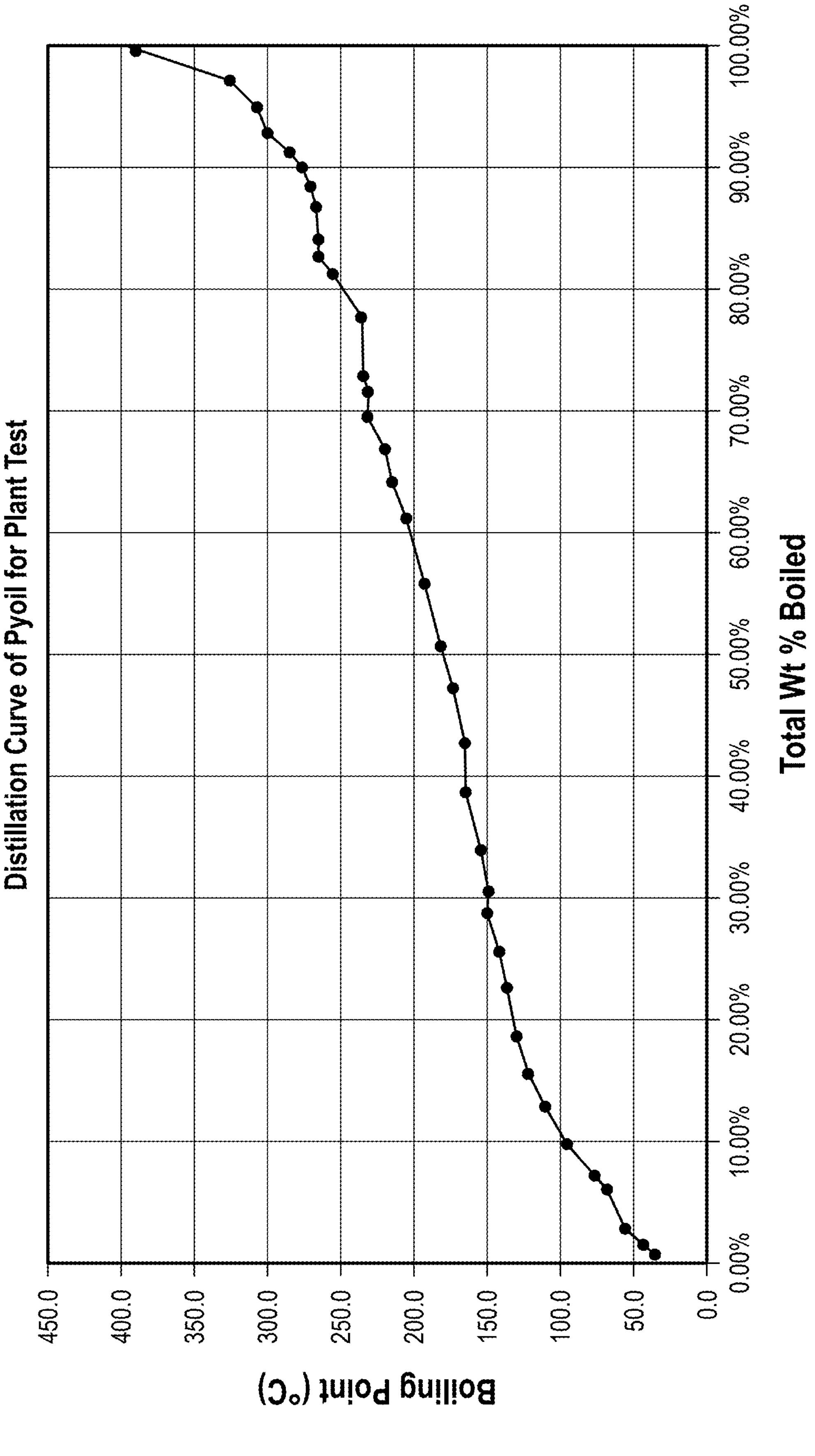
FIG. 23 is a graph of the boiling point curve of r-pyoil with an initial boiling point of about 40 °C.
Figure 24:
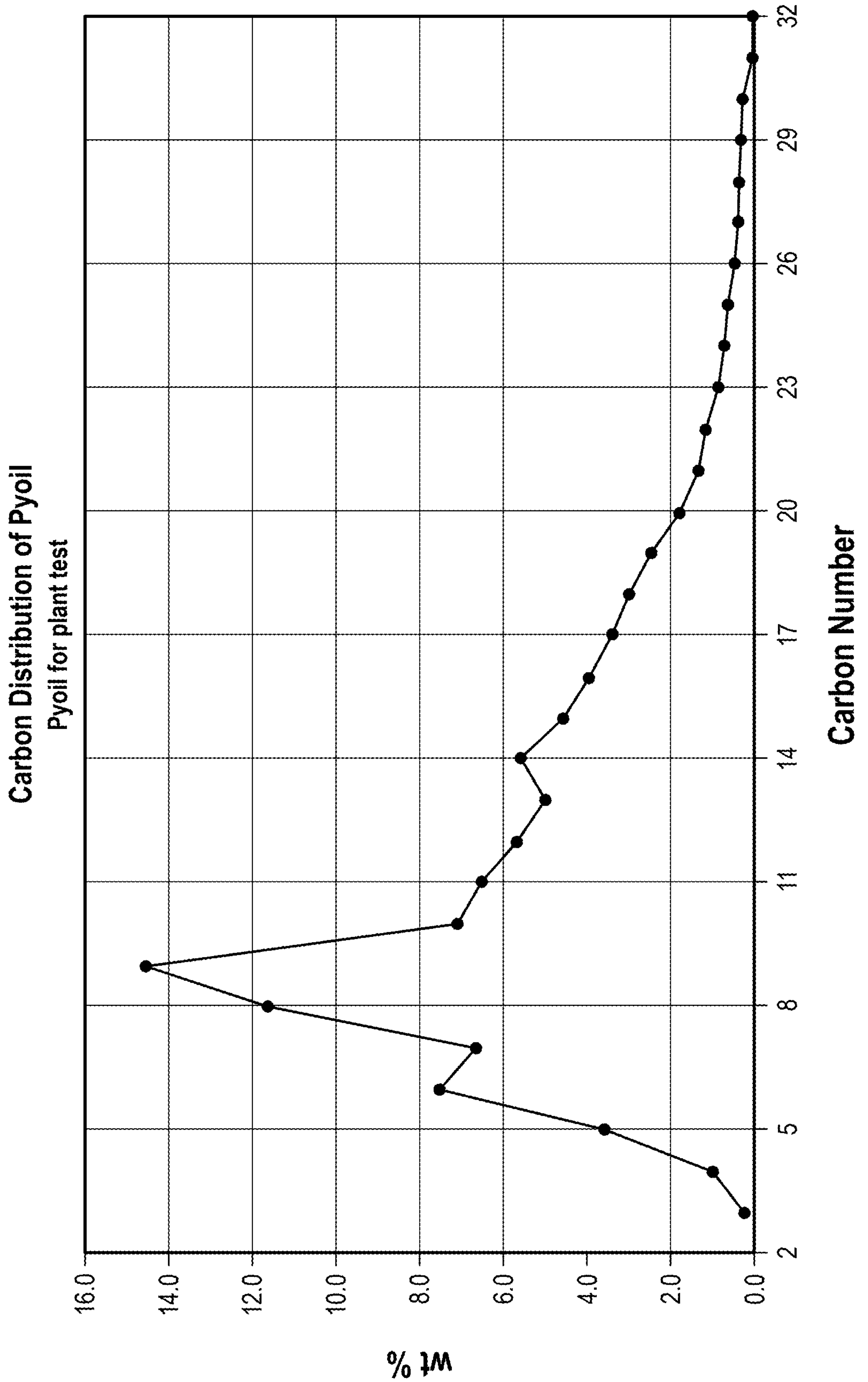
FIG. 24 is a graph of the carbon distribution of pyoil used in a plant test.
Figure 25:
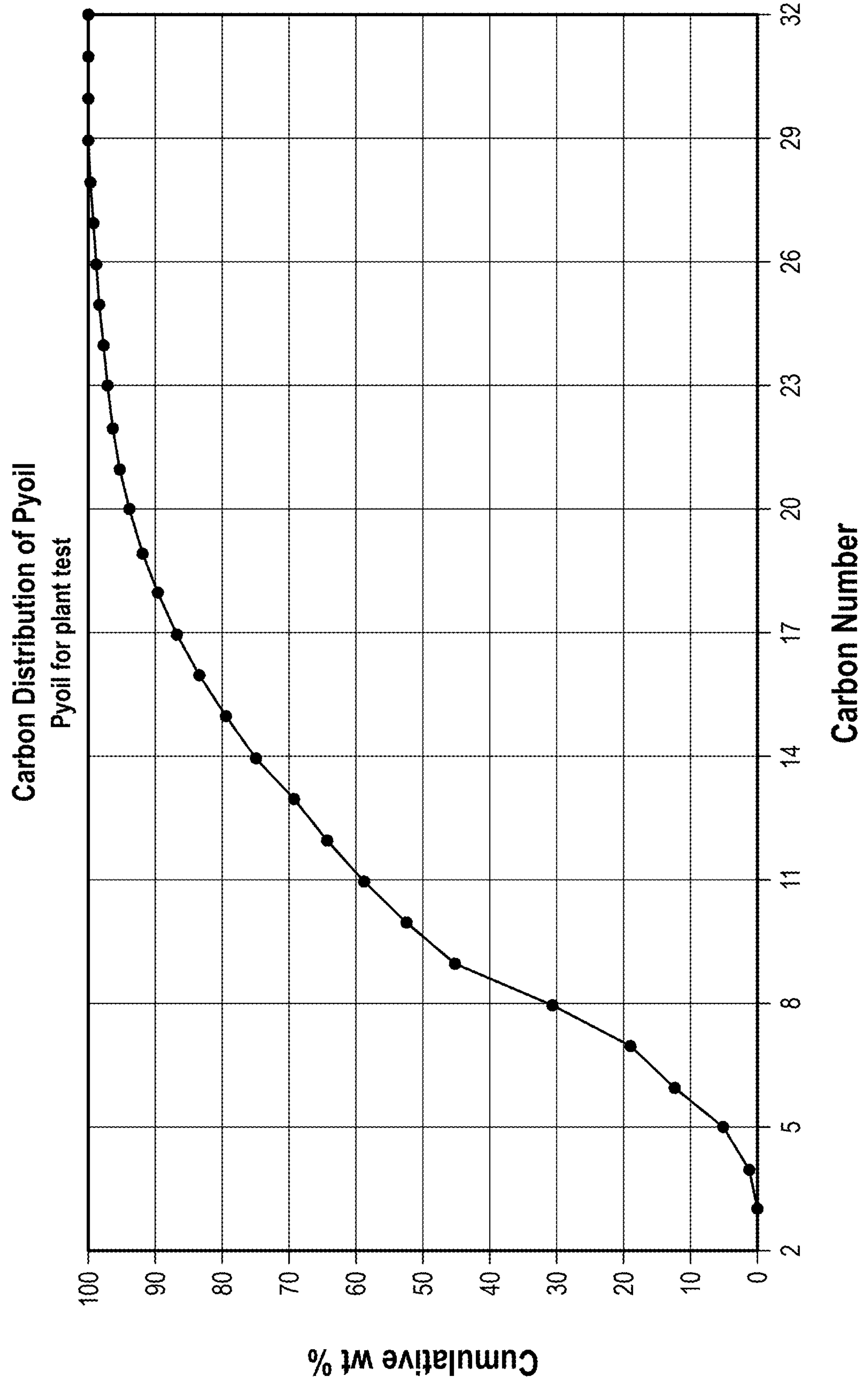
FIG. 25 is a graph of the carbon distribution of pyoil used in a plant test.

The r-pyoil properties are shown in and Table 15 and FIG. 23. The r-pyoil contained a small amount of aromatics, less than 8 wt. %, but a lot of alkanes (more than 50%), thus making this material as a preferred feedstock for steam cracking to light olefins. However, the r-pyoil had a wide distillation range, from initial boiling point of about 40 °C to an end point of about 400 °C, as shown in Table 15 and FIGS. 24 and 25, covering a wide range of carbon numbers (C4 to C30 as shown in Table 15). Another good characteristic of this r-pyoil is its low sulfur content of less than 100 ppm, but the r-pyoil had high nitrogen (327 ppm) and chlorine (201 ppm) content. The composition of the r-pyoil by gas chromatography analysis is shown in Table 16.

TABLE 15

Properties of r-pyoil for plant test.

| Physical Properties | |
|---|---|
| Density, 22.1° C., g/ml | 0.768 |
| Viscosity, 22° C., cP | 1.26 |
| Initial Boiling Point, ° C. | 45 |
| Flash Point, ° C. | Below - 1.1 |
| Pour Point, ° C. | −5.5 |

TABLE 15-continued

Properties of r-pyoil for plant test.

| Impurities | |
|---|---|
| Nitrogen, ppmw | 327 |
| Sulfur, ppmw | 74 |
| Chlorine, ppmw | 201 |
| **Hydrocarbons, wt %** | |
| Total Identified alkanes | 58.8 |
| Total Identified Aromatics | 7.2 |
| Total Identified Olefins | 16.7 |
| Total Identified Dienes | 1.1 |
| Total Identified Hydrocarbons | 83.5 |

TABLE 16 r-Pyoil composition.

| Component | wt % |
|---|---|
| Propane | 0.17 |
| 1,3-Butadiene | 0.97 |
| Pentene | 0.40 |
| Pentane | 3.13 |
| 2-methyl-pentene | 2.14 |
| 2-methyl-Pentane | 2.46 |
| Hexane | 1.83 |
| 2,4-dimethylpentene | 0.20 |
| Benzene | 0.17 |
| 5-methyl-1,3-cyclopentadiene | 0.17 |
| Heptene | 1.15 |
| Heptane | 2.87 |
| Toluene | 1.07 |
| 4-methylheptane | 1.65 |
| Octene | 1.51 |
| Octane | 2.77 |
| 2,4-dimethylheptene | 1.52 |
| 2,4-dimethylheptane | 3.98 |
| Ethylbenzene | 3.07 |
| m,p-xylene | 0.66 |
| Styrene | 1.11 |
| Mol. Weight = 140 | 1.73 |
| Nonane | 2.81 |
| Cumene | 0.96 |
| Decene/methylstyrene | 1.16 |
| Decane | 3.16 |
| Indene | 0.20 |
| Indane | 0.26 |
| C11-Alkene | 1.31 |
| C11-Alkane | 3.29 |
| Napthanlene | 0.00 |
| C12-Alkene | 1.29 |
| C12-Alkane | 3.21 |
| C13-Alkene | 1.19 |
| C13-Alkane | 2.91 |
| 2-methylnapthalene | 0.62 |
| C14-Alkene | 0.83 |
| C14-Alkane | 3.02 |
| Acenapthalene | 0.19 |
| C15-Alkene | 0.86 |
| C15-Alkane | 3.00 |
| C16-Alkene | 0.58 |
| C16-Alkane | 2.66 |
| C17-Alkene | 0.46 |
| C17-Alkane | 2.42 |
| C18-Alkene | 0.32 |
| C18-Alkane | 2.10 |
| C19-Alkene | 0.37 |
| C19-Alkane | 1.81 |
| C20-Alkene | 0.25 |
| C20-Alkane | 1.53 |
| C21-Alkene | 0.00 |
| C21-Alkane | 1.28 |
| C22-Alkane | 1.10 |
| C23-Alkane | 0.87 |
| C24-Alkane | 0.72 |

TABLE 16-continued

| r-Pyoil composition. | |
|---|---|
| Component | wt % |
| C25-Alkane | 0.57 |
| C26-Alkane | 0.47 |
| C27-Alkane | 0.36 |
| C28-Alkane | 0.28 |
| C29-Alkane | 0.22 |
| C30-Alkane | 0.17 |
| Total Identified | 83.5% |

Before the plant test started, eight (8) furnace conditions (more specifically speaking, eight conditions on the testing coils) were chosen. These included r-pyoil content, coil outlet temperature, total hydrocarbon feeding rate, and the ratio of steam to total hydrocarbon. The test plan, objective and furnace control strategy are shown in Table 17. "Float Mode" means the testing coil outlet temperature is not controlling the furnace fuel supply. The furnace fuel supply is controlled by the non-testing coil outlet temperature, or the coils that do not contain r-pyoil.

TABLE 17

Plan for the plant test of r-pyoil co-cracking with propane.

| Condition | COT, ° F. | Pyoil w % | Py/ C3H8 | TOTAL, KLB/HR | Pyoil/coil, GPM | Pyoil/coil, lb/hr | Stm/HC ratio | Propane/coil, klb/hr |
|---|---|---|---|---|---|---|---|---|
| Base-line | 1500 | 0 | 0.000 | 6.0 | 0.00 | 0 | 0.3 | 6.00 |
| 1A | Float Mode | 5 | 0.053 | 6.0 | 0.79 | 300 | 0.3 | 5.70 |
| 1B | Float Mode | 10 | 0.111 | 6.0 | 1.58 | 600 | 0.3 | 5.40 |
| 1C & 2A | Float Mode | 15 | 0.176 | 6.0 | 2.36 | 900 | 0.3 | 5.10 |
| 2B | Lower by at least 10 F. than the base-line | 15 | 0.176 | 6.0 | 2.36 | 900 | 0.3 | 5.10 |
| 3A & 2C | 1500 | 15 | 0.176 | 6.0 | 2.36 | 900 | 0.3 | 5.10 |
| 3B | 1500 | 15 | 0.176 | 6.9 | 2.72 | 1035 | 0.3 | 5.87 |
| 4A | 1500 | 15 | 0.176 | 6.0 | 2.36 | 900 | 0.4 | 5.10 |
| 4B | 1500 | 15 | 0.176 | 6.0 | 2.36 | 900 | 0.5 | 5.10 |
| 5A | Float Mode | 4.8 | 0.050 | 6.3 | 0.79 | 300 | 0.3 | 6.00 |
| 5B | At 2B COT | 4.8 | 0.050 | 6.3 | 0.79 | 302 | 0.3 | 6.00 |

Effect of Addition of r-Pyoil

The results of r-Pyoil addition can be observed differently depending on how propane flow, steam/HC ratio and furnace are controlled. Temperatures at crossover and coil outlet changed differently depending on how propane flow and steam flow are maintained and how the furnace (the fuel supply to the firebox) was controlled. There were six coils in the testing furnace. There were several ways to control the furnace temperature via the fuel supply to the firebox. One of them was to control the furnace temperature by an individual coil outlet temperature, which was used in the test. Both a testing coil and a non-testing coil were used to control the furnace temperature for different test conditions.

Example 59.1—At Fixed Propane Flow, Steam/HC Ratio and Furnace Fuel Supply (Condition 5A)

In order to check the r-pyoil 1052*a* addition effect, propane flow and steam/HC ratio were held constant, and furnace temperature was set to control by a non-testing coil (Coil-C) outlet temperature. Then r-pyoil 1052*a*, in liquid form, without preheating, was added into the propane line at about 5% by weight.

Temperature changes: After the r-pyoil 1052*a* addition, the crossover temperature dropped about 10 °F for A and B coil, COT dropped by about 7 °F as shown in Table 18. There are two reasons that the crossover and COT temperature dropped. One, there was more total flow in the testing coils due to r-pyoil 1052*a* addition, and two, r-pyoil 1052*a* evaporation from liquid to vapor in the coils at the convection section needed more heat thus dropping the temperature down. With a lower coil inlet temperature at the radiant section, the COT also dropped. The TLE exit temperature went up due to a higher total mass flow through the TLE on the process side.

Cracked gas composition change: As can be seen from the results in Table 18, methane and r-ethylene decreased by about 1.7 and 2.1 percentage points, respectively, while r-propylene and propane increased by 0.5 and 3.0 percentage points, respectively. The propylene concentration increased as did the propylene:ethylene ratio relative to the baseline of no pyoil addition. This was the case even though the propane concentration also increased. Others did not change much. The change in r-ethylene and methane was due to the lower propane conversion at the higher flow rate, which was shown by a much higher propane content in the cracked gas.

TABLE 18

Changes When Hydrocarbon Mass Flow Increases By Adding r-pyoil To Propane At 5% At Constant Propane Flow, Steam/HC Ratio And Firebox Condition.

| | Base-line | Base-line | 5A Add in Pyoil |
|---|---|---|---|
| A&B Propane flow, klb/hr | 11.87 | 11.86 | 11.85 |
| A&B Pyoil Flow, lb/hr | 0 | 0 | 593 |
| A&B Steam flow, lb/hr | 3562 | 3556 | 3737 |
| A&B total HC flow, klb/hr | 11.87 | 11.86 | 12.44 |
| Pyoil/(poil + propane), % | 0.0 | 0.0 | 4.8 |
| Steam/HC, ratio | 0.30 | 0.30 | 0.30 |
| A&B Crossover T, F | 1092 | 1091 | 1081 |

TABLE 18-continued

Changes When Hydrocarbon Mass Flow Increases By Adding r-pyoil To Propane At 5% At Constant Propane Flow, Steam/HC Ratio And Firebox Condition.

| | | | |
|---|---|---|---|
| A&B COT, F | 1499 | 1499 | 1492 |
| A&B TLE Exit T, F | 691 | 691 | 698 |
| A&B TLE Inlet, PSIG | 10.0 | 10.0 | 10.0 |
| A&B TLE Exit T, PSIG | 9.0 | 9.0 | 9.0 |
| Cracked Gas Product | wt % | wt % | wt % |
| Hydrogen | 1.26 | 1.39 | 1.29 |
| Methane | 18.83 | 18.89 | 17.15 |
| Ethane | 4.57 | 4.54 | 4.38 |
| Ethylene | 31.25 | 31.11 | 28.94 |
| Acetylene | 0.04 | 0.04 | 0.04 |
| Propane | 20.13 | 21.25 | 24.15 |
| Propylene | 17.60 | 17.88 | 18.36 |
| MAPD | 0.26 | 0.25 | 0.25 |
| Butanes | 0.11 | 0.12 | 0.15 |
| Butadiene | 1.73 | 1.67 | 1.65 |
| Butenes + CPD | 1.41 | 1.41 | 1.62 |
| Other C5s | 0.42 | 0.37 | 0.40 |
| C6s+ | 1.34 | 0.93 | 1.55 |
| CO2 | 0.046 | 0.022 | 0.007 |
| CO | 1.001 | 0.134 | 0.061 |
| Aver. M.W. | 24.5 | 24.2 | 25.1 |

Example 59.2 at Fixed Total HC Flow, Steam/HC Ratio and Furnace Fuel Supply (Conditions 1A, 1B, & 1C)

In order to check how the temperatures and crack gas composition changed when the total mass of hydrocarbons to the coil was held constant while the percent of r-pyoil 1052*a* in the coil varied, steam flow to the testing coil was held constant in AUTO mode, and the furnace was set to control by a non-testing coil (Coil-C) outlet temp to allow the testing coils to be in Float Mode. The r-pyoil 1052*a*, in liquid form, without preheating, was added into propane line at about 5, 10 and 15% by weight, respectively. When r-pyoil 1052*a* flow was increased, propane flow was decreased accordingly to maintain the same total mass flow of hydrocarbon to the coil. Steam/HC ratio was maintained at 0.30 by a constant steam flow.

Temperature Change: As the r-pyoil 1052*a* content increased to 15%, crossover temperature dropped modestly by about 5 °F, COT increased greatly by about 15 °F, and TLE exit temperature just slightly increased by about 3 °F, as shown in Table 19.

Cracked gas composition change: As r-pyoil 1052*a* content in the feed increased to 15%, methane, ethane, r-ethylene, r-butadiene and benzene in cracked gas all went up by about 0.5, 0.2, 2.0, 0.5, and 0.6 percentage points, respectively. r-Ethylene/r-propylene ratio went up. Propane dropped significantly by about 3.0 percentage points, but r-propylene did not change much, as shown in Table 19A. These results showed the propane conversion increased. The increased propane conversion was due to the higher COT. When the total hydrocarbon feed to coil, steam/HC ratio and furnace fuel supply are held constant, the COT should go down when crossover temperature drops. However, what was seen in this test was opposite. The crossover temperature declined but COT went up, as shown in Table 19a. This indicates that r-pyoil 1052*a* cracking does not need as much heat as propane cracking on the same mass basis.

TABLE 19A

Variation of R-pyoil content and its effect on cracked gas and temperatures (Steam/HC ratio and furnace firebox were held constant).

| | Base-line | Base-line | 1A, 5% Pyoil | 1A, 5% Pyoil | 1B, 10% Pyoil | 1B, 10% Pyoil | 1C, 15% Pyoil | 1C, 15% pyoil |
|---|---|---|---|---|---|---|---|---|
| A&B Propane flow, klb/hr | 11.87 | 11.86 | 11.25 | 11.25 | 10.66 | 10.68 | 10.06 | 10.07 |
| A&B Pyoil Flow, lb/hr | 0 | 0 | 537 | 536 | 1074 | 1074 | 1776 | 1778 |
| A&B Steam flow, lb/hr | 3562 | 3556 | 3544 | 3543 | 3523 | 3523 | 3562 | 3560 |
| A&B total HC flow, klb/hr | 11.87 | 11.86 | 11.79 | 11.78 | 11.74 | 11.75 | 11.84 | 11.85 |
| Pyoil/(poil + propane), % | 0.0 | 0.0 | 4.6 | 4.6 | 9.2 | 9.1 | 15.0 | 15.0 |
| Steam/HC, ratio | 0.30 | 0.30 | 0.30 | 0.30 | 0.30 | 0.30 | 0.30 | 0.30 |
| A&B Crossover T, F | 1092 | 1091 | 1092 | 1092 | 1090 | 1090 | 1088 | 1087 |
| A&B COT, F | 1499 | 1499 | 1503 | 1503 | 1509 | 1509 | 1514 | 1514 |
| A&B TLE Exit T, F | 691 | 691 | 692 | 692 | 692 | 692 | 693 | 693 |
| A&B TLE Inlet, PSIG | 10.0 | 10.0 | 10.5 | 10.5 | 10.0 | 10.0 | 10.0 | 10.0 |
| A&B TLE Exit T, PSIG | 9.0 | 9.0 | 9.0 | 9.0 | 9.0 | 9.0 | 9.0 | 9.0 |
| Cracked Gas Product | wt % | wt % | wt % | wt % | wt % | wt % | wt % | wt % |
| Hydrogen | 1.26 | 1.39 | 1.40 | 1.32 | 1.33 | 1.28 | 1.31 | 1.18 |
| Methane | 18.83 | 18.89 | 18.96 | 18.74 | 19.31 | 19.08 | 19.61 | 19.16 |
| Ethane | 4.57 | 4.54 | 4.59 | 4.69 | 4.70 | 4.81 | 4.67 | 4.85 |
| Ethylene | 31.25 | 31.11 | 31.52 | 31.62 | 32.50 | 32.63 | 33.06 | 33.15 |
| Acetylene | 0.04 | 0.04 | 0.04 | 0.04 | 0.05 | 0.05 | 0.05 | 0.05 |
| Propane | 20.13 | 21.25 | 20.00 | 19.95 | 18.58 | 18.65 | 16.97 | 17.54 |
| Propylene | 17.60 | 17.88 | 17.85 | 17.86 | 17.79 | 17.85 | 17.58 | 17.81 |
| MAPD | 0.26 | 0.25 | 0.27 | 0.27 | 0.29 | 0.29 | 0.30 | 0.30 |
| Butanes | 0.11 | 0.12 | 0.11 | 0.11 | 0.10 | 0.10 | 0.10 | 0.10 |
| Butadiene | 1.73 | 1.67 | 1.86 | 1.86 | 2.04 | 2.03 | 2.23 | 2.17 |
| Butenes + CPD | 1.41 | 1.41 | 1.52 | 1.52 | 1.59 | 1.57 | 1.67 | 1.65 |
| Other C5s | 0.42 | 0.37 | 0.38 | 0.38 | 0.38 | 0.37 | 0.40 | 0.39 |
| C6s+ | 1.34 | 0.93 | 1.37 | 1.50 | 1.24 | 1.21 | 1.95 | 1.56 |
| CO2 | 0.046 | 0.022 | 0.012 | 0.016 | 0.011 | 0.011 | 0.007 | 0.008 |
| CO | 1.001 | 0.134 | 0.107 | 0.107 | 0.085 | 0.088 | 0.086 | 0.084 |
| Aver. M.W. | 24.5 | 24.2 | 24.2 | 24.4 | 24.2 | 24.4 | 24.2 | 24.6 |

Example 59.3 at Constant COT and Steam/HC Ratio (Conditions 2B, & 5B)

In the previous test and comparison, effect of r-pyoil 1052*a* addition on cracked gas composition was influenced not only by r-pyoil 1052*a* content but also by the change of COT because when r-pyoil 1052*a* was added, COT changed accordingly (it was set to Float Mode). In this comparison test, COT was held constant. The test conditions and cracked gas composition are listed in Table 19B. By comparing the data in Table 19B, the same trend in cracked gas composition was found as in the case Example 59.2. When r-pyoil 1052*a* content in the hydrocarbon feed was increased, methane, ethane, r-ethylene, r-butadiene in cracked gas went up, but propane dropped significantly while r-propylene did not change much.

TABLE 19B

Changing r-Pyoil 1052a content in HC feed at constant coil outlet temperature.

| | 5B, Pyoil 5% @ low T | 2B, 15% Pyoil | 2B, 15% Pyoil |
|---|---|---|---|
| A&B Propane flow, klb/hr | 11.85 | 10.07 | 10.07 |
| A&B Pyoil Flow, lb/hr | 601 | 1778 | 1777 |
| A&B Steam flow, lb/hr | 3738 | 3560 | 3559 |
| A&B total HC flow, klb/hr | 12.45 | 11.85 | 11.85 |
| Pyoil/(poil + propane), % | 4.8 | 15.0 | 15.0 |
| Steam/HC, ratio | 0.30 | 0.30 | 0.30 |
| A&B Crossover T, F | 1062 | 1055 | 1059 |
| A&B COT, F | 1478 | 1479 | 1479 |
| A&B TLE Exit T, F | 697 | 688 | 688 |
| A&B TLE Inlet, PSIG | 10.0 | 10.0 | 10.0 |
| A&B TLE Exit T, PSIG | 9.0 | 9.0 | 9.0 |

TABLE 19B-continued

Changing r-Pyoil 1052a content in HC feed at constant coil outlet temperature.

| Cracked Gas Product | wt % | wt % | wt % |
|---|---|---|---|
| Hydrogen | 1.20 | 1.12 | 1.13 |
| Methane | 16.07 | 16.60 | 16.23 |
| Ethane | 4.28 | 4.81 | 4.65 |
| Ethylene | 27.37 | 29.33 | 28.51 |
| Acetylene | 0.03 | 0.04 | 0.04 |
| Propane | 27.33 | 24.01 | 25.51 |
| Propylene | 18.57 | 18.45 | 18.59 |
| MAPD | 0.23 | 0.27 | 0.25 |
| Butanes | 0.17 | 0.14 | 0.16 |
| Butadiene | 1.50 | 1.94 | 1.76 |
| Butenes + CPD | 1.63 | 1.65 | 1.73 |
| Other C5s | 0.40 | 0.35 | 0.35 |
| C6s+ | 1.17 | 1.21 | 1.03 |
| CO2 | 0.007 | 0.010 | 0.007 |
| CO | 0.047 | 0.065 | 0.054 |
| Aver. M.W. | 25.8 | 25.7 | 25.9 |
| C2H4/C3H6, wt/wt | 1.47 | 1.59 | 1.53 |

Example 59.4 Effect of COT on Effluent Composition with R-Pyoil 1052*a* in Feed (Conditions 1C, 2B, 2C, 5A & 5B)

r-Pyoil 1052*a* in the hydrocarbon feed was held constant at 15% for 2B, and 2C. r-pyoil for 5A and 5B were reduced to 4.8%. The total hydrocarbon mass flow and steam to HC ratio were both held constant.

On cracked gas composition. When COT increased from 1479 °F to 1514 °F (by 35 °F), r-ethylene and r-butadiene in the cracked gas went up by about 4.0 and 0.4 percentage points, respectively, and r-propylene went down by about 0.8 percentage points, as shown in Table 20.

When r-pyoil 1052*a* content in the hydrocarbon feed was reduced to 4.8%, the COT effect on the cracked gas composition followed the same trend as that with 15% r-Pyoil 1052*a*.

TABLE 20

Effect of COT on cracked gas composition.
(Steam/HC ratio, R-pyoil 1052a content in the feed and total hydrocarbon mass flow were all held constant)

| | 1C, 15% Pyoil | 1C, 15% pyoil | 2B, 15% Pyoil | 2B, 15% Pyoil | 2C, 15% Pyoil | 2C, 15% Pyoil | 5A, Add in Pyoil 5% to $C_3H_8$ | 5B, Pyoil 5%@low T |
|---|---|---|---|---|---|---|---|---|
| A&B Propane flow, klb/hr | 10.06 | 10.07 | 10.07 | 10.07 | 10.07 | 10.06 | 11.85 | 11.85 |
| A&B Pyoil Flow, lb/hr | 1776 | 1778 | 1778 | 1777 | 1777 | 1776 | 593 | 601 |
| A&B Steam flow, lb/hr | 3562 | 3560 | 3560 | 3559 | 3560 | 3559 | 3737 | 3738 |
| A&B total HC flow, klb/hr | 11.84 | 11.85 | 11.85 | 11.85 | 11.84 | 11.84 | 12.44 | 12.45 |
| Pyoil/(poil + propane), % | 15.0 | 15.0 | 15.0 | 15.0 | 15.0 | 15.0 | 4.8 | 4.8 |
| Steam/HC, ratio | 0.30 | 0.30 | 0.30 | 0.30 | 0.30 | 0.30 | 0.30 | 0.30 |
| A&B Crossover T, F | 1088 | 1087 | 1055 | 1059 | 1075 | 1076 | 1081 | 1062 |
| A&B COT, F | 1514 | 1514 | 1479 | 1479 | 1497 | 1497 | 1492 | 1478 |
| A&B TLE Exit T, F | 693 | 693 | 688 | 688 | 690 | 691 | 698 | 697 |
| A&B TLE Inlet, PSIG | 10.0 | 10.0 | 10.0 | 10.0 | 10.0 | 10.0 | 10.0 | 10.0 |
| A&B TLE Exit T, PSIG | 9.0 | 9.0 | 9.0 | 9.0 | 9.0 | 9.0 | 9.0 | 9.0 |
| Cracked Gas Product | wt % | wt % | wt % | wt % | wt % | wt % | wt % | wt % |
| Hydrogen | 1.31 | 1.18 | 1.12 | 1.13 | 1.26 | 1.25 | 1.29 | 1.20 |
| Methane | 19.61 | 19.16 | 16.60 | 16.23 | 18.06 | 17.87 | 17.15 | 16.07 |
| Ethane | 4.67 | 4.85 | 4.81 | 4.65 | 4.72 | 4.75 | 4.38 | 4.28 |
| Ethylene | 33.06 | 33.15 | 29.33 | 28.51 | 31.03 | 30.73 | 28.94 | 27.37 |
| Acetylene | 0.05 | 0.05 | 0.04 | 0.04 | 0.04 | 0.04 | 0.04 | 0.03 |
| Propane | 16.97 | 17.54 | 24.01 | 25.51 | 21.17 | 21.10 | 24.15 | 27.33 |
| Propylene | 17.58 | 17.81 | 18.45 | 18.59 | 18.29 | 18.30 | 18.36 | 18.57 |
| MAPD | 0.30 | 0.30 | 0.27 | 0.25 | 0.27 | 0.28 | 0.25 | 0.23 |
| Butanes | 0.10 | 0.10 | 0.14 | 0.16 | 0.13 | 0.13 | 0.15 | 0.17 |
| Butadiene | 2.23 | 2.17 | 1.94 | 1.76 | 1.87 | 1.99 | 1.65 | 1.50 |
| Butenes + CPD | 1.67 | 1.65 | 1.65 | 1.73 | 1.71 | 1.77 | 1.62 | 1.63 |
| Other C5s | 0.40 | 0.39 | 0.35 | 0.35 | 0.37 | 0.40 | 0.40 | 0.40 |

TABLE 20-continued

Effect of COT on cracked gas composition.
(Steam/HC ratio, R-pyoil 1052a content in the feed and total hydrocarbon mass flow were all held constant)

| | | | | | | | | |
|---|---|---|---|---|---|---|---|---|
| C6s+ | 1.95 | 1.56 | 1.21 | 1.03 | 1.00 | 1.30 | 1.55 | 1.17 |
| CO2 | 0.007 | 0.008 | 0.010 | 0.007 | 0.009 | 0.009 | 0.007 | 0.007 |
| CO | 0.086 | 0.084 | 0.065 | 0.054 | 0.070 | 0.072 | 0.061 | 0.047 |
| Aver. M.W. | 24.2 | 24.6 | 25.7 | 25.9 | 24.8 | 24.9 | 25.1 | 25.8 |

Example 59.5 Effect of Steam/HC Ratio (Conditions 4A & 4B)

Steam/HC ratio effect is listed in Table 21A. In this test, r-pyoil 1052*a* content in the feed was held constant at 15%. COT in the testing coils was held constant in SET mode, while the COTs at non-testing coils were allowed to float. Total hydrocarbon mass flow to each coil was held constant.

On temperature. When steam/HC ratio was increased from 0.3 to 0.5, the crossover temperature dropped by about 17 °F since the total flow in the coils in the convection section increased due to more dilution steam, even though the COT of the testing coil was held constant. Due to the same reason, TLE exit temperature went up by about 13F.

On cracked gas composition. In the cracked gas, methane and r-ethylene were reduced by 1.6 and 1.4 percentage points, respectively, and propane was increased by 3.7 percentage points. The increased propane in the cracked gas indicated propane conversion dropped. This was due to, firstly, a shorter residence time, since in the 4B condition, the total moles (including steam) going into the coils was about 1.3 times of that in 2 °C condition (assuming the average molecular weight of r-pyoil 1052*a* was 160), and secondly, to the lower crossover temperature which was the inlet temperature for the radiant coil, making the average cracking temperature lower.

TABLE 21A

Effect of steam/HC ratio. (r-Pyoil in the HC feed at 15%, total hydrocarbon mass flow and COT were held constant).

| | 2C, 15% Pyoil | 2C, 15% Pyoil | 4A, Stm ratio 0.4 | 4B, Stm ratio 0.5 |
|---|---|---|---|---|
| A&B Propane flow, klb/hr | 10.07 | 10.06 | 10.08 | 10.08 |
| A&B Pyoil Flow, lb/hr | 1777 | 1776 | 1778 | 1778 |
| A&B Steam flow, lb/hr | 3560 | 3559 | 4748 | 5933 |
| A&B total HC flow, klb/hr | 11.84 | 11.84 | 11.85 | 11.85 |
| Pyoil/(poil + propane), % | 15.0 | 15.0 | 15.0 | 15.0 |
| Steam/HC, ratio | 0.30 | 0.30 | 0.40 | 0.50 |
| A&B Crossover T, F | 1075 | 1076 | 1063 | 1058 |
| A&B COT, F | 1497 | 1497 | 1498 | 1498 |
| A&B TLE Exit T, F | 690 | 691 | 698 | 703 |
| A&B Feed Pres, PSIG | 69.5 | 69.5 | 67.0 | 67.0 |
| A&B TLE Inlet, PSIG | 10.0 | 10.0 | 10.0 | 11.0 |
| A&B TLE Exit T, PSIG | 9.0 | 9.0 | 9.0 | 9.0 |
| Cracked Gas Product | wt % | wt % | wt % | wt % |
| Hydrogen | 1.26 | 1.25 | 0.87 | 1.12 |
| Methane | 18.06 | 17.87 | 16.30 | 16.18 |
| Ethane | 4.72 | 4.75 | 4.55 | 4.38 |
| Ethylene | 31.03 | 30.73 | 29.92 | 29.52 |
| Acetylene | 0.04 | 0.04 | 0.05 | 0.05 |
| Propane | 21.17 | 21.10 | 23.40 | 24.88 |
| Propylene | 18.29 | 18.30 | 18.67 | 18.49 |
| MAPD | 0.27 | 0.28 | 0.29 | 0.28 |
| Butanes | 0.13 | 0.13 | 0.15 | 0.16 |
| Butadiene | 1.87 | 1.99 | 2.01 | 1.85 |
| Butenes + CPD | 1.71 | 1.77 | 1.89 | 1.81 |
| Other C5s | 0.37 | 0.40 | 0.43 | 0.37 |
| C6s+ | 1.00 | 1.30 | 1.38 | 0.84 |

TABLE 21A-continued

Effect of steam/HC ratio. (r-Pyoil in the HC feed at 15%, total hydrocarbon mass flow and COT were held constant).

| | | | | |
|---|---|---|---|---|
| CO2 | 0.009 | 0.009 | 0.026 | 0.008 |
| CO | 0.070 | 0.072 | 0.070 | 0.061 |

On cracked gas composition. In the cracked gas, methane and r-ethylene were reduced by 1.6 and 1.4 percentage points, respectively, and propane was increased Renormalized cracked gas composition. In order to see what the lighter product composition could be if ethane and propane in the cracked gas would be recycled, the cracked gas composition in Table 21A was renormalized by taking off propane or ethane+ propane, respectively. The resulting composition is listed in Table 21B. It can be seen, olefin (r-ethylene+r-propylene) content wentup with steam/HC ratio.

TABLE 21B

Renormalized cracked gas composition. (R-pyoil in the HC feed at 15%, total hydrocarbon mass flow and COT were held constant).

| | 2C, 15% Pyoil | 4A, Stm ratio 0.4 | 4B, Stm ratio 0.5 |
|---|---|---|---|
| A&B Propane flow, klb/hr | 10.07 | 10.08 | 10.08 |
| Pyoil/(poil + propane), % | 15.0 | 15.0 | 15.0 |
| Steam/HC, ratio | 0.30 | 0.40 | 0.50 |
| A&B Crossover T, F | 1075 | 1063 | 1058 |
| A&B COT, F | 1497 | 1498 | 1498 |
| Renorm. w/o Propane | wt % | wt % | wt % |
| Hydrogen | 1.60 | 1.14 | 1.49 |
| Methane | 22.91 | 21.28 | 21.54 |
| Ethane | 5.99 | 5.94 | 5.83 |
| Ethylene | 39.36 | 39.06 | 39.29 |
| Acetylene | 0.05 | 0.06 | 0.06 |
| Propylene | 23.21 | 24.37 | 24.62 |
| MAPD | 0.34 | 0.38 | 0.38 |
| Butanes | 0.17 | 0.20 | 0.21 |
| Butadiene | 2.37 | 2.63 | 2.46 |
| Butenes + CPD | 2.16 | 2.47 | 2.41 |
| Other C5s | 0.46 | 0.56 | 0.50 |
| C6s+ | 1.27 | 1.80 | 1.12 |
| CO2 | 0.011 | 0.033 | 0.010 |
| CO | 0.089 | 0.091 | 0.081 |
| C2H4 + C3H6 | 62.57 | 63.43 | 63.91 |
| Renorm. w/o C2H6 + C3H8 | wt % | wt % | wt % |
| Hydrogen | 1.70 | 1.21 | 1.58 |
| Methane | 24.37 | 22.62 | 22.87 |
| Ethylene | 41.87 | 41.52 | 41.73 |
| Acetylene | 0.06 | 0.06 | 0.06 |
| Propylene | 24.69 | 25.91 | 26.15 |
| MAPD | 0.36 | 0.40 | 0.40 |
| Butanes | 0.18 | 0.21 | 0.22 |
| Butadiene | 2.52 | 2.79 | 2.61 |
| Butenes + CPD | 2.30 | 2.62 | 2.55 |
| Other C5s | 0.49 | 0.60 | 0.53 |
| C6s+ | 1.35 | 1.91 | 1.19 |
| CO2 | 0.012 | 0.035 | 0.011 |

TABLE 21B-continued

Renormalized cracked gas composition. (R-pyoil in the HC feed at 15%, total hydrocarbon mass flow and COT were held constant).

| | | | |
|---|---|---|---|
| CO | 0.094 | 0.097 | 0.086 |
| C2H4 + C3H6 | 66.55 | 67.43 | 67.87 |

Effect of total hydrocarbon feed flow (Conditions 2C & 3B) An increase in total hydrocarbon flow to the coil means a higher throughput but a shorter residence time, which reduces conversion. With r-pyoil 1052*a* at 15% in the HC feed, a 10% increase of the total HC feed brought about a slight increase in the propylene:ethylene ratio along with an increase in the concentration of propane without a change in ethane, when COT was held constant. Other changes were seen on methane and r-ethylene. Each dropped about 0.5~0.8 percentage points. The results are listed in Table 22.

TABLE 22

Comparison of more feed to coil (Steam/HC ratio = 0.3, COT is held constant at 1497 F.).

| | 2C, 15% Pyoil | 2C, 15% Pyoil | 3B, 10% more FD | 3B, 10% more FD |
|---|---|---|---|---|
| A&B Propane flow, klb/hr | 10.07 | 10.06 | 11.09 | 11.09 |
| A&B Pyoil Flow, lb/hr | 1777 | 1776 | 1956 | 1957 |
| A&B Steam flow, lb/hr | 3560 | 3559 | 3916 | 3916 |
| A&B total HC flow, klb/hr | 11.84 | 11.84 | 13.04 | 13.05 |
| Pyoil/(poil + propane), % | 15.0 | 15.0 | 15.0 | 15.0 |
| Steam/HC, ratio | 0.30 | 0.30 | 0.30 | 0.30 |
| A&B Crossover T, F | 1075 | 1076 | 1066 | 1065 |
| A&B COT, F | 1497 | 1497 | 1497 | 1497 |
| A&B TLE Exit T, F | 690 | 691 | 698 | 699 |
| A&B TLE Inlet, PSIG | 10.0 | 10.0 | 10.3 | 10.3 |
| A&B TLE Exit T, PSIG | 9.0 | 9.0 | 9.0 | 9.0 |
| Cracked Gas Product | wt % | wt % | wt % | wt % |
| Hydrogen | 1.26 | 1.25 | 1.19 | 1.24 |
| Methane | 18.06 | 17.87 | 17.23 | 17.31 |
| Ethane | 4.72 | 4.75 | 4.76 | 4.79 |
| Ethylene | 31.03 | 30.73 | 30.02 | 29.95 |
| Acetylene | 0.04 | 0.04 | 0.04 | 0.04 |
| Propane | 21.17 | 21.10 | 22.51 | 22.31 |
| Propylene | 18.29 | 18.30 | 18.44 | 18.28 |
| MAPD | 0.27 | 0.28 | 0.28 | 0.28 |
| Butanes | 0.13 | 0.13 | 0.15 | 0.14 |
| Butadiene | 1.87 | 1.99 | 1.93 | 1.95 |
| Butenes + CPD | 1.71 | 1.77 | 1.82 | 1.82 |
| Other C5s | 0.37 | 0.40 | 0.41 | 0.42 |
| C6s+ | 1.00 | 1.30 | 1.15 | 1.39 |
| CO2 | 0.009 | 0.009 | 0.009 | 0.008 |
| CO | 0.070 | 0.072 | 0.065 | 0.066 |

r-pyoil 1052*a* is successfully co-cracked with propane in the same coil on a commercial scale furnace.

What is claimed is:

1. A method of making a recycle content glycol ether composition ("r-GE"), said method comprising:

pyrolyzing a recycled waste ("pr-AO") at a temperature of at least 725 °C with hydrogen;

reacting a recycle content alkylene oxide composition, at least 5 wt. % of which is derived directly or indirectly from pyrolyzing the recycled waste ("pr-AO") to produce a glycol ether effluent comprising r-GE.

2. A method of making glycol ether, said method comprising:

a) a glycol ether manufacturer obtaining an alkylene oxide composition from a supplier and either:

i) from said supplier, also obtaining a pyrolysis recycle content allotment obtained at a pyrolysis temperature of at least 725 °C, wherein the pyrolysis recycle content allotment is a pyrolysis recycle content value that is an allocation or a credit; or ii) from any person or entity, obtaining a pyrolysis recycle content allotment, wherein the person or the entity only transfers the pyrolysis recycle content allotment and does not supply an alkylene oxide composition; and b) said glycol ether manufacturer making a glycol ether composition ("GE") from any alkylene oxide composition obtained from any source; and c) either:

i) applying said pyrolysis recycle content allotment to GE made by the supply of alkylene oxide obtained in step (a); or ii) applying said pyrolysis recycle content allotment to GE not made by the supply of alkylene oxide obtained in step (a), or iii) depositing said pyrolysis recycle content allotment into a recycle inventory from which is deducted a recycle content value and applying at least a portion of said value to:

1) GE to thereby obtain r-GE, or 2) to a compound or composition other than GE, or 3) both;

whether or not the recycle content value is obtained from a pyrolysis recycle content allotment obtained in step a(i) or step a(ii).

3. A method of making a recycle content glycol ether composition ("r-GE"), said method comprising:

a) reacting any alkylene oxide composition in a synthetic process to make a glycol ether composition ("GE"); and b) pyrolyzing a recycle waste at a pyrolysis temperature of at least 725 °C to produce a recycle content; applying a recycle content value to at least a portion of said GE to thereby obtain a recycle content glycol ether composition ("r-GE"); and c) obtaining said recycle content value by deducting at least a portion of said recycle content value from a recycle inventory, further said recycle inventory also containing a pyrolysis recycle content allotment or a pyrolysis recycle content allotment deposit having been made into the recycle inventory prior to the deduction, wherein the pyrolysis recycle content allotment is a pyrolysis recycle content value that is an allocation or a credit; and d) optionally communicating to a third party that said r-GE has a recycle content or is obtained or derived from recycled waste.

4. The method according to claim 3, said method further comprising:

e) pyrolyzing a pyrolysis feed comprising a recycled waste material to thereby form a pyrolysis effluent comprising recycle pyoil (r-pyoil) and/or a recycle pygas ("r-pygas");

f) optionally cracking a cracker feed comprising at least a portion of the r-pyoil to thereby produce a cracker effluent comprising r-olefins; or optionally cracking a cracker feed without r-pyoil to make olefins and applying a recycle content value to the olefins so made by deducting a recycle content value from a recycle inventory and applying it to the olefins to make r-olefins; and g) reacting any olefin volume in a synthetic process to make an alkylene oxide composition; and h) reacting at least a portion of any alkylene oxide composition in a synthetic process to make a glycol ether composition; and j) applying a recycle content value to at least a portion of said glycol ether composition based on:

i) feeding a pyrolysis recycle content alkylene oxide composition ("pr-AO") as a feedstock or ii) depositing at least a portion of an allotment obtained from any one or more of steps a) or b) into a recycle inventory and deducting from said inventory a recycle content value and applying at least a portion of said value to GE to thereby obtain said r-GE.

5. The method according to claim 3, wherein said recycle content value is derived directly or indirectly from cracking a r-pyoil or obtained from a r-pygas.

6. The method according to claim 3, wherein said r-GE is derived directly or indirectly from cracking r-pyoil in a gas fed cracker furnace.

7. The method according to claim 3, wherein the GE composition is prepared by reacting, in the presence of a catalyst, r-AO with an alcohol.

8. The method according to claim 3, wherein at least a portion of the alkylene oxide composition is derived directly or indirectly from the pyrolysis of recycled waste and/or through the cracking of r-pyoil to thereby obtain an r-AO composition.

9. The method according to claim 3, wherein the glycol ether is made by a glycol ether manufacturer and the recycle content is apportioned among products made by a glycol ether manufacturer or the products made by any one entity or a combinations of entities among the Family of Entities of which the glycol ether manufacturer is a part, and wherein the method for apportioning is an asymmetric distribution of recycle content values among their product(s).

10. The method according to claim 3, wherein the glycol ether is made by a glycol ether manufacturer and the recycle content is apportioned among products made by a glycol ether manufacturer or the products made by any one entity or a combinations of entities among the Family of Entities of which the glycol ether manufacturer is a part, and wherein the method for apportioning is applied symmetrically or asymmetrically across a combination of GE and other products.

11. The method according to claim 3, wherein the AO is supplied by an AO supplier that transfers a recycle content allotment to the GE manufacturer and a supply of AO to the GE manufacturer.

12. The method according to claim 3, wherein the alkylene oxide of step a) is a recycled alkylene oxide (r-AO).

13. The method according to claim 3, wherein a GE manufacturer or a person or entity among its Family of Entities obtains a supply of alkylene oxide (AO) and an allotment, and at least a portion of the allotment is either:

e) applied to make the GE;

f) applied to make a GE not made from the AO; or g) deposited into a recycle inventory from which is deducted a recycle content value and applying at least a portion of the recycle content value to:

i) GE to thereby obtain r-GE, or ii) to a compound or composition other than GE, or iii) both; or h) deposited into a recycle inventory and stored.

14. The method according to claim 3 further comprising:

a) an olefin supplier who either:

i) cracks a cracker feedstock comprising recycle pyoil to make an olefin composition, or ii) makes a pygas at least a portion of which is obtained by pyrolyzing a recycled waste stream (r-pygas), or iii) both; and b) a glycol ether manufacturer:

i) obtaining an allotment derived directly or indirectly with said r-olefin or said r-pygas from the supplier or a third-party transferring said allotment, ii) making glycol ether from alkylene oxide, and iii) associating at least a portion of the allotment with at least a portion of the glycol ether, whether or not the alkylene oxide used to make the glycol ether contains r-alkylene oxide.

15. The method according to claim 3, further comprising:

e) making a r-olefin by either cracking a r-pyoil or separating an olefin from a r-pygas; and f) converting at least a portion of the r-olefin in a synthetic process to make alkylene oxide, and g) converting at least a portion of any or said alkylene oxide to glycol ether; and h) applying a recycle content value to said glycol ether to make a r-GE; and j) optionally, also making a r-pyoil or r-pygas or both by pyrolyzing a recycle feedstock.

16. The method according to claim 3, further comprising:

e) an identifier associated with said GE, said identifier being a representation that said GE has recycle content or is made from a source having recycle content.

* * * * *